US007396913B2

(12) United States Patent
DeVries et al.

(10) Patent No.: US 7,396,913 B2
(45) Date of Patent: Jul. 8, 2008

(54) ERYTHROPOIETIN RECEPTOR BINDING ANTIBODIES

(75) Inventors: Peter J. DeVries, Des Plaines, IL (US); David H. Ostrow, Lake Zurich, IL (US); Edward B. Reilly, Libertyville, IL (US); Larry L. Green, San Francisco, CA (US); James Wieler, Beverly, MA (US)

(73) Assignee: Abbott Laboratories, Abbott Park, IL (US)

( * ) Notice: Subject to any disclaimer, the term of this patent is extended or adjusted under 35 U.S.C. 154(b) by 376 days.

(21) Appl. No.: 10/684,109

(22) Filed: Oct. 10, 2003

(65) Prior Publication Data

US 2004/0175379 A1 Sep. 9, 2004

Related U.S. Application Data

(60) Provisional application No. 60/418,031, filed on Oct. 14, 2002.

(51) Int. Cl.
*C01K 16/00* (2006.01)
*A61K 39/395* (2006.01)

(52) U.S. Cl. .............. 530/387.1; 530/387.3; 530/387.9; 530/388.15; 530/388.22; 424/130.1; 424/133.1; 424/141.1; 424/143.1

(58) Field of Classification Search ........................ None
See application file for complete search history.

(56) References Cited

U.S. PATENT DOCUMENTS

| 4,667,016 | A |   | 5/1987  | Lai et al. |
|-----------|---|---|---------|-----------|
| 4,703,008 | A |   | 10/1987 | Lin |
| 5,278,065 | A |   | 1/1994  | D'Andrea et al. |
| 5,885,574 | A | * | 3/1999  | Elliott ..................... 424/133.1 |
| 6,103,879 | A |   | 8/2000  | Chaovapong et al. |
| 6,153,190 | A |   | 11/2000 | Young et al. |
| 6,309,636 | B1| * | 10/2001 | do Couto et al. ......... 424/133.1 |
| 6,319,499 | B1|   | 11/2001 | Elliott |
| 2003/0215444 | A1 |   | 11/2003 | Elliott |

FOREIGN PATENT DOCUMENTS

| EP | 733962 | 9/1996 |
|----|--------|--------|
| EP | 1146056 A1 | 10/2001 |
| WO | 9008822 | 8/1990 |
| WO | WO9505469 | 2/1995 |
| WO | WO9603438 A1 | 2/1996 |
| WO | WO9942127 | 8/1999 |
| WO | WO0061164 | 10/2000 |
| WO | WO0061637 A1 | 10/2000 |
| WO | WO0066632 | 11/2000 |

OTHER PUBLICATIONS

Cacia et al., Biochemidtry, 1996, vol. 35, pp. 1897-1903.*
Rudikoff et al., Proc. Natl. Acad. Sci, USA, 1982, vol. 79:1979-1983.*
Alberts et al., The Cell, 2002, Garland Science, 4th edition, esp. pp. 161, Fig. 3-42.*
D'Andrea, et al., "Expression Cloning of the Murine Erythropoietin Receptor", *Cell*, 57:277-285 (1989).
Erslev, A., "Erythropoietin Coming of Age", *The New Engl. Journ. Of Med.*, 316(2)_101-103 (1987).
Jones, S. S., et al., "Human Erythropoietin Receptor: Cloning, Expression, and Biologic Characterization", *Blood*, 76(1):31-35 (1990).
Koury, M.J. & Boundurant, M.C., "Erythropoietin Retards DNA Breakdown and Prevents Programmed Death in Erythroid Progenitor Cells", *Science*, 248:378-381 (1990).
Liboi, E., et al., "Erythropoietin receptor signals both proliferation and erythroid-specific differentiation", *Proc. Natl. Acad. Sci. USA*, 90:11351-11355 (1993).
Mayeux, P., et al., "Structure of the Murine Erythropoietin Receptor Complex", *The Houm. Of Biol. Chem.*, 266(34):23380-23385 (1991).
McCaffery, P. J., et al., "Subunit Structure of the Erythropoietin Receptor", *The Journ. Of Biol. Chem.*, 264(18):10507-10512 (1989).
Miyake, T., et al., "Purification of Human Erythropoietin", *The Journ. Of Biol. Chem.*, 252(15):5558-5564 (1977).
Winkelmann, J. C., et al., "The Gene for the Human Erythropoietin Receptor: Analysis of the Coding Sequence and Assignment to Chromosome 19p", *Blood*, 76(1)24-30 (1990).

* cited by examiner

Primary Examiner—Elizabeth C. Kemmerer
Assistant Examiner—Xiaozhen Xie
(74) Attorney, Agent, or Firm—Irene M. Reininger

(57) ABSTRACT

The present invention relates to antibodies and antibody fragments thereof that bind to and activate an erythropoietin receptor. The present invention also relates to methods of modulating the endogenous activity of an erythropoietin receptor in a mammal using said antibodies as well as pharmaceutical compositions containing said antibodies.

11 Claims, 79 Drawing Sheets

FIGURE 1

```
                                             MetLysHisLeuTrp
 801                                         ATGAAGCATCTGTG
                                             TACTTCGTAGACAC

·PhePheLeuLeuLeuValAlaAlaProArgTrpValLeuSerGlnValGln
 851   GTTCTTCCTTCTCCTAGTGGCAGCTCCCAGATGGGTCCTGTCCCAGGTGC
       CAAGAAGGAAGAGGATCACCGTCGAGGGTCTACCCAGGACAGGGTCCACG

··LeuGlnGluSerGlyProGlyLeuValLysProSerGluThrLeuSer
 901   AGCTGCAGGAGTCGGGCCCAGGACTGGTGAAGCCTTCGGAGACCCTGTCC
       TCGACGTCCTCAGCCCGGGTCCTGACCACTTCGGAAGCCTCTGGGACAGG

LeuThrCysThrValSerGlyAlaSerIleSerSerTyrTyrTrpSerTrp
 951   CTCACCTGCACTGTCTCTGGTGCCTCCATCAGTAGTTACTACTGGAGCTG
       GAGTGGACGTGACAGAGACCACGGAGGTAGTCATCAATGATGACCTCGAC

·IleArgGlnProProGlyLysGlyLeuGluTrpIleGlyTyrIleTyrTyr
1001   GATCCGGCAGCCCCCAGGGAAGGGACTGGAGTGGATTGGGTATATCTATT
       CTAGGCCGTCGGGGGTCCCTTCCCTGACCTCACCTAACCCATATAGATAA

··SerGlySerThrAsnTyrAsnProSerLeuLysSerArgValThrIle
1051   ACAGTGGGAGCACCAACTACAACCCCTCCCTCAAGAGTCGAGTCACCATA
       TGTCACCCTCGTGGTTGATGTTGGGGAGGGAGTTCTCAGCTCAGTGGTAT

SerValAspThrSerLysAsnGlnPheSerLeuLysLeuArgSerValThr
1101   TCAGTAGACACGTCCAAGAACCAGTTCTCCCTGAAGCTGAGGTCTGTGAC
       AGTCATCTGTGCAGGTTCTTGGTCAAGAGGGACTTCGACTCCAGACACTG

·AlaAlaAspThrAlaValTyrTyrCysAlaArgGluArgLeuGlyIleGly
1151   CGCTGCGGACACGGCCGTGTATTACTGTGCGAGAGAGCGACTGGGGATCG
       GCGACGCCTGTGCCGGCACATAATGACACGCTCTCTCGCTGACCCCTAGC

··AspTyrTrpGlyGlnGlyThrLeuValThrValSerSerAlaSerThr
1201   GGGACTACTGGGGCCAAGGAACCCTGGTCACCGTCTCCTCAGCCTCCACC
       CCCTGATGACCCCGGTTCCTTGGGACCAGTGGCAGAGGAGTCGGAGGTGG

LysGlyProSerValPheProLeuAlaProCysSerArgSerThrSerGlu
1251   AAGGGCCCATCGGTCTTCCCCCTGGCGCCCTGCTCTAGAAGCACCTCCGA
       TTCCCGGGTAGCCAGAAGGGGGACCGCGGGACGAGATCTTCGTGGAGGCT

·SerThrAlaAlaLeuGlyCysLeuValLysAspTyrPheProGluProVal
1301   GAGCACAGCCGCCCTGGGCTGCCTGGTCAAGGACTACTTCCCCGAACCGG
       CTCGTGTCGGCGGGACCCGACGGACCAGTTCCTGATGAAGGGGCTTGGCC

··ThrValSerTrpAsnSerGlyAlaLeuThrSerGlyValHisThrPhe
1351   TGACGGTGTCGTGGAACTCAGGCGCTCTGACCAGCGGCGTGCACACCTTC
       ACTGCCACAGCACCTTGAGTCCGCGAGACTGGTCGCCGCACGTGTGGAAG
```

FIGURE 1 Continuation

```
       ProAlaValLeuGlnSerSerGlyLeuTyrSerLeuSerSerValValThr
1401   CCAGCTGTCCTACAGTCCTCAGGACTCTACTCCCTCAGCAGCGTGGTGAC
       GGTCGACAGGATGTCAGGAGTCCTGAGATGAGGGAGTCGTCGCACCACTG

·ValProSerSerAsnPheGlyThrGlnThrTyrThrCysAsnValAspHis
1451   CGTGCCCTCCAGCAACTTCGGCACCCAGACCTACACCTGCAACGTAGATC
       GCACGGGAGGTCGTTGAAGCCGTGGGTCTGGATGTGGACGTTGCATCTAG

··LysProSerAsnThrLysValAspLysThrVal
1501   ACAAGCCCAGCAACACCAAGGTGGACAAGACAGTTGGTGAGAGGCCAGCT
       TGTTCGGGTCGTTGTGGTTCCACCTGTTCTGTCAACCACTCTCCGGTCGA

1551   CAGGGAGGGAGGGTGTCTGCTGGAAGCCAGGCTCAGCCCTCCTGCCTGGA
       GTCCCTCCCTCCCACAGACGACCTTCGGTCCGAGTCGGGAGGACGGACCT

1601   CGCACCCCGGCTGTGCAGCCCCAGCCCAGGGCAGCAAGGCAGGCCCCATC
       GCGTGGGGCCGACACGTCGGGGTCGGGTCCCGTCGTTCCGTCCGGGGTAG

1651   TGTCTCCTCACCCGGAGGCCTCTGCCCGCCCACTCATGCTCAGGGAGAG
       ACAGAGGAGTGGGCCTCCGGAGACGGGCGGGGTGAGTACGAGTCCCTCTC

1701   GGTCTTCTGGCTTTTTCCACCAGGCTCCAGGCAGGCACAGGCTGGGTGCC
       CCAGAAGACCGAAAAAGGTGGTCCGAGGTCCGTCCGTGTCCGACCCACGG

1751   CCTACCCCAGGCCCTTCACACACAGGGGCAGGTGCTTGGCTCAGACCTGC
       GGATGGGGTCCGGGAAGTGTGTGTCCCCGTCCACGAACCGAGTCTGGACG

1801   CAAAAGCCATATCCGGGAGGACCCTGCCCCTGACCTAAGCCGACCCCAAA
       GTTTTCGGTATAGGCCCTCCTGGGACGGGGACTGGATTCGGCTGGGGTTT

1851   GGCCAAACTGTCCACTCCCTCAGCTCGGACACCTTCTCTCCTCCCAGATC
       CCGGTTTGACAGGTGAGGGAGTCGAGCCTGTGGAAGAGAGGAGGGTCTAG

GluArgLysCysCysValGluCys
1901   CGAGTAACTCCCAATCTTCTCTCTGCAGAGCGCAAATGTTGTGTCGAGTG
       GCTCATTGAGGGTTAGAAGAGAGACGTCTCGCGTTTACAACACAGCTCAC

·ProProCysPro
1951   CCCACCGTGCCCAGGTAAGCCAGCCCAGGCCTCGCCTCCAGCTCAAGGC
       GGGTGGCACGGGTCCATTCGGTCGGGTCCGGAGCGGGAGGTCGAGTTCCG

2001   GGGACAGGTGCCCTAGAGTAGCCTGCATCCAGGGACAGGCCCCAGCTGGG
       CCCTGTCCACGGGATCTCATCGGACGTAGGTCCCTGTCCGGGGTCGACCC
```

FIGURE 1 Continuation

```
                                            AlaProProValAlaGlyPro
2051  TGCTGACACGTCCACCTCCATCTCTTCCTCAGCACCACCTGTGGCAGGAC
      ACGACTGTGCAGGTGGAGGTAGAGAAGGAGTCGTGGTGGACACCGTCCTG

··SerValPheLeuPheProProLysProLysAspThrLeuMetIleSer
2101  CGTCAGTCTTCCTCTTCCCCCCAAAACCCAAGGACACCCTCATGATCTCC
      GCAGTCAGAAGGAGAAGGGGGGTTTTGGGTTCCTGTGGGAGTACTAGAGG

ArgThrProGluValThrCysValValValAspValSerHisGluAspPro
2151  CGGACCCCTGAGGTCACGTGCGTGGTGGTGGACGTGAGCCACGAAGACCC
      GCCTGGGGACTCCAGTGCACGCACCACCACCTGCACTCGGTGCTTCTGGG

·GluValGlnPheAsnTrpTyrValAspGlyValGluValHisAsnAlaLys
2201  CGAGGTCCAGTTCAACTGGTACGTGGACGGCGTGGAGGTGCATAATGCCA
      GCTCCAGGTCAAGTTGACCATGCACCTGCCGCACCTCCACGTATTACGGT

··ThrLysProArgGluGluGlnPheAsnSerThrPheArgValValSer
2251  AGACAAAGCCACGGGAGGAGCAGTTCAACAGCACGTTCCGTGTGGTCAGC
      TCTGTTTCGGTGCCCTCCTCGTCAAGTTGTCGTGCAAGGCACACCAGTCG

ValLeuThrValValHisGlnAspTrpLeuAsnGlyLysGluTyrLysCys
2301  GTCCTCACCGTTGTGCACCAGGACTGGCTGAACGGCAAGGAGTACAAGTG
      CAGGAGTGGCAACACGTGGTCCTGACCGACTTGCCGTTCCTCATGTTCAC

·LysValSerAsnLysGlyLeuProAlaProIleGluLysThrIleSerLys
2351  CAAGGTCTCCAACAAAGGCCTCCCAGCCCCCATCGAGAAAACCATCTCCA
      GTTCCAGAGGTTGTTTCCGGAGGGTCGGGGGTAGCTCTTTTGGTAGAGGT

··ThrLys
2401  AAACCAAAGGTGGGACCCGCGGGGTATGAGGGCCACATGGACAGAGGCCG
      TTTGGTTTCCACCCTGGGCGCCCCATACTCCCGGTGTACCTGTCTCCGGC

2451  GCTCGGCCCACCCTCTGCCCTGGGAGTGACCGCTGTGCCAACCTCTGTCC
      CGAGCCGGGTGGGAGACGGGACCCTCACTGGCGACACGGTTGGAGACAGG

GlyGlnProArgGluProGlnValTyrThrLeuProProSerArg
2501  CTACAGGGCAGCCCCGAGAACCACAGGTGTACACCCTGCCCCCATCCCGG
      GATGTCCCGTCGGGGCTCTTGGTGTCCACATGTGGGACGGGGGTAGGGCC

GluGluMetThrLysAsnGlnValSerLeuThrCysLeuValLysGlyPhe
2551  GAGGAGATGACCAAGAACCAGGTCAGCCTGACCTGCCTGGTCAAAGGCTT
      CTCCTCTACTGGTTCTTGGTCCAGTCGGACTGGACGGACCAGTTTCCGAA

·TyrProSerAspIleAlaValGluTrpGluSerAsnGlyGlnProGluAsn
2601  CTACCCCAGCGACATCGCCGTGGAGTGGGAGAGCAATGGGCAGCCGGAGA
      GATGGGGTCGCTGTAGCGGCACCTCACCCTCTCGTTACCCGTCGGCCTCT

··AsnTyrLysThrThrProProMetLeuAspSerAspGlySerPhePhe
```

FIGURE 1 Continuation

```
2651   ACAACTACAAGACCACACCTCCCATGCTGGACTCCGACGGCTCCTTCTTC
       TGTTGATGTTCTGGTGTGGAGGGTACGACCTGAGGCTGCCGAGGAAGAAG

LeuTyrSerLysLeuThrValAspLysSerArgTrpGlnGlnGlyAsnVal
2701   CTCTACAGCAAGCTCACCGTGGACAAGAGCAGGTGGCAGCAGGGGAACGT
       GAGATGTCGTTCGAGTGGCACCTGTTCTCGTCCACCGTCGTCCCCTTGCA

·PheSerCysSerValMetHisGluAlaLeuHisAsnHisTyrThrGlnLys
2751   CTTCTCATGCTCCGTGATGCATGAGGCTCTGCACAACCACTACACGCAGA
       GAAGAGTACGAGGCACTACGTACTCCGAGACGTGTTGGTGATGTGCGTCT

··SerLeuSerLeuSerProGlyLys
2801   AGAGCCTCTCCCTGTCTCCGGGTAAA
       TCTCGGAGAGGGACAGAGGCCCATTT
```

FIGURE 2

```
         MetArgValProAlaGlnLeuLeuGlyLeuLeuLeuLeuTrp
901      ATGAGGGTCCCCGCTCAGCTCCTGGGGCTCCTGCTGCTCT
         TACTCCCAGGGGCGAGTCGAGGACCCCGAGGACGACGAGA

··PheProGlyAlaArgCysLysLeuAspIleGlnLeuThrGlnSerPro
951      GGTTCCCAGGTGCCAGGTGTAAGCTTGACATCCAGCTGACCCAATCTCCA
         CCAAGGGTCCACGGTCCACATTCGAACTGTAGGTCGACTGGGTTAGAGGT

SerSerLeuSerAlaSerValGlyAspArgValThrIleThrCysArgAla
1001     TCCTCCCTGTCTGCATCTGTAGGAGACAGAGTCACCATCACTTGCCGGGC
         AGGAGGGACAGACGTAGACATCCTCTGTCTCAGTGGTAGTGAACGGCCCG

·SerGlnGlyIleArgAsnAspLeuGlyTrpTyrGlnGlnLysProGlyLys
1051     AAGTCAGGGCATTAGAAATGATTTAGGCTGGTATCAGCAGAAACCAGGGA
         TTCAGTCCCGTAATCTTTACTAAATCCGACCATAGTCGTCTTTGGTCCCT

··AlaProLysArgLeuIleTyrAlaAlaSerSerLeuGlnSerGlyVal
1101     AAGCCCCTAAGCGCCTGATCTATGCTGCATCCAGTTTGCAAAGTGGGGTC
         TTCGGGGATTCGCGGACTAGATACGACGTAGGTCAAACGTTTCACCCCAG

ProSerArgPheSerGlySerGlySerGlyThrGluPheThrLeuThrIle
1151     CCATCAAGGTTCAGCGGCAGTGGATCTGGGACAGAATTCACTCTCACAAT
         GGTAGTTCCAAGTCGCCGTCACCTAGACCCTGTCTTAAGTGAGAGTGTTA

·SerSerLeuGlnProGluAspPheAlaThrTyrTyrCysLeuGlnHisAsn
1201     CAGCAGCCTGCAGCCTGAAGATTTTGCAACTTATTACTGTCTACAGCATA
         GTCGTCGGACGTCGGACTTCTAAAACGTTGAATAATGACAGATGTCGTAT

··ThrTyrProProThrPheGlyGlnGlyThrLysValGluIleLysArg
1251     ATACTTACCCTCCGACGTTCGGCCAAGGGACCAAGGTGGAAATCAAACGA
         TATGAATGGGAGGCTGCAAGCCGGTTCCCTGGTTCCACCTTTAGTTTGCT

ThrValAlaAlaProSerValPheIlePheProProSerAspGluGlnLeu
1301     ACTGTGGCTGCACCATCTGTCTTCATCTTCCCGCCATCTGATGAGCAGTT
         TGACACCGACGTGGTAGACAGAAGTAGAAGGCGGTAGACTACTCGTCAA

·LysSerGlyThrAlaSerValValCysLeuLeuAsnAsnPheTyrProArg
1351     GAAATCTGGAACTGCTAGCGTTGTGTGCCTGCTGAATAACTTCTATCCCA
         CTTTAGACCTTGACGATCGCAACACACGGACGACTTATTGAAGATAGGGT

··GluAlaLysValGlnTrpLysValAspAsnAlaLeuGlnSerGlyAsn
1401     GAGAGGCCAAAGTACAGTGGAAGGTGGATAACGCCCTCCAATCGGGTAAC
         CTCTCCGGTTTCATGTCACCTTCCACCTATTGCGGGAGGTTAGCCCATTG
```

FIGURE 2 Continuation

```
     SerGlnGluSer
1451 TCCCAGGAGAGT
     AGGGTCCTCTCA
```

FIGURE 3

```
                              MetGluLeuGlyLeu
801                           ATGGAATTGGGGCT
                              TACCTTAACCCCGA

·ArgTrpValPheLeuValAlaLeuLeuArgGlyValGlnCysGlnValGln
851     CCGCTGGGTTTTCCTCGTTGCTCTTTTAAGAGGTGTCCAGTGTCAGGTGC
        GGCGACCCAAAAGGAGCAACGAGAAAATTCTCCACAGGTCACAGTCCACG

··LeuValGluSerGlyGlyGlyValValGlnProGlyArgSerLeuArg
901     AGCTGGTGGAGTCTGGGGGAGGCGTGGTCCAGCCTGGGAGGTCCCTGAGA
        TCGACCACCTCAGACCCCCTCCGCACCAGGTCGGACCCTCCAGGGACTCT

LeuSerCysValAlaSerGlyPheThrPheSerSerTyrGlyMetHisTrp
951     CTCTCCTGTGTAGCCTCTGGATTCACCTTCAGTAGCTATGGCATGCACTG
        GAGAGGACACATCGGAGACCTAAGTGGAAGTCATCGATACCGTACGTGAC

·ValArgGlnAlaProGlyLysGlyLeuGluTrpValAlaValIleSerTyr
1001    GGTCCGCCAGGCTCCAGGCAAGGGGCTGGAGTGGGTGGCAGTTATATCAT
        CCAGGCGGTCCGAGGTCCGTTCCCCGACCTCACCCACCGTCAATATAGTA

··AspGlySerAsnLysTyrTyrAlaAspSerValLysGlyArgPheThr
1051    ATGATGGAAGTAATAAATACTATGCAGACTCCGTGAAGGGCCGATTCACC
        TACTACCTTCATTATTTATGATACGTCTGAGGCACTTCCCGGCTAAGTGG

IleSerArgAspAsnSerLysAsnThrLeuTyrLeuGlnMetAsnSerLeu
1101    ATCTCCAGAGACAATTCCAAGAACACGCTGTATCTGCAAATGAACAGCCT
        TAGAGGTCTCTGTTAAGGTTCTTGTGCGACATAGACGTTTACTTGTCGGA

·ArgValGluAspThrAlaValTyrTyrCysAlaArgAspHisGlyGlyArg
1151    GAGAGTTGAGGACACGGCTGTGTATTACTGTGCGAGAGATCACGGTGGGA
        CTCTCAACTCCTGTGCCGACACATAATGACACGCTCTCTAGTGCCACCCT

··TyrValTyrAspTyrGlyMetAspValTrpGlyGlnGlyThrThrVal
1201    GGTACGTCTACGACTACGGTATGGACGTCTGGGGCCAAGGGACCACGGTC
        CCATGCAGATGCTGATGCCATACCTGCAGACCCCGGTTCCCTGGTGCCAG

ThrValSerSerAlaSerThrLysGlyProSerValPheProLeuAlaPro
1251    ACCGTCTCCTCAGCCTCCACCAAGGGCCCATCGGTCTTCCCCCTGGCGCC
        TGGCAGAGGAGTCGGAGGTGGTTCCCGGGTAGCCAGAAGGGGGACCGCGG

·CysSerArgSerThrSerGluSerThrAlaAlaLeuGlyCysLeuValLys
1301    CTGCTCTAGAAGCACCTCCGAGAGCACAGCCGCCCTGGGCTGCCTGGTCA
        GACGAGATCTTCGTGGAGGCTCTCGTGTCGGCGGGACCCGACGGACCAGT

··AspTyrPheProGluProValThrValSerTrpAsnSerGlyAlaLeu
1351    AGGACTACTTCCCCGAACCGGTGACGGTGTCGTGGAACTCAGGCGCTCTG
        TCCTGATGAAGGGGCTTGGCCACTGCCACAGCACCTTGAGTCCGCGAGAC
```

FIGURE 3 Continuation

```
         ThrSerGlyValHisThrPheProAlaValLeuGlnSerSerGlyLeuTyr
1401     ACCAGCGGCGTGCACACCTTCCCAGCTGTCCTACAGTCCTCAGGACTCTA
         TGGTCGCCGCACGTGTGGAAGGGTCGACAGGATGTCAGGAGTCCTGAGAT

·SerLeuSerSerValValThrValProSerSerAsnPheGlyThrGlnThr
1451     CTCCCTCAGCAGCGTGGTGACCGTGCCCTCCAGCAACTTCGGCACCCAGA
         GAGGGAGTCGTCGCACCACTGGCACGGGAGGTCGTTGAAGCCGTGGGTCT

··TyrThrCysAsnValAspHisLysProSerAsnThrLysValAspLys
1501     CCTACACCTGCAACGTAGATCACAAGCCCAGCAACACCAAGGTGGACAAG
         GGATGTGGACGTTGCATCTAGTGTTCGGGTCGTTGTGGTTCCACCTGTTC

ThrVal
1551     ACAGTTGGTGAGAGGCCAGCTCAGGGAGGGAGGGTGTCTGCTGGAAGCCA
         TGTCAACCACTCTCCGGTCGAGTCCCTCCCTCCCACAGACGACCTTCGGT

1601     GGCTCAGCCCTCCTGCCTGGACGCACCCCGGCTGTGCAGCCCCAGCCCAG
         CCGAGTCGGGAGGACGGACCTGCGTGGGGCCGACACGTCGGGGTCGGGTC

1651     GGCAGCAAGGCAGGCCCCATCTGTCTCCTCACCCGGAGGCCTCTGCCCGC
         CCGTCGTTCCGTCCGGGGTAGACAGAGGAGTGGGCCTCCGGAGACGGGCG

1701     CCCACTCATGCTCAGGGAGAGGGTCTTCTGGCTTTTTCCACCAGGCTCCA
         GGGTGAGTACGAGTCCCTCTCCCAGAAGACCGAAAAAGGTGGTCCGAGGT

1751     GGCAGGCACAGGCTGGGTGCCCCTACCCCAGGCCCTTCACACACAGGGGC
         CCGTCCGTGTCCGACCCACGGGGATGGGGTCCGGGAAGTGTGTGTCCCCG

1801     AGGTGCTTGGCTCAGACCTGCCAAAAGCCATATCCGGGAGGACCCTGCCC
         TCCACGAACCGAGTCTGGACGGTTTTCGGTATAGGCCCTCCTGGGACGGG

1851     CTGACCTAAGCCGACCCCAAAGGCCAAACTGTCCACTCCCTCAGCTCGGA
         GACTGGATTCGGCTGGGGTTTCCGGTTTGACAGGTGAGGGAGTCGAGCCT

Glu
1901     CACCTTCTCTCCTCCCAGATCCGAGTAACTCCCAATCTTCTCTCTGCAGA
         GTGGAAGAGAGGAGGGTCTAGGCTCATTGAGGGTTAGAAGAGAGACGTCT

·ArgLysCysCysValGluCysProProCysPro
1951     GCGCAAATGTTGTGTCGAGTGCCCACCGTGCCCAGGTAAGCCAGCCCAGG
         CGCGTTTACAACACAGCTCACGGGTGGCACGGGTCCATTCGGTCGGGTCC

2001     CCTCGCCCTCCAGCTCAAGGCGGGACAGGTGCCCTAGAGTAGCCTGCATC
         GGAGCGGGAGGTCGAGTTCCGCCCTGTCCACGGGATCTCATCGGACGTAG

2051     CAGGGACAGGCCCCAGCTGGGTGCTGACACGTCCACCTCCATCTCTTCCT
         GTCCCTGTCCGGGGTCGACCCACGACTGTGCAGGTGGAGGTAGAGAAGGA
```

FIGURE 3 Continuation

```
              AlaProProValAlaGlyProSerValPheLeuPheProProLysPro
2101  CAGCACCACCTGTGGCAGGACCGTCAGTCTTCGTCTTCCCCCCAAAACCC
      GTCGTGGTGGACACCGTCCTGGCAGTCAGAAGGAGAAGGGGGGTTTTGGG

LysAspThrLeuMetIleSerArgThrProGluValThrCysValValVal
2151  AAGGACACCCTCATGATCTCCCGGACCCCTGAGGTCACGTGCGTGGTGGT
      TTCCTGTGGGAGTACTAGAGGGCCTGGGGACTCCAGTGCACGCACCACCA

·AspValSerHisGluAspProGluValGlnPheAsnTrpTyrValAspGly
2201  GGACGTGAGCCACGAAGACCCCGAGGTCCAGTTCAACTGGTACGTGGACG
      CCTGCACTCGGTGCTTCTGGGGCTCCAGGTCAAGTTGACCATGCACCTGC

··ValGluValHisAsnAlaLysThrLysProArgGluGluGlnPheAsn
2251  GCGTGGAGGTGCATAATGCCAAGACAAAGCCACGGGAGGAGCAGTTCAAC
      CGCACCTCCACGTATTACGGTTCTGTTTCGGTGCCCTCCTCGTCAAGTTG

SerThrPheArgValValSerValLeuThrValValHisGlnAspTrpLeu
2301  AGCACGTTCCGTGTGGTCAGCGTCCTCACCGTTGTGCACCAGGACTGGCT
      TCGTGCAAGGCACACCAGTCGCAGGAGTGGCAACACGTGGTCCTGACCGA

·AsnGlyLysGluTyrLysCysLysValSerAsnLysGlyLeuProAlaPro
2351  GAACGGCAAGGAGTACAAGTGCAAGGTCTCCAACAAAGGCCTCCCAGCCC
      CTTGCCGTTCCTCATGTTCACGTTCCAGAGGTTGTTTCCGGAGGGTCGGG

··IleGluLysThrIleSerLysThrLys
2401  CCATCGAGAAAACCATCTCCAAAACCAAAGGTGGGACCCGCGGGGTATGA
      GGTAGCTCTTTTGGTAGAGGTTTTGGTTTCCACCCTGGGCGCCCCATACT

2451  GGGCCACATGGACAGAGGCCGGCTCGGCCCACCCTCTGCCCTGGGAGTGA
      CCCGGTGTACCTGTCTCCGGCCGAGCCGGGTGGGAGACGGGACCCTCACT

GlyGlnProArgGluProGlnVal
2501  CCGCTGTGCCAACCTCTGTCCCTACAGGGCAGCCCCGAGAACCACAGGTG
      GGCGACACGGTTGGAGACAGGGATGTCCCGTCGGGGCTCTTGGTGTCCAC

TyrThrLeuProProSerArgGluGluMetThrLysAsnGlnValSerLeu
2551  TACACCCTGCCCCCATCCCGGGAGGAGATGACCAAGAACCAGGTCAGCCT
      ATGTGGGACGGGGGTAGGGCCCTCCTCTACTGGTTCTTGGTCCAGTCGGA

·ThrCysLeuValLysGlyPheTyrProSerAspIleAlaValGluTrpGlu
2601  GACCTGCCTGGTCAAAGGCTTCTACCCCAGCGACATCGCCGTGGAGTGGG
      CTGGACGGACCAGTTTCCGAAGATGGGGTCGCTGTAGCGGCACCTCACCC

··SerAsnGlyGlnProGluAsnAsnTyrLysThrThrProProMetLeu
2651  AGAGCAATGGGCAGCCGGAGAACAACTACAAGACCACACCTCCCATGCTG
      TCTCGTTACCCGTCGGCCTCTTGTTGATGTTCTGGTGTGGAGGGTACGAC

AspSerAspGlySerPhePheLeuTyrSerLysLeuThrValAspLysSer
2701  GACTCCGACGGCTCCTTCTTCCTCTACAGCAAGCTCACCGTGGACAAGAG
```

FIGURE 3 Continuation

```
     CTGAGGCTGCCGAGGAAGAAGGAGATGTCGTTCGAGTGGCACCTGTTCTC

·ArgTrpGlnGlnGlyAsnValPheSerCysSerValMetHisGluAlaLeu
2751 CAGGTGGCAGCAGGGGAACGTCTTCTCATGCTCCGTGATGCATGAGGCTC
     GTCCACCGTCGTCCCCTTGCAGAAGAGTACGAGGCACTACGTACTCCGAG

··HisAsnHisTyrThrGlnLysSerLeuSerLeuSerProGlyLys
2801 TGCACAACCACTACACGCAGAAGAGCCTCTCCCTGTCTCCGGGTAAA
     ACGTGTTGGTGATGTGCGTCTTCTCGGAGAGGGACAGAGGCCCATTT
```

FIGURE 4

```
        MetArgValProAlaGlnLeuLeuGlyLeuLeuLeuLeuTrpPhePro
 901    ATGAGGGTCCCCGCTCAGCTCCTGGGGCTCCTGCTGCTCTGGTTCC
        TACTCCCAGGGGCGAGTCGAGGACCCCGAGGACGACGAGACCAAGG

··GlySerArgCysAspIleGlnMetThrGlnSerProSerSerValSer
 951    CAGGTTCCAGATGCGACATCCAGATGACCCAATCTCCATCTTCCGTGTCT
        GTCCAAGGTCTACGCTGTAGGTCTACTGGGTTAGAGGTAGAAGGCACAGA

AlaSerIleGlyAspArgValSerIleThrCysArgAlaSerGlnGlyIle
1001    GCATCTATAGGAGACAGAGTCTCCATCACTTGTCGGGCGAGTCAGGGTAT
        CGTAGATATCCTCTGTCTCAGAGGTAGTGAACAGCCCGCTCAGTCCCATA

·SerSerTrpLeuAlaTrpTyrGlnGlnLysProGlyLysAlaProThrLeu
1051    TAGCAGCTGGTTAGCCTGGTATCAGCAGAAACCAGGGAAAGCCCCTACGC
        ATCGTCGACCAATCGGACCATAGTCGTCTTTGGTCCCTTTCGGGGATGCG

··LeuIleTyrAlaAlaSerThrLeuGlnArgGlyValProSerArgPhe
1101    TCCTTATCTATGCTGCATCCACTTTGCAACGTGGGGTCCCATCAAGGTTC
        AGGAATAGATACGACGTAGGTGAAACGTTGCACCCCAGGGTAGTTCCAAG

SerGlySerGlySerGlyThrAspPheThrLeuThrIleSerSerLeuGln
1151    AGCGGCAGTGGATCTGGGACAGATTTCACTCTCACCATCAGCAGCCTGCA
        TCGCCGTCACCTAGACCCTGTCTAAAGTGAGAGTGGTAGTCGTCGGACGT

·ProGluAspPheAlaThrTyrPheCysGlnGlnAlaAsnSerPheProPhe
1201    GCCTGAAGATTTTGCAACTTACTTTTGTCAACAGGCTAACAGTTTCCCAT
        CGGACTTCTAAAACGTTGAATGAAAACAGTTGTCCGATTGTCAAAGGGTA

··ThrPheGlyProGlyThrLysValAspIleLysArgThrValAlaAla
1251    TCACTTTCGGCCCTGGGACCAAAGTGGATATCAAACGAACTGTGGCTGCA
        AGTGAAAGCCGGGACCCTGGTTTCACCTATAGTTTGCTTGACACCGACGT

ProSerValPheIlePheProProSerAspGluGlnLeuLysSerGlyThr
1301    CCATCTGTCTTCATCTTCCCGCCATCTGATGAGCAGTTGAAATCTGGAAC
        GGTAGACAGAAGTAGAAGGGCGGTAGACTACTCGTCAACTTTAGACCTTG

·AlaSerValValCysLeuLeuAsnAsnPheTyrProArgGluAlaLysVal
1351    TGCTAGCGTTGTGTGCCTGCTGAATAACTTCTATCCCAGAGAGGCCAAAG
        ACGATCGCAACACACGGACGACTTATTGAAGATAGGGTCTCTCCGGTTTC

··GlnTrpLysValAspAsnAlaLeuGlnSerGlyAsnSerGlnGluSer
1401    TACAGTGGAAGGTGGATAACGCCCTCCAATCGGGTAACTCCCAGGAGAGT
        ATGTCACCTTCCACCTATTGCGGGAGGTTAGCCCATTGAGGGTCCTCTCA

ValThrGluGlnAspSerLysAspSerThrTyrSerLeuSerSerThrLeu
1451    GTCACAGAGCAGGACAGCAAGGACAGCACCTACAGCCTCAGCAGCACCCT
        CAGTGTCTCGTCCTGTCGTTCCTGTCGTGGATGTCGGAGTCGTCGTGGGA
```

FIGURE 4 Continuation

```
          ·ThrLeuSerLysAlaAspTyrGluLysHisLysValTyrAlaCysGluVal
    1501  GACGCTGAGCAAAGCAGACTACGAGAAACACAAAGTCTACGCCTGCGAAG
          CTGCGACTCGTTTCGTCTGATGCTCTTTGTGTTTCAGATGCGGACGCTTC

··ThrHisGlnGlyLeuSerSerProValThrLysSerPheAsnArgGly
    1551  TCACCCATCAGGGCCTGAGCTCGCCCGTCACAAAGAGCTTCAACAGGGGA
          AGTGGGTAGTCCCGGACTCGAGCGGGCAGTGTTTCTCGAAGTTGTCCCCT

GluCys
    1601  GAGTGT
          CTCACA
```

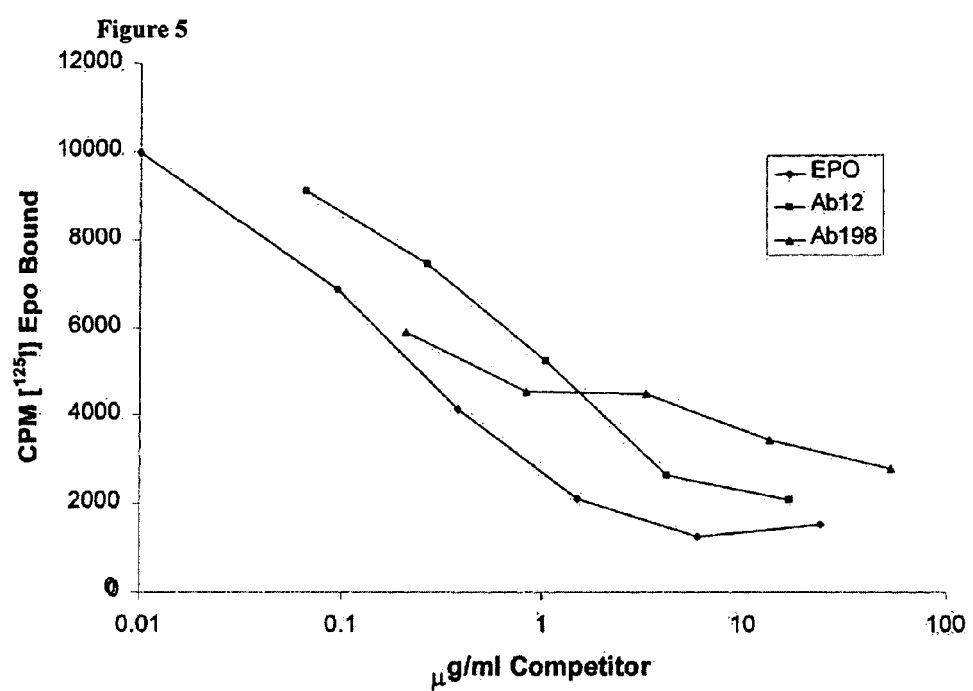

Erythropoietic Activity of Ab Candidates on F36e Human Erythroleukemic Cell Line No Epo Control     3 U/ml Epo     500 ng/ml Ab12

150 colonies / dish     48 colonies / dish

Figure 10
No Epo Control 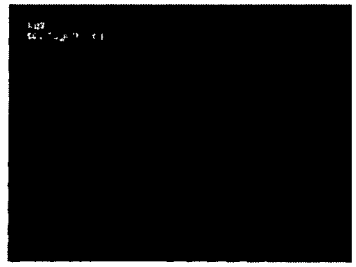 3 U/ml Epo 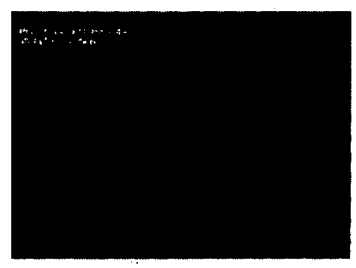 3200 ng/ml Ab12 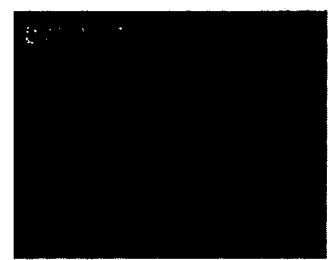

FIGURE 18

A.-- ABT2-SCX-003 Nucleotide sequence of heavy chain variable region:

5'CAGGTGCAGCTGGTGGAGTCTGGGGGAGGCGTGGTCCAGCCTGGGAGGTCC
CTGAGACTCTCCTGTGCAGCCTCTGGATTCACCTTCAGTAGCTATGGCATGCA
CTGGGTCCGCCAGGCTCCAGGCAAGGGGCTGGAGTGGGTGGCAGTTATATCA
TATGATGGAAGTAATAAATACTATGCAGACTCCGTGAAGGGCCGATTCACCA
TCTCCAGAGACAATTCCAAGAACACGCTGTATCTGCAAATGAACAGCCTGAG
AGTTGAGGACACGGCTGTGTATTACTGTGCGAGAGATCACGGTGGGAGGTAC
GTCTACGACTACGGTATGGACGTCTGGGGCCAAGGGACCACGGTCACCGTCT
CCTCAG 3'

B-- ABT2-SCX-003 Amino acid sequence of heavy chain variable region:

QVQLVESGGGVVQPGRSLRLSCAASGFTFSSYGMHWVRQAPGKGLEWVAVISY

DGSNKYYADSVKGRFTISRDNSKNTLYLQMNSLRVEDTAVYYCARDHGGRYVY

DYGMDVWGQGTTVTVSS

C-- ABT2-SCX-003 Nucleotide sequence of light chain variable region:

5'GACATCCAGATGACCCAATCTCCATCTTCCGTGTCTGCATCTGTAGGAGACA
GAGTCTCCATCACTTGTCGGGCGAGTCAGGGTATTAGCAGCTGGTTAGTCTGG
TATCAGCAGAAACCAGGGAAAGCCCCTGCGCTCCTAATCTATGCTGCATCCA
GTTTGCAGCGTGGGGTCCCATCAAGGTTCAGCGGCAGTGGATCTGGGACAGA
CTTCACTCTCACCATCAGCAGCCTGCAGCCTGAAGATTTTGCAACTTACTTTT
GTCAACAGGCTAACAGTTTCCCATTCACTTTCGGCCCTGGGACCAAAGTGGAT
ATCAAAC3'

D-- ABT2-SCX-003 Amino acid sequence of light chain variable region:

DIQMTQSPSSVSASVGDRVSITCRASQGISSWLVWYQQKPGKAPALLIYAASSLQ
RGVPSRFSGSGSGTDFTLTISSLQPEDFATYFCQQANSFPFTFGPGTKVDIK

FIGURE 19

A-- ABT2-SCX-012 Nucleotide sequence of heavy chain variable region:

5'CAGGTGCAGCTGCAGGAGTCGGGCCCAGGACTGGTGAAGCCTTCGGAGACC
CTGTCCCTCACCTGCACTGTCTCTGGTGCCTCCATCAGTAGTTACTACTGGAG
CTGGATCCGGCAGCCCCCAGGGAAGGGACTGGAGTGGATTGGGTATATCTAT
TACAGTGGGAGCACCAACTACAACCCCTCCCTCAAGAGTCGAGTCACCATAT
CAGTAGACACGTCCAAGAACCAGTTCTCCCTGAAGCTGAGGTCTGTGACCGC
TGCGGACACGGCCGTGTATTACTGTGCGAGAGAGCGACTGGGGATCGGGGAC
TACTGGGGCCAAGGAACCCTGGTCACCGTCTCCTCAG3'

B-- ABT2-SCX-012 Amino acid sequence of heavy chain variable region:

QVQLQESGPGLVKPSETLSLTCTVSGASISSYYWSWIRQPPGKGLEWIGYIYYSGS
TNYNPSLKSRVTISVDTSKNQFSLKLRSVTAADTAVYYCARERLGIGDYWGQGT
LVTVSS

C-- ABT2-SCX-012 Nucleotide sequence of light chain variable region:

5'GACATCCAGCTGACCCAATCTCCATCCTCCCTGTCTGCATCTGTAGGAGACA
GAGTCACCATCACTTGCCGGGCAAGTCAGGGCATTAGAAATGATTTAGGCTG
GTATCAGCAGAAACCAGGGAAAGCCCCTAAGCGCCTGATCTATGCTGCATCC
AGTTTGCAAAGTGGGGTCCCATCAAGGTTCAGCGGCAGTGGATCTGGGACAG
AATTCACTCTCACAATCAGCAGCCTGCAGCCTGAAGATTTTGCAACTTATTAC
TGTCTACAGCATAATACTTACCCTCCGACGTTCGGCCAAGGGACCAAGGTGG
AAATCAAAC3'

D-- ABT2-SCX-012 Amino acid sequence of light chain variable region:

DIQLTQSPSSLSASVGDRVTITCRASQGIRNDLGWYQQKPGKAPKRLIYAASSLQS
GVPSRFSGSGSGTEFTLTISSLQPEDFATYYCLQHNTYPPTFGQGTKVEIK

FIGURE 20

A-- ABT2-SCX-022 Nucleotide sequence of heavy chain variable region:

5'CAGGTGCAGCTGGTGGAGTCTGGGGGAGGCGTGGTCCAGCCTGGGAGGTCC
CTGAGACTCTCCTGTGCAGCCTCTGGATTCACCTTCAGTAGCTATGGCATGCA
CTGGGTCCGCCAGGCTCCAGGCAAGGGGCTGGAGTGGGTGGTAGTTATATCA
TATGATGGAAGTAATAAATACTATGCAGACTCCGTGAAGGGCCGATTCACCA
TCTCCAGAGACAATTCCAAGAACACGCTGTATCTGCAAATGAACAGCCTGAG
AGTTGAGGACACGGCTGTGTATTACTGTGCGAGAGATCACGGTGGGAGGTAC
GTCTACGACTACGGTATGGACGTCTGGGGCCAAGGGACCACGGTCACCGTCT
CCTCAG3'

B-- ABT2-SCX-022 Amino acid sequence of heavy chain variable region:

QVQLVESGGGVVQPGRSLRLSCAASGFTFSSYGMHWVRQAPGKGLEWVVVISY
DGSNKYYADSVKGRFTISRDNSKNTLYLQMNSLRVEDTAVYYCARDHGGRYVY
DYGMDVWGQGTTVTVSS

C-- ABT2-SCX-022 Nucleotide sequence of light chain variable region:

5'GACATCCAGATGACCCAATCTCCATCTTCCGTGTCTGCATCTGTAGGAGACA
GAGTCTCCATCACTTGTCGGGCGAGTCAGGGTATTAGCAGCTGGTTAGCCTG
GTATCAGCAGAAACCAGGGAAAGCCCCTACGCTCCTAATCTATGCTGCATCC
AGTTTGCAACGTGGGGTCCCATCAAGGTTCAGCGGCAGTGGATCTGGGACAG
ATTTCACTCTCACCATCAGCAGCCTGCAGCCTGAAGATTTTGCAACTTACTTT
TGTCAACAGGCTAACAGTTTCCCATTCACTTTCGGCCCTGGGACCAAAGTGGA
TATCAAAC3'

D-- ABT2-SCX-022 Amino acid sequence of light chain variable region:

DIQMTQSPSSVSASVGDRVSITCRASQGISSWLAWYQQKPGKAPTLLIYAASSLQ
RGVPSRFSGSGSGTDFTLTISSLQPEDFATYFCQQANSFPFTFGPGTKVDIK

FIGURE 21

A— ABT2-SCX-054 Nucleotide sequence of heavy chain variable region:

5'CAGGTGCAGCTGGTGGAGTCGGGGGGAGGCGTGGTCCAGCCTGGGAGGTC
CCTGAGACTCTCCTGTGCAGCGTCTGGATTCACCTTCAGTAAATATGGCATGC
ACTGGGTCCGCCAGGCTCCAGGCAAGGGGCTGGAGTGGGTGGCAGTTTTATG
GTATGATGGAAGTAATAAATACTATGCAGACTCCGTGAAGGGCCGATTCACC
ATCTCCAGAGACAATTCCAAGAACACGCTGTATCTGCAAATGAACAGCCTGA
GAGCCGAGGACACGGCTGTGTATTACTGTGCGAGAGGTCCGTACTACTTTGA
CTACTGGGGCCAGGGAACCCTGGTCACCGTCTCCTCAG3'

B— ABT2-SCX-054 Amino acid sequence of heavy chain variable region:
QVQLVESGGGVVQPGRSLRLSCAASGFTFSKYGMHWVRQAPGKGLEWVAVLW
YDGSNKYYADSVKGRFTISRDNSKNTLYLQMNSLRAEDTAVYYCARGPYYFDY
WGQGTLVTVSS C— ABT2-SCX-054 Nucleotide sequence of light chain variable region:

5'GAAATTGTGTTGACGCAGTCTCCAGGCACCCTGTCTTTGTCTCCAGGGGAAA
GAGCCACCCTCTCCTGCAGGGCCAGTCAGAGTGTTAGCAGCAGCTACTTAGC
CTGGTACCAGCAGAAACCTGGCCAGGCTCCCAGGCTCCTCATCTATGGTGCA
TCCAGCAGGGCCACTGGCATCCCAGACAGGTTCAGTGGCAGTGGGTCTGGGA
CAGACTTCACTGTCACCATCAGCAGACTGGAACCTGAAGATTTTGCAGTGTAT
TACTGTCAGCAGTATGGTAGTTCACCGTGGACGTTCGGCCAAGGGACCAAGG
TGGAAATCAAAC3'

D— ABT2-SCX-054 Amino acid sequence of light chain variable region:

EIVLTQSPGTLSLSPGERATLSCRASQSVSSSYLAWYQQKPGQAPRLLIYGASSRA
TGIPDRFSGSGSGTDFTVTISRLEPEDFAVYYCQQYGSSPWTFGQGTKVEIK

FIGURE 22

A-- ABT2-SCX-060 Nucleotide sequence of heavy chain variable region:

5'CAGGTGCAGCTGGTGGAGTCTGGGGGAGGCGTGGTCCAGCCTGGGAGGTCC
CTGAGACTCTCCTGTGCAGCCTCTGGATTCACCTTCAGTAGCTATGGCATGCA
CTGGGTCCGCCAGGCTCCAGGCAAGGGGCTGGAGTGGGTGGCAGTTATATCA
TATGATGGAAGTAATAAATACTATGCAGACTCCGTGAAGGGCCGATTCACCA
TCTCCAGAGACAATTCCAAGAACACGCTGTATCTGCAAATGAACAGCCTGAG
AGTTGAGGACACGGCTGTGTATTACTGTGCGAGAGATCACGGTGGGAGGTAC
GTCTACGACTACGGTATGGACGTCTGGGGCCAAGGGACCACGGTCACCGTCT
CCTCAG3'

B-- ABT2-SCX-060 Amino acid sequence of heavy chain variable region:
QVQLVESGGGVVQPGRSLRLSCAASGFTFSSYGMHWVRQAPGKGLEWVAVISY
DGSNKYYADSVKGRFTISRDNSKNTLYLQMNSLRVEDTAVYYCARDHGGRYVY
DYGMDVWGQGTTVTVSS C-- ABT2-SCX-060 Nucleotide sequence of light chain variable region:

5'GACATCCAGATGACCCAATCTCCATCTTCCGTGTCCGCATCTGTAGGAGACA
GAGTCTCCATCACTTGTCGGGCGAGTCAGGGTATTAGCAGCTGGTTAGCCTG
GTATCAGCAGAAACCAGGGAAAGCCCCTACGCTCCTAATCTATGCTGCATCC
AGTTTGCAACGTGGGGTCCCATCAAGGTTCAGCGGCAGTGGATCTGGGACAG
ATTTCACTCTCACCATCAGCAGCCTGCAGCCTGAAGATTTTGCAACTTACTTT
TGTCAACAGGCTAACAGTTTCCCATTCACTTTCGGCCCTGGGACCAAAGTGGA
TATCAAAC3'

D-- ABT2-SCX-060 Amino acid sequence of light chain variable region:
DIQMTQSPSSVSASVGDRVSITCRASQGISSWLAWYQQKPGKAPTLLIYAASSLQ
RGVPSRFSGSGSGTDFTLTISSLQPEDFATYFCQQANSFPFTFGPGTKVDIK

FIGURE 23

A-- ABT2-SCX-102 Nucleotide sequence of heavy chain variable region:

5'CAGGTGCAGCTGGTGGAGTCTGGGGGAGGCGTGGTCCAGCCTGGGAGGTCC
CTGAGACTCTCCTGTGCAGCCTCTGGATTCACCTTCAGTAGCTATGGCATGCA
CTGGGTCCGCCAGGCTCCAGGCAAGGGGCTGGAGTGGGTGGCAGTTATATCA
TATGATGGAAGTAATAAATACTATGCAGACTCCGTGAAGGGCCGATTCACCA
TCTCCAGAGACAATTCCAAGAACACGCTGTATCTGCAAATGAACAGCCTGAG
AGTTGAGGACACGGCTGTGTATTACTGTGCGAGAGATCACGGTGGGAGGTAC
GTCTACGACTACGGTATGGACGTCTGGGGCCAAGGGACCACGGTCACCGTCT
CCTCAG3'

B-- ABT2-SCX-102 Amino acid sequence of heavy chain variable region:
QVQLVESGGGVVQPGRSLRLSCAASGFTFSSYGMHWVRQAPGKGLEWVAVISY
DGSNKYYADSVKGRFTISRDNSKNTLYLQMNSLRVEDTAVYYCARDHGGRYVY
DYGMDVWGQGTTVTVSS C-- ABT2-SCX-102 Nucleotide sequence of light chain variable region:

5'GACATCCAGATGACCCAATCTCCATCTTCCGTGTCTGCATCTGTAGGAGACA
GAGTCTCCATCACTTGTCGGGCGAGTCAGGGTATTAGCAGCTGGTTAGCCTG
GTATCAGCAGAAACCAGGGAAAGCCCCTAAGCGCCTGATCTATGCTGCATCC
AGTTTGCAACGTGGGGTCCCATCAAGGTTCAGCGGCAGTGGATCTGGGACAG
ATTTCACTCTCACCATCAGCAGCCTGCAGCCTGAAGATTTTGCAACTTACTTT
TGTCAACAGGCTAACAGTTTCCCATTCACTTTCGGCCCTGGGACCAAAGTGGA
TATCAAAC3'

D-- ABT2-SCX-102 Amino acid sequence of light chain variable region:
DIQMTQSPSSVSASVGDRVSITCRASQGISSWLAWYQQKPGKAPKRLIYAASSLQ
RGVPSRFSGSGSGTDFTLTISSLQPEDFATYFCQQANSFPFTFGPGTKVDIK

FIGURE 24

A-- ABT2-SCX-135 Nucleotide sequence of heavy chain variable region:

5'CAGGTGCAGCTGGTGGAGTCTGGGGGAGGCGTGGTCCAGCCTGGGAGGTCC
CTGAGACTCTCCTGTGCAGCCTCTGGATTCACCTTCAGTAGCTATGGCATGCA
CTGGGTCCGCCAGGCTCCAGGCAAGGGGCTGGAGTGGGTGGCAGTTATATCA
TATGATGGAAGTAATAAATACTATGCAGACTCCGTGAAGGGCCGATTCACCA
TCTCCAGAGACAATTCCAAGAACACGCTGTATCTGCAAATGAACAGCCTGAG
AGTTGAGGACACGGCTGTGTATTACTGTGCGAGAGATCACGGTGGGAGGTAC
GTCTACGACTACGGTATGGACGTCTGGGGCCAAGGGACCACGGTCACCGTCT
CCTCAG 3'

B-- ABT2-SCX-135 Amino acid sequence of heavy chain variable region:

QVQLVESGGGVVQPGRSLRLSCAASGFTFSSYGMHWVRQAPGKGLEWVAVISY
DGSNKYYADSVKGRFTISRDNSKNTLYLQMNSLRVEDTAVYYCARDHGGRYVY
DYGMDVWGQGTTVTVSS

C-- ABT2-SCX-135 Nucleotide sequence of light chain variable region:

5'GACATCCAGATGACCCAGTCTCCATCTTCCGTGTCTACATCTGTAGGAGACA
GAGTCTCCATCACTTGTCGGGCGAGTCAGGGTATTGGCAGCTGGTTAGCCTG
GTATCAGCAGAAACCAGGGCAAGCCCCTACGCTCCTAATCTATGCTGCATCC
AGTTTGCAACGTGGGGTCCCATCAAGATTCAGCGGCAGTGGATCTGGGACAG
ATTTCACTCTCACCATCAACAGCCTGCAGCCTGAAGATTTTGCAACTTACTTT
TGTCAACAGGCTAACAGTTTCCCATTCACTTTCGGCCCTGGGACCAAAGTGGA
TGTCAAAC3'

D-- ABT2-SCX-135 Amino acid sequence of light chain variable region:
DIQMTQSPSSVSTSVGDRVSITCRASQGIGSWLAWYQQKPGQAPTLLIYAASSLQ
RGVPSRFSGSGSGTDFTLTINSLQPEDFATYFCQQANSFPFTFGPGTKVDVK

FIGURE 25

A-- ABT2-SCX-145 Nucleotide sequence of heavy chain variable region:

5'CAGGTGCAGCTGGTGGAGTCTGGGGGAGGCGTGGTCCAGCCTGGGAGGTCC
CTGAGACTCTCCTGTGCAGCCTCTGGATTCACCTTCAGTAGCTATGGCATGCA
CTGGGTCCGCCAGGCTCCAGGCAAGGGGCTGGAGTGGGTGGCAGTTATATCA
TATGATGGAAGTAATAAATACTATGCAGACTCCGTGAAGGGCCGATTCACCA
TCTCCAGAGACAATTCCAAGAACACGCTGTATCTGCAAATGAACAGCCTGAG
AGTTGAGGACACGGCTGTGTATTACTGTGCGAGAGATCACGGTGGGAGGTAC
GTCTACGACTACGGTATGGACGTCTGGGGCCAAGGGACCACGGTCACCGTCT
CCTCAG3'

B-- ABT2-SCX-145 Amino acid sequence of heavy chain variable region:

QVQLVESGGGVVQPGRSLRLSCAASGFTFSSYGMHWVRQAPGKGLEWVAVISY
DGSNKYYADSVKGRFTISRDNSKNTLYLQMNSLRVEDTAVYYCARDHGGRYVY
DYGMDVWGQGTTVTVSS

C-- ABT2-SCX-145 Nucleotide sequence of light chain variable region:

5'GACATCCAGATGACCCAGTCTCCATCTTCCGTGTCTGCATCTGTAGGAGACA
GAGTCTCCATCACTTGTCGGGCGAGTCAGGGTATTGGCAGCTGGTTAGCCTG
GTATCAGCAGAAACCAGGGCAAGCCCCTACGCTCCTAATCTATGCTGCATCC
AGTTTGCAACGTGGGGTCCCATCAAGATTCAGCGGCAGTGGATCTGGGACAG
ATTTCACTCTCACCATCAACAGCCTGCAGCCTGAAGATTTTGCAACTTACTTT
TGTCAACAGGCTAACAGTTTCCCATTCACTTTCGGCCCTGGGACCAAAGTGGA
TGTCAAAC3'

D-- ABT2-SCX-145 Amino acid sequence of light chain variable region:
DIQMTQSPSSVSASVGDRVSITCRASQGIGSWLAWYQQKPGQAPTLLIYAASSLQ
RGVPSRFSGSGSGTDFTLTINSLQPEDFATYFCQQANSFPFTFGPGTKVDVK

FIGURE 26

A-- ABT2-SCX-198 Nucleotide sequence of heavy chain variable region:

5'CAGGTGCAGCTGGTGGAGTCTGGGGGAGGCGTGGTCCAGCCTGGGAGGTCC
CTGAGACTCTCCTGTGTAGCCTCTGGATTCACCTTCAGTAGCTATGGCATGCA
CTGGGTCCGCCAGGCTCCAGGCAAGGGGCTGGAGTGGGTGGCAGTTATATCA
TATGATGGAAGTAATAAATACTATGCAGACTCCGTGAAGGGCCGATTCACCA
TCTCCAGAGACAATTCCAAGAACACGCTGTATCTGCAAATGAACAGCCTGAG
AGTTGAGGACACGGCTGTGTATTACTGTGCGAGAGATCACGGTGGGAGGTAC
GTCTACGACTACGGTATGGACGTCTGGGGCCAAGGGACCACGGTCACCGTCT
CCTCAG3'

B-- ABT2-SCX-198 Amino acid sequence of heavy chain variable region:

QVQLVESGGGVVQPGRSLRLSCVASGFTFSSYGMHWVRQAPGKGLEWVAVISY
DGSNKYYADSVKGRFTISRDNSKNTLYLQMNSLRVEDTAVYYCARDHGGRYVY
DYGMDVWGQGTTVTVSS

C-- ABT2-SCX-198 Nucleotide sequence of light chain variable region:

5'GACATCCAGATGACCCAATCTCCATCTTCCGTGTCTGCATCTATAGGAGACA
GAGTCTCCATCACTTGTCGGGCGAGTCAGGGTATTAGCAGCTGGTTAGCCTG
GTATCAGCAGAAACCAGGGAAAGCCCCTACGCTCCTTATCTATGCTGCATCC
ACTTTGCAACGTGGGGTCCCATCAAGGTTCAGCGGCAGTGGATCTGGGACAG
ATTTCACTCTCACCATCAGCAGCCTGCAGCCTGAAGATTTTGCAACTTACTTT
TGTCAACAGGCTAACAGTTTCCCATTCACTTTCGGCCCTGGGACCAAAGTGGA
TATCAAAC3'

D-- ABT2-SCX-198 Amino acid sequence of light chain variable region:

DIQMTQSPSSVSASIGDRVSITCRASQGISSWLAWYQQKPGKAPTLLIYAASTLQR
GVPSRFSGSGSGTDFTLTISSLQPEDFATYFCQQANSFPFTFGPGTKVDIK

FIGURE 27

A-- ABT2-SCX-254 Nucleotide sequence of heavy chain variable region:

5'CAGGTGCAGCTGGTGGAGTCTGGGGGAGGCGTGGTCCAGCCTGGGAGGTCC
CTGAGACTCTCCTGTGCAGCGTCTGGATTCACCTTCAGTAGCTATGGCATGCA
CTGGGTCCGCCAGGCTCCAGGCAAGGGGCTGGAGTGGGTGGCAGTTATATGG
TTTGATGGAAATAATAAATTCTATGCAGACTCCGTGAAGGGCCGATTCACCA
TCTCCAGAGACAATTCCAAGAACACGCTGTATCTGCAAATGAACAGCCTGAG
AGTCGAGGACACGGCTGTGTATTACTGTGCGCGAGGCGGGAGCTACTGGGAC
TACTGGGGCCAGGGAACCCTGGTCACCGTCTCCTCAG3'

B-- ABT2-SCX-254 Amino acid sequence of heavy chain variable region:
QVQLVESGGGVVQPGRSLRLSCAASGFTFSSYGMHWVRQAPGKGLEWVAVIWF
DGNNKFYADSVKGRFTISRDNSKNTLYLQMNSLRVEDTAVYYCARGGSYWDY
WGQGTLVTVSS C-- ABT2-SCX-254 Nucleotide sequence of light chain variable region:

5'GATATTGTGATGACCCAGACTCCACTCTTCTCATTTGTCATGATTGGACAGC
CGGCCTCCATCTCCTGCAGGTCTAGGCAAAGCCTCGTACACAGTGATGGAAA
CACCTACTTGAATTGGCTTCAGCAGAGGCCAGGCCAGCCTCCAAGACTCCTA
ATTTATAAGACTTCTAACCGGTTCTCTGGGGTCCCAGATAGATTCAGTGGCAG
TGGGGCAGGGACAGATTTCACACTGAAAATCAGCAGGGTGGAAGCTGAGGA
TGTCGGGGTTTATTACTGTATGCAAGCTACACAATTTCCTATCACGTTCGGCC
AAGGGACACGACTGGAGATTAAA3'

D-- ABT2-SCX-254 Amino acid sequence of light chain variable region:
DIVMTQTPLFSFVMIGQPASISCRSRQSLVHSDGNTYLNWLQQRPGQPPRLLIYKT
SNRFSGVPDRFSGSGAGTDFTLKISRVEAEDVGVYYCMQATQFPITFGQGTRLEI
K

FIGURE 28

A-- ABT2-SCX-267 Nucleotide sequence of heavy chain variable region:

5'CAGGTGCAGCTGGTGGAGTCTGGGGGAGGCGTGGTCCAGCCTGGGAGGTCC
CTGAGACTCTCCTGTGCAGCCTCTGGATTCACCTTCAGTAGCTATGGCATGCA
CTGGGTCCGCCAGGCTCCAGGCAAGGGGCTGGAGTGGGTGGCAGTTATATCA
TATGATGGAAGTAATAAATACTATGCAGACTCCGTGAAGGGCCGATTCACCA
TCTCCAGAGACAATTCCAAGAACACGCTGTATCTGCAAATGAACAGCCTGAG
AGTTGAGGACACGGCTGTGTATTACTGTGCGAAAGATCACGGTGGGAGGTAC
GTCTACGACTACGGTATGGACGTCTGGGGCCAAGGGACCACGGTCACCGTCT
CCTCAG3'

B-- ABT2-SCX-267 Amino acid sequence of heavy chain variable region:

QVQLVESGGGVVQPGRSLRLSCAASGFTFSSYGMHWVRQAPGKGLEWVAVISY
DGSNKYYADSVKGRFTISRDNSKNTLYLQMNSLRVEDTAVYYCAKDHGGRYV
YDYGMDVWGQGTTVTVSS

C-- ABT2-SCX-267 Nucleotide sequence of light chain variable region:

5'GACATCCAGATGACCCAGTCTCCATCTTCCGTGTCTGCATCTGTAGGAGACA
GAGTCTCCATCACTTGTCGGGCGAGTCAGGGTATTGGCAGCTGGTTAGCCTG
GTATCAGCAGAAACCAGGGCAAGCCCCTACGCTCCTAATCTATGCTGCCTCC
AGTTTGCAACGTGGGGTCCCATCAAGATTCAGCGGCAGTGGATCTGGGACAG
ATTTCACTCTCACCATCAACAGCCTGCAGCCTGAAGATTTTGCAACTTACTTT
TGTCAACAGGCTAACAGTTTCCCATTCACTTTCGGCCCTGGGACCAAAGTGGA
TGTCAAAC3'

D-- ABT2-SCX-267 Amino acid sequence of light chain variable region:

DIQMTQSPSSVSASVGDRVSITCRASQGIGSWLAWYQQKPGQAPTLLIYAASSLQ
RGVPSRFSGSGSGTDFTLTINSLQPEDFATYFCQQANSFPFTFGPGTKVDVK

FIGURE 29

| Single Cell | V Heavy/D/J | FR1 | CDR1 | FR2 | CDR2 |
|---|---|---|---|---|---|
| - | Germline | QVQLVESGGGVVQPGRSLRLSCAAS | GFTFSSYGMH | WVRQAPGKGLEWVA | VISYDGSNKYYADSVKG |
| 3 | VH3-30(V3-30)/D4-23/LH6b | ---------------------- | ---------- | --------------- | -------------------- |
| 22 | | ---------------------- | ---------- | ------------V-- | -------------------- |
| 60 | | ---------------------- | ---------- | --------------- | -------------------- |
| 102 | | ---------------------- | ---------- | --------------- | -------------------- |
| 135 | | ---------------------- | ---------- | --------------- | -------------------- |
| 145 | | ---------------------- | ---------- | --------------- | -------------------- |
| 198 | | --------------------V-- | ---------- | --------------- | -------------------- |
| - | Germline | QVQLVESGGGVVQPGRSLRLSCAAS | GFTFSSYGMH | WVRQAPGKGLEWVA | VISYDGSNKYYADSVKG |
| 267 | VH3-30.5(DP-49)/D4-23/JH6b | ---------------------- | ---------- | --------------- | -------------------- |
| - | Germline | QVQLVESGGGVVQPGRSLRLSCAAS | GFTFSSYGMH | WVRQAPGKGLEWVA | VISYDGSNKYYADSVKG |
| 54 | VH3-33(DP-50)/DIR3/JH4b | ---------------------- | ----K---- | --------------- | -L------------------ |
| 254 | VH3-33(DP-50)/D21-10rc/JH4b | ---------------------- | ---------- | --------------- | ---F--N--F--------- |
| - | Germline | QVQLQESGPGLVKPSETLSLTCTVS | GGSISSYYWS | WIRQPPGKGLEWIG | YIYYSGSTHYNPSLKS |
| 12 | VH4-59(DP-71)/DIR4rc/JM4a | ---------------------- | -A-------- | --------------- | -------------------- |

| Single Cell | V Heavy/D/J | FR3 | CDR3 | FR4 |
|---|---|---|---|---|
| - | Germline | RFTISRDNSKNTLYLQMNSLRAEDTAVYYCAR | DHGGRVYDYGMDV | WGQGTTVTVSS |
| 3 | VH3-30(V3-30)/D4-23/LH6b | ----------------------V--------- | ------------- | ----------- |
| 22 | | ----------------------V--------- | ------------- | ----------- |
| 60 | | ----------------------V--------- | ------------- | ----------- |
| 102 | | ----------------------V--------- | ------------- | ----------- |
| 135 | | ----------------------V--------- | ------------- | ----------- |
| 145 | | ----------------------V--------- | ------------- | ----------- |
| 198 | | ----------------------V--------- | ------------- | ----------- |
| - | Germline | RFTISRDNSKNTLYLQMNSLRAEDTAVYYCAK | | WGQGTTVTVSS |
| 267 | VH3-30.5(DP-49)/D4-23/JH6b | ----------------------V--------- | ------------- | ----------- |
| - | Germline | RFTISRDNSKNTLYLQMNSLRAEDTAVYYCAR | | WGQGTLVTVSS |
| 54 | VH3-33(DP-50)/DIR3/JH4b | -------------------------------- | GPYYFDY | ----------- |
| 254 | VH3-33(DP-50)/D21-10rc/JH4b | ----------------------V--------- | GGSYWDY | ----------- |
| - | Germline | RVTISVDTSKNQFSLKLSSVTAADTAVYYCAR | | WGQGTLVTVSS |
| 12 | VH4-59(DP-71)/DIR4rc/JM4a | --------------R---------------- | ERLGIGDY | ----------- |

Figure 30

Comparison of Erythropoietic Activity of Gamma 1 Ab-12 versus Gamma 2 Ab-12 on F36e Human Erythroleukemic Cell Line

Ab-12 Increases Reticulocyte Count and Hematocrit in Transgenic Mice

Day 19 Hematocrit in Transgenic Mice Following Weekly Dosing with Ab-12 or Aranesp

\* P<0.001

Day 19 Hematocrit in Transgenic Mice Comparing Single vs. Weekly Dosing with Ab-12 or Aranesp

FIGURE 35

A. Ab390 nucleotide sequence of heavy chain variable region:

5' CAGGTGCAGCTGCAGGAGTCGGGCCCAGGACTGGTGAAGCCTTCGGAGACC
CTGTCCCTCACCTGCACTGTCTCTGGTGCCTCCATCAGTAATTACTACTGG
AGCTGGATCCGGCAGCCCCCAGGGAAGGGACTGGAGTGGATTGGGTATGTC
TCTTACAGTGGGAGTACGTACTACAACCCCTCCCTCAAGGGTCGAGTCACC
ATGTCAGTAGACACGTCCAAGAACCAGTTCTCCCTGAAGCTGAGCTCTGTG
ACCGCTGCGGACACGGCCGTGTATTACTGTGCGAGAGAAAAACTGGGGATT
GGAGACTACTGGGGCCAGGGAACCCTGGTCACCGTCTCCTCA3'

B. Ab390 Amino acid sequence of heavy chain variable region:

QVQLQESGPGLVKPSETLSLTCTVSGASISNYYWSWIRQPPGKGLEWIGYVSYSGS
TYYNPSLKGRVTMSVDTSKNQFSLKLSSVTAADTAVYYCAREKLGIGDYWGQGTLV
TVSS

C. Ab390 nucleotide sequence of light chain variable region:

5' GACATCCAGATGACCCAGTCTCCATCCTCCCTGTCTGCATCTGTAGGAGACA
GAGTCACCATCACTTGCCGGGCAAGTCAGGGCATTAAAAATGATTTAGGCTG
GTATCAGCAGAAACCAGGGAAAGCCCCTAAGCGCCTGATCTATGCTGCATCC
AGTTTGCAAAGTGGGGTCCCATCAAGGTTCAGCGGCAGTGGATCTGGGACAG
AATTCACTCTCACAATCAGCAGCCTGCAGCCTGAAGATTTTGCAACTTATTA
CTGTCTACAGCATAATAGTTATCCGTGCAGTTTTGGCCAGGGGACCAAGCTG
GAGATCAAAC3'

D. Ab390 Amino acid sequence of light chain variable region:

DIQMTQSPSSLSASVGDRVTITCRASQGIKNDLGWYQQKPGKAPKRLIYAASSLQS
GVPSRFSGSGSGTEFTLTISSLQPEDFATYYCLQHNSYPCSFGQGTKLEIK

FIGURE 36

A. Ab412 nucleotide sequence of heavy chain variable region:

5' CAGGTGCAGCTGCAGGAGTCGGGCCCAGGACTGGTGAAGCCTTCACAGACCC
TGTCCCTCACCTGCACTGTCTCTGGTGCCTCCATCAGCAGTGGTGCTTACTA
CTGGAGTTGGATCCGCCAGCACCCAGGGAAGGGCCTGGAGTGGATTGGGTAC
ATCTATAAGAGTGAGACCTCCTACTACAACCCGTCCCTCAAGAGTCGACTTA
CCCTATCAGTAGACACGTCTAAGAACCAGTTCTCCCTGAACCTGATCTCTGT
GACTGCCGCGGACACGGCCGTGTATTATTGTGCGAGAGATAAACTGGGGATC
GCGGACTACTGGGGCCAGGGAACCCTGGTCACCGTCTCCTCA3'

B. Ab412 Amino acid sequence of heavy chain variable region:

QVQLQESGPGLVKPSQTLSLTCTVSGASISSGAYYWSWIRQHPGKGLEWIGY
IYKSETSYYNPSLKSRLTLSVDTSKNQFSLNLISVTAADTAVYYCARDKLGI
ADYWGQGTLVTVSS

C. Ab412 nucleotide sequence of light chain variable region:

5' GACATCCAGATGACCCAGTCTCCATCCTCCCTGTCTGCATCTGTAGGAGACA
GAGTCACCATCACTTGCCGGGCAAGTCAGGACATTAGAAATGATTTAGGCTG
GTATCAGCAGAAACCAGGGAAAGCCCCTAAGCGCCTGATCTATGCTGCATCC
AATTTGCAAAGTGGGGTCCCATCAAGGTTCAGCGGCAGTGGATCTGGGACAG
AATTCACTCTCACAATCAGCAGCCTGCAGCCTGAAGATTTTGCAACTTATTA
CTGTCTACAGCATAATAGCTACCCTCCCACTTTCGGCGGAGGGACCAAGGTG
GAAATCAAAC3'

D. Ab412 Amino acid sequence of light chain variable region:

DIQMTQSPSSLSASVGDRVTITCRASQDIRNDLGWYQQKPGKAPKRLIYAAS
NLQSGVPSRFSGSGSGTEFTLTISSLQPEDFATYYCLQHNSYPPTFGGGTKV
EIK

FIGURE 37

A. Ab432 nucleotide sequence of heavy chain variable region:

5' CAGGTGCAGCTGCAGGAGTCGGGCCCAGGACTGGTGAAGCCTTCGGAGACCC
TGTCCCTCACCTGCACTGTCTCTGGTGTCTCCATCAGTAATTACTACTGGAG
CTGGATCCGGCAGTCCCCAGGGAAGGGACTGGAGTGGATTGGATATATCTAT
TACAGTGGGAGTCCCTATTACAACCCCTCCCTCAAGAGTCGAGTCACTATAT
CTGCAGACACGTCCAAGAACCAATTCTCCCTGAAGCTGAGCTCTGTGACCGC
TGCGGACACGGCCATTTATTACTGTGCGAGAGAAAAACTGGGGATTGGAGAC
TACTGGGGCCAGGGAACCCTGGTCACCGTCTCCTCAG3'

B. Ab432 Amino acid sequence of heavy chain variable region:

QVQLQESGPGLVKPSETLSLTCTVSGVSISNYYWSWIRQSPGKGLEWIGYIY
YSGSPYYNPSLKSRVTISADTSKNQFSLKLSSVTAADTAIYYCAREKLGIGD
YWGQGTLVTVSS

C. Ab430 nucleotide sequence of light chain variable region:

5' GACATCCAGATGACCCAGTCTCCATCCTCCCTGTCTGCATCTGTCGGAGACA
GAGTCACCATCACTTGCCGGGCAAGTCAGGGCATTAGAAATGATTTAGGCTG
GTATCAGCAGAAACCAGGGAAAGCCCCTAAGCGCCTGATCTATGCTGCATCC
AGTTTGCAAAGTGGGGTCCCATCAAGGTTCAGCGGCAGTGGATCTGGGACAG
AATTCACTCTCACAATCAGCAGCCTGCAGCCTGAAGATTTTGCAACTTATTA
CTGTCTACAGCATAATAGTTACCCTCCCACTTTCGGCCCTGGGACCAAGGTG
GATATCAAAC3'

D. Ab430 Amino acid sequence of light chain variable region:

DIQMTQSPSSLSASVGDRVTITCRASQGIRNDLGWYQQKPGKAPKRLIYAAS
SLQSGVPSRFSGSGSGTEFTLTISSLQPEDFATYYCLQHNSYPPTFGPGTKV
DIK

FIGURE 38

A. Ab467 nucleotide sequence of heavy chain variable region:

5' CAGGTGCAGCTGCAGGAGTCGGGCCCAGGACTGGTGAAGCCTTCGGAGACCC
TGTCCCTCACCTGCACTGTCTCTGGTGGCTCCATCAGTCGTTACTACTGGAG
CTGGATCCGGCAGCCCCCAGGGAAGGGACTGGAGTGGATTGGGTATGTCTCT
TACAGTGGGAGCACCTACTACAACCCCTCCCTCAAGAGTCGAGTCACCATAT
CAGTAGACACGTCCAAGAACCAGTTCTCCCTGAAGCTGAGCTCTGTGACCGC
TGCGGACACGGCCGTGTATTACTGTGCGAGAGATAAACTGGGGATTGGAGAC
TACTGGGGCCAGGGAACCCTGGTCACCGTCTCCTCAG3'

B. Ab467 Amino acid sequence of heavy chain variable region:

QVQLQESGPGLVKPSETLSLTCTVSGGSISRYYWSWIRQPPGKGLEWIGYVS
YSGSTYYNPSLKSRVTISVDTSKNQFSLKLSSVTAADTAVYYCARDKLGIGD
YWGQGTLVTVSS

C. Ab467 nucleotide sequence of light chain variable region:

5' GACATCCAGATGACCCAGTCTCCATCCTCCCTGTCTGCATCTGTAGGAGACA
GAGTCACCATCACTTGCCGGGCAAGTCAGGGCATTAGAAATGATTTAGGCTG
GTATCAGCAGAAACCGGGGAAAGCCCCTAAGCGCCTGATCTATGCTGCATCC
AGTTTGCAAAGTGGGGTCCCATCAAGGTTCAGCGGCAGTGGATCTGGGACAG
AATTCACTCTCACAATCAGCAGCCTGCAGCCTGAAGATTTTGCAACTTATTA
CTGTCTACAGCATAATAGTTACCCGTGCAGTTTTGGCCAGGGGACCAAGCTG
GAGATCAAAC3'

D. Ab467 Amino acid sequence of light chain variable region:

DIQMTQSPSSLSASVGDRVTITCRASQGIRNDLGWYQQKPGKAPKRLIYAAS
SLQSGVPSRFSGSGSGTEFTLTISSLQPEDFATYYCLQHNSYPCSFGQGTKL
EIK

FIGURE 39

A. Ab484 nucleotide sequence of heavy chain variable region:

5' CAGGTGCAGCTGCAGGAGTCGGGCCCAGGACTGGTGAAGCCTTTACAGACCC
TGTCCCTCACCTGCACTGTCTCTGGTGGCTCCATCAGCAGTGGTGTTTACTA
CTGGAGCTGGATCCGCCAGCACCCAGGGAAGGGCCTGGAGTGGATTGGGTAC
ATCTATAACAGTAAGACCTCCTATTATAATCCGTCCCTCAAGAGTCGACTTA
CCCTATCAGTAGACACGTCTAAGAACCAGTTCTCCCTGAACCTGATCTCTGT
GACTGCCGCGGACACGGCCGTGTATTACTGTGCGAGAGATAAATTGGGGATC
GCGGACTACTGGGGCCAGGGAACCCTGGTCACCGTCTCCTCAG3'

B. Ab484 Amino acid sequence of heavy chain variable region:

QVQLQESGPGLVKPLQTLSLTCTVSGGSISSGVYYWSWIRQHPGKGLEWIGY
IYNSKTSYYNPSLKSRLTLSVDTSKNQFSLNLISVTAADTAVYYCARDKLGI
ADYWGQGTLVTVSS

C. Ab484 nucleotide sequence of light chain variable region:

5' GACATCCAGATGACCCAGTCTCCATCCTCCCTGTCTGCATCTGTAGGAGACA
GAGTCACCATCACTTGCCGGACAAGTCAGGGCATTAGAAATGATTTAGGCTG
GTATCAGCAGAAACCAGGGAAAGCCCCTAAGCGCCTGATCTATGCTGCATCC
AGTTTGCAAAGTGGGGTCCCATCAAGGTTCAGCGGCAGTGGATCTGGGACAG
AATTCACTCTCACAATCAGCAGCCTGCAGCCTGAAGATTTTGCAACTTATTA
CTGTCTACAGCATAATAGCTACCCTCCCACTTTCGGCGGAGGGACCAAGGTG
GAGATCAAAC3'

D. Ab484 Amino acid sequence of light chain variable region:

DIQMTQSPSSLSASVGDRVTITCRTSQGIRNDLGWYQQKPGKAPKRLIYAAS
SLQSGVPSRFSGSGSGTEFTLTISSLQPEDFATYYCLQHNSYPPTFGGGTKV
EIK

| V_H | Origin (Kd) | Chain ID | V region/J region | FR1 | CDR1 | FR2 |
|---|---|---|---|---|---|---|
| 43H12 | 198 | 14325.3 | VH3-30/D4-23/JH6 | QVQLVESGGGVVQPGRSLRLSCAAS | GFTFSSYRMH | WVRQAPGKGLEWVA |
| 33G8 | 12 | 13308.1 | VH4-59/D1R4rc/JH4 | QVQLQESGPGLVKPSETLSLTCTVS | GGSISSYYWS | WIRQPPGKGLEWIG |
| 230A4 | 412 | 54995.1 | V4-31/D1R4rc/JR4 | QVQLQESGPFLVKPSQTLSLTCTVS | GGSISSGGYYWS | WIRQHPGKGLEWIG |
| 208A12 | 484 | 57130.1 | V4-30.1/D1R4rc/JH4 | QVQLQESGPGLVKPSQTLSLTCTVS | GGSISSGGYYWS | WIRQHPGKGLEWIG |
| 259C12 | 467 | 56977.2 | V4-59/D7-27/JH4 | QVQLQSGGRGLVKPSETLSLTCTVS | GGSISSYYWS | WIRQPPGKGLEWIG |
| 234D12 | 390 | 57141.2 | VH4-59/D7-27/JH4b | ------V---N--- | --A---N--- | ----------- |
| 223H2 | 432 | 57354.11 | VH4-59/D7-27/JH4b | ------V---N--- | --V---N--- | ---S------- |

| CDR2 | FR3 | CDR3 | FR4 |
|---|---|---|---|
| VISTDGSNKYYADSVKG | RFTISRDNSKNTLYLQMNSLRAEDTAVYYCAR | DWGGRYVYDYGMDV | WGQGTTVTVSS |
| YIYYSGSTYYNPSLKS | RVTISVDTSKNQFSLKLSSVTAADTAVYYCAR | ERLGIGDY | WGQGTLVTVSS |
| YIYYSGSTYYNPSLKS | RVTISVDTSKNQFSLKLSSVTAADTAVYYCAR | DRLGIADY | WGQGTLVTVSS |
| YIYYSGSTYYNPSLKG | RVTISVDTSKNQFSLKLSSVTAADTAVYYCAR | DRLGIADY | WGQGTLVTVSS |
| YIYYSGSTYYNPSLKG | RVTISVDTSKNQFSLKLSSVTAADTAVYYCAR | DKLGIGDY | WGQGTLVTVSS |
| -VS-----Y------- | ---N----------------------- | EKLGIGDY | ------------ |
| ------PY------- | ----A----------------J------ | EKLGIGDY | ------------ |

```
                    MetLysHisLeuTrpPhePheLeuLeuLeuValAla
  1                 ATGAAGCATCTGTGGTTCTTCCTTCTCCTGGTGG
                    TACTTCGTAGACACCAAGAAGGAAGAGGACCACC

··AlaProArgTrpValLeuSerGlnValGlnLeuGlnGluSerGlyPro
 51           CAGCTCCCAGATGGGTCCTGTCCCAGGTGCAGCTGCAGGAGTCGGGCCCA
              GTCGAGGGTCTACCCAGGACAGGGTCCACGTCGACGTCCTCAGCCCGGGT

GlyLeuValLysProSerGluThrLeuSerLeuThrCysThrValSerGly
101           GGACTGGTGAAGCCTTCGGAGACCCTGTCCCTCACCTGCACTGTCTCTGG
              CCTGACCACTTCGGAAGCCTCTGGGACAGGGAGTGGACGTGACAGAGACC

·AlaSerIleSerAsnTyrTyrTrpSerTrpIleArgGlnProProGlyLys
151           TGCCTCCATCAGTAATTACTACTGGAGCTGGATCCGGCAGCCCCCAGGGA
              ACGGAGGTAGTCATTAATGATGACCTCGACCTAGGCCGTCGGGGGTCCCT

··GlyLeuGluTrpIleGlyTyrValSerTyrSerGlySerThrTyrTyr
201           AGGGACTGGAGTGGATTGGGTATGTCTCTTACAGTGGGAGTACGTACTAC
              TCCCTGACCTCACCTAACCCATACAGAGAATGTCACCCTCATGCATGATG

AsnProSerLeuLysGlyArgValThrMetSerValAspThrSerLysAsn
251           AACCCCTCCCTCAAGGGTCGAGTCACCATGTCAGTAGACACGTCCAAGAA
              TTGGGGAGGGAGTTCCCAGCTCAGTGGTACAGTCATCTGTGCAGGTTCTT

·GlnPheSerLeuLysLeuSerSerValThrAlaAlaAspThrAlaValTyr
301           CCAGTTCTCCCTGAAGCTGAGCTCTGTGACCGCTGCGGACACGGCCGTGT
              GGTCAAGAGGGACTTCGACTCGAGACACTGGCGACGCCTGTGCCGGCACA

··TyrCysAlaArgGluLysLeuGlyIleGlyAspTyrTrpGlyGlnGly
351           ATTACTGTGCGAGAGAAAAACTGGGGATTGGAGACTACTGGGGCCAGGGA
              TAATGACACGCTCTCTTTTTGACCCCTAACCTCTGATGACCCCGGTCCCT

ThrLeuValThrValSerSerAlaSerThrLysGlyProSerValPhePro
401           ACCCTGGTCACCGTCTCCTCAGCCTCCACCAAGGGCCCATCGGTCTTCCC
              TGGGACCAGTGGCAGAGGAGTCGGAGGTGGTTCCCGGGTAGCCAGAAGGG

·LeuAlaProCysSerArgSerThrSerGluSerThrAlaAlaLeuGlyCys
451           CCTGGCGCCCTGCTCTAGAAGCACCTCCGAGAGCACAGCCGCCCTGGGCT
              GGACCGCGGGACGAGATCTTCGTGGAGGCTCTCGTGTCGGCGGGACCCGA

··LeuValLysAspTyrPheProGluProValThrValSerTrpAsnSer
501           GCCTGGTCAAGGACTACTTCCCCGAACCGGTGACGGTGTCGTGGAACTCA
              CGGACCAGTTCCTGATGAAGGGGCTTGGCCACTGCCACAGCACCTTGAGT

GlyAlaLeuThrSerGlyValHisThrPheProAlaValLeuGlnSerSer
551           GGCGCTCTGACCAGCGGCGTGCACACCTTCCCAGCTGTCCTACAGTCCTC
              CCGCGAGACTGGTCGCCGCACGTGTGGAAGGGTCGACAGGATGTCAGGAG
```

FIGURE 42 Continuation

```
           ·GlyLeuTyrSerLeuSerSerValValThrValProSerSerAsnPheGly
  601      AGGACTCTACTCCCTCAGCAGCGTGGTGACCGTGCCCTCCAGCAACTTCG
           TCCTGAGATGAGGGAGTCGTCGCACCACTGGCACGGGAGGTCGTTGAAGC

··ThrGlnThrTyrThrCysAsnValAspHisLysProSerAsnThrLys
  651      GCACCCAGACCTACACCTGCAACGTAGATCACAAGCCCAGCAACACCAAG
           CGTGGGTCTGGATGTGGACGTTGCATCTAGTGTTCGGGTCGTTGTGGTTC

ValAspLysThrVal
  701      GTGGACAAGACAGTTGGTGAGAGGCCAGCTCAGGGAGGGAGGGTGTCTGC
           CACCTGTTCTGTCAACCACTCTCCGGTCGAGTCCCTCCCTCCCACAGACG

751      TGGAAGCCAGGCTCAGCCCTCCTGCCTGGACGCACCCCGGCTGTGCAGCC
           ACCTTCGGTCCGAGTCGGGAGGACGGACCTGCGTGGGGCCGACACGTCGG

801      CCAGCCCAGGGCAGCAAGGCAGGCCCCATCTGTCTCCTCACCCGGAGGCC
           GGTCGGGTCCCGTCGTTCCGTCCGGGGTAGACAGAGGAGTGGGCCTCCGG

851      TCTGCGCGCCCCACTCATGCTCAGGGAGAGGGTCTTCTGGCTTTTTCCAC
           AGACGGGCGGGGTGAGTACGAGTCCCTCTCCCAGAAGACCGAAAAAGGTG

901      CAGGCTCCAGGCAGGCACAGGCTGGGTGCCCCTACCCCAGGCCCTTCACA
           GTCCGAGGTCCGTCCGTGTCCGACCCACGGGGATGGGGTCCGGGAAGTGT

951      CACAGGGGCAGGTGCTTGGCTCAGACCTGCCAAAAGCCATATCCGGGAGG
           GTGTCCCCGTCCACGAACCGAGTCTGGACGGTTTTCGGTATAGGCCCTCC

1001      ACCCTGCCCTGACCTAAGCCGACCCCAAAGGCCAAACTGTCCACTCCCT
           TGGGACGGGGACTGGATTCGGCTGGGGTTTCCGGTTTGACAGGTGAGGA

1051      CAGCTCGGACACCTTCTCTCCTCCCAGATCCGAGTAACTCCCAATCTTCT
           GTCGAGCCTGTGGAAGAGAGGAGGGTCTAGGCTCATTGAGGGTTAGAAGA

GluArgLysCysCysValGluCysProProCysPro
 1101      CTCTGCAGAGCGCAAATGTTGTGTCGAGTGCCCACCGTGCCCAGGTAAGC
           GAGACGTCTCGCGTTTACAACACAGCTCACGGGTGGCACGGGTCCATTCG

1151      CAGCCCAGGCCTCGCCCTCCAGCTCAAGGCGGGACAGGTGCCCTAGAGTA
           GTCGGGTCCGGAGCGGGAGGTCGAGTTCCGCCCTGTCCACGGGATCTCAT

1201      GCCTGCATCCAGGGACAGGCCCCAGCTGGGTGCTGACACGTCCACCTCCA
           CGGACGTAGGTCCCTGTCCGGGGTCGACCCACGACTGTGCAGGTGGAGGT

AlaProProValAlaGlyProSerValPheLeuPhePro
 1251      TCTCTTCCTCAGCACCACCTGTGGCAGGACCGTCAGTCTTCCTCTTCCCC
           AGAGAAGGAGTCGTGGTGGACACCGTCCTGGCAGTCAGAAGGAGAAGGGG

ProLysProLysAspThrLeuMetIleSerArgThrProGluValThrCys·
```

FIGURE 42 Continuation

```

1301   CCAAAACCCAAGGACACCCTCATGATCTCCCGGACCCCTGAGGTCACGTG
       GGTTTTGGGTTCCTGTGGGAGTACTAGAGGGCCTGGGGACTCCAGTGCAC

·ValValValAspValSerHisGluAspProGluValGlnPheAsnTrpTyr·
1351   CGTGGTGGTGGACGTGAGCCACGAAGACCCCGAGGTCCAGTTCAACTGGT
       GCACCACCACCTGCACTCGGTGCTTCTGGGGCTCCAGGTCAAGTTGACCA

···ValAspGlyValGluValHisAsnAlaLysThrLysProArgGluGlu
1401   ACGTGGACGGCGTGGAGGTGCATAATGCCAAGACAAAGCCACGGGAGGAG
       TGCACCTGCCGCACCTCCACGTATTACGGTTCTGTTTCGGTGCCCTCCTC

GlnPheAsnSerThrPheArgValValSerValLeuThrValValHisGln·
1451   CAGTTCAACAGCACGTTCCGTGTGGTCAGCGTCCTCACCGTTGTGCACCA
       GTCAAGTTGTCGTGCAAGGCACACCAGTCGCAGGAGTGGCAACACGTGGT

·AspTrpLeuAsnGlyLysGluTyrLysCysLysValSerAsnLysGlyLeu·
1501   GGACTGGCTGAACGGCAAGGAGTACAAGTGCAAGGTCTCCAACAAAGGCC
       CCTGACCGACTTGCCGTTCCTCATGTTCACGTTCCAGAGGTTGTTTCCGG

··ProAlaProIleGluLysThrIleSerLysThrLys
1551   TCCCAGCCCCCATCGAGAAAACCATCTCCAAAACCAAAGGTGGGACCCGC
       AGGGTCGGGGGTAGCTCTTTTGGTAGAGGTTTTGGTTTCCACCCTGGGCG

1601   GGGGTATGAGGGCCACATGGACAGAGGCCGGCTCGGCCCACCCTCTGCCC
       CCCCATACTCCCGGTGTACCTGTCTCCGGCCGAGCCGGGTGGGAGACGGG

GlyGlnProArgGlu
1651   TGGGAGTGACCGCTGTGCCAACCTCTGTCCCTACAGGGCAGCCCCGAGAA
       ACCCTCACTGGCGACACGGTTGGAGACAGGGATGTCCCGTCGGGGCTCTT

ProGlnValTyrThrLeuProProSerArgGluGluMetThrLysAsnGln·
1701   CCACAGGTGTACACCCTGCCCCCATCCCGGGAGGAGATGACCAAGAACCA
       GGTGTCCACATGTGGGACGGGGGTAGGGCCCTCCTCTACTGGTTCTTGGT

·ValSerLeuThrCysLeuValLysGlyPheTyrProSerAspIleAlaVal·
1751   GGTCAGCCTGACCTGCCTGGTCAAAGGCTTCTACCCCAGCGACATCGCCG
       CCAGTCGGACTGGACGGACCAGTTTCCGAAGATGGGGTCGCTGTAGCGGC

··GluTrpGluSerAsnGlyGlnProGluAsnAsnTyrLysThrThrPro
1801   TGGAGTGGGAGAGCAATGGGCAGCCGGAGAACAACTACAAGACCACACCT
       ACCTCACCCTCTCGTTACCCGTCGGCCTCTTGTTGATGTTCTGGTGTGGA

ProMetLeuAspSerAspGlySerPhePheLeuTyrSerLysLeuThrVal·
1851   CCCATGCTGGACTCCGACGGCTCCTTCTTCCTCTACAGCAAGCTCACCGT
       GGGTACGACCTGAGGCTGCCGAGGAAGAAGGAGATGTCGTTCGAGTGGCA

·AspLysSerArgTrpGlnGlnGlyAsnValPheSerCysSerValMetHis·
```

FIGURE 42 Continuation

```
1901   GGACAAGAGCAGGTGGCAGCAGGGGAACGTCTTCTCATGCTCCGTGATGC
       CCTGTTCTCGTCCACCGTCGTCCCCTTGCAGAAGAGTACGAGGCACTACG

..GluAlaLeuHisAsnHisTyrThrGlnLysSerLeuSerLeuSerPro
1951   ATGAGGCTCTGCACAACCACTACACGCAGAAGAGCCTCTCCCTGTCTCCG
       TACTCCGAGACGTGTTGGTGATGTGCGTCTTCTCGGAGAGGGACAGAGGC

GlyLys
2001   GGTAAA
       CCATTT
```

FIGURE 43

```
                MetArgLeuProAlaGlnLeuLeuGlyLeuLeuLeu
  1             ATGAGGCTCCCCGCTCAGCTCCTGGGGCTCCTGC
                TACTCCGAGGGGCGAGTCGAGGACCCCGAGGACG

··LeuTrpPheProGlyAlaArgCysAspIleGlnMetThrGlnSerPro
 51             TGCTCTGGTTCCCAGGTGCCAGGTGTGACATCCAGATGACCCAGTCTCCA
                ACGAGACCAAGGGTCCACGGTCCACACTGTAGGTCTACTGGGTCAGAGGT

SerSerLeuSerAlaSerValGlyAspArgValThrIleThrCysArgAla
101             TCCTCCCTGTCTGCATCTGTAGGAGACAGAGTCACCATCACTTGCCGGGC
                AGGAGGGACAGACGTAGACATCCTCTGTCTCAGTGGTAGTGAACGGCCCG

·SerGlnGlyIleLysAsnAspLeuGlyTrpTyrGlnGlnLysProGlyLys
151             AAGTCAGGGCATTAAAAATGATTTAGGCTGGTATCAGCAGAAACCAGGGA
                TTCAGTCCCGTAATTTTTACTAAATCCGACCATAGTCGTCTTTGGTCCCT

··AlaProLysArgLeuIleTyrAlaAlaSerSerLeuGlnSerGlyVal
201             AAGCCCCTAAGCGCCTGATCTATGCTGCATCCAGTTTGCAAAGTGGGGTC
                TTCGGGGATTCGCGGACTAGATACGACGTAGGTCAAACGTTTCACCCCAG

ProSerArgPheSerGlySerGlySerGlyThrGluPheThrLeuThrIle
251             CCATCAAGGTTCAGCGGCAGTGGATCTGGGACAGAATTCACTCTCACAAT
                GGTAGTTCCAAGTCGCCGTCACCTAGACCCTGTCTTAAGTGAGAGTGTTA

·SerSerLeuGlnProGluAspPheAlaThrTyrTyrCysLeuGlnHisAsn
301             CAGCAGCCTGCAGCCTGAAGATTTTGCAACTTATTACTGTCTACAGCATA
                GTCGTCGGACGTCGGACTTCTAAAACGTTGAATAATGACAGATGTCGTAT

··SerTyrProCysSerPheGlyGlnGlyThrLysLeuGluIleLysArg
351             ATAGTTATCCGTGCAGTTTTGGCCAGGGGACCAAGCTGGAGATCAAACGA
                TATCAATAGGCACGTCAAAACCGGTCCCCTGGTTCGACCTCTAGTTTGCT

ThrValAlaAlaProSerValPheIlePheProProSerAspGluGlnLeu
401             ACTGTGGCTGCACCATCTGTCTTCATCTTCCCGCCATCTGATGAGCAGTT
                TGACACCGACGTGGTAGACAGAAGTAGAAGGGCGGTAGACTACTCGTCAA

·LysSerGlyThrAlaSerValValCysLeuLeuAsnAsnPheTyrProArg
451             GAAATCTGGAACTGCTAGCGTTGTGTGCCTGCTGAATAACTTCTATCCCA
                CTTTAGACCTTGACGATCGCAACACACGGACGACTTATTGAAGATAGGGT

··GluAlaLysValGlnTrpLysValAspAsnAlaLeuGlnSerGlyAsn
501             GAGAGGCCAAAGTACAGTGGAAGGTGGATAACGCCCTCCAATCGGGTAAC
                CTCTCCGGTTTCATGTCACCTTCCACCTATTGCGGGAGGTTAGCCCATTG

SerGlnGluSerValThrGluGlnAspSerLysAspSerThrTyrSerLeu
551             TCCCAGGAGAGTGTCACAGAGCAGGACAGCAAGGACAGCACCTACAGCCT
                AGGGTCCTCTCACAGTGTCTCGTCCTGTCGTTCCTGTCGTGGATGTCGGA
```

FIGURE 43 Continuation

```
     ·SerSerThrLeuThrLeuSerLysAlaAspTyrGluLysHisLysValTyr
601  CAGCAGCACCCTGACGCTGAGCAAAGCAGACTACGAGAAACACAAAGTCT
     GTCGTCGTGGGACTGCGACTCGTTTCGTCTGATGCTCTTTGTGTTTCAGA

···AlaCysGluValThrHisGlnGlyLeuSerSerProValThrLysSer
651  ACGCCTGCGAAGTCACCCATCAGGGCCTGAGCTCGGCCGTCACAAAGAGC
     TGCGGACGCTTCAGTGGGTAGTCCCGGACTCGAGCGGGCAGTGTTTCTCG

PheAsnArgGlyGluCys
701  TTCAACAGGGGAGAGTGT
     AAGTTGTCCCCTCTCACA
```

FIGURE 44

```
                MetLysHisLeuTrpPhePheLeuLeuLeuValAla
  1             ATGAAACATCTGTGGTTCTTCCTCCTGCTGGTGG
                TACTTTGTAGACACCAAGAAGGAGGACGACCACC

··AlaProArgTrpValLeuSerGlnValGlnLeuGlnGluSerGlyPro
 51             CAGCTCCCAGATGGGTCCTGTCCCAGGTGCAGCTGCAGGAGTCGGGCCCA
                GTCGAGGGTCTACCCAGGACAGGGTCCACGTCGACGTCCTCAGCCCGGGT

GlyLeuValLysProSerGlnThrLeuSerLeuThrCysThrValSerGly
101             GGACTGGTGAAGCCTTCACAGACCCTGTCCCTCACCTGCACTGTCTCTGG
                CCTGACCACTTCGGAAGTGTCTGGGACAGGGAGTGGACGTGACAGAGACC

·AlaSerIleSerSerGlyAlaTyrTyrTrpSerTrpIleArgGlnHisPro
151             TGCCTCCATCAGCAGTGGTGCTTACTACTGGAGTTGGATCCGCCAGCACC
                ACGGAGGTAGTCGTCACCACGAATGATGACCTCAACCTAGGCGGTCGTGG

··GlyLysGlyLeuGluTrpIleGlyTyrIleTyrLysSerGluThrSer
201             CAGGGAAGGGCCTGGAGTGGATTGGGTACATCTATAAGAGTGAGACCTCC
                GTCCCTTCCCGGACCTCACCTAACCCATGTAGATATTCTCACTCTGGAGG

TyrTyrAsnProSerLeuLysSerArgLeuThrLeuSerValAspThrSer
251             TACTACAACCCGTCCCTCAAGAGTCGACTTACCCTATCAGTAGACACGTC
                ATGATGTTGGGCAGGGAGTTCTCAGCTGAATGGGATAGTCATCTGTGCAG

·LysAsnGlnPheSerLeuAsnLeuIleSerValThrAlaAlaAspThrAla
301             TAAGAACCAGTTCTCCCTGAACCTGATCTCTGTGACTGCCGCGGACACGG
                ATTCTTGGTCAAGAGGGACTTGGACTAGAGACACTGACGGCGCCTGTGCC

··ValTyrTyrCysAlaArgAspLysLeuGlyIleAlaAspTyrTrpGly
351             CCGTGTATTATTGTGCGAGAGATAAACTGGGGATCGCGGACTACTGGGGC
                GGCACATAATAACACGCTCTCTATTTGACCCCTAGCGCCTGATGACCCCG

GlnGlyThrLeuValThrValSerSerAlaSerThrLysGlyProSerVal
401             CAGGGAACCCTGGTCACCGTCTCCTCAGCCTCCACCAAGGGCCCATCGGT
                GTCCCTTGGGACCAGTGGCAGAGGAGTCGGAGGTGGTTCCCGGGTAGCCA

·PheProLeuAlaProCysSerArgSerThrSerGluSerThrAlaAlaLeu
451             CTTCCCCCTGGCGCCCTGCTCTAGAAGCACCTCCGAGAGCACAGCCGCCC
                GAAGGGGGACCGCGGGACGAGATCTTCGTGGAGGCTCTCGTGTCGGCGGG

··GlyCysLeuValLysAspTyrPheProGluProValThrValSerTrp
501             TGGGCTGCCTGGTCAAGGACTACTTCCCCGAACCGGTGACGGTGTCGTGG
                ACCCGACGGACCAGTTCCTGATGAAGGGGCTTGGCCACTGCCACAGCACC

AsnSerGlyAlaLeuThrSerGlyValHisThrPheProAlaValLeuGln
551             AACTCAGGCGCTCTGACCAGCGGCGTGCACACCTTCCCAGCTGTCCTACA
                TTGAGTCCGCGAGACTGGTCGCCGCACGTGTGGAAGGGTCGACAGGATGT
```

FIGURE 44 Continuation

```
            ·SerSerGlyLeuTyrSerLeuSerSerValValThrValProSerSerAsn
 601    GTCCTCAGGACTCTACTCCCTCAGCAGCGTGGTGACCGTGCCCTCCAGCA
        CAGGAGTCCTGAGATGAGGGAGTCGTCGCACCACTGGCACGGGAGGTCGT

··PheGlyThrGlnThrTyrThrCysAsnValAspHisLysProSerAsn
 651    ACTTCGGCACCCAGACCTACACGTGCAACGTAGATCACAAGCCCAGCAAC
        TGAAGCCGTGGGTCTGGATGTGGACGTTGCATCTAGTGTTCGGGTCGTTG

ThrLysValAspLysThrVal
 701    ACCAAGGTGGACAAGACAGTTGGTGAGAGGCCAGCTCAGGGAGGGAGGGT
        TGGTTCCACCTGTTCTGTCAACCACTCTCCGGTCGAGTCCCTCCCTCCCA

751    GTCTGCTGGAAGCCAGGCTCAGCCCTCCTGCCTGGACGCACCCCGGCTGT
        CAGACGACCTTCGGTCCGAGTCGGGAGGACGGACCTGCGTGGGGCCGACA

801    GCAGCCCCAGCCCAGGGCAGCAAGGCAGGCCCCATCTGTCTCCTCACCCG
        CGTCGGGGTCGGGTCCCGTCGTTCCGTCCGGGGTAGACAGAGGAGTGGGC

851    GAGGCCTCTGCCCGCCCCACTCATGCTCAGGGAGAGGGTCTTCTGGCTTT
        CTCCGGAGACGGGCGGGGTGAGTACGAGTCCCTCTCCCAGAAGACCGAAA

901    TTCCACCAGGCTCCAGGCAGGCACAGGCTGGGTGCCCCTACCCCAGGCCC
        AAGGTGGTCCGAGGTCCGTCCGTGTCCGACCCACGGGGATGGGGTCCGGG

951    TTCACACACAGGGGCAGGTGCTTGGCTCAGACCTGCCAAAAGCCATATCC
        AAGTGTGTGTCCCCGTCCACGAACCGAGTCTGGACGGTTTTCGGTATAGG

1001    GGGAGGACCCTGCCCCTGACCTAAGCCGACCCCAAAGGCCAAACTGTCCA
        CCCTCCTGGGACGGGGACTGGATTCGGCTGGGGTTTCCGGTTTGACAGGT

1051    CTCCCTCAGCTCGGACACCTTCTCTCCTCCCAGATCCGAGTAACTCCCAA
        GAGGGAGTCGAGCCTGTGGAAGAGAGGAGGGTCTAGGCTCATTGAGGGTT

GluArgLysCysCysValGluCysProProCysPro
1101    TCTTCTCTCTGCAGAGCGCAAATGTTGTGTCGAGTGCCCACCGTGCCCAG
        AGAAGAGAGACGTCTCGCGTTTACAACACAGCTCACGGGTGGCACGGGTC

1151    GTAAGCCAGCCCAGGCCTCGCCCTCCAGCTCAAGGCGGGACAGGTGCCCT
        CATTCGGTCGGGTCCGGAGCGGGAGGTCGAGTTCCGCCCTGTCCACGGGA

1201    AGAGTAGCCTGCATCCAGGGACAGGCCCCAGCTGGGTGCTGACACGTCCA
        TCTCATCGGACGTAGGTCCCTGTCCGGGGTCGACCCACGACTGTGCAGGT

AlaProProValAlaGlyProSerValPheLeu
1251    CCTCCATCTCTTCCTCAGCACCACCTGTGGCAGGACCGTCAGTCTTCCTC
        GGAGGTAGAGAAGGAGTCGTGGTGGACACCGTCCTGGCAGTCAGAAGGAG

PheProProLysProLysAspThrLeuMetIleSerArgThrProGluVal
```

FIGURE 44 Continuation

```
1301  TTCCCCCCAAAACCCAAGGACACCCTCATGATCTCCCGGACCCCTGAGGT
      AAGGGGGGTTTTGGGTTCCTGTGGGAGTACTAGAGGGCCTGGGGACTCCA

·ThrCysValValValAspValSerHisGluAspProGluValGlnPheAsn
1351  CACGTGCGTGGTGGTGGACGTGAGCCACGAAGACCCCGAGGTCCAGTTCA
      GTGCACGCACCACCACCTGCACTCGGTGCTTCTGGGGCTCCAGGTCAAGT

··TrpTyrValAspGlyValGluValHisAsnAlaLysThrLysProArg
1401  ACTGGTACGTGGACGGCGTGGAGGTGCATAATGCCAAGACAAAGCCACGG
      TGACCATGCACCTGCCGCACCTCCACGTATTACGGTTCTGTTTCGGTGCC

GluGluGlnPheAsnSerThrPheArgValValSerValLeuThrValVal
1451  GAGGAGCAGTTCAACAGCACGTTCCGTGTGGTCAGCGTCCTCACCGTTGT
      CTCCTCGTCAAGTTGTCGTGCAAGGCACACCAGTCGCAGGAGTGGCAACA

·HisGlnAspTrpLeuAsnGlyLysGluTyrLysCysLysValSerAsnLys
1501  GCACCAGGACTGGCTGAACGGCAAGGAGTACAAGTGCAAGGTCTCCAACA
      CGTGGTCCTGACCGACTTGCCGTTCCTCATGTTCACGTTCCAGAGGTTGT

··GlyLeuProAlaProIleGluLysThrIleSerLysThrLys
1551  AAGGCCTCCCAGCCCCCATCGAGAAAACCATCTCCAAAACCAAAGGTGGG
      TTCCGGAGGGTCGGGGGTAGCTCTTTTGGTAGAGGTTTTGGTTTCCACCC

1601  ACCCGCGGGGTATGAGGGCCACATGGACAGAGGCCGGCTCGGCCCACCCT
      TGGGCGCCCCATACTCCCGGTGTACCTGTCTCCGGCCGAGCCGGGTGGGA

GlyGlnPro
1651  CTGCCCTGGGAGTGACCGCTGTGCCAACCTCTGTCCCTACAGGGCAGCCC
      GACGGGACCCTCACTGGCGACACGGTTGGAGACAGGGATGTCCCGTCGGG

ArgGluProGlnValTyrThrLeuProProSerArgGluGluMetThrLys
1701  CGAGAACCACAGGTGTACACCCTGCCCCCATCCCGGGAGGAGATGACCAA
      GCTCTTGGTGTCCACATGTGGGACGGGGGTAGGGCCCTCCTCTACTGGTT

·AsnGlnValSerLeuThrCysLeuValLysGlyPheTyrProSerAspIle
1751  GAACCAGGTCAGCCTGACCTGCCTGGTCAAAGGCTTCTACCCCAGCGACA
      CTTGGTCCAGTCGGACTGGACGGACCAGTTTCCGAAGATGGGGTCGCTGT

··AlaValGluTrpGluSerAsnGlyGlnProGluAsnAsnTyrLysThr
1801  TCGCCGTGGAGTGGGAGAGCAATGGGCAGCCGGAGAACAACTACAAGACC
      AGCGGCACCTCACCCTCTCGTTACCCGTCGGCCTCTTGTTGATGTTCTGG

ThrProProMetLeuAspSerAspGlySerPhePheLeuTyrSerLysLeu
1851  ACACCTCCCATGCTGGACTCCGACGGCTCCTTCTTCCTCTACAGCAAGCT
      TGTGGAGGGTACGACCTGAGGCTGCCGAGGAAGAAGGAGATGTCGTTCGA

·ThrValAspLysSerArgTrpGlnGlnGlyAsnValPheSerCysSerVal
1901  CACCGTGGACAAGAGCAGGTGGCAGCAGGGGAACGTCTTCTCATGCTCCG
```

FIGURE 44 Continuation

```
      GTGGCACCTGTTCTCGTCCACCGTCGTCCCCTTGCAGAAGAGTACGAGGC

··MetHisGluAlaLeuHisAsnHisTyrThrGlnLysSerLeuSerLeu
1951  TGATGCATGAGGCTCTGCACAACCACTACACGCAGAAGAGCCTCTCCCTG
      ACTACGTACTCCGAGACGTGTTGGTGATGTGCGTCTTCTCGGAGAGGGAC

SerProGlyLys
2001  TCTCCGGGTAAA
      AGAGGCCCATTT
```

FIGURE 45

```
                    MetArgValProAlaGlnLeuLeuGlyLeuLeuLeu
  1                 ATGAGGGTCCCCGCTCAGCTCCTGGGGCTCCTGC
                    TACTCCCAGGGGCGAGTCGAGGACCCCGAGGACG

··LeuTrpPheProGlyAlaArgCysAspIleGlnMetThrGlnSerPro
 51                 TGCTCTGGTTCCCAGGCGCCAGGTGTGACATCCAGATGACCCAGTCTCCA
                    ACGAGACCAAGGGTCCGCGGTCCACACTGTAGGTCTACTGGGTCAGAGGT

SerSerLeuSerAlaSerValGlyAspArgValThrIleThrCysArgAla
101                 TCCTCCCTGTCTGCATCTGTAGGAGACAGAGTCACCATCACTTGCCGGGC
                    AGGAGGGACAGACGTAGACATCCTCTGTCTCAGTGGTAGTGAACGGCCCG

·SerGlnAspIleArgAsnAspLeuGlyTrpTyrGlnGlnLysProGlyLys
151                 AAGTCAGGACATTAGAAATGATTTAGGCTGGTATCAGCAGAAACCAGGGA
                    TTCAGTCCTGTAATCTTTACTAAATCCGACCATAGTCGTCTTTGGTCCCT

··AlaProLysArgLeuIleTyrAlaAlaSerAsnLeuGlnSerGlyVal
201                 AAGCCCCTAAGCGCCTGATCTATGCTGCATCCAATTTGCAAAGTGGGGTC
                    TTCGGGGATTCGCGGACTAGATACGACGTAGGTTAAACGTTTCACCCCAG

ProSerArgPheSerGlySerGlySerGlyThrGluPheThrLeuThrIle
251                 CCATCAAGGTTCAGCGGCAGTGGATCTGGGACAGAATTCACTCTCACAAT
                    GGTAGTTCCAAGTCGCCGTCACCTAGACCCTGTCTTAAGTGAGAGTGTTA

·SerSerLeuGlnProGluAspPheAlaThrTyrTyrCysLeuGlnHisAsn
301                 CAGCAGCCTGCAGCCTGAAGATTTTGCAACTTATTACTGTCTACAGCATA
                    GTCGTCGGACGTCGGACTTCTAAAACGTTGAATAATGACAGATGTCGTAT

··SerTyrProProThrPheGlyGlyGlyThrLysValGluIleLysArg
351                 ATAGCTACCCTCCCACTTTCGGCGGAGGGACCAAGGTGGAAATCAAACGA
                    TATCGATGGGAGGGTGAAAGCCGCCTCCCTGGTTCCACCTTTAGTTTGCT

ThrValAlaAlaProSerValPheIlePheProProSerAspGluGlnLeu
401                 ACTGTGGCTGCACCATCTGTCTTCATCTTCCCGCCATCTGATGAGCAGTT
                    TGACACCGACGTGGTAGACAGAAGTAGAAGGGCGGTAGACTACTCGTCAA

·LysSerGlyThrAlaSerValValCysLeuLeuAsnAsnPheTyrProArg
451                 GAAATCTGGAACTGCTAGCGTTGTGTGCCTGCTGAATAACTTCTATCCCA
                    CTTTAGACCTTGACGATCGCAACACACGGACGACTTATTGAAGATAGGGT

··GluAlaLysValGlnTrpLysValAspAsnAlaLeuGlnSerGlyAsn
501                 GAGAGGCCAAAGTACAGTGGAAGGTGGATAACGCCCTCCAATCGGGTAAC
                    CTCTCCGGTTTCATGTCACCTTCCACCTATTGCGGGAGGTTAGCCCATTG

SerGlnGluSerValThrGluGlnAspSerLysAspSerThrTyrSerLeu
551                 TCCCAGGAGAGTGTCACAGAGCAGGACAGCAAGGACAGCACCTACAGCCT
                    AGGGTCCTCTCACAGTGTCTCGTCCTGTCGTTCCTGTCGTGGATGTCGGA
```

FIGURE 45 Continuation

```
      ·SerSerThrLeuThrLeuSerLysAlaAspTyrGluLysHisLysValTyr
601   CAGCAGCACCCTGACGCTGAGCAAAGCAGACTACGAGAAACACAAAGTCT
      GTCGTCGTGGGACTGCGACTCGTTTCGTCTGATGCTCTTTGTGTTTCAGA

··AlaCysGluValThrHisGlnGlyLeuSerSerProValThrLysSer
651   ACGCCTGCGAAGTCACCCATGAGGGCCTGAGCTCGCCCGTCACAAAGAGC
      TGCGGACGCTTCAGTGGGTAGTCCCGGACTCGAGCGGGCAGTGTTTCTCG

PheAsnArgGlyGluCys
701   TTCAACAGGGGAGAGTGT
      AAGTTGTCCCCTCTCACA
```

FIGURE 46

```
                    MetLysHisLeuTrpPhePheLeuLeuLeuValAla
1                   ATGAAACACCTGTGGTTCTTCCTTCTCCTGGTGG
                    TACTTTGTGGACACCAAGAAGGAAGAGGACCACC

··AlaProArgTrpValLeuSerGlnValGlnLeuGlnGluSerGlyPro
51        CAGCTCCCAGATGGGTCCTGTCCCAGGTGCAGCTGCAGGAGTCGGGCCCA
          GTCGAGGGTCTACCCAGGACAGGGTCCACGTCGACGTCCTCAGCCCGGGT

GlyLeuValLysProSerGluThrLeuSerLeuThrCysThrValSerGly
101       GGACTGGTGAAGCCTTCGGAGACCCTGTCCCTCACCTGCACTGTCTCTGG
          CCTGACCACTTCGGAAGCCTCTGGGACAGGGAGTGGACGTGACAGAGACC

·ValSerIleSerAsnTyrTyrTrpSerTrpIleArgGlnSerProGlyLys
151       TGTCTCCATCAGTAATTACTACTGGAGCTGGATCCGGCAGTCCCCAGGGA
          ACAGAGGTAGTCATTAATGATGACCTCGACCTAGGCCGTCAGGGGTCCCT

··GlyLeuGluTrpIleGlyTyrIleTyrTyrSerGlySerProTyrTyr
201       AGGGACTGGAGTGGATTGGATATATCTATTACAGTGGGAGTCCCTATTAC
          TCCCTGACCTCACCTAACCTATATAGATAATGTCACCCTCAGGGATAATG

AsnProSerLeuLysSerArgValThrIleSerAlaAspThrSerLysAsn
251       AACCCCTCCCTCAAGAGTCGAGTCACTATATCTGCAGACACGTCCAAGAA
          TTGGGGAGGGAGTTCTCAGCTCAGTGATATAGACGTCTGTGCAGGTTCTT

·GlnPheSerLeuLysLeuSerSerValThrAlaAlaAspThrAlaIleTyr
301       CCAATTCTCCCTGAAGCTGAGCTCTGTGACCGCTGCGGACACGGCCATTT
          GGTTAAGAGGGACTTCGACTCGAGACACTGGCGACGCCTGTGCCGGTAAA

··TyrCysAlaArgGluLysLeuGlyIleGlyAspTyrTrpGlyGlnGly
351       ATTACTGTGCGAGAGAAAAACTGGGGATTGGAGACTACTGGGGCCAGGGA
          TAATGACACGCTCTCTTTTTGACCCCTAACCTCTGATGACCCCGGTCCCT

ThrLeuValThrValSerSerAlaSerThrLysGlyProSerValPhePro
401       ACCCTGGTCACCGTCTCCTCAGCCTCCACCAAGGGCCCATCGGTCTTCCC
          TGGGACCAGTGGCAGAGGAGTCGGAGGTGGTTCCCGGGTAGCCAGAAGGG

·LeuAlaProCysSerArgSerThrSerGluSerThrAlaAlaLeuGlyCys
451       CCTGGCGCCCTGCTCTAGAAGCACCTCCGAGAGCACAGCCGCCCTGGGCT
          GGACCGCGGGACGAGATCTTCGTGGAGGCTCTCGTGTCGGCGGGACCCGA

··LeuValLysAspTyrPheProGluProValThrValSerTrpAsnSer
501       GCCTGGTCAAGGACTACTTCCCCGAACCGGTGACGGTGTCGTGGAACTCA
          CGGACCAGTTCCTGATGAAGGGGCTTGGCCACTGCCACAGCACCTTGAGT

GlyAlaLeuThrSerGlyValHisThrPheProAlaValLeuGlnSerSer
551       GGCGCTCTGACCAGCGGCGTGCACACCTTCCCAGCTGTCCTACAGTCCTC
          CCGCGAGACTGGTCGCCGCACGTGTGGAAGGGTCGACAGGATGTCAGGAG
```

FIGURE 46 Continuation

```
     ·GlyLeuTyrSerLeuSerSerValValThrValProSerSerAsnPheGly
601  AGGACTCTACTCCCTCAGCAGCGTGGTGACCGTGCCTCCAGCAACTTCG
     TCCTGAGATGAGGGAGTCGTCGCACCACTGGCACGGGAGGTCGTTGAAGC

··ThrGlnThrTyrThrCysAsnValAspHisLysProSerAsnThrLys
651  GCACCCAGACCTACACCTGCAACGTAGATCACAAGCCCAGCAACACCAAG
     CGTGGGTCTGGATGTGGACGTTGCATCTAGTGTTCGGGTCGTTGTGGTTC

ValAspLysThrVal
701  GTGGACAAGACAGTTGGTGAGAGGCCAGCTCAGGGAGGGAGGGTGTCTGC
     CACCTGTTCTGTCAACCACTCTCCGGTCGAGTCCCTCCCTCCCACAGACG

751  TGGAAGCCAGGCTCAGCCCTCCTGCCTGGACGCACCCCGGCTGTGCAGCC
     ACCTTCGGTCCGAGTCGGGAGGACGGACCTGCGTGGGGCCGACACGTCGG

801  CCAGCCCAGGGCAGCAAGGCAGGCCCCATCTGTCTCCTCACCCGGAGGCC
     GGTCGGGTCCCGTCGTTCCGTCCGGGGTAGACAGAGGAGTGGGCCTCCGG

851  TCTGCCCGCCCCACTCATGCTCAGGGAGAGGGTCTTCTGGCTTTTTCCAC
     AGACGGGCGGGGTGAGTACGAGTCCCTCTCCCAGAAGACCGAAAAAGGTG

901  CAGGCTCCAGGCAGGCACAGGCTGGGTGCCCCTACCCCAGGCCCTTCACA
     GTCCGAGGTCCGTCCGTGTCCGACCCACGGGGATGGGGTCCGGGAAGTGT

951  CACAGGGGCAGGTGCTTGGCTCAGACCTGCCAAAAGCCATATCCGGGAGG
     GTGTCCCCGTCCACGAACCGAGTCTGGACGGTTTTCGGTATAGGCCCTCC

1001 ACCCTGCCCCTGACCTAAGCCGACCCCAAAGGCCAAACTGTCCACTCCCT
     TGGGACGGGGACTGGATTCGGCTGGGGTTTCCGGTTTGACAGGTGAGGGA

1051 CAGCTCGGACACCTTCTCTCCTCCCAGATCCGAGTAACTCCCAATCTTCT
     GTCGAGCCTGTGGAAGAGAGGAGGGTCTAGGCTCATTGAGGGTTAGAAGA

GluArgLysCysCysValGluCysProProCysPro
1101 CTCTGCAGAGCGCAAATGTTGTGTCGAGTGCCCACCGTGCCCAGGTAAGC
     GAGACGTCTCGCGTTTACAACACAGCTCACGGGTGGCACGGGTCCATTCG

1151 CAGCCCAGGCCTCGCCCTCCAGCTCAAGGCGGGACAGGTGCCCTAGAGTA
     GTCGGGTCCGGAGCGGGAGGTCGAGTTCCGCCCTGTCCACGGGATCTCAT

1201 GCCTGCATCCAGGGACAGGCCCCAGCTGGGTGCTGACACGTCCACCTCCA
     CGGACGTAGGTCCCTGTCCGGGGTCGACCCACGACTGTGCAGGTGGAGGT

AlaProProValAlaGlyProSerValPheLeuPhePro
1251 TCTCTTCCTCAGCACCACCTGTGGCAGGACCGTCAGTCTTCCTCTTCCCC
     AGAGAAGGAGTCGTGGTGGACACCGTCCTGGCAGTCAGAAGGAGAAGGGG

ProLysProLysAspThrLeuMetIleSerArgThrProGluValThrCys
1301 CCAAAACCCAAGGACACCCTCATGATCTCCCGGACCCCTGAGGTCACGTG
```

FIGURE 46 Continuation

```
     GGTTTTGGGTTCCTGTGGGAGTACTAGAGGGCCTGGGGACTCCAGTGCAC

·ValValValAspValSerHisGluAspProGluValGlnPheAsnTrpTyr
1351     CGTGGTGGTGGACGTGAGCCACGAAGACCCCGAGGTCCAGTTCAACTGGT
         GCACCACCACCTGCACTCGGTGCTTCTGGGGCTCCAGGTCAAGTTGACCA

··ValAspGlyValGluValHisAsnAlaLysThrLysProArgGluGlu
1401     ACGTGGACGGCGTGGAGGTGCATAATGCCAAGACAAAGCCACGGGAGGAG
         TGCACCTGCCGCACCTCCACGTATTACGGTTCTGTTTCGGTGCCCTCCTC

GlnPheAsnSerThrPheArgValValSerValLeuThrValValHisGln
1451     CAGTTCAACAGCACGTTCCGTGTGGTCAGCGTCCTCACCGTTGTGCACCA
         GTCAAGTTGTCGTGCAAGGCACACCAGTCGCAGGAGTGGCAACACGTGGT

·AspTrpLeuAsnGlyLysGluTyrLysCysLysValSerAsnLysGlyLeu
1501     GGACTGGCTGAACGGCAAGGAGTACAAGTGCAAGGTCTCCAACAAAGGCC
         CCTGACCGACTTGCCGTTCCTCATGTTCACGTTCCAGAGGTTGTTTCCGG

··ProAlaProIleGluLysThrIleSerLysThrLys
1551     TCCCAGCCCCCATCGAGAAAACCATCTCCAAAACCAAAGGTGGGACCCGC
         AGGGTCGGGGGTAGCTCTTTTGGTAGAGGTTTTGGTTTCCACCCTGGGCG

1601     GGGGTATGAGGGCCACATGGACAGAGGCCGGCTCGGCCCACCCTCTGCCC
         CCCCATACTCCCGGTGTACCTGTCTCCGGCCGAGCCGGGTGGGAGACGGG

GlyGlnProArgGlu
1651     TGGGAGTGACCGCTGTGCCAACCTCTGTCCCTACAGGGCAGCCCCGAGAA
         ACCCTCACTGGCGACACGGTTGGAGACAGGGATGTCCCGTCGGGGCTCTT

ProGlnValTyrThrLeuProProSerArgGluGluMetThrLysAsnGln
1701     CCACAGGTGTACACCCTGCCCCCATCCCGGGAGGAGATGACCAAGAACCA
         GGTGTCCACATGTGGGACGGGGGTAGGGCCCTCCTCTACTGGTTCTTGGT

·ValSerLeuThrCysLeuValLysGlyPheTyrProSerAspIleAlaVal
1751     GGTCAGCCTGACCTGCCTGGTCAAAGGCTTCTACCCCAGCGACATCGCCG
         CCAGTCGGACTGGACGGACCAGTTTCCGAAGATGGGGTCGCTGTAGCGGC

··GluTrpGluSerAsnGlyGlnProGluAsnAsnTyrLysThrThrPro
1801     TGGAGTGGGAGAGCAATGGGCAGCCGGAGAACAACTACAAGACCACACCT
         ACCTCACCCTCTCGTTACCCGTCGGCCTCTTGTTGATGTTCTGGTGTGGA

ProMetLeuAspSerAspGlySerPhePheLeuTyrSerLysLeuThrVal
1851     CCCATGCTGGACTCCGACGGCTCCTTCTTCCTCTACAGCAAGCTCACCGT
         GGGTACGACCTGAGGCTGCCGAGGAAGAAGGAGATGTCGTTCGAGTGGCA

·AspLysSerArgTrpGlnGlnGlyAsnValPheSerCysSerValMetHis
1901     GGACAAGAGCAGGTGGCAGCAGGGGAACGTCTTCTCATGCTCCGTGATGC
         CCTGTTCTCGTCCACCGTCGTCCCCTTGCAGAAGAGTACGAGGCACTACG
```

FIGURE 46 Continuation

```
      ··GluAlaLeuHisAsnHisTyrThrGlnLysSerLeuSerLeuSerPro
1951  ATGAGGCTCTGCACAACCACTACACGCAGAAGAGCCTCTCCCTGTCTCCG
      TACTCCGAGACGTGTTGGTGATGTGCGTCTTCTCGGAGAGGGACAGAGGC

GlyLys
2001  GGTAAA
      CCATTT
```

FIGURE 47

```
                    MetArgValProAlaGlnLeuLeuGlyLeuLeuLeu
  1                 ATGAGGGTCCCCGCTCAGCTCCTGGGGCTCCTGC
                    TACTCCCAGGGGCGAGTCGAGGACCCCGAGGACG

··LeuTrpPheProGlyAlaArgCysAspIleGlnMetThrGlnSerPro
 51                 TGCTCTGGTTCCCAGGTGCCAGGTGTGACATCCAGATGACCCAGTCTCCA
                    ACGAGACCAAGGGTCCACGGTCCACACTGTAGGTCTACTGGGTCAGAGGT

SerSerLeuSerAlaSerValGlyAspArgValThrIleThrCysArgAla
101                 TCCTCCCTGTCTGCATCTGTCGGAGACAGAGTCACCATCACTTGCCGGGC
                    AGGAGGGACAGACGTAGACAGCCTCTGTCTCAGTGGTAGTGAACGGCCCG

·SerGlnGlyIleArgAsnAspLeuGlyTrpTyrGlnGlnLysProGlyLys
151                 AAGTCAGGGCATTAGAAATGATTTAGGCTGGTATCAGCAGAAACCAGGGA
                    TTCAGTCCCGTAATCTTTACTAAATCCGACCATAGTCGTCTTTGGTCCCT

··AlaProLysArgLeuIleTyrAlaAlaSerSerLeuGlnSerGlyVal
201                 AAGCCCCTAAGCGCCTGATCTATGCTGCATCCAGTTTGCAAAGTGGGGTC
                    TTCGGGGATTCGCGGACTAGATACGACGTAGGTCAAACGTTTCACCCCAG

ProSerArgPheSerGlySerGlySerGlyThrGluPheThrLeuThrIle
251                 CCATCAAGGTTCAGCGGCAGTGGATCTGGGACAGAATTCACTCTCACAAT
                    GGTAGTTCCAAGTCGCCGTCACCTAGACCCTGTCTTAAGTGAGAGTGTTA

·SerSerLeuGlnProGluAspPheAlaThrTyrTyrCysLeuGlnHisAsn
301                 CAGCAGCCTGCAGCCTGAAGATTTTGCAACTTATTACTGTCTACAGCATA
                    GTCGTCGGACGTCGGACTTCTAAAACGTTGAATAATGACAGATGTCGTAT

··SerTyrProProThrPheGlyProGlyThrLysValAspIleLysArg
351                 ATAGTTACCCTCCCACTTTCGGCCCTGGGACCAAGGTGGATATCAAACGA
                    TATCAATGGGAGGGTGAAAGCCGGGACCCTGGTTCCACCTATAGTTTGCT

ThrValAlaAlaProSerValPheIlePheProProSerAspGluGlnLeu
401                 ACTGTGGCTGCACCATCTGTCTTCATCTTCCCGCCATCTGATGAGCAGTT
                    TGACACCGACGTGGTAGACAGAAGTAGAAGGGCGGTAGACTACTCGTCAA

·LysSerGlyThrAlaSerValValCysLeuLeuAsnAsnPheTyrProArg
451                 GAAATCTGGAACTGCTAGCGTTGTGTGCCTGCTGAATAACTTCTATCCCA
                    CTTTAGACCTTGACGATCGCAACACACGGACGACTTATTGAAGATAGGGT

···GluAlaLysValGlnTrpLysValAspAsnAlaLeuGlnSerGlyAsn
501                 GAGAGGCCAAAGTACAGTGGAAGGTGGATAACGCCCTCCAATCGGGTAAC
                    CTCTCCGGTTTCATGTCACCTTCCACCTATTGCGGGAGGTTAGCCCATTG

SerGlnGluSerValThrGluGlnAspSerLysAspSerThrTyrSerLeu
551                 TCCCAGGAGAGTGTCACAGAGCAGGACAGCAAGGACAGCACCTACAGCCT
                    AGGGTCCTCTCACAGTGTCTCGTCCTGTCGTTCCTGTCGTGGATGTCGGA
```

FIGURE 47 Continuation

```
     ·SerSerThrLeuThrLeuSerLysAlaAspTyrGluLysHisLysValTyr
601   CAGCAGCACCCTGACGCTGAGCAAAGCAGACTACGAGAAACACAAAGTCT
      GTCGTCGTGGGACTGCGACTCGTTTCGTCTGATGCTCTTTGTGTTTCAGA

··AlaCysGluValThrHisGlnGlyLeuSerSerProValThrLysSer
651   ACGCCTGCGAAGTCACCCATCAGGGCCTGAGCTCGCCCGTCACAAAGAGC
      TGCGGACGCTTCAGTGGGTAGTCCCGGACTCGAGCGGGCAGTGTTTCTCG

PheAsnArgGlyGluCys
701   TTCAACAGGGGAGAGTGT
      AAGTTGTCCCCTCTCACA
```

FIGURE 48

```
                        MetLysHisLeuTrpPhePheLeuLeuLeuValAla
  1                     ATGAAACATCTGTGGTTCTTCCTTCTCCTGGTGG
                        TACTTTGTAGACACCAAGAAGGAAGAGGACCACC

··AlaProArgTrpValLeuSerGlnValGlnLeuGlnGluSerGlyPro
  51       CAGCTCCCAGATGGGTCCTGTCCCAGGTGCAGCTGCAGGAGTCGGGCCCA
           GTCGAGGGTCTACCCAGGACAGGGTCCACGTCGACGTCCTCAGCCCGGGT

GlyLeuValLysProSerGluThrLeuSerLeuThrCysThrValSerGly
 101       GGACTGGTGAAGCCTTCGGAGACCCTGTCCCTCACCTGCACTGTCTCTGG
           CCTGACCACTTCGGAAGCCTCTGGGACAGGGAGTGGACGTGACAGAGACC

·GlySerIleSerArgTyrTyrTrpSerTrpIleArgGlnProProGlyLys
 151       TGGCTCCATCAGTCGTTACTACTGGAGCTGGATCCGGCAGCCCCCAGGGA
           ACCGAGGTAGTCAGCAATGATGACCTCGACCTAGGCCGTCGGGGGTCCCT

··GlyLeuGluTrpIleGlyTyrValSerTyrSerGlySerThrTyrTyr
 201       AGGGACTGGAGTGGATTGGGTATGTCTCTTACAGTGGGAGCACCTACTAC
           TCCCTGACCTCACCTAACCCATACAGAGAATGTCACCCTCGTGGATGATG

AsnProSerLeuLysSerArgValThrIleSerValAspThrSerLysAsn
 251       AACCCCTCCCTCAAGAGTCGAGTCACCATATCAGTAGACACGTCCAAGAA
           TTGGGGAGGGAGTTCTCAGCTCAGTGGTATAGTCATCTGTGCAGGTTCTT

·GlnPheSerLeuLysLeuSerSerValThrAlaAlaAspThrAlaValTyr
 301       CCAGTTCTCCCTGAAGCTGAGCTCTGTGACCGCTGCGGACACGGCCGTGT
           GGTCAAGAGGGACTTCGACTCGAGACACTGGCGACGCCTGTGCCGGCACA

··TyrCysAlaArgAspLysLeuGlyIleGlyAspTyrTrpGlyGlnGly
 351       ATTACTGTGCGAGAGATAAACTGGGGATTGGAGACTACTGGGGCCAGGGA
           TAATGACACGCTCTCTATTTGACCCCTAACCTCTGATGACCCCGGTCCCT

ThrLeuValThrValSerSerAlaSerThrLysGlyProSerValPhePro
 401       ACCCTGGTCACCGTCTCCTCAGCCTCCACCAAGGGCCCATCGGTCTTCCC
           TGGGACCAGTGGCAGAGGAGTCGGAGGTGGTTCCCGGGTAGCCAGAAGGG

·LeuAlaProCysSerArgSerThrSerGluSerThrAlaAlaLeuGlyCys
 451       CCTGGCGCCCTGCTCTAGAAGCACCTCCGAGAGCACAGCCGCCCTGGGCT
           GGACCGCGGGACGAGATCTTCGTGGAGGCTCTCGTGTCGGCGGGACCCGA

··LeuValLysAspTyrPheProGluProValThrValSerTrpAsnSer
 501       GCCTGGTCAAGGACTACTTCCCCGAACCGGTGACGGTGTCGTGGAACTCA
           CGGACCAGTTCCTGATGAAGGGGCTTGGCCACTGCCACAGCACCTTGAGT

GlyAlaLeuThrSerGlyValHisThrPheProAlaValLeuGlnSerSer
 551       GGCGCTCTGACCAGCGGCGTGCACACCTTCCCAGCTGTCCTACAGTCCTC
           CCGCGAGACTGGTCGCCGCACGTGTGGAAGGGTCGACAGGATGTCAGGAG
```

FIGURE 48 Continuation

```
     ·GlyLeuTyrSerLeuSerSerValValThrValProSerSerAsnPheGly
601  AGGACTCTACTCCCTCAGCAGCGTGGTGACCGTGCCCTCCAGCAACTTCG
     TCCTGAGATGAGGGAGTCGTCGCACCACTGGCACGGGAGGTCGTTGAAGC

··ThrGlnThrTyrThrCysAsnValAspHisLysProSerAsnThrLys
651  GCACCCAGACCTACACCTGCAACGTAGATCACAAGCCCAGCAACACCAAG
     CGTGGGTCTGGATGTGGACGTTGCATCTAGTGTTCGGGTCGTTGTGGTTC

ValAspLysThrVal
701  GTGGACAAGACAGTTGGTGAGAGGCCAGCTCAGGGAGGGAGGGTGTCTGC
     CACCTGTTCTGTCAACCACTCTCCGGTCGAGTCCCTCCCTCCCACAGACG

751  TGGAAGCCAGGCTCAGCCCTCCTGCCTGGACGCACCCCGGCTGTGCAGCC
     ACCTTCGGTCCGAGTCGGGAGGACGGACCTGCGTGGGCCGACACGTCGG

801  CCAGCCCAGGGCAGCAAGGCAGGCCCCATCTGTCTCCTCACCCGGAGGCC
     GGTCGGGTCCCGTCGTTCCGTCCGGGGTAGACAGAGGAGTGGGCCTCCGG

851  TCTGCCCGCCCCACTCATGCTCAGGGAGAGGGTCTTCTGGCTTTTTCCAC
     AGACGGGCGGGGTGAGTACGAGTCCCTCTCCCAGAAGACCGAAAAAGGTG

901  CAGGCTCCAGGCAGGCACAGGCTGGGTGCCCCTACCCCAGGCCCTTCACA
     GTCCGAGGTCCGTCCGTGTCCGACCCACGGGGATGGGGTCCGGGAAGTGT

951  CACAGGGGCAGGTGCTTGGCTCAGACCTGCCAAAAGCCATATCCGGGAGG
     GTGTCCCCGTCCACGAACCGAGTCTGGACGGTTTTCGGTATAGGCCCTCC

1001 ACCCTGCCCCTGACCTAAGCCGACCCCAAAGGCCAAACTGTCCACTCCCT
     TGGGACGGGGACTGGATTCGGCTGGGGTTTCCGGTTTGACAGGTGAGGGA

1051 CAGCTCGGACACCTTCTCTCCTCCCAGATCCGAGTAACTCCCAATCTTCT
     GTCGAGCCTGTGGAAGAGAGGAGGGTCTAGGCTCATTGAGGGTTAGAAGA

GluArgLysCysCysValGluCysProProCysPro
1101 CTCTGCAGAGCGCAAATGTTGTGTCGAGTGCCCACCGTGCCCAGGTAAGC
     GAGACGTCTCGCGTTTACAACACAGCTCACGGGTGGCACGGGTCCATTCG

1151 CAGCCCAGGCCTCGCCCTCCAGCTCAAGGCGGGACAGGTGCCCTAGAGTA
     GTCGGGTCCGGAGCGGGAGGTCGAGTTCCGCCCTGTCCACGGGATCTCAT

1201 GCCTGCATCCAGGGACAGGCCCCAGCTGGGTGCTGACACGTCCACCTCCA
     CGGACGTAGGTCCCTGTCCGGGGTCGACCCACGACTGTGCAGGTGGAGGT

AlaProProValAlaGlyProSerValPheLeuPhePro
1251 TCTCTTCCTCAGCACCACCTGTGGCAGGACCGTCAGTCTTCCTCTTCCCC
     AGAGAAGGAGTCGTGGTGGACACCGTCCTGGCAGTCAGAAGGAGAAGGGG

ProLysProLysAspThrLeuMetIleSerArgThrProGluValThrCys
```

FIGURE 48 Continuation

```
1301   CCAAAACCCAAGGACACCCTCATGATCTCCCGGACCCCTGAGGTCACGTG
       GGTTTTGGGTTCCTGTGGGAGTACTAGAGGGCCTGGGGACTCCAGTGCAC

·ValValValAspValSerHisGluAspProGluValGlnPheAsnTrpTyr
1351   CGTGGTGGTGGACGTGAGCCACGAAGACCCCGAGGTCCAGTTCAACTGGT
       GCACCACCACCTGCACTCGGTGCTTCTGGGGCTCCAGGTCAAGTTGACCA

··ValAspGlyValGluValHisAsnAlaLysThrLysProArgGluGlu
1401   ACGTGGACGGCGTGGAGGTGCATAATGCCAAGACAAAGCCACGGGAGGAG
       TGCACCTGCCGCACCTCCACGTATTACGGTTCTGTTTCGGTGCCCTCCTC

GlnPheAsnSerThrPheArgValValSerValLeuThrValValHisGln
1451   CAGTTCAACAGCACGTTCCGTGTGGTCAGCGTCCTCACCGTTGTGCACCA
       GTCAAGTTGTCGTGCAAGGCACACCAGTCGCAGGAGTGGCAACACGTGGT

·AspTrpLeuAsnGlyLysGluTyrLysCysLysValSerAsnLysGlyLeu
1501   GGACTGGCTGAACGGCAAGGAGTACAAGTGCAAGGTCTCCAACAAAGGCC
       CCTGACCGACTTGCCGTTCCTCATGTTCACGTTCCAGAGGTTGTTTCCGG

··ProAlaProIleGluLysThrIleSerLysThrLys
1551   TCCCAGCCCCCATCGAGAAAACCATCTCCAAAACCAAAGGTGGGACCCGC
       AGGGTCGGGGGTAGCTCTTTTGGTAGAGGTTTTGGTTTCCACCCTGGGCG

1601   GGGGTATGAGGGCCACATGGACAGAGGCCGGCTCGGCCCACCCTCTGCCC
       CCCCATACTCCCGGTGTACCTGTCTCCGGCCGAGCCGGGTGGGAGACGGG

GlyGlnProArgGlu
1651   TGGGAGTGACCGCTGTGCCAACCTCTGTCCCTACAGGGCAGCCCCGAGAA
       ACCCTCACTGGCGACACGGTTGGAGACAGGGATGTCCCGTCGGGGCTCTT

ProGlnValTyrThrLeuProProSerArgGluGluMetThrLysAsnGln
1701   CCACAGGTGTACACCCTGCCCCCATCCCGGGAGGAGATGACCAAGAACCA
       GGTGTCCACATGTGGGACGGGGGTAGGGCCCTCCTCTACTGGTTCTTGGT

·ValSerLeuThrCysLeuValLysGlyPheTyrProSerAspIleAlaVal
1751   GGTCAGCCTGACCTGCCTGGTCAAAGGCTTCTACCCCAGCGACATCGCCG
       CCAGTCGGACTGGACGGACCAGTTTCCGAAGATGGGGTCGCTGTAGCGGC

··GluTrpGluSerAsnGlyGlnProGluAsnAsnTyrLysThrThrPro
1801   TGGAGTGGGAGAGCAATGGGCAGCCGGAGAACAACTACAAGACCACACCT
       ACCTCACCCTCTCGTTACCCGTCGGCCTCTTGTTGATGTTCTGGTGTGGA

ProMetLeuAspSerAspGlySerPhePheLeuTyrSerLysLeuThrVal
1851   CCCATGCTGGACTCCGACGGCTCCTTCTTCCTCTACAGCAAGCTCACCGT
       GGGTACGACCTGAGGCTGCCGAGGAAGAAGGAGATGTCGTTCGAGTGGCA

·AspLysSerArgTrpGlnGlnGlyAsnValPheSerCysSerValMetHis·
1901   GGACAAGAGCAGGTGGCAGCAGGGGAACGTCTTCTCATGCTCCGTGATGC
```

FIGURE 48 Continuation

CCTGTTCTCGTCCACCGTCGTCCCCTTGCAGAAGAGTACGAGGCACTACG

```
       ··GluAlaLeuHisAsnHisTyrThrGlnLysSerLeuSerLeuSerPro
1951   ATGAGGCTCTGCACAACCACTACACGCAGAAGAGCCTCTCCCTGTCTCCG
       TACTCCGAGACGTGTTGGTGATGTGCGTCTTCTCGGAGAGGGACAGAGGC

GlyLys
2001   GGTAAA
       CCATTT
```

FIGURE 49

```
                    MetArgLeuProAlaGlnLeuLeuGlyLeuLeuLeu
  1                 ATGAGGCTCCCTGCTCAGCTCCTGGGGCTCCTGC
                    TACTCCGAGGGACGAGTCGAGGACCCCGAGGACG

··LeuTrpPheProGlyAlaArgCysAspIleGlnMetThrGlnSerPro
 51                 TGCTCTGGTTCCCAGGTGCCAGGTGTGACATCCAGATGACCCAGTCTCCA
                    ACGAGACCAAGGGTCCACGGTCCACACTGTAGGTCTACTGGGTCAGAGGT

SerSerLeuSerAlaSerValGlyAspArgValThrIleThrCysArgAla
101                 TCCTCCCTGTCTGCATCTGTAGGAGACAGAGTCACCATCACTTGCCGGGC
                    AGGAGGGACAGACGTAGACATCCTCTGTCTCAGTGGTAGTGAACGGCCCG

·SerGlnGlyIleArgAsnAspLeuGlyTrpTyrGlnGlnLysProGlyLys
151                 AAGTCAGGGCATTAGAAATGATTTAGGCTGGTATCAGCAGAAACCGGGGA
                    TTCAGTCCCGTAATCTTTACTAAATCCGACCATAGTCGTCTTTGGCCCCT

··AlaProLysArgLeuIleTyrAlaAlaSerSerLeuGlnSerGlyVal
201                 AAGCCCCTAAGCGCCTGATCTATGCTGCATCCAGTTTGCAAAGTGGGGTC
                    TTCGGGGATTCGCGGACTAGATACGACGTAGGTCAAACGTTTCACCCCAG

ProSerArgPheSerGlySerGlySerGlyThrGluPheThrLeuThrIle
251                 CCATCAAGGTTCAGCGGCAGTGGATCTGGGACAGAATTCACTCTCACAAT
                    GGTAGTTCCAAGTCGCCGTCACCTAGACCCTGTCTTAAGTGAGAGTGTTA

·SerSerLeuGlnProGluAspPheAlaThrTyrTyrCysLeuGlnHisAsn
301                 CAGCAGCCTGCAGCCTGAAGATTTTGCAACTTATTACTGTCTACAGCATA
                    GTCGTCGGACGTCGGACTTCTAAAACGTTGAATAATGACAGATGTCGTAT

··SerTyrProCysSerPheGlyGlnGlyThrLysLeuGluIleLysArg
351                 ATAGTTACCCGTGCAGTTTTGGCCAGGGGACCAAGCTGGAGATCAAACGA
                    TATCAATGGGCACGTCAAAACCGGTCCCCTGGTTCGACCTCTAGTTTGCT

ThrValAlaAlaProSerValPheIlePheProProSerAspGluGlnLeu
401                 ACTGTGGCTGCACCATCTGTCTTCATCTTCCCGCCATCTGATGAGCAGTT
                    TGACACCGACGTGGTAGACAGAAGTAGAAGGGCGGTAGACTACTCGTCAA

·LysSerGlyThrAlaSerValValCysLeuLeuAsnAsnPheTyrProArg
451                 GAAATCTGGAACTGCTAGCGTTGTGTGCCTGCTGAATAACTTCTATCCCA
                    CTTTAGACCTTGACGATCGCAACACACGGACGACTTATTGAAGATAGGGT

··GluAlaLysValGlnTrpLysValAspAsnAlaLeuGlnSerGlyAsn
501                 GAGAGGCCAAAGTACAGTGGAAGGTGGATAACGCCCTCCAATCGGGTAAC
                    CTCTCCGGTTTCATGTCACCTTCCACCTATTGCGGGAGGTTAGCCCATTG

SerGlnGluSerValThrGluGlnAspSerLysAspSerThrTyrSerLeu
551                 TCCCAGGAGAGTGTCACAGAGCAGGACAGCAAGGACAGCACCTACAGCCT
                    AGGGTCCTCTCACAGTGTCTCGTCCTGTCGTTCCTGTCGTGGATGTCGGA
```

FIGURE 49 Continuation

```
     ·SerSerThrLeuThrLeuSerLysAlaAspTyrGluLysHisLysValTyr
601   CAGCAGCACCCTGACGCTGAGCAAAGCAGACTACGAGAAACACAAAGTCT
      GTCGTCGTGGGACTGCGACTCGTTTCGTCTGATGCTCTTTGTGTTTCAGA

··AlaCysGluValThrHisGlnGlyLeuSerSerProValThrLysSer
651   ACGCCTGCGAAGTCACCCATCAGGGCCTGAGCTCGCCCGTCACAAAGAGC
      TGCGGACGCTTCAGTGGGTAGTCCCGGACTCGAGCGGGCAGTGTTTCTCG

PheAsnArgGlyGluCys
701   TTCAACAGGGGAGAGTGT
      AAGTTGTCCCCTCTCACA
```

FIGURE 50

```
                    MetLysHisLeuTrpPhePheLeuLeuLeuValAla
  1                 ATGAAGCATCTGTGGTTCTTCCTCCTGCTGGTGG
                    TACTTCGTAGACACCAAGAAGGAGGACGACCACC
```

```
                 ··AlaProArgTrpValLeuSerGlnValGlnLeuGlnGluSerGlyPro
 51              CAGCTCCCAGATGGGTCCTGTCCCAGGTGCAGCTGCAGGAGTCGGGCCCA
                 GTCGAGGGTCTACCCAGGACAGGGTCCACGTCGACGTCCTCAGCCCGGGT
```

```
                 GlyLeuValLysProLeuGlnThrLeuSerLeuThrCysThrValSerGly
101              GGACTGGTGAAGCCTTTACAGACCCTGTCCCTCACCTGCACTGTCTCTGG
                 CCTGACCACTTCGGAAATGTCTGGGACAGGGAGTGGACGTGACAGAGACC
```

```
                 ·GlySerIleSerSerGlyValTyrTyrTrpSerTrpIleArgGlnHisPro
151              TGGCTCCATCAGCAGTGGTGTTTACTACTGGAGCTGGATCCGCCAGCACC
                 ACCGAGGTAGTCGTCACCACAAATGATGACCTCGACCTAGGCGGTCGTGG
```

```
                 ··GlyLysGlyLeuGluTrpIleGlyTyrIleTyrAsnSerLysThrSer
201              CAGGGAAGGGCCTGGAGTGGATTGGGTACATCTATAACAGTAAGACCTCC
                 GTCCCTTCCCGGACCTCACCTAACCCATGTAGATATTGTCATTCTGGAGG
```

```
                 TyrTyrAsnProSerLeuLysSerArgLeuThrLeuSerValAspThrSer
251              TATTATAATCCGTCCCTCAAGAGTCGACTTACCCTATCAGTAGACACGTC
                 ATAATATTAGGCAGGGAGTTCTCAGCTGAATGGGATAGTCATCTGTGCAG
```

```
                 ·LysAsnGlnPheSerLeuAsnLeuIleSerValThrAlaAlaAspThrAla
301              TAAGAACCAGTTCTCCCTGAACCTGATCTCTGTGACTGCCGCGGACACGG
                 ATTCTTGGTCAAGAGGGACTTGGACTAGAGACACTGACGGCGCCTGTGCC
```

```
                 ··ValTyrTyrCysAlaArgAspLysLeuGlyIleAlaAspTyrTrpGly
351              CCGTGTATTACTGTGCGAGAGATAAATTGGGGATCGCGGACTACTGGGGC
                 GGCACATAATGACACGCTCTCTATTTAACCCCTAGCGCCTGATGACCCCG
```

```
                 GlnGlyThrLeuValThrValSerSerAlaSerThrLysGlyProSerVal
401              CAGGGAACCCTGGTCACCGTCTCCTCAGCCTCCACCAAGGGCCCATCGGT
                 GTCCCTTGGGACCAGTGGCAGAGGAGTCGGAGGTGGTTCCCGGGTAGCCA
```

```
                 ·PheProLeuAlaProCysSerArgSerThrSerGluSerThrAlaAlaLeu
451              CTTCCCCCTGGCGCCCTGCTCTAGAAGCACCTCCGAGAGCACAGCCGCCC
                 GAAGGGGGACCGCGGGACGAGATCTTCGTGGAGGCTCTCGTGTCGGCGGG
```

```
                 ··GlyCysLeuValLysAspTyrPheProGluProValThrValSerTrp
501              TGGGCTGCCTGGTCAAGGACTACTTCCCCGAACCGGTGACGGTGTCGTGG
                 ACCCGACGGACCAGTTCCTGATGAAGGGGCTTGGCCACTGCCACAGCACC
```

```
                 AsnSerGlyAlaLeuThrSerGlyValHisThrPheProAlaValLeuGln
551              AACTCAGGCGCTCTGACCAGCGGCGTGCACACCTTCCCAGCTGTCCTACA
                 TTGAGTCCGCGAGACTGGTCGCCGCACGTGTGGAAGGGTCGACAGGATGT
```

FIGURE 50 Continuation

```
                ·SerSerGlyLeuTyrSerLeuSerSerValValThrValProSerSerAsn
 601    GTCCTCAGGACTCTACTCCCTCAGCAGCGTGGTGACCGTGCCGTCCAGCA
        CAGGAGTCCTGAGATGAGGGAGTCGTCGCACCACTGGCACGGGAGGTCGT

··PheGlyThrGlnThrTyrThrCysAsnValAspHisLysProSerAsn
 651    ACTTCGGCACCCAGACCTACACCTGCAACGTAGATCACAAGCCCAGCAAC
        TGAAGCCGTGGGTCTGGATGTGGACGTTGCATCTAGTGTTCGGGTCGTTG

ThrLysValAspLysThrVal
 701    ACCAAGGTGGACAAGACAGTTGGTGAGAGGCCAGCTCAGGGAGGGAGGGT
        TGGTTCCACCTGTTCTGTCAACCACTCTCCGGTCGAGTCCCTCCCTCCCA

751    GTCTGCTGGAAGCCAGGCTCAGCCCTCCTGCCTGGACGCACCCCGGCTGT
        CAGACGACCTTCGGTCCGAGTCGGGAGGACGGACCTGCGTGGGGCCGACA

801    GCAGCCCCAGCCCAGGGCAGCAAGGCAGGCCCCATCTGTCTCCTCACCCG
        CGTCGGGGTCGGGTCCCGTCGTTCCGTCCGGGGTAGACAGAGGAGTGGGC

851    GAGGCCTCTGCCCGCCCGACTCATGCTCAGGGAGAGGGTCTTCTGGCTTT
        CTCCGGAGACGGGCGGGGTGAGTACGAGTCCCTCTCCCAGAAGACCGAAA

901    TTCCACCAGGCTCCAGGCAGGCACAGGCTGGGTGCCCCTACCCCAGGCCC
        AAGGTGGTCCGAGGTCCGTCCGTGTCCGACCCACGGGGATGGGGTCCGGG

951    TTCACACACAGGGGCAGGTGCTTGGCTCAGACCTGCCAAAAGCCATATCC
        AAGTGTGTGTCCCCGTCCACGAACCGAGTCTGGACGGTTTTCGGTATAGG

1001    GGGAGGACCCTGCCGCTGACCTAAGCCGACCCCAAAGGCCAAACTGTCCA
        CCCTCCTGGGACGGGGACTGGATTCGGCTGGGGTTTCCGGTTTGACAGGT

1051    CTCCCTCAGCTCGGACACCTTCTCTCCTCCCAGATCCGAGTAACTCCCAA
        GAGGGAGTCGAGCCTGTGGAAGAGAGGAGGGTCTAGGCTCATTGAGGGTT

GluArgLysCysCysValGluCysProProCysPro
1101    TCTTCTCTCTGCAGAGCGCAAATGTTGTGTCGAGTGCCCACCGTGCCCAG
        AGAAGAGAGACGTCTCGCGTTTACAACACAGCTCACGGGTGGCACGGGTC

1151    GTAAGCCAGCCCAGGCCTCGCCCTCCAGCTCAAGGCGGGACAGGTGCCCT
        CATTCGGTCGGGTCCGGAGCGGGAGGTCGAGTTCCGCCCTGTCCACGGGA

1201    AGAGTAGCCTGCATCCAGGGACAGGCCCCAGCTGGGTGCTGACACGTCCA
        TCTCATCGGACGTAGGTCCCTGTCCGGGGTCGACCCACGACTGTGCAGGT

AlaProProValAlaGlyProSerValPheLeu
1251    CCTCCATCTCTTCCTCAGCACCACCTGTGGCAGGACCGTCAGTCTTCCTC
        GGAGGTAGAGAAGGAGTCGTGGTGGACACCGTCCTGGCAGTCAGAAGGAG

PheProProLysProLysAspThrLeuMetIleSerArgThrProGluVal
```

FIGURE 50 Continuation

```
1301  TTCCCCCCAAAACCCAAGGACACCCTCATGATCTCCCGGACCCCTGAGGT
      AAGGGGGGTTTTGGGTTCCTGTGGGAGTACTAGAGGGCCTGGGGACTCCA

·ThrCysValValValAspValSerHisGluAspProGluValGlnPheAsn
1351  CACGTGCGTGGTGGTGGACGTGAGCCACGAAGACCCCGAGGTCCAGTTCA
      GTGCACGCACCACCACCTGCACTCGGTGCTTCTGGGGCTCCAGGTCAAGT

··TrpTyrValAspGlyValGluValHisAsnAlaLysThrLysProArg
1401  ACTGGTACGTGGACGGCGTGGAGGTGCATAATGCCAAGACAAAGCCACGG
      TGACCATGCACCTGCCGCACCTCCACGTATTACGGTTCTGTTTCGGTGCC

GluGluGlnPheAsnSerThrPheArgValValSerValLeuThrValVal
1451  GAGGAGCAGTTCAACAGCACGTTCCGTGTGGTCAGCGTCCTCACCGTTGT
      CTCCTCGTCAAGTTGTCGTGCAAGGCACACCAGTCGCAGGAGTGGCAACA

·HisGlnAspTrpLeuAsnGlyLysGluTyrLysCysLysValSerAsnLys
1501  GCACCAGGACTGGCTGAACGGCAAGGAGTACAAGTGCAAGGTCTCCAACA
      CGTGGTCCTGACCGACTTGCCGTTCCTCATGTTCACGTTCCAGAGGTTGT

··GlyLeuProAlaProIleGluLysThrIleSerLysThrLys
1551  AAGGCCTCCCAGCCCGCATCGAGAAAACCATCTCCAAAACCAAAGGTGGG
      TTCCGGAGGGTCGGGGGTAGCTCTTTTGGTAGAGGTTTTGGTTTCCACCC

1601  ACCCGCGGGGTATGAGGGCCACATGGACAGAGGCCGGCTCGGCCCACCCT
      TGGGCGCCCCATACTCCCGGTGTACCTGTCTCCGGCCGAGCCGGGTGGGA

GlyGlnPro
1651  CTGCCCTGGGAGTGACCGCTGTGCCAACCTCTGTCCCTACAGGGCAGCCC
      GACGGGACCCTCACTGGCGACACGGTTGGAGACAGGGATGTCCCGTCGGG

ArgGluProGlnValTyrThrLeuProProSerArgGluGluMetThrLys
1701  CGAGAACCACAGGTGTACACCCTGCCCCCATCCCGGGAGGAGATGACCAA
      GCTCTTGGTGTCCACATGTGGGACGGGGGTAGGGCCCTCCTCTACTGGTT

·AsnGlnValSerLeuThrCysLeuValLysGlyPheTyrProSerAspIle
1751  GAACCAGGTCAGCCTGACCTGCCTGGTCAAAGGCTTCTACCCCAGCGACA
      CTTGGTCCAGTCGGACTGGACGGACCAGTTTCCGAAGATGGGGTCGCTGT

··AlaValGluTrpGluSerAsnGlyGlnProGluAsnAsnTyrLysThr
1801  TCGCCGTGGAGTGGGAGAGCAATGGGCAGCCGGAGAACAACTACAAGACC
      AGCGGCACCTCACCCTCTCGTTACCCGTCGGCCTCTTGTTGATGTTCTGG

ThrProProMetLeuAspSerAspGlySerPhePheLeuTyrSerLysLeu
1851  ACACCTCCCATGCTGGACTCCGACGGCTCCTTCTTCCTCTACAGCAAGCT
      TGTGGAGGGTACGACCTGAGGCTGCCGAGGAAGAAGGAGATGTCGTTCGA

·ThrValAspLysSerArgTrpGlnGlnGlyAsnValPheSerCysSerVal
1901  CACCGTGGACAAGAGCAGGTGGCAGCAGGGGAACGTCTTCTCATGCTCCG
```

FIGURE 50 Continuation

```
         GTGGCACCTGTTCTCGTCCACCGTCGTCCCCTTGCAGAAGAGTACGAGGC

··MetHisGluAlaLeuHisAsnHisTyrThrGlnLysSerLeuSerLeu
1951     TGATGCATGAGGCTCTGCACAACCACTACACGCAGAAGAGCCTCTCCCTG
         ACTACGTACTCCGAGACGTGTTGGTGATGTGCGTCTTCTCGGAGAGGGAC

SerProGlyLys
2001     TCTCCGGGTAAA
         AGAGGCCCATTT
```

FIGURE 51

```
                MetArgValProAlaGlnLeuLeuGlyLeuLeuLeu
1               ATGAGGGTCCCTGCTCAGCTCCTGGGGCTCCTGC
                TACTCCCAGGGACGAGTCGAGGACCCCGAGGACG

··LeuTrpPheProGlyAlaArgCysAspIleGlnMetThrGlnSerPro
51              TGCTCTGGTTCCCAGGTGCCAGGTGTGACATCCAGATGACCCAGTCTCCA
                ACGAGACCAAGGGTCCACGGTCCACACTGTAGGTCTACTGGGTCAGAGGT

SerSerLeuSerAlaSerValGlyAspArgValThrIleThrCysArgThr
101             TCCTCCCTGTCTGCATCTGTAGGAGACAGAGTCACCATCACTTGCCGGAC
                AGGAGGGACAGACGTAGACATCCTCTGTCTCAGTGGTAGTGAACGGCCTG

·SerGlnGlyIleArgAsnAspLeuGlyTrpTyrGlnGlnLysProGlyLys
151             AAGTCAGGGCATTAGAAATGATTTAGGCTGGTATCAGCAGAAACCAGGGA
                TTCAGTCCCGTAATCTTTACTAAATCCGACCATAGTCGTCTTTGGTCCCT

···AlaProLysArgLeuIleTyrAlaAlaSerSerLeuGlnSerGlyVal
201             AAGCCCCTAAGCGCCTGATCTATGCTGCATCCAGTTTGCAAAGTGGGGTC
                TTCGGGGATTCGCGGACTAGATACGACGTAGGTCAAACGTTTCACCCCAG

ProSerArgPheSerGlySerGlySerGlyThrGluPheThrLeuThrIle
251             CCATCAAGGTTCAGCGGCAGTGGATCTGGGACAGAATTCACTCTCACAAT
                GGTAGTTCCAAGTCGCCGTCACCTAGACCCTGTCTTAAGTGAGAGTGTTA

·SerSerLeuGlnProGluAspPheAlaThrTyrTyrCysLeuGlnHisAsn
301             CAGCAGCCTGCAGCCTGAAGATTTTGCAACTTATTACTGTCTACAGCATA
                GTCGTCGGACGTCGGACTTCTAAAACGTTGAATAATGACAGATGTCGTAT

··SerTyrProProThrPheGlyGlyGlyThrLysValGluIleLysArg
351             ATAGCTACCCTCCCACTTTCGGCGGAGGGACCAAGGTGGAGATCAAACGA
                TATCGATGGGAGGGTGAAAGCCGCCTCCCTGGTTCCACCTCTAGTTTGCT

ThrValAlaAlaProSerValPheIlePheProProSerAspGluGlnLeu
401             ACTGTGGCTGCACCATCTGTCTTCATCTTCCCGCCATCTGATGAGCAGTT
                TGACACCGACGTGGTAGACAGAAGTAGAAGGGCGGTAGACTACTCGTCAA

·LysSerGlyThrAlaSerValValCysLeuLeuAsnAsnPheTyrProArg
451             GAAATCTGGAACTGCTAGCGTTGTGTGCCTGCTGAATAACTTCTATCCCA
                CTTTAGACCTTGACGATCGCAACACACGGACGACTTATTGAAGATAGGGT

··GluAlaLysValGlnTrpLysValAspAsnAlaLeuGlnSerGlyAsn
501             GAGAGGCCAAAGTACAGTGGAAGGTGGATAACGCCCTCCAATCGGGTAAC
                CTCTCCGGTTTCATGTCACCTTCCACCTATTGCGGGAGGTTAGCCCATTG

SerGlnGluSerValThrGluGlnAspSerLysAspSerThrTyrSerLeu
551             TCCCAGGAGAGTGTCACAGAGCAGGACAGCAAGGACAGCACCTACAGCCT
                AGGGTCCTCTCACAGTGTCTCGTCCTGTCGTTCCTGTCGTGGATGTCGGA
```

FIGURE 51 Continuation

```
      ·SerSerThrLeuThrLeuSerLysAlaAspTyrGluLysHisLysValTyr
601   CAGCAGCACCCTGACGCTGAGCAAAGCAGACTACGAGAAACACAAAGTCT
      GTCGTCGTGGGACTGCGACTCGTTTCGTCTGATGCTCTTTGTGTTTCAGA

··AlaCysGluValThrHisGlnGlyLeuSerSerProValThrLysSer
651   ACGCCTGCGAAGTCACCCATCAGGGCCTGAGCTCGCCCGTCACAAAGAGC
      TGCGGACGCTTCAGTGGGTAGTCCCGGACTCGAGCGGGCAGTGTTTCTCG

PheAsnArgGlyGluCys
701   TTCAACAGGGGAGAGTGT
      AAGTTGTCCCCTCTCACA
```

ERYTHROPOIETIN RECEPTOR BINDING ANTIBODIES

APPLICATION HISTORY

This application claims priority to U.S. Provisional Application Ser. No. 60/418,031, filed Oct. 14, 2002, hereby incorporated by reference in its entirety.

TECHNICAL FIELD OF THE INVENTION

The present invention relates to antibodies that recognize, bind to and, preferably, activate the erythropoietin receptor.

BACKGROUND OF THE INVENTION

Erythropoietin ("EPO") is a glycoprotein that is the primary regulator of erythropoiesis. Specifically, EPO is responsible for promoting the growth, differentiation and survival of erythroid progenitors, which give rise to mature red blood cells. In response to changes in the level of oxygen in the blood and tissues, erythropoietin appears to stimulate both proliferation and differentiation of immature erythroblasts. It also functions as a growth factor, stimulating the mitotic activity of erythroid progenitor cells, such as erythrocyte burst forming and colony-forming units. It also acts as a differentiation factor, triggering transformation of an erythrocyte colony-forming-unit into a proerythroblast (See Erslev, A., *New Eng. J. Med.*, 316:101-103 (1987)).

EPO has a molecular weight of about 34,000 daltons and can occur in three forms—alpha, beta and asialo. During mid- to late gestation, EPO is synthesized in the fetal liver. Subsequently, EPO is synthesized in the kidney, circulates in the plasma and is excreted in the urine.

Human urinary EPO has been isolated and purified (See, Miyake et al., *J. Biol. Chem.*, 252:5558 (1977)). Moreover, methods for identifying, cloning and expressing genes encoding EPO (See U.S. Pat. No. 4,703,008) as well as purifying recombinant EPO from a cell medium (See U.S. Pat. No. 4,667,016) are known in the art.

The activity of EPO is mediated through the binding and activation of a cell surface receptor referred to as the erythropoietin receptor. The EPO receptor belongs to the cytokine receptor superfamily and is believed to contain at least two distinct polypeptides, a 55-72 kDa species and a 85-100 kDa species (See U.S. Pat. No. 6,319,499, Mayeux et al., *J. Biol. Chem*, 266:23380 (1991), McCaffery et al., *J. Biol. Chem.*, 264:10507 (1991)). Other studies have revealed other polypeptide complexes of EPO receptor having molecular weights such as 110, 130 and 145 kDa (See U.S. Pat. No. 6,319,499).

Both the murine and human EPO receptors have been cloned and expressed (See D'Andrea et al., *Cell*, 57:277 (1989); Jones et al., *Blood*, 76:31 (1990); Winkelmann et al., *Blood*, 76:24 (1990); WO 90/08822/U.S. Pat. No. 5,278,065). The full length human EPO receptor is a 483 amino acid transmembrane protein with an approximately 25 amino acid signal peptide (See U.S. Pat. No. 6,319,499). The human receptor demonstrates about a 82% amino acid sequence homology with the murine receptor. Id.

In the absence of ligand the EPO receptor exists in a preformed dimer. The binding of EPO to its receptor causes a conformational change such that the cytoplasmic domains are placed in close proximity. While not completely understood, it is believed that this "dimerization" plays a role in the activation of the receptor. The activation of the EPO receptor results in a number of biological effects. Some of these activities include stimulation of proliferation, stimulation of differentiation and inhibition of apoptosis (See U.S. Pat. No. 6,319,499, Liboi et al., *PNAS USA*, 90:11351 (1993), Koury, *Science*, 248:378 (1990)).

It is the relationship between the EPO receptor dimerization and activation that can be used to identify compounds (i.e. such as antibodies) other than EPO that are capable of: (1) dimerizing the EPO receptor; and (2) activating the receptor. These compounds would be useful in treating mammals suffering from anemia and in identifying mammals having a dysfunctional EPO receptor.

SUMMARY OF THE INVENTION

In one embodiment, the invention relates to antibodies that bind to the human erythropoietin receptor. In one embodiment, the antibodies comprise a heavy chain variable region that is selected from the group consisting of SEQ ID NOS: 3, 7, 11, 15, 19, 31, 35, 39, 43, 47, 51, 55 and fragments thereof. In another embodiment, the antibodies comprise a light chain variable region that is selected from the group consisting of SEQ ID NOS: 5, 9, 13, 17, 21, 23, 25, 27, 29, 33, 37, 41, 45, 49, 53, 57 and fragments thereof.

In another embodiment, the present invention relates to an isolated antibody that is capable of binding a human erythropoietin receptor in a mammal. Such an antibody comprises a heavy chain variable region or a light chain variable region that comprises a continuous sequence from CDR1 through CDR3. The amino acid sequence of the heavy chain variable region comprising the continuous sequence from CDR1 through CDR3 is selected from the group consisting of: SEQ ID NO:58, SEQ ID NO:59, SEQ ID NO:60, SEQ ID NO:61 and fragments thereof. The amino acid sequence of the light chain variable region comprising the continuous sequence from CDR1 through CDR3 is selected from the group consisting of: SEQ ID NO:62, SEQ ID NO:63, SEQ ID NO:64, SEQ ID NO:65, SEQ ID NO:66, SEQ ID NO:67, SEQ ID NO:68 and fragments thereof.

In another embodiment, the present invention relates to an antibody that activates an endogenous activity of a human erythropoietin receptor in a mammal but does not interact with a peptide having an amino acid sequence of PGNYSFSYQLEDEPWKLCRLHQAPTARGAV (SEQ ID NO:1).

In another embodiment, the present invention relates to an antibody that is capable of activating an endogenous activity of a human erythropoietin receptor in a mammal, wherein said antibody or antibody fragment thereof exhibits a binding affinity within one hundred fold of the binding affinity of endogenous human erythropoietin to the erythropoietin receptor.

In yet another embodiment, the present invention relates to an antibody or antibody fragment thereof that activates an endogenous activity of a human erythropoietin receptor in a mammal. The antibody or antibody fragment thereof comprises at least one human heavy chain variable region having the amino acid sequence of SEQ ID NO:3 or antibody fragment thereof, and/or at least one human light chain variable region having the amino acid sequence of SEQ ID NO:5 or antibody fragment thereof, provided that said antibody or antibody fragment thereof does not interact with a peptide having an amino acid sequence of PGNYSFSYQLEDEPWKLCRLHQAPTARGAV (SEQ ID NO:1).

In yet another embodiment, the present invention relates to an antibody or antibody fragment thereof that activates an endogenous activity of a human erythropoietin receptor in a mammal. The antibody or antibody fragment thereof comprises at least one heavy chain variable region having the amino acid sequence of SEQ ID NO:7 or antibody fragment thereof, and/or at least one light chain variable region having the amino acid sequence of SEQ ID NO:9 or antibody fragment thereof, provided that said antibody or antibody fragment thereof does not interact with a peptide having an amino acid sequence of PGNYSFSYQLEDEPWKLCRLHQAPTARGAV (SEQ ID NO:1).

This embodiment also includes other heavy chain variable regions selected from the group consisting of SEQ ID NO: 11, 15, 19,31, 35, 39, 43,47, 51, and 55 or an antibody fragment of any of these aforementioned SEQ ID NOS, wherein said antibody or antibody fragment thereof does not interact with a peptide having an amino acid sequence of SEQ ID NO:1. Other light chain variable regions included in this embodiment may be selected from the group consisting of SEQ ID NO: 13, 17, 21, 23, 25,27, 29,33, 37, 41, 45, 49, 53 and 57 or an antibody fragment of any of these aforementioned SEQ ID NOS, wherein said antibody or antibody fragment thereof does not interact with a peptide having an amino acid sequence of SEQ ID NO:1.

In yet another embodiment, the invention provides an antibody or antibody fragment thereof that activates an endogenous activity of a human erythropoietin receptor in a mammal, the antibody comprising the amino acid sequences of at least one heavy chain variable region and at least one light chain variable region selected from the group consisting of SEQ ID NO:11/SEQ ID NO:13, SEQ ID NO:15/SEQ ID NO:17, SEQ ID NO:19/SEQ ID NO:21, SEQ ID NO:11/SEQ ID NO:23, SEQ ID NO:11/SEQ ID NO:25, SEQ ID NO:11/SEQ ID NO:27, SEQ ID NO:11/SEQ ID NO:29, SEQ ID NO:31/SEQ ID NO:33, SEQ ID NO:35/SEQ ID NO:37, SEQ ID NO:39/SEQ ID NO:41, SEQ ID NO:43/SEQ ID NO:45, SEQ ID NO:47/SEQ ID NO:49, SEQ ID NO:51/SEQ ID NO:53 and SEQ ID NO:55/SEQ ID NO:57 or antibody fragment thereof, wherein said antibody or antibody fragment thereof does not interact with a peptide having an amino acid sequence of SEQ ID NO:1.

In yet another embodiment, the present invention relates to a method of activating an endogenous activity of a human erythropoietin receptor in a mammal. The method involves the step of administering to a mammal a therapeutically effective amount of an antibody or antibody fragment thereof to activate the EPO receptor. The antibody or antibody fragment thereof does not interact with a peptide having an amino acid sequence of PGNYSFSYQLEDEPWKLCRLHQAPTARGAV (SEQ ID NO:1).

In yet a further embodiment, the present invention relates to a method of modulating an endogenous activity of a human erythropoietin receptor in a mammal. The method involves administering to a mammal a therapeutically effective amount of an antibody or antibody fragment thereof to modulate the endogenous activity of a human erythropoietin receptor in a mammal but does not interact with a peptide having an amino acid sequence of PGNYSFSYQLEDEPWKLCRLHQAPTARGAV (SEQ ID NO:1).

In yet a further embodiment, the present invention relates to a method of treating a mammal suffering from pure red cell aplasia induced by neutralizing anti-erythropoietin antibodies. The method involves administering to a mammal in need of treatment a therapeutically effective amount of an antibody or antibody fragment thereof to activate said receptor, wherein said antibody or antibody fragment thereof does not interact with a peptide having an amino acid sequence of PGNYSFSYQLEDEPWKLCRLHQAPTARGAV (SEQ ID NO:1).

In yet a further embodiment, the present invention relates to pharmaceutical compositions. The pharmaceutical compositions of the present invention contain a therapeutically effective amount of an antibody or antibody fragment thereof and a pharmaceutically acceptable excipient. The antibody or antibody fragment contained in the pharmaceutical composition activates an endogenous activity of a human erythropoietin receptor in a mammal but does not interact with a peptide having an amino acid sequence of PGNYSFSYQLEDEPWKLCRLHQAPTARGAV (SEQ ID NO:1).

In yet a further embodiment, the present invention relates to an IgG2 antibody or antibody fragment that binds to and activates the erythropoietin receptor. The IgG2 antibodies or antibody fragments of this embodiment bind to and interact with any epitope that is involved in activating the EPO receptor. Such antibodies may be polyclonal or monoclonal antibodies or any antibody fragment thereof. The IgG2 antibodies may be chimeric, humanized or human antibodies.

In yet a further embodiment, the present invention provides a method of activating an endogenous activity of a human erythropoietin receptor in a mammal comprising the step of administering to a mammal a therapeutically effective amount of an IgG2 antibody or antibody fragment of the invention to activate the receptor.

In yet a further embodiment, the present invention provides a method of modulating an endogenous activity of a human erythropoietin receptor in a mammal comprising the step of administering to a mammal a therapeutically effective amount of an IgG2 antibody or antibody fragment of the invention to modulate the receptor.

In yet another embodiment, the present invention provides a method of treating a mammal suffering aplasia, the method comprising the step of administering to a mammal in need of treatment a therapeutically effective amount of an IgG2 antibody or antibody fragment of the invention to activate the receptor.

In yet another embodiment, the present invention provides a method of treating a mammal suffering aplasia, the method comprising the step of administering to a mammal in need of treatment a therapeutically effective amount of an IgG2 antibody or antibody fragment of the invention to modulate the receptor.

In yet another embodiment, the present invention provides a pharmaceutical composition comprising a therapeutically effective amount of an IgG2 antibody or antibody fragment of the invention and a pharmaceutically acceptable excipient.

Finally, the present invention relates to isolated and purified polynucleotide and amino acid sequences. The isolated and purified polynucleotide sequences can be selected from the group consisting of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56 and fragments, complements and degenerate codon equivalents thereof.

The present invention further relates to isolated and purified amino acid sequences selected from the group consisting of: SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68 and fragments and complements and thereof.

BRIEF DESCRIPTION OF THE FIGURES

FIG. 1 shows the isolated and purified polynucleotide (top strand and bottom strands, SEQ ID NO:69 and SEQ ID NO:70, respectively) and amino acid sequence of the heavy chain of human antibody Ab12. The amino acid sequence comprises SEQ ID NOS:71 through 74. The sequence of the constant region alone is shown as SEQ ID NO:75. The variable chain ends at nucleotide 1283. The variable/constant joining region (underlined) is at nucleotides 1284-1289. The constant region is from nucleotides 1290-2826.

FIG. 2 shows the isolated and purified polynucleotide (top strand and bottom strands, SEQ ID NO:76 and SEQ ID NO:77, respectively) and amino acid sequence of the light chain of human antibody Ab12. The amino acid sequence comprises SEQ ID NOS:78. The sequence of the constant region alone is shown as SEQ ID NO: 79. The variable chain ends at nucleotide1363. The variable/constant joining region (underlined) is at nucleotides 1364-1369. The constant region is from nucleotides 1370-1618.

FIG. 3 shows the isolated and purified polynucleotide (top strand and bottom strands, SEQ ID NO:80 and SEQ ID NO:81, respectively) and amino acid sequence of the heavy chain of human antibody Ab198. The amino acid sequence comprises SEQ ID NOS:82 and SEQ ID NOS 72 through 74. The variable chain ends at nucleotide 1304. The variable/constant joining region (underlined) is at nucleotides 1305-1310. The constant region is from nucleotides 1311-2847.

FIG. 4 shows the isolated and purified polynucleotide (top strand and bottom strands, SEQ ID NO:83 and SEQ ID NO:84, respectively) and amino acid sequence of the light chain of human antibody Ab198. The amino acid sequence comprises SEQ ID NOS:78. The variable chain ends at nucleotide 1351. The variable/constant joining region (underlined) is at nucleotides 1352-1357. The constant region is from nucleotides 1358-1606.

FIG. 5 shows the competition of Ab12 with $^{125}$I-labeled EPO for binding to Chinese Hamster Ovary cells expressing recombinant EPO receptor.

FIG. 10 shows that Ab198 induces the formation of CFU-E colonies from cynomologous bone marrow-derived erythroid progenitor cells.

FIG. 18 is a series of representations of the heavy chain and light chain variable region nucleotide and amino acid sequences of the human anti-EPO-R antibody expressed by the cell line designated ABT2-SCX-003 of the invention, with FIG. 18A (SEQ ID NO:10) representing the nucleotide sequence encoding the variable region of the heavy chain, FIG. 18B (SEQ ID NO:11) representing the amino acid sequence encoded by the nucleotide sequence shown in FIG. 18A, FIG. 18C (SEQ ID NO:12) representing the nucleotide sequence encoding the variable region of the light chain, and FIG. 18D (SEQ ID NO:13) representing the amino acid sequence encoded by the nucleotide sequence shown in FIG. 18C.

FIG. 19 is a series of representations of the heavy chain and light chain variable region nucleotide and amino acid sequences of the human anti-EPO-R antibody expressed by the cell line designated ABT2-SCX-012 (also referred to herein as Ab12) of the invention, with FIG. 19A (SEQ ID NO:2) representing the nucleotide sequence encoding the variable region of the heavy chain, FIG. 19B (SEQ ID NO:3) representing the amino acid sequence encoded by the nucleotide sequence shown in FIG. 19A, FIG. 19C (SEQ ID NO:4) representing the nucleotide sequence encoding the variable region of the light chain, and FIG. 19D (SEQ ID NO:5) representing the amino acid sequence encoded by the nucleotide sequence shown in FIG. 19C.

FIG. 20 is a series of representations of the heavy chain and light chain variable region nucleotide and amino acid sequences of the human anti-EPO-R antibody expressed by the cell line designated ABT2-SCX-022 of the invention, with FIG. 20A (SEQ ID NO:14) representing the nucleotide sequence encoding the variable region of the heavy chain, FIG. 20B (SEQ ID NO:15) representing the amino acid sequence encoded by the nucleotide sequence shown in FIG. 20A, FIG. 20C (SEQ ID NO:16) representing the nucleotide sequence encoding the variable region of the light chain, and FIG. 20D (SEQ ID NO:17) representing the amino acid sequence encoded by the nucleotide sequence shown in FIG. 20C.

FIG. 21 is a series of representations of the heavy chain and light chain variable region nucleotide and amino acid sequences of the human anti-EPO-R antibody expressed by the cell line designated ABT2-SCX-054 of the invention, with FIG. 21A (SEQ ID NO:18) representing the nucleotide sequence encoding the variable region of the heavy chain, FIG. 21B (SEQ ID NO:19) representing the amino acid sequence encoded by the nucleotide sequence shown in FIG. 21A, FIG. 21C (SEQ ID NO:20) representing the nucleotide sequence encoding the variable region of the light chain, and FIG. 21D (SEQ ID NO:21) representing the amino acid sequence encoded by the nucleotide sequence shown in FIG. 21C.

FIG. 22 is a series of representations of the heavy chain and light chain variable region nucleotide and amino acid sequences of the human anti-EPO-R antibody expressed by the cell line designated ABT2-SCX-060 of the invention, with FIG. 22A (SEQ ID NO:10) representing the nucleotide sequence encoding the variable region of the heavy chain, FIG. 22B (SEQ ID NO:11) representing the amino acid sequence encoded by the nucleotide sequence shown in FIG. 22A, FIG. 22C (SEQ ID NO:22) representing the nucleotide sequence encoding the variable region of the light chain, and FIG. 22D (SEQ ID NO:23) representing the amino acid sequence encoded by the nucleotide sequence shown in FIG. 22C.

FIG. 23 is a series of representations of the heavy chain and light chain variable region nucleotide and amino acid sequences of the human anti-EPO-R antibody expressed by the cell line designated ABT2-SCX-102 of the invention, with FIG. 23A (SEQ ID NO:10) representing the nucleotide sequence encoding the variable region of the heavy chain, FIG. 23B (SEQ ID NO:11) representing the amino acid sequence encoded by the nucleotide sequence shown in FIG. 23A, FIG. 23C (SEQ ID NO:24) representing the nucleotide sequence encoding the variable region of the light chain, and FIG. 23D (SEQ ID NO:25) representing the amino acid sequence encoded by the nucleotide sequence shown in FIG. 23C.

FIG. 24 is a series of representations of the heavy chain and light chain variable region nucleotide and amino acid sequences of the human anti-EPO-R antibody expressed by the cell line designated ABT2-SCX-135 of the invention, with FIG. 24A (SEQ ID NO:10) representing the nucleotide sequence encoding the variable region of the heavy chain, FIG. 24B (SEQ ID NO:11) representing the amino acid sequence encoded by the nucleotide sequence shown in FIG. 24A, FIG. 24C (SEQ ID NO:26) representing the nucleotide sequence encoding the variable region of the light chain, and FIG. 24D (SEQ ID NO:27) representing the amino acid sequence encoded by the nucleotide sequence shown in FIG. 24C.

FIG. 25 is a series of representations of the heavy chain and light chain variable region nucleotide and amino acid sequences of the human anti-EPO-R antibody expressed by the cell line designated ABT2-SCX-145 of the invention, with FIG. 25A (SEQ ID NO:10) representing the nucleotide sequence encoding the variable region of the heavy chain, FIG. 25B (SEQ ID NO:11) representing the amino acid sequence encoded by the nucleotide sequence shown in FIG. 25A, FIG. 25C (SEQ ID NO:28) representing the nucleotide sequence encoding the variable region of the light chain, and FIG. 25D (SEQ ID NO:29) representing the amino acid sequence encoded by the nucleotide sequence shown in FIG. 25C.

FIG. 26 is a series of representations of the heavy chain and light chain variable region nucleotide and amino acid sequences of the human anti-EPO-R antibody expressed by the cell line designated ABT2-SCX-198 (also referred to herein as Ab198) of the invention, with FIG. 26A (SEQ ID NO:6) representing the nucleotide sequence encoding the variable region of the heavy chain, FIG. 26B (SEQ ID NO:7) representing the amino acid sequence encoded by the nucleotide sequence shown in FIG. 26A, FIG. 26C (SEQ ID NO:8) representing the nucleotide sequence encoding the variable region of the light chain, and FIG. 26D (SEQ ID NO:9) representing the amino acid sequence encoded by the nucleotide sequence shown in FIG. 26C.

FIG. 27 is a series of representations of the heavy chain and light chain variable region nucleotide and amino acid sequences of the human anti-EPO-R antibody expressed by the cell line designated ABT2-SCX-254 of the invention, with FIG. 27A (SEQ ID NO:30) representing the nucleotide sequence encoding the variable region of the heavy chain, FIG. 27B (SEQ ID NO:31) representing the amino acid sequence encoded by the nucleotide sequence shown in FIG. 27A, FIG. 27C (SEQ ID NO:32) representing the nucleotide sequence encoding the variable region of the light chain, and FIG. 27D (SEQ ID NO:33) representing the amino acid sequence encoded by the nucleotide sequence shown in FIG. 27C.

FIG. 28 is a series of representations of the heavy chain and light chain variable region nucleotide and amino acid sequences of the human anti-EPO-R antibody expressed by the cell line designated ABT2-SCX-267 of the invention, with FIG. 28A (SEQ ID NO:34) representing the nucleotide sequence encoding the variable region of the heavy chain, FIG. 28B (SEQ ID NO:35) representing the amino acid sequence encoded by the nucleotide sequence shown in FIG. 28A, FIG. 28C (SEQ ID NO:36) representing the nucleotide sequence encoding the variable region of the light chain, and FIG. 28D (SEQ ID NO:37) representing the amino acid sequence encoded by the nucleotide sequence shown in FIG. 28C.

FIG. 29 is a table showing amino acid sequence alignments of heavy chain variable regions of anti-EPOr mAbs generated according to the invention with their associated germline variable region sequences and identifying framework regions and complementarity determining regions.

FIG. 30 is a table showing amino acid sequence alignments of light chain variable regions of anti-EPOr mAbs generated according to the invention with their associated germline variable region sequences and identifying framework regions and complementarity determining regions.

FIG. 35 is a series of representations of the heavy chain and light chain variable region nucleotide and amino acid sequences of the human anti-EPO-R antibody expressed by the cell line designated ABT2-SCX-390 of the invention, with FIG. 35A (SEQ ID NO:38) representing the nucleotide sequence encoding the variable region of the heavy chain, FIG. 35B (SEQ ID NO:39) representing the amino acid sequence encoded by the nucleotide sequence shown in FIG. 35A, FIG. 35C (SEQ ID NO:40) representing the nucleotide sequence encoding the variable region of the light chain, and FIG. 35D (SEQ ID NO:41) representing the amino acid sequence encoded by the nucleotide sequence shown in FIG. 35C.

FIG. 36 is a series of representations of the heavy chain and light chain variable region nucleotide and amino acid sequences of the human anti-EPO-R antibody expressed by the cell line designated ABT2-SCX-412 of the invention, with FIG. 36A (SEQ ID NO:42) representing the nucleotide sequence encoding the variable region of the heavy chain, FIG. 36B (SEQ ID NO:43) representing the amino acid sequence encoded by the nucleotide sequence shown in FIG. 36A, FIG. 36C (SEQ ID NO:44) representing the nucleotide sequence encoding the variable region of the light chain, and FIG. 36D (SEQ ID NO:45) representing the amino acid sequence encoded by the nucleotide sequence shown in FIG. 36C.

FIG. 37 is a series of representations of the heavy chain and light chain variable region nucleotide and amino acid sequences of the human anti-EPO-R antibody expressed by the cell line designated ABT2-SCX430/432 of the invention, with FIG. 37A (SEQ ID NO:46) representing the nucleotide sequence encoding the variable region of the heavy chain, FIG. 37B (SEQ ID NO:47) representing the amino acid sequence encoded by the nucleotide sequence shown in FIG. 37A, FIG. 37C (SEQ ID NO:48) representing the nucleotide sequence encoding the variable region of the light chain, and FIG. 37D (SEQ ID NO:49) representing the amino acid sequence encoded by the nucleotide sequence shown in FIG. 37C.

FIG. 38 is a series of representations of the heavy chain and light chain variable region nucleotide and amino acid sequences of the human anti-EPO-R antibody expressed by the cell line designated ABT2-SCX467 of the invention, with FIG. 38A (SEQ ID NO:50) representing the nucleotide sequence encoding the variable region of the heavy chain, FIG. 38B (SEQ ID NO:51) representing the amino acid sequence encoded by the nucleotide sequence shown in FIG. 38A, FIG. 38C (SEQ ID NO:52) representing the nucleotide sequence encoding the variable region of the light chain, and FIG. 38D (SEQ ID NO:53) representing the amino acid sequence encoded by the nucleotide sequence shown in FIG. 38C.

FIG. 39 is a series of representations of the heavy chain and light chain variable region nucleotide and amino acid sequences of the human anti-EPO-R antibody expressed by the cell line designated ABT2-SCX484 of the invention, with FIG. 39A (SEQ ID NO:54) representing the nucleotide sequence encoding the variable region of the heavy chain, FIG. 39B (SEQ ID NO:55) representing the amino acid sequence encoded by the nucleotide sequence shown in FIG. 39A, FIG. 39C (SEQ ID NO:56) representing the nucleotide sequence encoding the variable region of the light chain, and FIG. 39D (SEQ ID NO:57) representing the amino acid sequence encoded by the nucleotide sequence shown in FIG. 39C.

FIG. 40 is a table showing amino acid sequence alignments of heavy chain variable regions of anti-EPOr mAbs generated according to the invention with their associated germline variable region sequences and identifying framework regions and complementarity determining regions.

Figure 41:
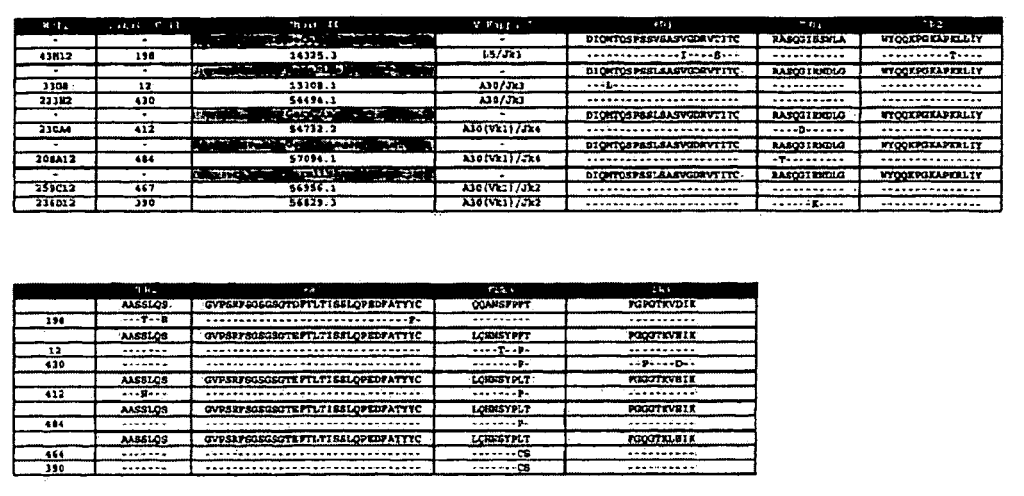

FIG. 41 is a table showing amino acid sequence alignments of light chain variable regions of anti-EPOr mAbs generated according to the invention with their associated germline variable region sequences and identifying framework regions and complementarity determining regions.

FIG. 42 shows the isolated and purified polynucleotide (top strand and bottom strands, SEQ ID NO:86 and SEQ ID NO:87, respectively) and amino acid sequence of the heavy chain of human antibody Ab390. The amino acid sequence comprises SEQ ID NOS:88 and SEQ ID NOS 72 through 74. The variable chain ends at nucleotide 463. The variable/constant joining region (underlined) is at nucleotides 464-469. The constant region is from nucleotides 470-2006.

FIG. 43 shows the isolated and purified polynucleotide (top strand and bottom strands, SEQ ID NO:89 and SEQ ID NO:90, respectively) and amino acid sequence of the light chain of human antibody Ab390. The amino acid sequence comprises SEQ ID NOS:91. The variable chain ends at nucleotide 463. The variable/constant joining region (underlined) is at nucleotides 464469. The constant region is from nucleotides 470-718.

FIG. 44 shows the isolated and purified polynucleotide (top strand and bottom strands, SEQ ID NO:92 and SEQ ID NO:93, respectively) and amino acid sequence of the heavy chain of human antibody Ab412. The amino acid sequence comprises SEQ ID NOS:94 and SEQ ID NOS 72 through 74. The variable chain ends at nucleotide 469. The variable/constant joining region (underlined) is at nucleotides 470-475. The constant region is from nucleotides 476-2012.

FIG. 45 shows the isolated and purified polynucleotide (top strand and bottom strands, SEQ ID NO:95 and SEQ ID NO:96, respectively) and amino acid sequence of the light chain of human antibody Ab412. The amino acid sequence comprises SEQ ID NOS:97. The variable chain ends at nucleotide 463. The variable/constant joining region (underlined) is at nucleotides 464-469. The constant region is from nucleotides 470-718.

FIG. 46 shows the isolated and purified polynucleotide (top strand and bottom strands, SEQ ID NO:98 and SEQ ID NO:99, respectively) and amino acid sequence of the heavy chain of human antibody Ab432. The amino acid sequence comprises SEQ ID NOS:100 and SEQ ID NOS 72 through 74. The variable chain ends at nucleotide 463. The variable/constant joining region (underlined) is at nucleotides 464-469. The constant region is from nucleotides 470-2006.

FIG. 47 shows the isolated and purified polynucleotide (top strand and bottom strands, SEQ ID NO:101 and SEQ ID NO:102, respectively) and amino acid sequence of the light chain of human antibody Ab430. The amino acid sequence comprises SEQ ID NOS:103. The variable chain ends at nucleotide 463. The variable/constant joining region (underlined) is at nucleotides 464-469. The constant region is from nucleotides 470-718.

FIG. 48 shows the isolated and purified polynucleotide (top strand and bottom strands, SEQ ID NO:104 and SEQ ID NO:105, respectively) and amino acid sequence of the heavy chain of human antibody Ab467. The amino acid sequence comprises SEQ ID NOS:106 and SEQ ID NOS 72 through 74. The variable chain ends at nucleotide 463. The variable/constant joining region (underlined) is at nucleotides 464-469. The constant region is from nucleotides 470-2006.

FIG. 49 shows the isolated and purified polynucleotide (top strand and bottom strands, SEQ ID NO:107 and SEQ ID NO:108, respectively) and amino acid sequence of the light chain of human antibody Ab467. The amino acid sequence comprises SEQ ID NOS:109. The variable chain ends at nucleotide 463. The variable/constant joining region (underlined) is at nucleotides 464-469. The constant region is from nucleotides 470-718.

FIG. 50 shows the isolated and purified polynucleotide (top strand and bottom strands, SEQ ID NO:110 and SEQ ID NO:111, respectively) and amino acid sequence of the heavy chain of human antibody Ab484. The amino acid sequence comprises SEQ ID NOS:112 and SEQ ID NOS 72 through 74. The variable chain ends at nucleotide 469. The variable/constant joining region (underlined) is at nucleotides 470-475. The constant region is from nucleotides 470-2012.

FIG. 51 shows the isolated and purified polynucleotide (top strand and bottom strands, SEQ ID NO:113 and SEQ ID NO:114, respectively) and amino acid sequence of the light chain of human antibody Ab484. The amino acid sequence comprises SEQ ID NOS:115. The variable chain ends at nucleotide 463. The variable/constant joining region (underlined) is at nucleotides 464469. The constant region is from nucleotides 470-718.

DETAILED DESCRIPTION OF THE INVENTION

Definitions

Figure 6:
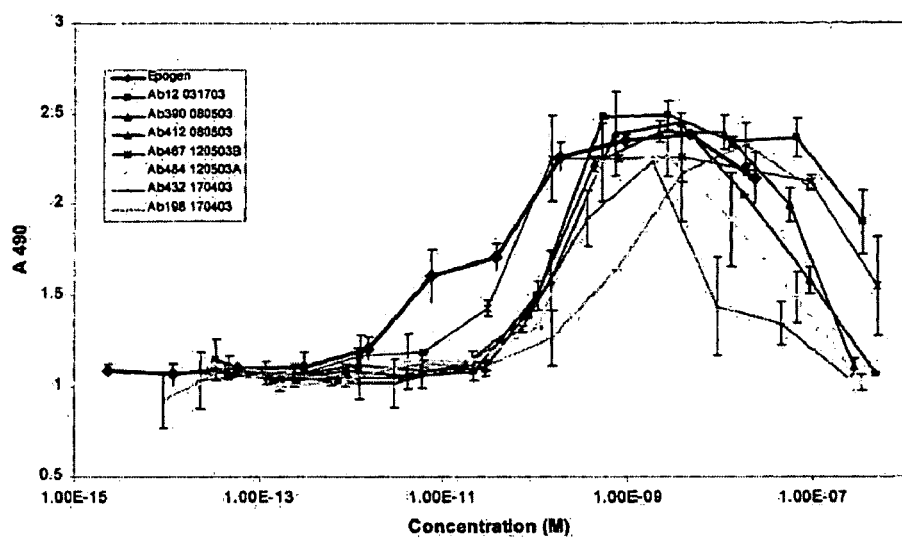
FIG. 6 shows the results of an EPO dependent human cell proliferation assay using Ab12 and Ab198.

As used herein, the term "antibody" or "immunoglobulin" refers to single chain, two-chain, and multi-chain proteins and glycoproteins that belong to the classes of polyclonal, monoclonal, chimeric and human or humanized. The term "antibody" also includes synthetic and genetically engineered variants thereof.

As used herein, the term "antibody fragment" refers to Fab, Fab', F(ab')$_2$ and Fv fragments, as well as any portion of an antibody having specificity toward at least one desired epitope.

As used herein, the term "gamma-2", "gamma-2 isotype" or "IgG2" refers to subclass 2 of immunoglobulin G (IgG), as well as any antibody fragment thereof. The four subclasses of IgG molecules are well characterized and well known to those of ordinary skill in the art. (See for example, Molecular Biology of the Cell, $2^{nd}$ Edition by Bruce Alberts et al., 1989) Panels of monoclonal antibodies are available that recognize all human isotypes (IgA, IgG, IgD IgE, and IgM) and subisotypes (IgA1, IgA2, IgG1, IgG2, IgG3, and IgG4) of human immunoglobulins.

As used herein, the term "humanized antibody" refers to an antibody that is derived from a non-human antibody (i.e murine) that retains or substantially retains the antigen-binding properties of the parent antibody but is less immunogenic in humans.

As used herein, the term "human antibody" refers to an antibody that possesses a sequence that is derived from a human germ-line immunoglobulin sequence, such as antibodies derived from transgenic mice having human immunoglobulin genes (e.g., XenoMouse® mice), human phage display libraries, or human B cells.

As used herein, the term "epitope" refers to any protein determinate capable of specifically binding to an antibody or T-cell receptors. Epitopic determinants usually consist of chemically active surface groupings of molecules such as amino acids or sugar side chains and usually have specific three dimensional structural characteristics, as well as specific charge characteristics.

As used herein, the term "endogenous" refers to a product or activity arising in the body or cell as opposed to a product or activity coming from outside.

As used herein the phrase, a polynucleotide "derived from" or "specific for a designated sequence refers to a polynucleotide sequence that comprises a contiguous sequence of approximately at least 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The sequence may be complementary or identical to a sequence that is unique to a particular polynucleotide sequence as determined by techniques known in the art. Regions from which sequences may be derived, include but are not limited to, regions encoding specific epitopes, as well as non-translated and/or non-transcribed regions.

The derived polynucleotide will not necessarily be derived physically from the nucleotide sequence of interest under study, but may be generated in any manner, including, but not limited to, chemical synthesis, replication, reverse transcription or transcription, that is based on the information provided by the sequence of bases in the region(s) from which the polynucleotide is derived. As such, it may represent either a sense or an antisense orientation of the original polynucleotide. In addition, combinations of regions corresponding to that of the designated sequence may be modified in ways known in the art to be consistent with the intended use.

As used herein, the phrase "encoded by" refers to a nucleic acid sequence that codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences that are immunologically identifiable with a polypeptide encoded by the sequence. Thus, a "polypeptide," "protein" or "amino acid" sequence has at least about 50%, 60%, 70%, 75%, 80%, 85%, 90%, 95% or more identity to the antibodies of the present invention. Further, the antibodies of the present invention may have at least about 60%, 70%, 75%, 80%, 85%, 90% or 95% similarity to a polypeptide or amino sequences of the antibodies of the present invention. The amino acid sequences of the antibodies of the present invention can be selected from the group consisting of SEQUENCE ID NOS: 3, 5, 7, 9, 11, 13, 15, 17, 19, 21, 23, 25, 27, 29, 31, 33, 35, 37, 39, 41, 43, 45, 47, 49, 51, 53, 55 and 57. Preferred amino acid sequences of the antibodies of the present invention are selected from the group consisting of SEQ ID NOS: 3, 5, 7, 9, 51 and 53.

As used herein, the phrase "recombinant polypeptide," "recombinant protein," or "a polypeptide produced by recombinant techniques", which terms may be used interchangeably herein, describes a polypeptide that by virtue of its origin or manipulation is not associated with all or a portion of the polypeptide with which it is associated in nature and/or is linked to a polypeptide other than that to which it is lined in nature. A recombinant or encoded polypeptide or protein is not necessarily translated from a designated nucleic acid sequence. It also may be generated in any manner, including chemical synthesis or expression of a recombinant expression system.

As used herein, the phrase "synthetic peptide" refers to a polymeric form of amino acids of any length, which may be chemically synthesized by methods well known in the art (See U.S. Pat. Nos. 4,816,513, 5,854,389, 5,891,993 and 6,184,344).

As used herein, the term "polynucleotide" refers to a polymeric form of nucleotides of any length, either ribonucleotides or deoxyribonucleotides. This term refers only to the primary structure of the molecule. Thus, the term includes double and single-stranded DNA as well as double- and single-stranded RNA. It also includes modifications, such as methylation or capping and unmodified forms of the polynucleotide. The terms "polynucleotide", "oligomer," "oligonucleotide," and "oligo," are used interchangeably herein.

As used herein the phrase "purified polynucleotide" refers to a polynucleotide of interest or fragment thereof that is essentially free, e.g. contains less than about 50%, 60%, 70%, 75%, 80%, 85%, 90%, 95% of the protein with which the polynucleotide is naturally associated. Techniques for purifying polynucleotides of interest are well known in the art and include, for example, disruption of the cell containing the polynucleotide with a chaotropic agent and separation of the polynucleotide(s) and proteins by ion-exchange chromatography, affinity chromatography and sedimentation according to density.

As used herein, the phrase "purified polypeptide" or "purified protein" means a polypeptide of interest or fragment thereof which is essentially free of, e.g., contains less than about 50%, 60%, 70%, 75%, 80%, 85%, 90%, 95%, cellular components with which the polypeptide of interest is naturally associated. Methods for purifying polypeptides of interest are known in the art.

As used herein, the term "isolated" refers to material that is removed from its original environment (e.g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

As used herein, the term "polypeptide" and "protein" are used interchangeably and refer to at least one molecular chain of amino acids linked through covalent and/or non-covalent bonds. The terms do not refer to a specific length of the product. Thus, peptides, oligopeptides and proteins are included within the definition of polypeptide. The terms include post-translational modifications of the polypeptide, including, but not limited to, glycosylations, acetylations, phosphorylations and the like. In addition, protein fragments, analogs, mutated or variant proteins, fusion proteins and the like are included within the meaning of polypeptide.

As used herein, the phrase "recombinant host cells," "host cells," "cells," "cell lines," "cell cultures," and other such terms denoting microorganisms or higher eukaryotic cell lines cultured as unicellular entities refer to cells that can be, or have been, used as recipients for recombinant vector or other transferred DNA, and include the original progeny of the original cell that has been transfected.

As used herein, the term "replicon" refers to any genetic element, such as a plasmid, a chromosome or a virus, that behaves as an autonomous unit of polynucleotide replication within a cell.

As used herein, the term "operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequence.

As used herein, the term "vector" refers to a replicon in which another polynucleotide segment is attached, such as to bring about the replication and/or expression of the attached segment.

As used herein, the term "control sequence" refers to a polynucleotide sequence that is necessary to effect the expression of a coding sequence to which it is ligated. The nature of such control sequences differs depending upon the host organism. In prokaryotes, such control sequences generally include a promoter, a ribosomal binding site and terminators and, in some instances, enhancers. The term "control sequence" thus is intended to include at a minimum all components whose presence is necessary for expression, and also may include additional components whose presence is advantageous, for example, leader sequences.

The term "transfection" refers to the introduction of an exogenous polynucleotide into a prokaryotic or eucaryotic host cell, irrespective of the method used for the introduction. The term "transfection" refers to both stable and transient introduction of the polynucleotide, and encompasses direct uptake of polynucleotides, transformation, transduction and f-mating. Once introduced into the host cell, the exogenous polynucleotide may be maintained as a non-integrated replicon, for example, a plasmid, or alternatively, may be integrated into the host genome.

As used herein, the term "treatment" refers to prophylaxis and/or therapy.

As used herein, the term "purified product" refers to a preparation of the product which has been isolated from the cellular constituents with which the product is normally associated and from other types of cells that may be present in the sample of interest.

As used herein, the phrase "activation of an erythropoietin (EPO) receptor" refers to one or more molecular processes which an EPO receptor undergoes that result in the transduction of a signal to the interior of a receptor-bearing cell. Ultimately, this signal brings about one or more changes in cellular physiology. Activation of the EPO receptor typically results in the proliferation or differentiation of EPO receptor-bearing cells, such as, but not limited to, erythroid progenitor cells. A number of events are involved in the activation of the EPO receptor, such as, but not limited to, the dimerization of the receptor.

The structural unit of an antibody is a tetramer. Each tetramer is composed of two identical pairs of polypeptide chains, each pair having one "light" (25 kDa) and one "heavy" chain (about 50-70 kDa). The amino-terminal portion of each chain includes a variable region that is primarily responsible for antigen recognition. The carboxy-terminal portion of the chain defines a constant region that is responsible for the effector function of the antibody. Human light chains are classified as kappa and lambda light chains. Heavy chains are classified as mu, delta, gamma, alpha, or epsilon and define the antibody's isotype as IgM, IgD, IgG, IgA, and IgE. IgG immunoglobulins are classified further into four subclasses (IgG1, IgG2, IgG3 and IgG4) having gamma-1, gamma-2, gamma-3 and gamma4 heavy chains, respectively. Most of the therapeutic human, chimeric or humanized antibodies available are of the IgG1 antibody type including Herceptin for breast cancer, Rituxan for Non-Hodgkins lymphoma and Humira and Remicade for rheumatoid arthritis (See Glennie, M. J. et al., *Drug Discovery Today*, 8:503 (2003).

Within the light and heavy chains, the variable and constant regions are joined by a "J" region with the heavy chain also include a "D" region. The variable regions of each light/heavy chain pair form the antigen binding site. Thereupon, an intact antibody has two binding sites, which, except in bifunctional or bispecific antibodies, are the same. Bifunctional or bispecific antibodies are artificial hybrid antibodies that have two different heavy/light chain pairs and two different binding sites. Bifunctional or bispecific antibodies can be produced using routine techniques known in the art.

The structure of the chains of an antibody exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both the light and heavy chains comprise the domains FR1, CDR1, FR2, CDR2, FR3, CDR3 and FR4.

U.S. Pat. No. 6,319,499 describes antibodies that bind to and activate an erythropoietin receptor (EPO-R). The antibodies specifically identified in this patent are Mabs 71 and 73. Mab 71 binds to a peptide designated "SE-3" having the amino acid sequence of PGNYSFSYQLEDEPWKLCRL-HQAPTARGAV (SEQ ID NO:1) (See Example 3). SE-3 is located on the human EPO-R between amino acid residues 49-78. According to U.S. Pat. No. 6,319,499, when this region of the EPO-R (i.e. amino acid residues 49-79) is bound with a cross linker such as Mab 71, this results in the activation of the EPO receptor. Example 6 in U.S. Pat. No. 6,319, 499 states that Mab 71 binds "significant amounts of peptide SE-3" compared to other peptides tested. This example further states that this "indicates that Mab 71 binds to a region of the human EPO-R containing or overlapping residues 49 to 78." Mabs 71 and 73 are murine antibodies. Although rodent and human antibodies may both provide precision for target specificity, human antibodies interact far more effectively with the natural defenses of the body and do not elicit anti-antibody responses to the same extent as rodent antibodies (Winter, G. and Milstein, C. *Nature* 349: 293 (1991). Additionally, the flexibility of human IgG subclasses differ (Roux, K. H. et al., *J. Immunol.* 159: 3372 (1997) and this difference also extends to rodent IgG isotypes since rodent IgG isotypes differ from their human counterparts. Since protein flexibility may affect antibody-antigen recognition (Jimenez, R., et al. Proc. Natl. Acad Sci. USA, 100: 92 (2003), human IgG2 isotypes may result in antigen recognition mechanisms distinct from those of murine antibodies. Murine IgG isotypes generally differ from those of humans.

In one embodiment, the present invention relates to an antibody or antibody fragment that binds to the erythropoietin receptor. The antibody or antibody fragment that binds to the erythropoietin receptor comprises at least one heavy chain having an amino acid sequence selected from the group consisting of: SEQ ID NOS: 3, 7, 11, 15, 19, 31, 35, 39, 43, 47, 51, 55 and fragments thereof. In a second embodiment, the antibody or antibody fragment that binds to the erythropoietin receptor comprises at least one light chain having an amino acid sequence selected from the group consisting of: SEQ ID NOS: 5, 9, 13, 17, 21, 23, 25, 27, 29, 33, 37, 41, 45, 49, 53, 57 and fragments thereof.

In a third embodiment, the present invention relates to an isolated antibody that is capable of binding a human erythropoietin receptor in a mammal. More specifically, the antibody comprises a heavy chain variable region or a light chain variable region which comprises a continuous sequence from CDR1 through CDR3. The amino acid sequence of the heavy chain variable region comprising the continuous sequence from CDR1 through CDR3 is selected from the group consisting of: SEQ ID NO:58, SEQ ID NO:59, SEQ ID NO:60 and SEQ ID NO:61, and fragments thereof. The amino acid sequence of the light chain variable region comprising the continuous sequence from CDR1 through CDR3 is selected from the group consisting of: SEQ ID NO:62, SEQ ID NO:63, SEQ ID NO:64, SEQ ID NO:65, SEQ ID NO:66, SEQ ID NO:67, and SEQ ID NO:68, and fragments thereof. In addition, the present invention relates to an isolated antibody which comprises a heavy chain variable region or a light chain variable region which comprises at least one CDR. More specifically, the antibody comprises a heavy chain variable region comprising at least one CDR selected from the group consisting of amino acid residues 99-112 of SEQ ID NO:11, 26-35 of SEQ ID NO:3, 50-65 of SEQ ID NO:3, 98-105 of SEQ ID NO:3, 26-35 of SEQ ID NO:19, 50-66 of SEQ ID NO:19, 99-105 of SEQ ID NO:19, 50-66 of SEQ ID NO:31, 99-105 of SEQ ID NO:31, 26-35 of SEQ ID NO:39, 50-65 of SEQ ID NO:39, 98-105 of SEQ ID NO:39, 26-37 of SEQ ID NO:43, 52-67 of SEQ ID NO:43, 100-107 of SEQ ID NO:43, 26-35 of SEQ ID NO:47, 50-65 of SEQ ID NO:47, 26-35 of SEQ ID NO:51, 50-65 of SEQ ID NO:51, 98-105 of SEQ ID NO:51, 26-37 of SEQ ID NO:55 and 52-67 of SEQ ID NO:55 or a light chain variable region comprising at least one CDR selected from the group consisting of amino acid residues 24-34 of SEQ ID NO:13, 50-56 of SEQ ID NO:13, 89-97 of SEQ ID NO:5, 24-34 of SEQ ID NO:27, 50-56 of SEQ ID NO:9, 24-39 of SEQ ID NO:33, 55-61 of SEQ ID NO:33, 24-34 of SEQ ID NO:41, 89-97 of SEQ ID NO:41, 24-34 of SEQ ID NO:45, 50-56 of SEQ ID NO:45, 89-97 of SEQ ID NO:45, 89-97 of SEQ ID NO:49 and 24-34 of SEQ ID NO:57.

In a fourth embodiment, the present invention relates to an antibody or antibody fragment that binds to and activates the erythropoietin receptor. The antibodies of the present invention bind to at least one epitope that is involved in activating the EPO receptor (Example 4). Unlike other antibodies or fragments known in the art that bind to and activate an erythropoietin receptor, such as the antibodies described in U.S. Pat. No. 6,319,499, the antibodies of the present invention do not interact with the peptide designated SE-3. Surprisingly, the antibodies of the present invention are erythropoietic even though the antibodies do not bind to the SE-3 peptide. Therefore, the human antibodies of the present invention interact with at least one different epitope on the human EPO receptor than the antibodies described in U.S. Pat. No. 6,319,499.

In a fifth embodiment, the present invention relates to an IgG2 antibody or antibody fragment that binds to and activates the erythropoietin receptor. The IgG2 antibodies or antibody fragments of this embodiment bind to and interact with any epitope that is involved in activating the EPO receptor.

"Additionally, as demonstrated by the BIAcore results shown in Example 3, the antibodies of the present invention exhibit a binding affinity to the erythropoietin receptor within one hundred fold of the binding affinity of endogenous human erythropoietin to the erythropoietin receptor. A high (~1 nM) and low (~1 μM) affinity of the EPO receptor for EPO has been reported resulting from two nonequivalent receptor binding sites on EPO (See Phio, J. S. et al., *Biochemistry*, 35:1681 (1996))."

The antibodies of the present invention can be polyclonal antibodies, monoclonal antibodies, chimeric antibodies (See U.S. Pat. No. 6,020,153) or human or humanized antibodies or antibody fragments thereof. Synthetic and genetically engineered variants (See U.S. Pat. No. 6,331,415) of any of the foregoing are also contemplated by the present invention. Preferably, however, the antibodies of the present invention are human or humanized antibodies. The advantage of human or humanized antibodies is that they potentially decrease or eliminate the immunogenicity of the antibody in a host recipient, thereby permitting an increase in the bioavailability and a reduction in the possibility of adverse immune reaction, thus potentially enabling multiple antibody administrations.

Humanized antibodies include chimeric or CDR-grafted antibodies. Also, human antibodies can be produced using genetically engineered strains of animals in which the antibody gene expression of the animal is suppressed and functionally replaced with human antibody gene expression.

Methods for making humanized and human antibodies are known in the art. One method for making human antibodies employs the use of transgenic animals, such as a transgenic mouse. These transgenic animals contain a substantial portion of the human antibody producing genome inserted into their own genome and the animal's own endogenous antibody production is rendered deficient in the production of antibodies. Methods for making such transgenic animals are known in the art. Such transgenic animals can be made using XenoMouse® technology or by using a "minilocus" approach. Methods for making Xenomice™ are described in U.S. Pat. Nos. 6,162,963, 6,150,584, 6,114,598 and 6,075,181. Methods for making transgenic animals using the "minilocus"

approach are described in U.S. Pat. Nos. 5,545,807, 5,545,806 and 5,625,825. Also see International Publication No. WO93/12227.

Using the XenoMouse® technology, human antibodies can be obtained by immunizing a XenoMouse® mouse (Abgenix, Fremont, Calif.) with an antigen of interest. The lymphatic cells (such as B-cells) are recovered from the mice that express antibodies. These recovered cells can be fused with myeloid-type cell line to prepare immortal hybridoma cell lines. These hybridoma cell lines can be screened and selected to identify hybridoma cell lines that produce antibodies specific to the antigen of interest. Alternatively, the antibodies can be expressed in cell lines other than hybridoma cell lines. More specifically, sequences encoding particular antibodies can be cloned from cells producing the antibodies and used for transformation of a suitable mammalian host cell.

Transformation can be by any known method for introducing polynucleotides into a host cell, including, for example, packaging the polynucleotide in a virus or into a viral vector and transducing a host cell with a virus or vector or by transfection procedures known in the art such as those described in U.S. Pat. Nos. 4,399,216, 4,912,040, 4,740,461 and 4,959,455. For example, one or more genes encoding the heavy chain can be expressed in a cell and one or more genes encoding the light chain can be expressed in a second cell. The resulting heavy and light chains can then be fused together to form the antibodies of the present invention using techniques known in the art. Alternatively, genes encoding for parts of the heavy and light chains can be ligated using restriction endonucleases to reconstruct the gene coding for each chain. Such a gene can then be expressed in a cell to produce the antibodies of the present invention.

The transformation procedure used will depend upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) into liposomes and direct microinjection of the DNA molecule.

Mammalian cell lines that can be used as hosts for expression are well known in the art and include, but are not limited to, Chinese hamster ovary (CHO) cells, HeLa cells, baby hamster kidney (BHK) cells, monkey kidney cells (COS), human hepatocellular carcinoma cells bacterial cells, such as *E. coli*, yeast cells, such as *Saccharomyces cerevisiae*, etc.

Humanized antibodies can also be made using a CDR-grafted approach. Such humanized antibodies are well known in the art. Generally, humanized antibodies are produced by obtaining nucleic acid sequences that encode the variable heavy and variable light sequences of an antibody that binds to the EPO receptor, identifying the complementary determining region or "CDR" in the variable heavy and variable light sequences and grafting the CDR nucleic acid sequences on to human framework nucleic acid sequences. (See, for example, U.S. Pat. Nos. 4,816,567 and 5,225,539).

The human framework that is selected is one that is suitable for in vivo administration, meaning that it does not exhibit immunogenicity. For example, such a determination can be made by prior experience with in vivo usage of such antibodies and studies of amino acid similarities.

Methods for cloning nucleic acids are known in the art. These methods involve amplification of the antibody sequences to be cloned using appropriate primers by polymerase chain reaction (PCR). Primers that are suitable for amplifying antibody nucleic acid sequences and specifically murine variable heavy and variable light sequences are known in the art.

Once the CDRs and FRs of the cloned antibody sequences that are to be humanized are identified, the amino acid sequences encoding the CDRs are identified and the corresponding nucleic acid sequences grafted on to selected human FRs. This can be done using known primers and linkers, the selection of which are known in the art.

After the CDRs are grafted onto selected human FRs, the resulting "humanized" variable heavy and variable light sequences are expressed to produce a humanized Fv or humanized antibody that binds to the EPO receptor. Typically, the humanized variable heavy and light sequences are expressed as a fusion protein with human constant domain sequences so an intact antibody that binds to the EPO receptor is obtained. However, a humanized Fv antibody can be produced that does not contain the constant sequences. Fusion of the human constant sequence to the humanized variable region is preferred.

The EPO receptor that is bound by and preferably activated using the antibodies of the present invention is preferably a mammalian EPO receptor, most preferably a human EPO receptor. The present invention also contemplates the use of analogs of the EPO receptor, such as those described in U.S. Pat. No. 5,292,654. Human EPO receptor can be purchased from R & D Systems (Minneapolis, Minn.).

An example of two (2) antibodies that (1) bind to and activate the EPO receptor; (2) do not interact with a peptide having an amino acid sequence of PGNYSFSYQLEDEPWKLCRLHQAPTARGAV (SEQ ID NO: 1); and (3) exhibit a binding affinity within one hundred fold of the binding affinity of endogeous human EPO to the EPO receptor, are the human antibodies designated Ab12 and Ab198. Ab12 and Ab198 are human antibodies that were developed using the XenoMouse® XenoMax technology described herein (See Example 1).

In another embodiment, the present invention relates to polynucleotide and polypeptide sequences that encode for the antibodies described herein. Preferably, such polynucleotides encode for both the variable and constant regions of each of the heavy and light chains, although other combinations are also contemplated by the present invention.

The present invention also contemplates oligonucleotide fragments derived from the disclosed polynucleotides and nucleic acid sequences complementary to these polynucleotides. The polynucleotides can be in the form of RNA or DNA. Polynucleotides in the form of DNA, cDNA, genomic DNA, nucleic acid analogs and synthetic DNA are within the scope of the present invention. The DNA may be double-stranded or single-stranded, and if single stranded, may be the coding (sense) strand or non-coding (anti-sense) strand. The coding sequence that encodes the polypeptide may be identical to the coding sequence provided herein or may be a different coding sequence which coding sequence, as a result of the redundancy or degeneracy of the genetic code, encodes the same polypeptide as the DNA provided herein.

Preferably, the polynucleotides encode at least one heavy chain variable region and at least one light chain variable region of the present invention. Examples of such polynucleotides are shown in SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54 and 56 as well as fragments, complements and degenerate codon equivalents thereof. For example, SEQ ID NO: 2 encodes for the heavy chain of Ab12 (variable region) and SEQ ID NO:4 encodes for the light chain of Ab12 (variable region). SEQ ID NO:6 encodes for the heavy chain of Ab 198

(variable region) and SEQ ID NO: 8 encodes for the light chain of Ab198 (variable region).

The present invention also includes variant polynucleotides containing modifications such as polynucleotide deletions, substitutions or additions, and any polypeptide modification resulting from the variant polynucleotide sequence. A polynucleotide of the present invention may also have a coding sequence that is a naturally occurring variant of the coding sequence provided herein.

It is contemplated that polynucleotides will be considered to hybridize to the sequences provided herein if there is at least 50%, 60%, 70%, 75%, 80%, 85%, 90%, 95% identity between the polynucleotide and the sequence.

The present invention further relates to polypeptides that encode for the antibodies of the present invention as well as fragments, analogs and derivatives of such polypeptides. The polypeptides of the present invention may be recombinant polypeptides, naturally purified polypeptides or synthetic polypeptides. The fragment, derivative or analogs of the polypeptides of the present invention may be one in which one or more of the amino acid residues is substituted with a conserved or non-conserved amino acid residue (preferably a conserved amino acid residue) and such substituted amino acid residue may or may not be one encoded by the genetic code; or it may be one in which one or more of the amino acid residues includes a substituent group; or it may be on in which the polypeptide is fused with another compound, such as a compound to increase the half-life of the polypeptide (for example, polyethylene glycol); or it may be one in which the additional amino acids are fused to the polypeptide, such as a leader or secretory sequence or a sequence that is employed for purification of the polypeptide or a proprotein sequence. Such fragments, derivatives and analogs are within the scope of the present invention.

A polypeptide of the present invention may have an amino acid sequence that is identical to that of the antibodies described herein or that is different by minor variations due to one or more amino acid substitutions. The variation may be a "conservative change" typically in the range of about 1 to 5 amino acids, wherein the substituted amino acid has similar structural or chemical properties, e.g., replacement of leucine with isoleucine or threonine with serine. In contrast, variations may include nonconservative changes, e.g., replacement of a glycine with a tryptophan. Similar minor variations may also include amino acid deletions or insertions or both. Guidance in determining which and how many amino acid residues may be substituted, inserted, or deleted without changing biological or immunological activity may be found using computer programs well known in the art, for example DNASTAR software (DNASTAR, Inc., Madison, Wis.).

Preferably, the polypeptides encode at least one heavy chain variable region or at least one light chain variable region of the antibodies of the present invention. More preferably, the polypeptides encode at least one heavy chain variable region and one light chain variable region of the antibodies of the present invention. Examples of such polypeptides are those having the amino acid sequences shown in SEQ ID NOS: 3, 5, 7, 9, 11, 13, 15, 17, 19, 21, 23, 25, 27, 29, 31, 33, 35, 37, 39, 41, 43, 45, 46, 47, 49, 51, 53, 55, 57, 58, 59, 60, 61, 62, 63, 64, 65, 66, 67, 68, and fragments thereof. Specifically, the heavy chain of Ab 12 has the amino acid sequence shown in SEQ ID NO: 3 and the light chain has the amino acid sequence shown in SEQ ID NO:5. The amino acid sequence of the heavy chain of Ab198 is shown in SEQ ID NO:7 and the light chain has the amino acid sequence shown in SEQ ID NO:9.

The present invention also provides vectors that include the polynucleotides of the present invention, host cells which are genetically engineered with vectors of the present invention and the production of the antibodies of the present invention by recombinant techniques.

Host cells are genetically engineered (transfected, transduced or transformed) with vectors, such as, cloning vectors or expression vectors. The vector may be in the form of a plasmid, a viral particle, a phage, etc. The engineered host cells can be cultured in conventional nutrient media modified as appropriate for activating promoters, selecting transfected cells, etc. The culture conditions, such as temperature, pH and the like, are those previously used with the host cell selected for expression, and will be apparent to those of skilled in the art.

The polynucleotides of the present invention can be employed to produce the polypeptides and hence the antibodies of the present invention. The polynucleotide sequences of the present invention can be included in any one of a variety of expression vehicles, in particular, vectors or plasmids for expressing a polypeptide. Such vectors include chromosomal, nonchromosomal and synthetic DNA sequences, derivatives of SV40, bacterial plasmids, phage DNA, yeast plasmids, vectors derived from combinations of plasmids and phage DNA, viral DNA such as vaccinia, adenovirus, fowl pox virus and pseudorabies. However, any other plasmid or vector may be used so long as it is replicable and viable in the host.

The appropriate DNA sequence may be inserted into the vector by a variety of procedures. In general, the DNA sequence is inserted into appropriate restriction endonuclease sites by procedures known in the art. The polynucleotide sequence in the expression vector is operatively linked to an appropriate expression control sequence (i.e. promoter) to direct mRNA synthesis. Examples of such promoters include, but are not limited to, the LTR or the SV40 promoter, the *E. coli* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression. For example, the vector can contain enhancers, which are transcription-stimulating DNA sequences of viral origin, such as those derived form simian virus such as SV40, polyoma virus, bovine papilloma virus or Moloney sarcoma virus, or genomic, origin. The vector preferably also contains an origin of replication. The vector can be constructed to contain an exogenous origin of replication or, such an origin of replication can be derived from SV40 or another viral source, or by the host cell chromosomal replication mechanism.

In addition, the vectors preferably contain a marker gene for selection of transfected host cells such as dihydrofolate reductase or antibiotics, such as GA418 (geneticin, a neomycin-derivative) or hygromycin, or genes which complement a genetic lesion of the host cells such as the absence of thymidine kinase, hypoxanthine phosphoribosyl transferase, dihydrofolate reductase, etc.

Suitable vectors for use in the present invention are known in the art. Any plasmid or vector can be used in the present invention as long as it is replicable and is viable in the host. Examples of vectors that can be used include those that are suitable for mammalian hosts and based on viral replication systems, such as simian virus 40 (SV40), Rous sarcoma virus (RSV), adenovirus 2, bovine papilloma virus (BPV), papovavirus BK mutant (BKV), or mouse and human cytomegalovirus (CVM).

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Preferably, the host cells provide a suitable environment for the production of active antibodies, since the biosynthesis of functional tetrameric antibody molecules requires correct nascent polypeptide chain folding, glycosylation, and assembly. Example of suitable host cells, include mammalian cells, such as COS-7 cells, Bowes melanoma cells, Chinese hamster ovary (CHO) cells, embryonic lung cells L-132, and mammalian cells of lymphoid origin, such as myeloma or lymphoma cells. The host cells can be transfected with a vector containing a polynucleotide sequence encoding the H-chain alone, with a second vector encoding the light chain alone (such as by using two different vectors as discussed previously). Preferably, the host cells are transfected with two different vectors.

Introduction of the vectors into the host cell can be effected by calcium phosphate transfection, DEAE-Dextran mediated transfection or electroporation (L. David et al., *Basic Methods in Molecular Biology* $2^{nd}$ Edition, Appleton and Lang, Paramount Publishing, East Norwalk, Conn. (1994)).

In order to obtain the antibodies of the present invention, one or more polynucleotide sequences that encode for the light and heavy chain variable regions and light and heavy chain constant regions of the antibodies of the present invention should be incorporated into a vector. Polynucleotide sequences encoding the light and heavy chains of the antibodies of the present invention can be incorporated into one or multiple vectors and then incorporated into the host cells.

Cell lines expressing Ab12 and Ab467 antibodies were deposited with the American Type Culture Collection (ATCC), 10801 University Boulevard, Manassas, Va. 20110, under the terms of the Budapest Treaty, on Sep. 30, 2003 and were accorded accession numbers PTA-5554 and PTA-5555. These deposits are provided for the convenience of those skilled in the art and are neither an admission that such deposits are required to practice the invention nor that equivalent embodiments are not within the skill of the art in view of the present disclosure. The public availability of these deposits is not a grant of a license to make, use or sell the deposited materials under this or any other patents. The nucleic acid sequences of the deposited materials are incorporated in the present disclosure by reference and are controlling if in conflict with any sequence described herein.

The antibodies of the present invention have a number of uses. In general, the antibodies may be used to treat any condition treatable by erythropoietin or a biologically active variant or analog thereof. For example, antibodies of the invention are useful for treating disorders characterized by low red blood cell levels and/or decreased hemoglobin levels (e.g. anemia). In addition, the antibodies of the invention may be used for treating disorders characterized by decreased or subnormal levels of oxygen in the blood or tissue, such as, for example, hypoxemia or chronic tissue hypoxia and/or diseases characterized by inadequate blood circulation or reduced blood flow. Antibodies of the invention also may be useful in promoting wound healing or for protecting against neural cell and/or tissue damage, resulting from brain/spinal cord injury, stroke and the like. Non-limiting examples of conditions that may be treatable by the antibodies of the invention include anemia, such as chemotherapy-induced anemia, cancer associated anemia, anemia of chronic disease, HIV-associated anemia, bone marrow transplant-associated anemia and the like, heart failure, ischemic heart disease and renal failure. As such, the invention includes methods of treating any of the aforementioned diseases or conditions comprising the step of administering to a mammal a therapeutically effective amount of said antibody. Preferably, the mammal is a human.

The antibodies of the present invention also can be used to identify and diagnose mammals that have a dysfunctional EPO receptor. Mammals that have a dysfunctional EPO receptor are characterized by disorders such as anemia. Preferably, the mammal being identified and diagnosed is a human. Additionally, the antibodies of the present invention can be used in the treatment of anemia in mammals suffering from red blood cell aplasia. Red blood cell aplasia may result from the formation of neutralizing anti-erythropoietin antibodies in patients during treatment with recombinant erythropoietin (Casadevall, N. et al., n. Eng. J. Med. 346: 469 (2002)). The method involves the step of administering to a mammal suffering from said aplasia and in need of treatment a therapeutically effective amount of the antibodies of the present invention.

In another embodiment of the invention, the EPO receptor antibodies and antibody fragments of the invention also can be used to detect EPO receptor (e.g., in a biological sample, such as tissue specimens, intact cells, or extracts thereof), using a conventional immunoassay, such as an enzyme linked immunosorbent assay (ELISA), a radioimmunoassay (RIA) or tissue immunohistochemistry. The invention provides a method for detecting EPO receptor in a biological sample comprising contacting a biological sample with an antibody or antibody fragment of the invention and detecting either the antibody (or antibody portion), to thereby detect EPO receptor in the biological sample. The antibody or antibody fragment is directly or indirectly labeled with a detectable substance to facilitate detection of the bound or unbound antibody or antibody fragment. A variety of immunoassay formats may be practiced (such as competitive assays, direct or indirect sandwich immunoassays and the like) and are well known to those of ordinary skill in the art.

Suitable detectable substances include various enzymes, prosthetic groups, fluorescent materials, luminescent materials and radioactive materials. Examples of suitable enzymes include horseradish peroxidase, alkaline phosphatase, B-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine, dansyl chloride or phycoerythrin; and an example of a luminescent material includes luminol; and examples of suitable radioactive material include $^{125}$I, $^{131}$I, $^{35}$S. or $^3$H.

In yet another embodiment, the present invention relates to a pharmaceutical composition containing a therapeutically effective amount of the antibody of the present invention along with a pharmaceutically acceptable carrier or excipient. As used herein, "pharmaceutically acceptable carrier" or "pharmaceutically acceptable excipient" includes any and all solvents, dispersion media, coating, antibacterial and antifungal agents, isotonic and absorption delaying agents, and the like that are physiologically compatible. Examples of pharmaceutically acceptable carriers or excipients include one or more of water, saline, phosphate buffered saline, dextrose, glycerol, ethanol and the like as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the of the antibody or antibody portion also may be included. Optionally, disintegrating agents can be included, such as cross-linked polyvinyl pyrrolidone, agar, alginic acid or a salt thereof, such as sodium alginate and the like. In addition to the excipients, the pharmaceutical composition can include one or more of the following, carrier proteins such as serum albumin, buffers, binding agents, sweeteners and other flavoring agents; coloring agents and polyethylene glycol.

The compositions of this invention may be in a variety of forms. They include, for example, liquid, semi-solid and solid dosage forms, such as liquid solutions (e.g. injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody or antibody fragment is administered by intramuscular or subcutaneous injection.

Other suitable routes of administration for the pharmaceutical composition include, but are not limited to, rectal, transdermal, vaginal, transmucosal or intestinal administration.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e. antibody or antibody fragment) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antibody fragments of the invention can be administered by a variety of methods known in the art, although for many therapeutic applications, the preferred route/mode of administration is intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g. *Sustained and Controlled Release Drug Delivery Systems*, J. R. Robinson, ed., Marcel Dekker, Inc., New York, 1978).

In certain embodiments, an antibody or antibody portion of the invention may be orally administered, for example, with an inert diluent or an assimilable edible carrier. The compound (and other ingredients if desired) may also be enclosed in a hard or soft shell gelatin capsule, compressed into tablets, buccal tablets, troches, capsules, elixiers, suspensions, syrups, wafers, and the like. To administer an antibody or antibody fragment of the invention by other than parenteral administration, it may be necessary to coat the compound with, or co-administer the compound with, a material to prevent its inactivation.

Supplementary active compounds also can be incorporated into the compositions. In certain embodiments, an antibody or antibody fragment of the invention is coformulated with and/or coadministered with one or more additional therapeutic agents. For example, an EPO receptor antibody or antibody fragment of the invention may be coformulated and/or coadministerd with one or more additional antibodies that bind other targets (e.g., antibodies that bind other cytokines or that bind cell surface molecules) or one or more cytokines. Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

As used herein, the term "therapeutically effective amount" means an amount of antibody or antibody fragment that produces the effects for which it is administered. The exact dose will be ascertainable by one skilled in the art. As known in the art, adjustments based on age, body weight, sex, diet, time of administration, drug interaction and severity of condition may be necessary and will be ascertainable with routine experimentation by those skilled in the art. A therapeutically effective amount is also one in which the therapeutically beneficial effects outweigh any toxic or detrimental effects of the antibody or antibody fragment. A "prophylactically effective amount" refers to an amount effective, at dosages and for periods of time necessary to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be tested; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

By way of example, and not of limitation, examples of the present invention shall now be given.

EXAMPLE 1

Generation of Human Erythropoietin Receptor Antibodies

Antigen Preparation. The antigen used for immunization of XenoMouse® animals was coupled to a universal T-cell epitope (TCE) (*J.Immunol.*, 148(5):1499 (1992)) using two different methods. A mixture containing an equal amount of each was used as the immunogen.

1) 2.3 mg of Dithiothreitol (DTT), and 200 mcg of cysteine coupled TCE (*J.Immunol.*, 148(5):1499 (1992)) are mixed at room temperature for 30 minutes. DTT is removed by centrifugation through a Sephadex G10 (Pharmacia, Upsala, Sweden) chromatography column. The reduced cysteine coupled TCE is added to 200 mcg soluble extracellular domain of human EpoR (R&D Systems, Minneapolis, Minn.) re-suspended in Phosphate Buffered Saline (PBS) (8.1 mM $Na_2HPO_4$, 1.6 mM $NaH_2PO_4$, 136 mM NaCl, 2.6 mM KCl, pH 7.4) and 33 mcg of Sulfosuccinimidyl 4-(N-maleimidomethyl)-cyclohexane-1-carboxylate (sulfo SMCC), and mixed 4° C. over night. Un-reacted EpoR was removed by centrifugation through a 10 KDa cut off Centricon column (Millipore, Bedford, Mass.).

2) The soluble extracellular domain (200 mcg) of human EpoR (R&D Systems, Minneapolis, Minn.) was re-suspended in PBS and mixed with 4 mcg of TCE-BPA (p-Benzoyl Phenylalanine) and incubated under UV light (362 nM) at room temperature for 45 minutes. The un-reacted EpoR was removed by centrifugation through a 10 KDa cut off Centricon column (Millipore, Bedford, Mass.).

Immunization of animals. Monoclonal antibodies of the invention, including Ab12 and Ab198 (also referred to herein as AB-ABT2-XG2-012 and AB-ABT2-XG2-198, respectively) were developed by immunizing XenoMouse® mice (XenoMouse® XG2, Abgenix, Inc., Fremont, Calif. and Vancouver, BC) with soluble EpoR coupled to a TCE as described above. The initial immunization was with 20 mcg of antigen and mixed 1:1 v/v with Complete Freund's Adjuvant (CFA) (Sigma, St Louis, Mo.) per mouse. The subsequent immunizations were with 20 mcg of antigen mixed 1:1 v/v with incomplete Freund's (IFA). In particular, each animal was immunized at the base of tail and by intraperitoneal injection on days 0, 14, 28 and 42.

Biotinylation of EpoR. 300 mcg of EpoR (Abbott CHO cell derived ref.#RB69084:4) was re-suspended in 990 mcL of PBS pH 8.6 and added to 100 mcg of biotin-NHS (Pierce, Rockford, Ill.) dissolved in DMSO (Dimethyl Sulfoxide) incubated for forty minutes at room temperature (RT). Free biotin and buffer was removed by centrifugation through a 5 kDa Centricon column with several washes with PBS pH 7.4 and re-suspended in an appropriate volume to a final concentration was 600 mcg/mL.

Selection of animals for harvest. Anti-EpoR antibody titers were determined by ELISA. 0.7 mcg/ml biotin EpoR (described above) was coated onto streptavadin plates (Sigma, St Louis, Mo.) at room teperature for 1 hour. The solution containing unbound biotin EpoR was removed and all plates were washed five times with $dH_2O$. XenoMouse® sera from the EpoR immunized animals, or naïve XenMouse® animals, were titrated in 2% milk/PBS at a 1:2 dilution in duplicate from a 1:100 initial dilution. The last well was left blank, and plates were washed five times with $dH_2O$. A goat anti-human IgG Fc-specific horseradish peroxidase (HRP)(Pierce, Rockford, Ill.) conjugated antibody was added at a final concentration of 1 mcg/mL for 1 hour at room temperature. The plates were washed five times with $dH_2O$. The plates were developed with the addition of TMB chromogenic substrate (KPL, Gaithersburg, Md.) for 30 minutes and the ELISA was stopped by the addition of 1 M phosphoric acid. The specific titers obtained from XenoMouse® animals were determined from the optical density at 450 nm and are shown in Table 1. The titer represents the reciprocal dilution of the serum and therefore the higher the number the greater the humoral immune response to EpoR.

TABLE 1

| Mouse I.D. | Titer |
|---|---|
| 11 | 1600 |
| 12 | 12800 |
| 13 | 51200 |
| 14 | 102400 |
| 15 | 102400 |
| 16 | 0 |
| 17 | 102400 |
| 18 | 3200 |
| 19 | 102400 |
| 20 | 2560 |

XenoMouse® animal 14 was selected for harvest based on the serology data in Table 1.

Culture and selection of B cells. B cells from the harvested animals were cultured and those secreting EpoR-specific antibodies were isolated essentially as described in Babcook et al., *Proc. Natl. Acad. Sci. USA*, 93:7843-7848 (1996). ELISA, performed as described above for sera titers, was used to identify EpoR-specific wells. Fifty plates cultured at 500 cells/well were screened on biotin EpoR to identify the antigen-specific wells. The data as shown in Table 2 demonstrated the presence of 701 wells with ODs significantly over background (0.05).

TABLE 2

| Optical Density | Number of Positives |
|---|---|
| 0.1 | 701 |
| 0.2 | 273 |
| 0.3 | 163 |
| 0.4 | 130 |
| 0.5 | 102 |
| 0.6 | 91 |
| 0.7 | 76 |
| 0.8 | 70 |
| 0.9 | 67 |
| 1.0 | 65 |

TABLE 2-continued

| Optical Density | Number of Positives |
|---|---|
| 2.0 | 25 |
| 3.0 | 7 |

These data indicated a very low frequency of hits and indicated that the wells were monoclonal for antigen-specificity. These 701 positive wells were re-screened on biotin EpoR and 137 wells (shown in bold in Table 3 below) were found to repeat as real antigen-specific wells with ODs significantly over background (0.05).

TABLE 3

| Optical Density | Number of Positives |
|---|---|
| 0.1 | 207 |
| 0.15 | 137 |
| 0.2 | 110 |
| 0.3 | 94 |
| 0.4 | 85 |
| 0.5 | 79 |
| 0.6 | 71 |
| 0.7 | 63 |
| 0.8 | 57 |
| 0.9 | 53 |
| 1.0 | 50 |
| 2.0 | 32 |
| 3.0 | 13 |

Agonist activity assay. Proliferation of an Epo responsive cell line was used as the basis for the agonist screen. These 137 wells were then screened for agonist activity using the human erythroleukemia cell line UT-7/Epo (Abbott ref#.RB29454-174). 12.5 mcL of supernatant were added to 1×105 cells per well in RPMI 1640 (10% FCS) to a final volume of 50 mcL in a half-area 96 well plate. The well size is half the area of a typical 96 well plate. Proliferation was identified visually and compared to cells in media containing a titration of human Epo or no Epo as a base line control. Eleven wells with proliferation activity were identified.

EpoR-specific Hemolytic Plaque Assay. A number of specialized reagents are needed to conduct the assay. These reagents were prepared as follows.

Biotinylation of Sheep red blood cells (SRBC): SRBC are stored in RPMI media as a 25% stock. A 250 ul SRBC packed-cell pellet was obtained by aliquoting 1.0 ml of the stock into a 15-ml falcon tube, spinning down the cells and removing the supernatant. The cell pellet was then re-suspended in 4.75 ml PBS at pH 8.6 in a 50 ml tube. In a separate 50 ml tube, 2.5 mg of Sulfo-NHS biotin was added to 45 ml of PBS at pH 8.6. Once the biotin had completely dissolved, 5 ml of SRBCs were added and the tube rotated at RT for 1 hour. The SRBCs were centrifuged at 3000 g for 5 min, the supernatant drawn off and 25 mls PBS at pH 7.4 as a wash. The wash cycle was repeated 3 times, then 4.75 ml immune cell media (RPMI 1640 with 10% FCS) was added to the 250 ul biotinylated-SRBC (B-SRBC) pellet to gently re-suspend the B-SRBC (5% B-SRBC stock). Stock was stored at 4° C. until needed.

Streptavidin (SA) coating of B-SRBC: One ml of the 5% B-SRBC stock was transferred into to a fresh eppendorf tube. The B-SRBC cells were pelleted with a pulse spin at 8000 rpm (6800 rcf) in a microfuge, the supernatant drawn off, the pellet re-suspended in 1.0 ml PBS at pH 7.4, and the centrifugation repeated. The wash cycle was repeated 2 times, then the B-SRBC pellet was resuspended in 1.0 ml of PBS at pH 7.4 to give a final concentration of 5% (v/v). 10 ul of a 10 mg/ml streptavidin (CalBiochem, San Diego, Calif.) stock solution was added and the tube mixed and rotated at RT for 20 min. The washing steps were repeated and the SA-SRBC were re-suspended in 1 ml PBS pH 7.4 (5% (v/v)).

EpoR coating of SA-SRBC: The SA-SRBC were coated with biotinylated EpoR at 10 ug/ml, the mixed and rotated at RT for 20 min. The SRBC were washed twice with 1.0 ml of PBS at pH 7.4 as above. The EpoR-coated SRBC were re-suspended in RPMI (+10% FCS) to a final concentration of 5% (v/v).

Determination of the quality of EpoR-SRBC by immunofluorescence (IF): 10 ul of 5% SA-SRBC and 10 ul of 5% PTH-coated SRBC were each added to separate fresh 1.5 ml eppendorf tube containing 40 ul of PBS. The murine anti-EpoR antibody (R&D Systems Cat. #MAB307) was added to each sample of SRBCs at 20 ug/ml. The tubes were rotated at RT for 25 min, and the cells were then washed three times with 100 ul of PBS. The cells were re-suspended in 50 ul of PBS and incubated with 40 mcg/mL Gt-anti mouse IgG Fc antibody conjugated to Alexa488 (Molecular Probes, Eugene, Oreg.). The tubes were rotated at RT for 25 min, and then washed with 100 ul PBS and the cells re-suspended in 10 ul PBS. 10 ul of the stained cells were spotted onto a clean glass microscope slide, covered with a glass coverslip, observed under fluorescent light, and scored on an arbitrary scale of 0-4.

Preparation of plasma cells: The contents of a single microculture well identified by the previous assays as containing a B cell clone secreting the immunoglobulin of interest were harvested. Using a 100-1000 ul pipettman, the contents of the well were recovered by adding 37C RPMI (+10% FCS). The cells were re-suspended by pipetting and then transferred to a fresh 1.5 ml eppendorf tube (final vol. approx 500-700 ul). The cells were centrifuged in a microfuge at 1500 rpm (240 rcf) for 2 minutes at room temperature, then the tube rotated 180 degrees and spun again for 2 minutes at 1500 rpm. The freeze media was drawn off and the immune cells resuspended in 100 ul RPMI (10% FCS), then centrifuged. This washing with RPMI (10% FCS) was repeated and the cells re-suspended in 60 ul RPMI (FCS) and stored on ice until ready to use.

Plague assay: Glass slides (2×3 inch) were prepared in advance with silicone edges and allowed to cure overnight at RT. Before use the slides were treated with approx. 5 ul of SigmaCoat (Sigma, Oakville, ON) wiped evenly over glass surface, allowed to dry and then wiped vigorously. To a 60 ul sample of cells was added 60 ul each of EpoR-coated SRBC (5% v/v stock), 4× guina pig complement (Sigma, Oakville, ON) stock prepared in RPMI with 10% FCS, and 4× enhancing sera stock (1:900 in RPMI with 10% FCS). The mixture (3-5 ul) was spotted onto the prepared slides and the spots covered with undiluted paraffin oil. The slides were incubated at 37° C. for a minimum of 45 minutes.

Plague assay results: The coating was determined qualitatively by immunofluorescent microscopy to be very high (4/4) using MAB307 to detect coating compared to a secondary detection reagent alone (0/4). There was no signal detected using the MAB307 antibody on red blood cells that were only coated with streptavidin (0/4). These red blood cells were then used to identify antigen-specific plasma cells from the fourteen wells identified in Table 4. After micromanipulation to rescue the antigen-specific plasma cells, the genes encoding the variable region genes were rescued by RT-PCR on a single plasma cell.

TABLE 4

| Plate ID | Single Cell numbers |
| --- | --- |
| 11G10 | ABT2-SCX-251-260 |
| 21D1 | ABT2-SCX-54 |
| 25C3 | ABT2-SCX-134-144 |
| 29G8 | ABT2-SCX-1-11 |
| 33G8 | ABT2-SCX-12-18 |
| 37A11 | ABT2-SCX-19-44 |
| 43H12 | ABT2-SCX-185-201, 233-239 |
| 16F7 | ABT2-SCX-267-278 |
| 24C3 | ABT2-SCX-55-77 |
| 24F8 | ABT2-SCX-82-102 |
| 34D4 | ABT2-SCX-145-168 |

Expression. After isolation of the single plasma cells, mRNA was extracted and reverse transcriptase PCR was conducted to generate cDNA. The cDNA encoding the variable heavy and light chains was specifically amplified using polymerase chain reaction. The variable heavy chain region was cloned into an IgG2 expression vector. This vector was generated by cloning the constant domain of human IgG2 into the multiple cloning site of pcDNA3.1+/Hygro (Invitrogen, Burlington, ON). The variable light chain region was cloned into an IgK expression vector. This vector was generated by cloning the constant domain of human IgK into the multiple cloning site of pcDNA3.1+/Neo (Invitrogen, Burlington, ON). The appropriate pairs of heavy chain and the light chain expression vectors were then co-lipofected into a 60 mm dish of 70% confluent human embryonal kidney 293 cells and the transfected cells were left to secrete a recombinant antibody for 24 hours. The supernatant (3 mL) was harvested from the HEK 293 cells and the secretion of an intact antibody (AB-ABT2-XG2-012 and AB-ABT2-XG2-198) was demonstrated with a sandwich ELISA to specifically detect human IgG (Table 5, fourth column). The specificity of AB-ABT2-XG2-012 and AB-ABT2-XG2-198 was assessed through binding of the recombinant antibody to biotinylated EpoR using ELISA (Table 5, fifth column).

TABLE 5

| Well ID | Single cell number | Secretion | Binding |
| --- | --- | --- | --- |
| 11G10 | ABT2-SCX-254 | 1:4 | 1:8 |
| 21D1 | ABT2-SCX-054 | >1:64 | >1:64 |
| 25C3 | ABT2-SCX-135 | 1:4 | 1:4 |
| 29G8 | ABT2-SCX-003 | >1:64 | >1:64 |
| 33G8 | ABT2-SCX-012 | >1:64 | >1:64 |
| 37A11 | ABT2-SCX-022 | >1:64 | >1:64 |
| 43H12 | ABT2-SCX-198 | >1:64 | >1:64 |
| 16F7 | ABT2-SCX-267 | >1:64 | >1:64 |
| 24C3 | ABT2-SCX-060 | >1:64 | >1:64 |
| 24F8 | ABT2-SCX-102 | >1:64 | >1:64 |
| 34D4 | ABT2-SCX-145 | >1:64 | >1:64 |

The ELISA for antigen specific antibody secretion was performed as follows. Control plates were coated with 2mg/mL Goat anti-human IgG H+L O/N. For the binding plates, biotin-EpoR (0.7 mcg/mL) was coated onto streptavadin 96 well plates (Sigma, St Louis, Mo.) for one hour at room temperature. The plates were washed five times with $dH_2O$. Recombinant antibodies were titrated 1:2 for 7 wells from the undiluted minilipofection supernatant. The plates were washed five times with $dH_2O$. A goat anti-human IgG Fc-specific HRP-conjugated antibody was added at a final concentration of 1 ug/mL for 1 hour at RT for the secretion and the binding ELISA. The plates were washed five times with $dH_2O$. The plates were developed with the addition of TMB chromogenic substrate (KPL, Gaithersburg, Md.) for 30 minutes and the ELISA was stopped by the addition of 1 M phosphoric acid. Each ELISA plate was analyzed to determine the optical density of each well at 450 nm.

Purification of AB-ABT2-XG2-012 and AB-ABT2-XG2-198. For larger scale production, the heavy and light chain expression vectors (2.5 ug of each chain/dish) were lipofected into ten 100 mm dishes that were 70% confluent with HEK 293 cells. The transfected cells were incubated at 37° C. for 4 days, the supernatant (6 mL) was harvested and replaced with 6 mL of fresh media. At day 7, the supernatant was removed and pooled with the initial harvest (120 mL total from 10 plates). The ABT2-XG2-012 and ABT2-XG2-198 antibody were purified from the supernatant using a Protein-A Sepharose (Amersham Biosciences, Piscataway, N.J.) affinity chromatography (1 mL). The antibody was eluted from the Protein-A column with 500 mcL of 0.1 M Glycine pH 2.5. The eluate was dialysed in PBS pH 7.4 and filter sterilized. The antibody was analyzed by non-reducing SDS-PAGE to assess purity and yield.

Figure 14:
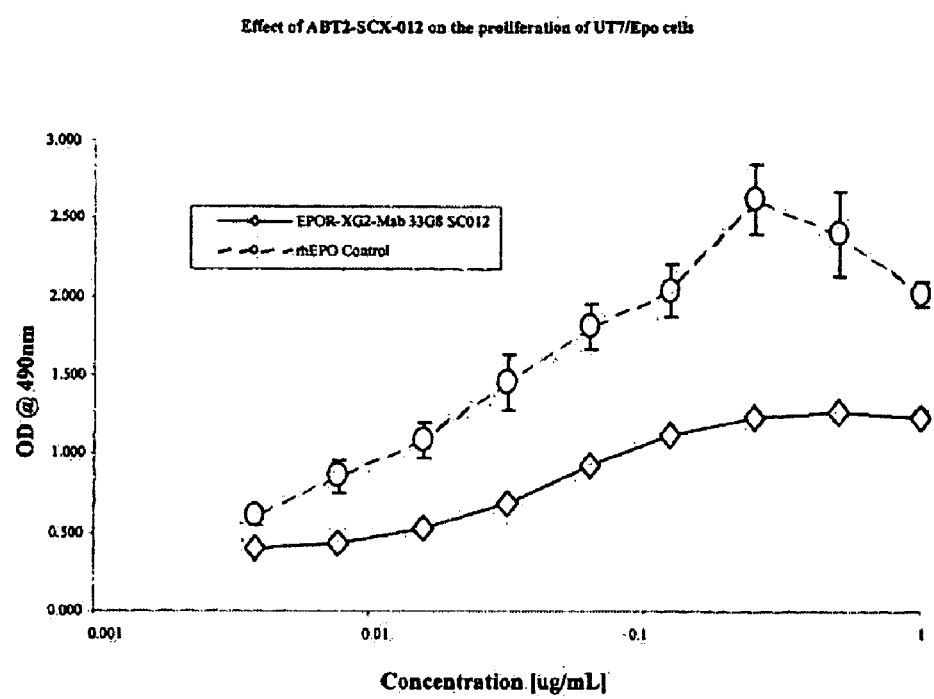
FIG. 14 shows the activity of various concentrations of Ab12 on the proliferation of UT7/EPO cells.
Figure 15:
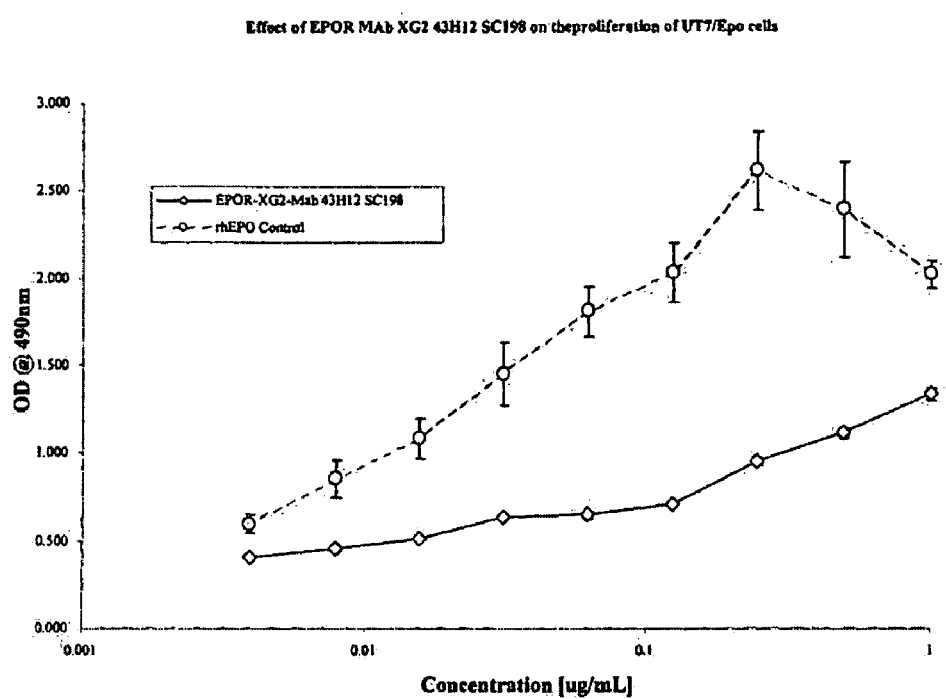
FIG. 15 shows the activity of various concentrations of Ab198 on the proliferation of UT7/EPO cells.

Agonist activity of recombinant antibodies. The ability of these recombinant antibodies to stimulate the proliferation of Epo responsive cells was examined using the UT-7/Epo cells with proliferation quantitated by MTS reagent (Promega, Madison, Wis.) measured at 490 nm as described in the Agonist Activity Assay above. ABT2-SCX-012 and ABT2-SCX-198 induced proliferation in comparison to cells in media without antibody and are shown below (FIGS. 14 and 15 respectively).

Figure 16:
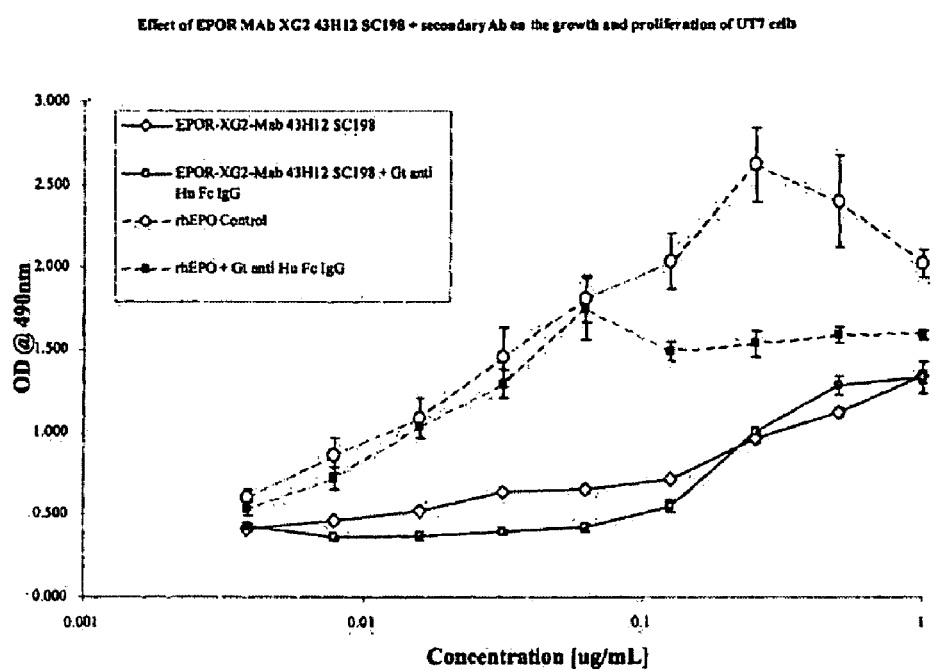
FIG. 16 shows the activity of various concentrations of Ab198 (with or without the addition of a secondary goat anti-human FC antibody) on the growth and proliferation of UT7/EPO cells.
Figure 17:
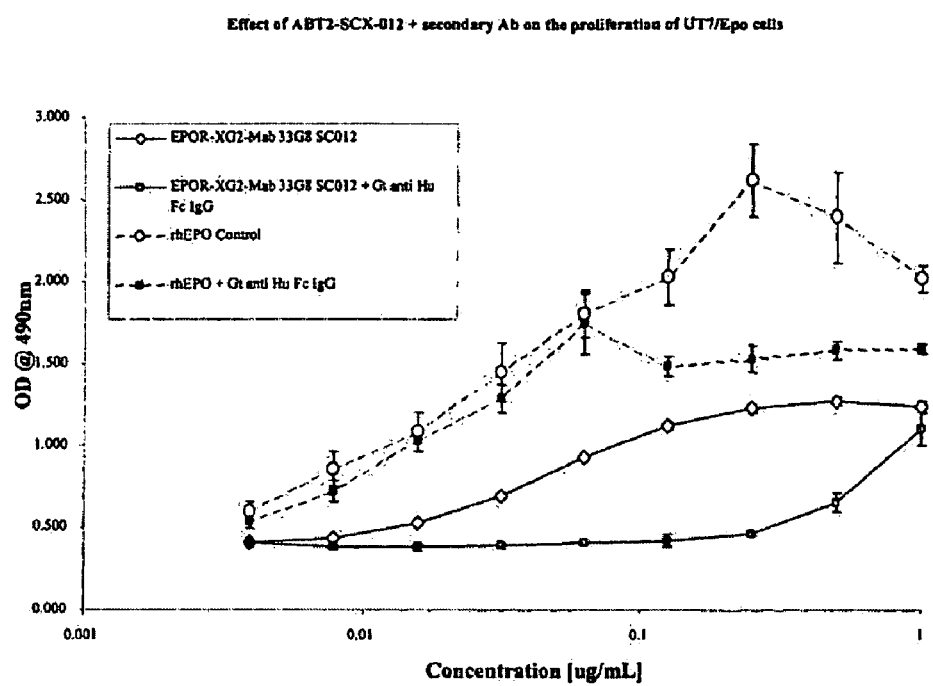
FIG. 17 shows the activity of various concentrations of Ab12 (with or without the addition of a secondary goat anti-human FC antibody) on the growth and proliferation of UT7/EPO cells.

Effect of anti-Human Fc. It is possible that the agonist activity of ABT2-SCX-012 and ABT2-SCX-198 are due to self-aggregation. In order to address this issue we induced aggregation by the addition of an anti-human Fc secondary antibody and the effect on the agonist activity of ABT2-SCX-012 and ABT2-SCX-198 was determined using the UT-7/Epo cells. As shown below the addition of a secondary antibody had no effect on the activity of ABT2-SCX-198 (FIG. 16) and inhibited the activity of ABT2-SCX-012 (FIG. 4 17).

Since the addition of secondary Ab inhibited the activity of ABT2-SCX-012 we concluded that aggregation of this antibody interferes with it's activity and thus it is unlikely that ABT2-SCX-012 has agonist activity due to aggregation. However, the results of ABT2-SCX-198 are more difficult to interpret. The lack of an effect could suggest that ABT2-SCX-198 is fully aggregated and thus the addition of secondary Ab has no further effects on its activity. Alternatively, the lack of effect suggests the activity of ABT2-SCX-198 is not perturbed by the conformational restrictions applied by a secondary antibody.

Sequence analysis of ABT2-SCX-012 and ABT2-SCX-198 The variable heavy chains and the variable light chains for antibodies ABT2-SCX-012 and ABT2-SCX-198 were sequenced to determine their DNA sequences. The complete sequence information for the anti-EpoR antibodies shown in FIGS. 1, 2, and 18-30 with nucleotide and amino acid sequences for each variable region of the heavy chain gamma and kappa light chains. FIGS. 1 and 2 provide full-length sequences, including the constant regions.

Figure 30:
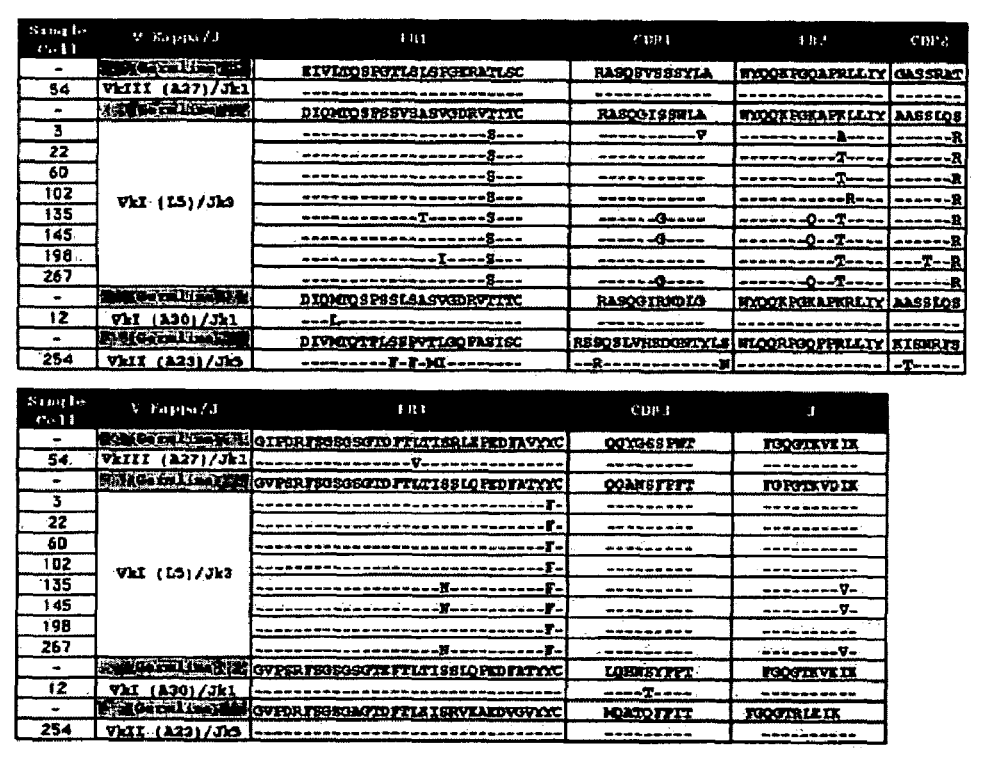

The variable heavy sequences were analyzed to determine the VH family, the D-region sequence and the J-region sequence. The sequences were then translated to determine the primary amino acid sequence (FIG. 29) and compared to the germline VH, D and J-region sequences to assess somatic hypermutations. The primary amino acid sequences of all the anti-EpoR antibody gamma chains are shown in FIG. 16. The germline sequences are shown above and the mutations are indicated with the new amino acid sequence. Unaltered amino acids are indicated with a dash (-). The light chain was analyzed similarly to determine the V and the J-regions and to identify any somatic mutations from germline kappa sequences (FIG. 30). The heavy chain of ABT2-SCX-012 was shown to utilize the VH 4-59 (DP-71), DIR4rc and the JH4a gene segments, while the light chain was shown to use the VkI (A30) and the Jk1 gene segments. The heavy chain of ABT2-SCX-198 was shown to utilize the VH 3-30 (V3-30), D4-23 and the JH6b gene segments, while the light chain was shown to use the VkI (L5) and the Jk3 gene segments.

EXAMPLE 2

Competition of Ab12 with $^{125}$I-Labeled EPO for Binding CHO Cells Expressing Recombinant EPO Receptor CHO cells expressing the full length recombinant human EPO receptor were plated at $5\times10^5$ cells/well in 24 well plates 72 hours prior to the assay. On the day of the assay, 95 ul of Ab12, Ab198, or EPO at indicated concentrations (shown in FIG. 5) diluted in RPMI 1640, 0.5% BSA, 1 mM Na $N_3$ and 5 ul (6 ng) of $^{125}$I-EPO (Amersham Cat. #IM178, Arlington Heights, Ill. 486 ci/mM) were added to the wells. After incubating at 37° C. for 1.5 hours, the wells were washed three times with cold HBSS and harvested using 0.5 ml 0.1N NaOH. Samples were counted in a Micromedic ME Plus gamma counter. The results are shown in FIG. 5. Specifically, the results show that Abs 12 and 198 competed with EPO for binding to the erythropoietin receptor.

EXAMPLE 3

Biacore Studies

The studies described below were performed on a Biacore 2000 utilizing the Biacontrol software version 3.1. (Biacore, Uppsala, Sweden). Binding analyses were performed with antibody immobilized directly to the chip surface and followed by injection of varying receptor concentrations.

Immobilization of Antibody

Immobilizations of antibody were performed using the default immobilization program in the Biacore software package. Antibodies were diluted to 10 ug/mL in the supplied acetate buffers to prescreen for the appropriate pH at which to conduct the immobilizations. For immobilizations, antibodies were diluted into the appropriate acetate buffer (10 mM acetate pH 4.0) and coupled directly to the chip surface using standard EDC chemistry at three different protein levels (500, 1000, and 1500 RU). The fourth flow cell was mock coupled with EDC to cap the carboxyl groups and provide a background surface as a negative control.

Binding Studies

Binding studies were performed by successive injections of varying concentrations of soluble human EPO receptor over the chip surface (500 RU immobilized protein). Binding analyses were performed in the supplied HBS-EP buffer [HBS buffer–10 mM HEPES pH=7.4, 150 mM NaCl, 3 mM EDTA, 0.005% Polysorbate 20 (v/v), Biacore] using receptor diluted to the desired concentrations (10-200 nM) using the running buffer (HBS-EP). Experiments were performed at a flow rate of 30 uL/min. The receptor was injected over a period of 3 minutes followed by a 15 minute dissociation period. Simultaneous injections over the flow cell created as a negative control were also performed. All injections were performed in triplicate.

Model Fitting

Data were fit to the models available in the BiaEvaluation 3.0.2 software package (Biacore). The data points from the experimental injections were corrected by subtraction of data points from simultaneous over the negative control surface. The corrected data were used to fit to the 1:1 (Langmuir) binding model as well as the bivalent analyte model available in the BiaEvaluation software package. Dissociation constants were calculated directly from fitting to the Langmuir binding model. For the bivalent analyte model, the dissociation constants were calculated indirectly using the calculated values for the kinetic dissociation and kinetic association constants, $k_d$ and $k_a$.

TABLE 6

| Antibody | kD |
|---|---|
| Ab 12 | 17.5 nM |
| Ab 198 | 13.9 nM |

EXAMPLE 4

EPO Dependent Human Cell Proliferation Assay

Figure 7:
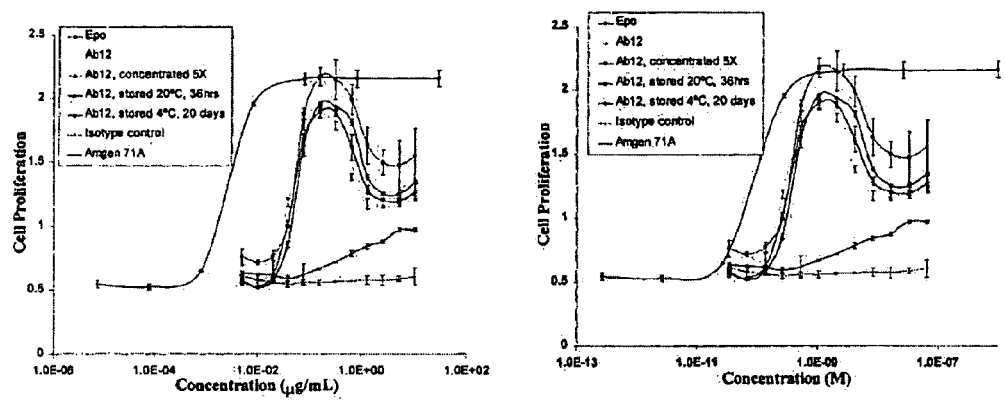
FIG. 7 shows that Ab12 remains active in inducing the proliferation of F36E cells after storage at 4° C. for up to 20 days.

Stock cultures of the human erythroleukemic cell line, F36E cells were maintained in RPMI 1640 media with 10% fetal bovine serum and 1 unit per mL of recombinant human erythropoietin. Prior to assays, cells were cultured overnight at a density of 4.0 to $5.0\times10^5$ cells per mL in growth medium without EPO. Cells were recovered, washed and resuspended at a density of $1.0\times10^6$ cells per mL in assay medium (RPMI 1640+10% FBS) and 50 uL of cells added to wells of a 96 well microtiter plate. 50 uL of each of Ab12, Ab 390, Ab 412, Ab 467, Ab 484, Ab 430/432 and Ab198 or EPO standards (recombinant human EPO (rHuEPO)) in assay medium were added to wells and the plates were incubated in a humidified incubator at 37° C. with a 5% $CO_2$ atmosphere. After 72 hours, 20 plL of Promega Cell Titer 96 Aqueous® reagent (as prepared per manufacturer's instructions, Madison, Wis.) was added to all wells. Plates were incubated at 37° C. with a 5% $CO_2$ atmosphere for 4 hours and the optical density at 490 nm was determined using a microplate reader (Wallac Victor 1420 Multilabel Counter, Wallac Company, Boston, Mass.). The results are shown in FIG. 6. All Abs stimulated proliferation of the F36E cell line. Maximal proliferative activity was similar to that observed with the EPO control and shown by a bell shaped curve as concentration increased. The results in FIG. 7 demonstrate that Ab12, after storage at 4° C. for up to 20 days, is active in inducing the proliferation of F36E cells. Proliferative activity was similar to that observed with the EPO control with the maximal response differing about tenfold on a molar equivalent basis

EXAMPLE 5

Human CD36+ CFUe Assay

Figure 8:
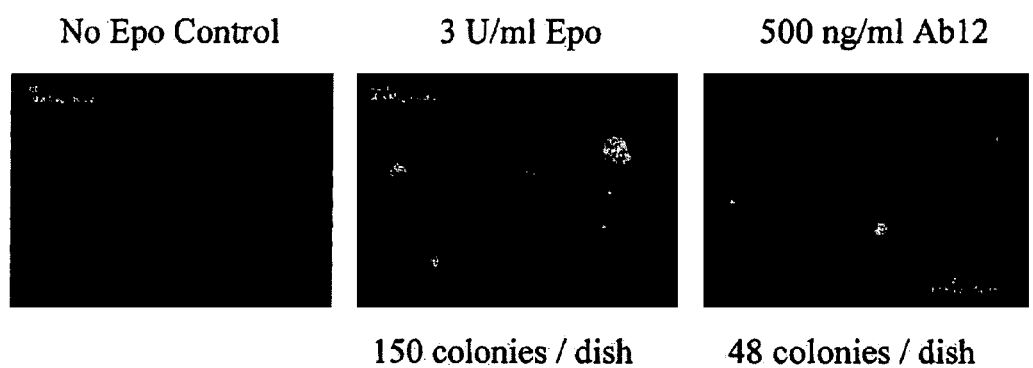
FIG. 8 shows that Ab12 induces the formation of CFU-E (colony forming unit-erythroid) from human 36$^+$ progenitor cells.

Frozen human CD36+ erythroid progenitor cells obtained from Poietics (Biowhittaker (Walkersville, Md.)) were thawed and $10^4$ cells/ml in IMDM-2% FBS. Cells (0.3 ml) were added to 0.3 ml tubes containing 2.4 ml Methoctilt (StemCell Technologies, Vancouver, Canada) Cat. #04230), 0.3 ml stem cell growth factor (Sigma, St. Louis, Mo. Cat. #S7901, 100 ug/ml), and 0.3 ml EPO (R&D Systems), Ab 12, or IMDM-2% FBS. After mixing, 1.1 ml of the Methocult suspension was added to a 35 mm non tissue culture treated sterile petri dish and incubated at 37° C., 5% $CO_2$ for 2 weeks. Colonies were identified microscopically. The results are shown in FIG. 8. Specifically, Ab 12 induced the formation of CFU-E colonies from human CD 36+ progenitor cells. The colonies, identified microscopically, were red in color. The size and number of the colonies is reduced compared to those observed with the EPO control probably due to a reduced proliferative signal.

EXAMPLE 6

Demonstration of Erythopoietic Activity in Liquid Cultures

CD34+ cells were enriched from human peripheral blood using a Direct CD34+ Progenitor Cell Isolation Kit (Miltenyi, Auburn, Calif.). Recovered cells were washed twice with alpha-medium and re-suspended in suspension culture media (alpha-media supplemented with 30% FCS, 1% deionized BSA, $10^{-5}$M β-mercaptoethanol, 10-6 M dexamethasone, 0.3 mg/mL human hollo-transferrin and 10 ng/mL human recombinant stem cell factor). Cells were plated out at a density of $1 \times 10^4$ cells/mL in duplicates in 6-well microplates with test antibody at concentrations ranging from 0.1-100 ng/mL. Plates were incubated at 37° C. and 5% $CO_2$ for two weeks. Duplicate samples from each well were recovered for cell counts and staining with benzidine (Reference Fibach, E., 1998 *Hemoglobin*, 22:5-6, 445-458).

Figure 9:
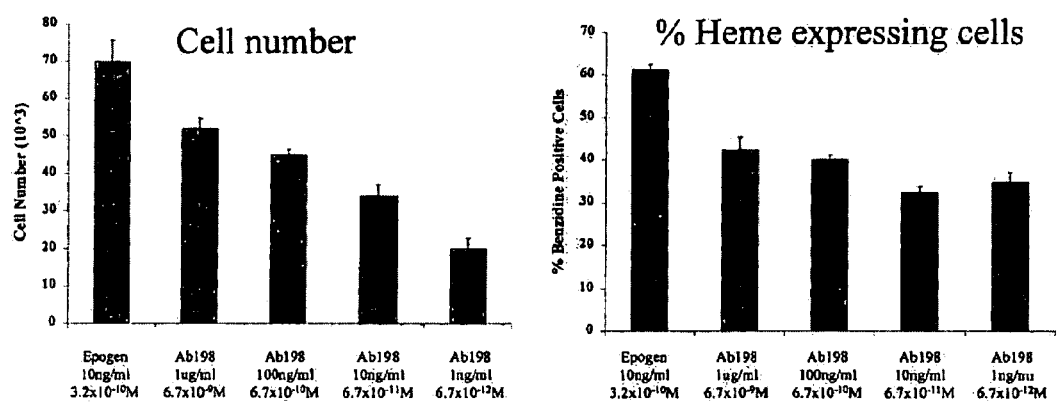
FIG. 9 shows the induction of proliferation of human erythroid producing cells with Ab198.

The results are shown in FIG. 9. Specifically, Ab198 induced the proliferation of human erythroid producing cells derived from progenitor cells in a dose dependent manner. The number of proliferating cells and the percentage expressing hemoglobin, as indicated by staining with benzidine, was reduced compared to the EPO treated controls again probably due to a reduced proliferative signal.

EXAMPLE 7

Cynomolgus Bone Marrow CFUe Assay

Bone marrow was harvested from cynomolgus monkeys and diluted 1:2 with PBS. Three ml of the diluted bone marrow was layered over six ml of Lymphoprep (Gibco (Invitrogen), Carlsbad, Calif. Cat. #1001967), centrifuged at 2700 rpm for 20 minutes and the buffy coat recovered and diluted in 10 ml IMDM-2% FBS. Cells were centrifuged and resuspended at $10^6$ cells/ml in IMDM-2% FBS. Cells (0.3 ml) were added to tubes containing 2.4 ml Methocult (StemCell Technologies, Vancouver, Canada) Cat. #04230), 0.3 ml stem cell growth factor (Sigma, Cat. #S7901, 100 ug/ml), 0.3 ml EPO (R&D Systems, Minneapolis, Minn.), test antibody (Ab198), or IMDM-2% FBS. After mixing, 1.1 ml of the Methocult suspension was added to a 35 mm non tissue culture treated sterile petri dish and incubated at 37° C., 5% $CO_2$ for 2 weeks. Colonies were identified microscopically. The results of this assay are shown in FIG. 10 demonstrate that Ab198 induced the formation of CFU-E colonies (although the number of colonies was reduced compared to that observed with the EPO control).

EXAMPLE 8

ELISA to Measure Binding of SE-3 Peptide 96 well polystyrene plates (Dynatec (Elk Grove Village, Ill.) Immunolon 4) were coated with 80 ul of 5 ug/ml soluble EPO receptor (sEPOR) (R&D Systems (Minneapolis, Minn.) Cat. #307-ER/LF), or peptide SE-3 (PGNYSFSYQLEDEP-WKLCRLHWAPTARGAV) (described in U.S. Pat. No. 6,319,499) diluted in 0.015M $Na_2CO_3$, 0.035M $NaHCO_3$, pH 9.4 for 2 hours at room temperature and overnight at 4° C. Plates were blocked for 30 minutes at room temperature with 100 ul of 5% BSA in PBS (Gibco (Invitrogen (Carlsbad, Calif.)) Cat.#10010). After removal of blocking solution, 50 ul of Ab12 at 5 ug/ml in PBS with 1% BSA was added to wells and plates were incubated at room temperature for 2 hours. Plates were washed three times using a Skatron 400 Plate Washer with PBS/0.05% Tween 20 and 50 ul of secondary antibody diluted in PBS/0.25% BSA/0.05% Tween 20 added to the wells. For Ab12, goat anti-human IgG (Fc)-HRP (Caltag (Burlingame, Calif.) Cat.#H10507) diluted 1:1000 was used and for Ab 71 A (available from the American Type Culture Collection HB11689, also described in U.S. Pat. No. 6,319,499), goat anti mouse IgG (Fc)-HRP (Jackson Laboratories (West Grove, Pa.) Cat.#115-035-164) diluted 1:5000 was used. After a 1 hour incubation at room temperature, plates were washed three times as before and 50 ul of OPD Developing Reagent (Sigma #P9187) added to each well. Color development was stopped by addition of 50 ul of 1N HCl to the wells and optical density measured at 490 nm on a Victor 1420 Multi-Label Counter.

Figure 11:
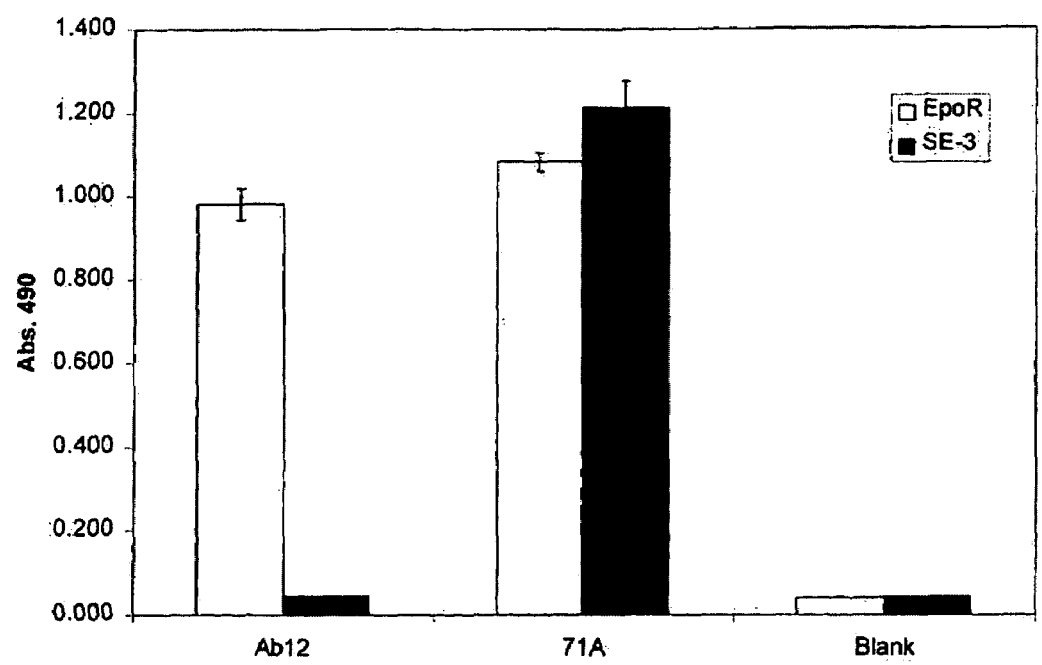
FIG. 11 shows that Ab12 does not interact with the peptide SE-3. Ab71A interacts with the SE-3 peptide.

FIG. 11 shows that Ab12 does not interact (i.e. bind) with SE-3 peptide. Ab 71A does interact (i.e. binds) with the SE-3 peptide Both Abs 12, and 71A interacted with immobilized erythropoietin receptor.

EXAMPLE 9

EPO Dependent Proliferation Assay

Figure 12:
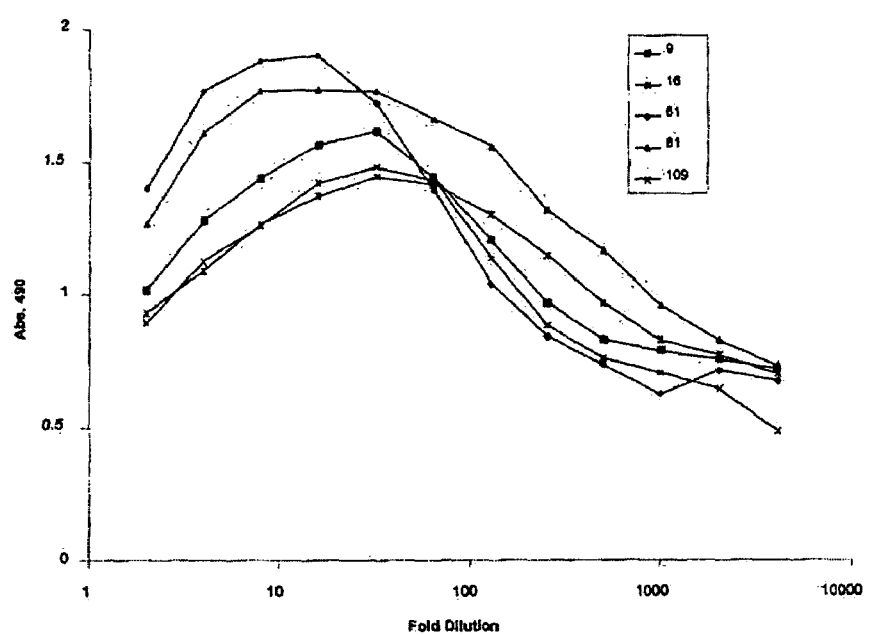
FIG. 12 shows that human Abs secreted by primary hybridomas induce the proliferation of F36E cells.

Primary hybridoma supernatants were diluted in assay medium and tested for their ability to stimulate the proliferation of the F36E human erythroleukemic cells as described in EXAMPLE 5. Results with five primary supernatants are shown in FIG. 12. These samples stimulated the proliferation of F36E cells.

EXAMPLE 10

ELISA to Measure Binding of Hybridoma Supernatants to SE-3 Peptide

Figure 13:
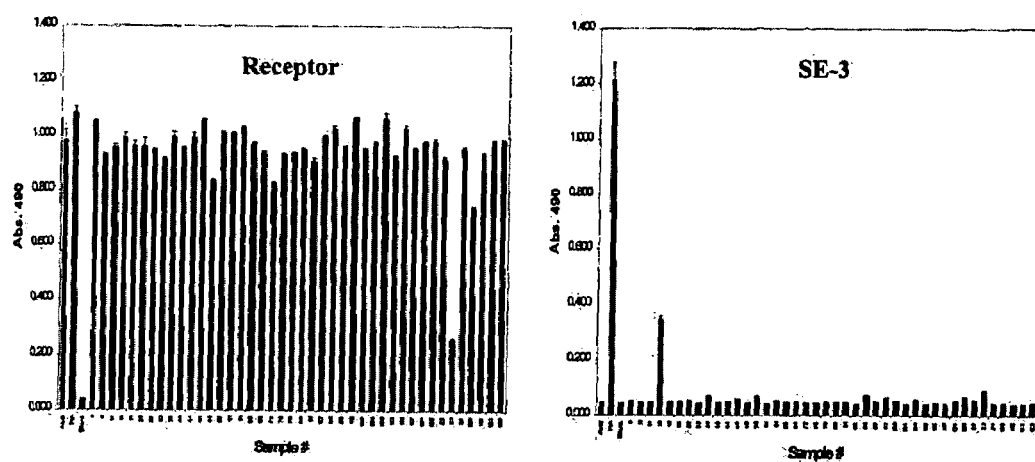
FIG. 13 shows that human Ab supernatants secreted by primary hybridomas interact with intact EPO receptor, but not with peptide SE-3.

Forty-two primary hybridoma supernatants were tested for their ability to bind to either immobilized EPO receptor or peptide SE-3 as described in EXAMPLE 10. FIG. 13 shows that whereas all the hybridoma supernatants tested interact with immobilized EPO receptor, only sample 16 interacted with SE-3 peptide at levels above background.

EXAMPLE 11

Comparison of Erythropoietic Activity of Gamma-1 Ab12 versus Gamma-2 Ab12

Figure 31:
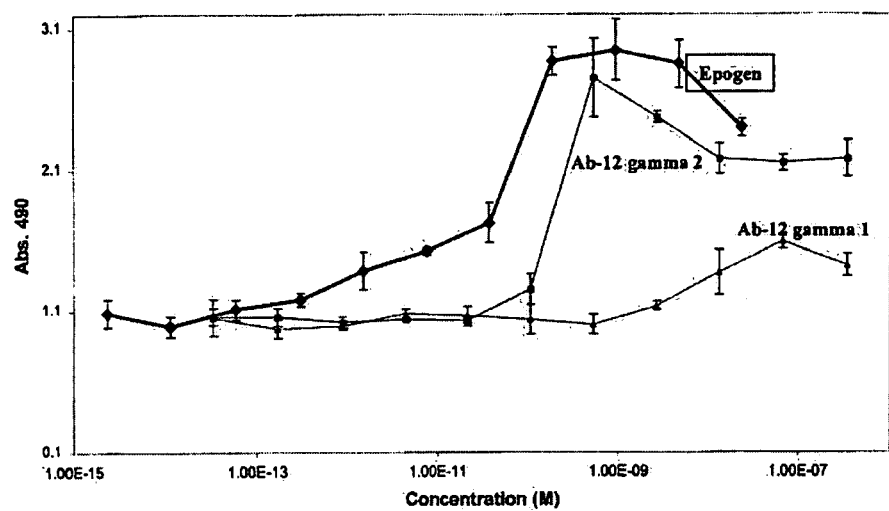
FIG. 31 is a graph comparing the erythropoietic activity, at various concentrations, of a gamma-1 Ab 12 monoclonal antibody (Mab) and a gamma-2 Ab 12 Mab on an F36e human erythroleukemic cell line.

Proliferation assays (as described in Example 4) were performed to compare the erythropoietic activity of gamma-1 Ab 12 and gamma-2 Ab 12 on F36e human erythroleukemic cells. The results are shown in FIG. 31. As FIG. 31 shows, gamma-2 Ab 12 was more effective at stimulating proliferation of the F36E cell line than gamma-1 Ab 12.

EXAMPLE 12

Effect of Ab 12 on Erythropoiesis in vivo (a) Construction of mEpoR –/–, hEopR+ transgenic mice: Transgenic mice that produced only human EpoR (hEpoR+, single allele) and no endogenous mouse EpoR (mEpoR –/–, double allele mutation) were generated as described in Liu, C. et al., *Jounal of Biological Chemistry*. 272:32395 (1997) and Yu, X., et al., *Blood*, 98(2):475 (2001). Breeding colonies were established to generate mice for in vivo studies of eryhthropoiesis.

(b) Multiple dosing regimen: In initial experiments, animals were subjected to a multiple dosing regimen of Ab 12 to determine whether the antibody would cause an increase in reticulocyte counts and/or % hematocrit. Five transgenic mice (mEpoR –/–, hEpoR+, were injected subcutaneously with either 5 μg or 50 μg of Ab 12 in 0.2 mL vehicle (phosphate buffered saline [PBS] containing 0.1% bovine serum albumin ([BSA]). Control animals also were injected in the same manner with equal volumes of the vehicle alone or vehicle containing 5U Epogen® (Amgen®, Thousand Oaks, Calif.). All animals were dosed over a three-week period in accordance with the following schedule:

| Week 1 | Week 2 | Week 3 |
|---|---|---|
| Monday, Tuesday, Wednesday, Friday | Monday, Wednesday, Friday | Monday, Wednesday |

Figure 32:
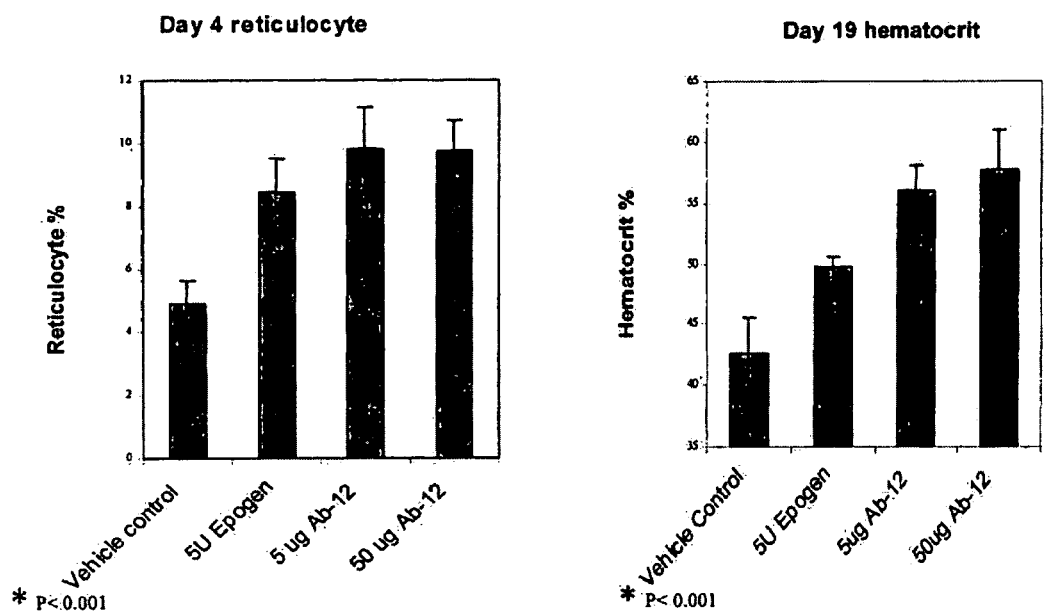
FIG. 32 is a graph showing the increase in percent reticulocyte and percent hematocrit in trangenic mice subjected to a multiple dosing regimen of vehicle, Epogen (5 U) or Ab 12 antibody (5 or 50 µg).

Sample bleeds were taken on day 4 (Thursday of week 1) for determining reticulocyte counts and on day 19 (Friday of week 3) for determining hematocrits. Reticulocyte counts and hematocrit determinations were made using methods well known in the art. As FIG. 32 shows, Ab 12 caused a statistically significant increase (over controls) in reticulocyte count and % hematocrit in animals receiving either 5 or 50 μg of Ab 12 antibody.

Figure 33:
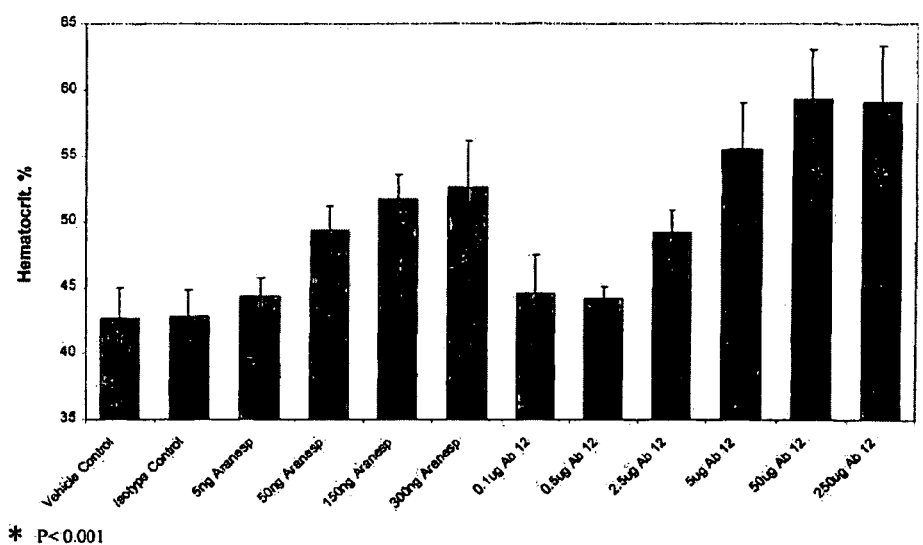
FIG. 33 is a graph showing the increase in percent hematocrit in transgenic mice subjected to a weekly dosing regimen (over 3 weeks) of various concentrations of Aranesp™ or Ab 12.

(c) Weekly dosing regimen: To assess whether the results seen under a multiple dosing regimen still would be observed in animals receiving fewer doses of Ab 12, transgenic mice were injected (as described in (b) above) with varying concentrations (0.5, 2.5, 5.0, 50 and 250 μg) of Ab 12 or a control, Aranesp™ (Amgen®, Thousand Oaks, Calif.), a more active variant of Epogen® on days 1, 8 and 15 and bled on days 4 and 19 for determination of reticulocyte count and hematocrit, respectively. Control animals received a single dose of vehicle only or a human IgG2 isotype control. FIG. 33 shows that Ab 12 caused a statistically significant increase (over vehicle and isotype controls) in pecent hematocrit with all but the lowest concentrations tested.

Figure 34:
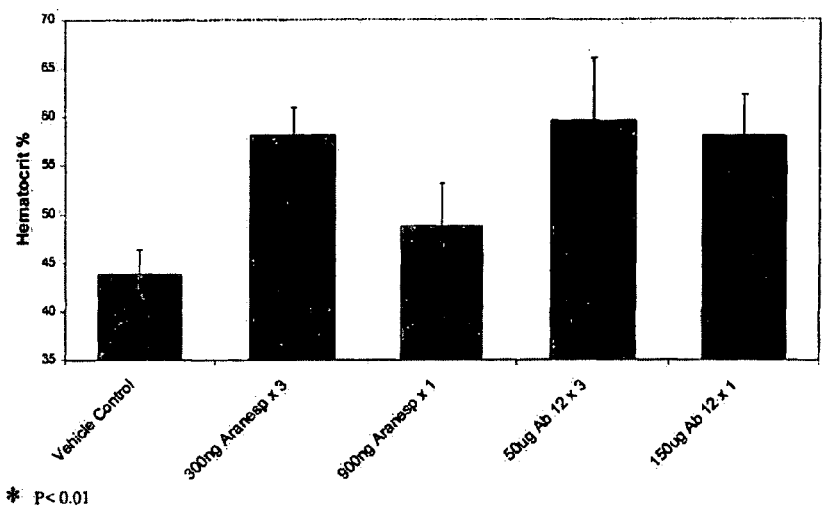
FIG. 34 is a graph showing the increase in percent hematocrit in transgenic mice subjected to single versus weekly dosing regimens of various concentrations of Aranesp™ or Ab 12.

(d) Single versus weekly dosing regimens: To determine whether a single dose of Ab-12 would have an effect on erythropoiesis after 3 weeks, transgenic mice were dosed with Ab 12 (50 μg), at one week intervals for 3 weeks or with a single dose of Ab 12 (150 μg) and bled on day 19 for determination of percent hematocrit. Control animals received vehicle alone, a single dose of Aranesp™ (900 ng) or 3 total doses of Aranesp™ injected at weekly intervals (300 ng×3). FIG. 34 shows that both dosing regimens of Ab 12 caused a statistically significant increase in percent hematocrit over the vehicle control. In contrast, the single dose regimen of Aranesp™ did not have this effect.

All abstracts, references, patents and published patent applications referred to herein are hereby incorporated by reference.

The present invention is illustrated by way of the foregoing description and examples. The foregoing description is intended as a non-limiting illustration, since many variations will become apparent to those skilled in the art in view thereof.

Changes can be made to the composition, operation and arrangement of the method of the present invention described herein without departing from the concept and scope of the invention.

What is claimed is:

1. An isolated antibody or antibody fragment thereof that activates an endogenous activity of a human erythropoietin receptor in a mammal, comprising: at least one heavy chain variable region having the amino acid sequence of SEQ ID NO:3 or antibody fragment thereof comprising the amino acid sequence of SEQ ID NO:3, and at least one light chain variable region having the amino acid sequence of SEQ ID NO:5 or antibody fragment thereof comprising the amino acid sequence of SEQ ID NO:5, wherein said antibody or antibody fragment thereof does not interact with a peptide having an amino acid sequence of SEQ ID NO:1.

2. An isolated antibody or antibody fragment thereof that activates an endogenous activity of a human erythropoietin receptor in a mammal, said antibody comprising: the amino acid sequences of at least one heavy chain variable region and at least one light chain variable region or antibody fragment thereof comprising SEQ ID NO:51 and SEQ ID NO:53, wherein said antibody or antibody fragment thereof does not interact with a peptide having an amino acid sequence of SEQ ID NO:1.

3. An isolated antibody or antibody fragment thereof capable of binding to a human erythropoietin receptor in a mammal, said antibody comprising: at least one heavy chain variable region having the amino acid sequence of SEQ ID NO: 3 and at least one light chain variable region having the amino acid sequence of SEQ ID NO: 5 or antibody fragment thereof comprising SEQ ID NO:3 and SEQ ID NO:5.

4. An isolated antibody or antibody fragment thereof capable of binding to a human erythropoietin receptor in a mammal, said antibody comprising: at least one heavy chain variable region having the amino acid sequence of SEQ ID NO:51 and at least one light chain variable region having the amino acid sequence of SEQ ID NO:53 or antibody fragment thereof comprising SEQ ID NO:51 and SEQ ID NO:53.

5. An isolated antibody capable of binding a human erythropoietin receptor in a mammal, said antibody comprising a heavy chain variable region comprising a continuous sequence from CDR1 through CDR3 having the amino acid sequence of: SEQ ID NO:58 and a light chain variable region comprising a continuous sequence from CDR1 through CDR3 having the amino acid sequence SEQ ID NO:62 and fragments thereof.

6. An isolated antibody or antibody fragment thereof that activates an endogenous activity of a human erythropoietin receptor in a mammal wherein said antibody is Ab12, wherein Ab12 has ATCC Accession No. PTA-5554.

7. A method of activating an endogenous activity of a human erythropoietin receptor in a mammal, the method comprising the step of administering to a mammal a therapeutically effective amount of the antibody or antibody fragment of claim 6 to activate said receptor.

8. A method of treating a mammal suffering red cell aplasia, the method comprising the step of administering to a mammal in need of treatment a therapeutically effective amount of the antibody or antibody fragment of claim 6 to activate the receptor.

9. A method of treating a mammal suffering anemia, the method comprising the steps of administering to a mammal in need of treatment a therapeutically effective amount of the antibody or antibody fragment of claim 6 to activate the receptor.

10. A pharmaceutical composition comprising a therapeutically effective amount of the antibody or antibody fragment of claim 6 and a pharmaceutically acceptable excipient.

11. The antibody fragment of claim 1, 2, 3, 4, 5 or 6, wherein the fragment is one selected from the group consisting of an Fab fragment, Fab' fragment, F(ab')$_2$ fragment and Fv fragment.

* * * * *

UNITED STATES PATENT AND TRADEMARK OFFICE
CERTIFICATE OF CORRECTION

PATENT NO. : 7,396,913 B2
APPLICATION NO. : 10/684109
DATED : July 8, 2008
INVENTOR(S) : DeVries et al.

It is certified that error appears in the above-identified patent and that said Letters Patent is hereby corrected as shown below:

Title Page, item (56), under "Other Publications", in column 2, line 1, delete "Biochemidtry" and insert -- Biochemistry --.

Title Page, item (56), under "Other Publications", in column 2, line 2, delete "Sci," and insert -- Sci., --.

Title Page, item (56), under "Other Publications", in column 2, line 28, delete "Blood, 76(1)24-30 (1990)." and insert -- Blood, 76(1):24-30 (1990). --.

Column 5, line 57, delete "cynomologous" and insert -- cynomolgus --.

Column 8, line 35, delete "trangenic" and insert -- transgenic --.

Column 9, line 8, delete "ABT2-SCX430/432" and insert -- ABT2-SCX-430/432 --.

Column 9, line 21, delete "ABT2-SCX467" and insert -- ABT2-SCX-467 --.

Column 9, line 34, delete "ABT2-SCX484" and insert -- ABT2-SCX-484 --.

Column 10, line 2, delete "464469." and insert -- 464-469. --.

Column 10, line 66, delete "464469." and insert -- 464-469. --.

Column 11, line 22, delete "IgD IgE," and insert -- IgD, IgE, --.

Column 11, line 26, delete "(i.e" and insert -- (i.e., --.

Column 13, line 62, delete "eucaryotic" and insert -- eukaryotic --.

Column 14, line 35, delete "gamma4" and insert -- gamma-4 --.

Signed and Sealed this

Tenth Day of August, 2010

David J. Kappos
*Director of the United States Patent and Trademark Office*

CERTIFICATE OF CORRECTION (continued)
U.S. Pat. No. 7,396,913 B2

Column 16, line 27, delete ""Additionally," and insert -- Additionally, --.

Column 16, line 35, delete "Phio,J. S." and insert -- Philo, J. S. --.

Column 16, line 36, delete "(1996))."" and insert -- (1996)). --.

Column 18, line 33, delete "endogeous" and insert -- endogenous --.

Column 20, line 54, delete "GA418" and insert -- G-418 --.

Column 24, lines 1-2, delete "skilledin" and insert -- skilled in --.

Column 24, line 10, delete "elixiers" and insert -- elixirs --.

Column 24, line 22, delete "coadministerd" and insert -- coadministered --.

Column 25, line 30, delete "Upsala," and insert -- Uppsala, --.

Column 26, line 7, delete "streptavadin" and insert -- streptavidin --.

Column 26, line 8, delete "room teperature" and insert -- room temperature --.

Column 28, line 13, delete "bv" and insert -- by --.

Column 28, line 36, delete "transfered" and insert -- transferred --.

Column 28, line 45, delete "Plague" and insert -- Plaque --.

Column 28, line 57, delete "Plague" and insert -- Plaque --.

Column 29, line 58, delete "streptavadin" and insert -- streptavidin --.

Column 30, line 38, delete "(FIG.4 17)." and insert -- (FIG. 17). --.

Column 32, line 40, delete "20 pIL" and insert -- 20 μL --.

Column 32, line 63, delete "Methoctilt" and insert -- Methocult --.

Column 33, line 13, delete "Erythopoietic" and insert -- Erythropoietic --.

Column 33, line 21, delete "10-6 M" and insert -- $10^{-6}$ M --.

Column 33, line 67, delete "Immunolon" and insert -- Immunolin --.

Column 35, line 9, delete "Jounal" and insert -- Journal --.

Column 35, line 9, delete "Chemistry." and insert -- Chemistry, --.

CERTIFICATE OF CORRECTION (continued)
U.S. Pat. No. 7,396,913 B2

Column 35, line 12, delete "eryhthropoiesis" and insert -- erythropoiesis --.

Column 36, line 13, delete "pecent" and insert -- percent --.

Columns 39-40, line 45, delete "Homo sapie ns" and insert -- Homo sapiens --.

Column 137, line 58, in claim 2, after "variable region" insert -- of SEQ ID NO:51/SEQ ID NO:53 --.

SEQUENCE LISTING

```
<160> NUMBER OF SEQ ID NOS: 115

<210> SEQ ID NO 1
<211> LENGTH: 30
<212> TYPE: PRT
<213> ORGANISM: Homo sapiens

<400> SEQUENCE: 1

Pro Gly Asn Tyr Ser Phe Ser Tyr Gln Leu Glu Asp Glu Pro Trp Lys
1               5                   10                  15

Leu Cys Arg Leu His Gln Ala Pro Thr Ala Arg Gly Ala Val
            20                  25                  30

<210> SEQ ID NO 2
<211> LENGTH: 349
<212> TYPE: DNA
<213> ORGANISM: Homo sapiens

<400> SEQUENCE: 2
caggtgcagc tgcaggagtc gggcccagga ctggtgaagc cttcggagac cctgtccctc      60
```

-continued

```
acctgcactg tctctggtgc ctccatcagt agttactact ggagctggat ccggcagccc      120
ccagggaagg gactggagtg gattgggtat atctattaca gtgggagcac caactacaac      180
ccctccctca agagtcgagt caccatatca gtagacacgt ccaagaacca gttctccctg      240
aagctgaggt ctgtgaccgc tgcggacacg gccgtgtatt actgtgcgag agagcgactg      300
gggatcgggg actactgggg ccaaggaacc ctggtcaccg tctcctcag                 349
```

<210> SEQ ID NO 3
<211> LENGTH: 116
<212> TYPE: PRT
<213> ORGANISM: Homo sapiens

<400> SEQUENCE: 3

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Ala Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Glu Arg Leu Gly Ile Gly Asp Tyr Trp Gly Gln Gly Thr Leu Val
            100                 105                 110

Thr Val Ser Ser
        115
```

<210> SEQ ID NO 4
<211> LENGTH: 322
<212> TYPE: DNA
<213> ORGANISM: Homo sapiens

<400> SEQUENCE: 4

```
gacatccagc tgacccaatc tccatcctcc ctgtctgcat ctgtaggaga cagagtcacc       60
atcacttgcc gggcaagtca gggcattaga aatgatttag gctggtatca gcagaaacca      120
gggaaagccc ctaagcgcct gatctatgct gcatccagtt tgcaaagtgg ggtcccatca      180
aggttcagcg gcagtggatc tgggacagaa ttcactctca caatcagcag cctgcagcct      240
gaagattttg caacttatta ctgtctacag cataatactt accctccgac gttcggccaa      300
gggaccaagg tggaaatcaa ac                                               322
```

<210> SEQ ID NO 5
<211> LENGTH: 107
<212> TYPE: PRT
<213> ORGANISM: Homo sapiens

<400> SEQUENCE: 5

```
Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45
```

```
Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Thr Tyr Pro Pro
                 85                  90                  95

Thr Phe Gly Gln Gly Thr Lys Val Glu Ile Lys
            100                 105

<210> SEQ ID NO 6
<211> LENGTH: 370
<212> TYPE: DNA
<213> ORGANISM: Homo sapiens

<400> SEQUENCE: 6
caggtgcagc tggtggagtc tgggggaggc gtggtccagc ctggggaggtc cctgagactc    60 tcctgtgtag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agttgaggac acggctgtgt attactgtgc gagagatcac   300
ggtggggagt acgtctacga ctacggtatg gacgtctggg gccaagggac cacggtcacc   360
gtctcctcag                                                          370

<210> SEQ ID NO 7
<211> LENGTH: 123
<212> TYPE: PRT
<213> ORGANISM: Homo sapiens

<400> SEQUENCE: 7

Gln Val Gln Leu Val Glu Ser Gly Gly Gly Val Val Gln Pro Gly Arg
 1               5                  10                  15

Ser Leu Arg Leu Ser Cys Val Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Asn Lys Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                 85                  90                  95

Ala Arg Asp His Gly Gly Arg Tyr Val Tyr Asp Tyr Gly Met Asp Val
                100                 105                 110

Trp Gly Gln Gly Thr Thr Val Thr Val Ser Ser
        115                 120

<210> SEQ ID NO 8
<211> LENGTH: 322
<212> TYPE: DNA
  ORGANISM: Homo sapie   ns

<400> SEQUENCE: 8
gacatccaga tgacccaatc tccatcttcc gtgtctgcat ctataggaga cagagtctcc    60
atcacttgtc gggcgagtca gggtattagc agctggttag cctggtatca gcagaaacca   120
```

```
gggaaagccc ctacgctcct tatctatgct gcatccactt tgcaacgtgg ggtcccatca    180
aggttcagcg gcagtggatc tgggacagat ttcactctca ccatcagcag cctgcagcct    240
gaagattttg caacttactt ttgtcaacag gctaacagtt tcccattcac tttcggccct    300
gggaccaaag tggatatcaa ac                                              322
```

<210> SEQ ID NO 9
<211> LENGTH: 107
<212> TYPE: PRT
<213> ORGANISM: Homo sapiens

<400> SEQUENCE: 9

```
Asp Ile Gln Met Thr Gln Ser Pro Ser Ser Val Ser Ala Ser Ile Gly
 1               5                  10                  15

Asp Arg Val Ser Ile Thr Cys Arg Ala Ser Gln Gly Ile Ser Ser Trp
            20                  25                  30

Leu Ala Trp Tyr Gln Gln Lys Pro Gly Lys Ala Pro Thr Leu Leu Ile
        35                  40                  45

Tyr Ala Ala Ser Thr Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asn Ser Phe Pro Phe
                85                  90                  95

Thr Phe Gly Pro Gly Thr Lys Val Asp Ile Lys
            100                 105
```

<210> SEQ ID NO 10
<211> LENGTH: 370
<212> TYPE: DNA
<213> ORGANISM: Homo sapiens

<400> SEQUENCE: 10

```
caggtgcagc tggtggagtc tgggggaggc gtggtccagc ctggggaggtc cctgagactc     60 tcctgtgcag cctctggatt caccttcagt agctatggca tgcactgggt ccgccaggct    120
ccaggcaagg ggctggagtg gtggcagtt atatcatatg atggaagtaa taaatactat    180
gcagactccg tgaagggccg attcaccatc tccagagaca attccaagaa cacgctgtat    240
ctgcaaatga acagcctgag agttgaggac acggctgtgt attactgtgc gagagatcac    300
ggtgggaggt acgtctacga ctacggtatg gacgtctggg gccaagggac cacggtcacc    360
gtctcctcag                                                           370
```

<210> SEQ ID NO 11
<211> LENGTH: 123
<212> TYPE: PRT
<213> ORGANISM: Homo sapiens

<400> SEQUENCE: 11

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Asp His Gly Gly Arg Tyr Val Tyr Asp Tyr Gly Met Asp Val
            100                 105                 110

Trp Gly Gln Gly Thr Thr Val Thr Val Ser Ser
        115                 120

<210> SEQ ID NO 12
<211> LENGTH: 322
<212> TYPE: DNA
<213> ORGANISM: Homo sapiens

<400> SEQUENCE: 12
gacatccaga tgacccaatc tccatcttcc gtgtctgcat ctgtaggaga cagagtctcc     60
atcacttgtc gggcgagtca gggtattagc agctggttag tctggtatca gcagaaacca    120
gggaaagccc ctgcgctcct aatctatgct gcatccagtt tgcagcgtgg ggtcccatca    180
aggttcagcg gcagtggatc tgggacagac ttcactctca ccatcagcag cctgcagcct    240
gaagattttg caacttactt ttgtcaacag gctaacagtt tcccattcac tttcggccct    300
gggaccaaag tggatatcaa ac                                             322

<210> SEQ ID NO 13
<211> LENGTH: 107
<212> TYPE: PRT
<213> ORGANISM: Homo sapiens

<400> SEQUENCE: 13

Asp Ile Gln Met Thr Gln Ser Pro Ser Val Ser Ala Ser Val Gly
1               5                   10                  15

Asp Arg Val Ser Ile Thr Cys Arg Ala Ser Gln Gly Ile Ser Ser Trp
            20                  25                  30

Leu Val Trp Tyr Gln Gln Lys Pro Gly Lys Ala Pro Ala Leu Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asn Ser Phe Pro Phe
                85                  90                  95

Thr Phe Gly Pro Gly Thr Lys Val Asp Ile Lys
            100                 105

<210> SEQ ID NO 14
<211> LENGTH: 370
<212> TYPE: DNA
<213> ORGANISM: Homo sapiens

<400> SEQUENCE: 14
caggtgcagc tggtggagtc tgggggaggc gtggtccagc ctgggaggtc cctgagactc     60
tcctgtgcag cctctggatt caccttcagt agctatggca tgcactgggt ccgccaggct    120
ccaggcaagg ggctggagtg ggtggtagtt atatcatatg atggaagtaa taaatactat    180
gcagactccg tgaagggccg attcaccatc tccagagaca attccaagaa cacgctgtat    240

```
ctgcaaatga acagcctgag agttgaggac acggctgtgt attactgtgc gagagatcac      300
ggtgggaggt acgtctacga ctacggtatg gacgtctggg gccaagggac cacggtcacc      360
gtctcctcag                                                              370
```

<210> SEQ ID NO 15
<211> LENGTH: 123
<212> TYPE: PRT
<213> ORGANISM: Homo sapiens

<400> SEQUENCE: 15

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Val Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Asp His Gly Gly Arg Tyr Val Tyr Asp Tyr Gly Met Asp Val
            100                 105                 110

Trp Gly Gln Gly Thr Thr Val Thr Val Ser Ser
        115                 120
```

<210> SEQ ID NO 16
<211> LENGTH: 322
<212> TYPE: DNA
<213> ORGANISM: Homo sapiens

<400> SEQUENCE: 16

```
gacatccaga tgacccaatc tccatcttcc gtgtctgcat ctgtaggaga cagagtctcc       60
atcacttgtc gggcgagtca gggtattagc agctggttag cctggtatca gcagaaacca      120
gggaaagccc ctacgctcct aatctatgct gcatccagtt tgcaacgtgg gtcccatca       180 aggttcagcg gcagtggatc tgggacagat ttcactctca ccatcagcag cctgcagcct      240
gaagattttg caacttactt ttgtcaacag gctaacagtt tcccattcac tttcggccct      300
gggaccaaag tggatatcaa ac                                               322
```

<210> SEQ ID NO 17
<211> LENGTH: 107
<212> TYPE: PRT
<213> ORGANISM: Homo sapiens

<400> SEQUENCE: 17

```
Asp Ile Gln Met Thr Gln Ser Pro Ser Ser Val Ser Ala Ser Val Gly
 1               5                  10                  15

Asp Arg Val Ser Ile Thr Cys Arg Ala Ser Gln Gly Ile Ser Ser Trp
            20                  25                  30

Leu Ala Trp Tyr Gln Gln Lys Pro Gly Lys Ala Pro Thr Leu Leu Ile
        35                  40                  45

Tyr Ala Ala Ser Ser Leu Gln Arg Gly Val Pro Ser Arg Phe Ser Gly
    50                  55                  60
```

-continued

```
Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Ala Asn Ser Phe Pro Phe
                 85                  90                  95

Thr Phe Gly Pro Gly Thr Lys Val Asp Ile Lys
            100                 105
```

<210> SEQ ID NO 18
<211> LENGTH: 349
<212> TYPE: DNA
<213> ORGANISM: Homo sapiens

<400> SEQUENCE: 18

| | |
|---|---|
| caggtgcagc tggtggagtc gggggggaggc gtggtccagc ctgggaggtc cctgagactc | 60 |
| tcctgtgcag cgtctggatt caccttcagt aaatatggca tgcactgggt ccgccaggct | 120 |
| ccaggcaagg gctggagtg gtggcagtt ttatggtatg atggaagtaa taaatactat | 180 |
| gcagactccg tgaagggccg attcaccatc tccagagaca attccaagaa cacgctgtat | 240 |
| ctgcaaatga acagcctgag agccgaggac acggctgtgt attactgtgc gagaggtccg | 300 |
| tactactttg actactgggg ccagggaacc ctggtcaccg tctcctcag | 349 |

<210> SEQ ID NO 19
<211> LENGTH: 116
<212> TYPE: PRT
<213> ORGANISM: Homo sapiens

<400> SEQUENCE: 19

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Lys Tyr
                 20                  25                  30

Gly Met His Trp Val Arg Gln Ala Pro Gly Lys Gly Leu Glu Trp Val
             35                  40                  45

Ala Val Leu Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Pro Tyr Tyr Phe Asp Tyr Trp Gly Gln Gly Thr Leu Val
            100                 105                 110

Thr Val Ser Ser
        115
```

<210> SEQ ID NO 20
<211> LENGTH: 325
<212> TYPE: DNA
<213> ORGANISM: Homo sapiens

<400> SEQUENCE: 20

| | |
|---|---|
| gaaattgtgt tgacgcagtc tccaggcacc ctgtctttgt ctccagggga aagagccacc | 60 |
| ctctcctgca gggccagtca gagtgttagc agcagctact tagcctggta ccagcagaaa | 120 |
| cctggccagg ctcccaggct cctcatctat ggtgcatcca gcagggccac tggcatccca | 180 |
| gacaggttca gtggcagtgg gtctgggaca gacttcactg tcaccatcag cagactggaa | 240 |
| cctgaagatt ttgcagtgta ttactgtcag cagtatggta gttcaccgtg acgttcggc | 300 |

```
caagggacca aggtggaaat caaac                                            325
```

<210> SEQ ID NO 21
<211> LENGTH: 108
<212> TYPE: PRT
<213> ORGANISM: Homo sapiens

<400> SEQUENCE: 21

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Val Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 22
<211> LENGTH: 322
<212> TYPE: DNA
<213> ORGANISM: Homo sapiens

<400> SEQUENCE: 22

```
gacatccaga tgacccaatc tccatcttcc gtgtccgcat ctgtaggaga cagagtctcc    60
atcacttgtc gggcgagtca gggtattagc agctggttag cctggtatca gcagaaacca   120
gggaaagccc ctacgctcct aatctatgct gcatccagtt tgcaacgtgg ggtcccatca   180
aggttcagcg gcagtggatc tgggacagat ttcactctca ccatcagcag cctgcagcct   240
gaagattttg caacttactt ttgtcaacag gctaacagtt tcccattcac tttcggccct   300
gggaccaaag tggatatcaa ac                                            322
```

<210> SEQ ID NO 23
<211> LENGTH: 107
<212> TYPE: PRT
<213> ORGANISM: Homo sapiens

<400> SEQUENCE: 23

```
Asp Ile Gln Met Thr Gln Ser Pro Ser Ser Val Ser Ala Ser Val Gly
 1               5                  10                  15

Asp Arg Val Ser Ile Thr Cys Arg Ala Ser Gln Gly Ile Ser Ser Trp
            20                  25                  30

Leu Ala Trp Tyr Gln Gln Lys Pro Gly Lys Ala Pro Thr Leu Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asn Ser Phe Pro Phe
                85                  90                  95
```

Thr Phe Gly Pro Gly Thr Lys Val Asp Ile Lys
            100                 105

<210> SEQ ID NO 24
<211> LENGTH: 322
<212> TYPE: DNA
<213> ORGANISM: Homo sapiens

<400> SEQUENCE: 24
gacatccaga tgacccaatc tccatcttcc gtgtctgcat ctgtaggaga cagagtctcc    60
atcacttgtc gggcgagtca gggtattagc agctggttag cctggtatca gcagaaacca   120
gggaaagccc ctaagcgcct gatctatgct gcatccagtt tgcaacgtgg ggtcccatca   180
aggttcagcg gcagtggatc tgggacagat ttcactctca ccatcagcag cctgcagcct   240
gaagattttg caacttactt ttgtcaacag gctaacagtt tcccattcac tttcggccct   300
gggaccaaag tggatatcaa ac                                             322

<210> SEQ ID NO 25
<211> LENGTH: 107
<212> TYPE: PRT
<213> ORGANISM: Homo sapiens

<400> SEQUENCE: 25

Asp Ile Gln Met Thr Gln Ser Pro Ser Ser Val Ser Ala Ser Val Gly
 1               5                  10                  15

Asp Arg Val Ser Ile Thr Cys Arg Ala Ser Gln Gly Ile Ser Ser Trp
            20                  25                  30

Leu Ala Trp Tyr Gln Gln Lys Pro Gly Lys Ala Pro Lys Arg Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asn Ser Phe Pro Phe
                85                  90                  95

Thr Phe Gly Pro Gly Thr Lys Val Asp Ile Lys
            100                 105

<210> SEQ ID NO 26
<211> LENGTH: 322
<212> TYPE: DNA
<213> ORGANISM: Homo sapiens

<400> SEQUENCE: 26
gacatccaga tgacccagtc tccatcttcc gtgtctacat ctgtaggaga cagagtctcc    60
atcacttgtc gggcgagtca gggtattggc agctggttag cctggtatca gcagaaacca   120
gggcaagccc ctacgctcct aatctatgct gcatccagtt tgcaacgtgg ggtcccatca   180
agattcagcg gcagtggatc tgggacagat ttcactctca ccatcaacag cctgcagcct   240
gaagattttg caacttactt ttgtcaacag gctaacagtt tcccattcac tttcggccct   300
gggaccaaag tggatgtcaa ac                                             322

<210> SEQ ID NO 27
<211> LENGTH: 107
<212> TYPE: PRT

<210> SEQ ID NO 27
<211> LENGTH: 107
<212> TYPE: PRT
<213> ORGANISM: Homo sapiens

<400> SEQUENCE: 27

```
Asp Ile Gln Met Thr Gln Ser Pro Ser Ser Val Ser Thr Val Gly
  1               5                  10                  15

Asp Arg Val Ser Ile Thr Cys Arg Ala Ser Gln Gly Ile Gly Ser Trp
             20                  25                  30

Leu Ala Trp Tyr Gln Gln Lys Pro Gly Gln Ala Pro Thr Leu Leu Ile
         35                  40                  45

Tyr Ala Ala Ser Ser Leu Gln Arg Gly Val Pro Ser Arg Phe Ser Gly
 50                  55                  60

Ser Gly Ser Gly Thr Asp Phe Thr Leu Thr Ile Asn Ser Leu Gln Pro
 65                  70                  75                  80

Glu Asp Phe Ala Thr Tyr Phe Cys Gln Gln Ala Asn Ser Phe Pro Phe
             85                  90                  95

Thr Phe Gly Pro Gly Thr Lys Val Asp Val Lys
            100                 105
```

<210> SEQ ID NO 28
<211> LENGTH: 322
<212> TYPE: DNA
<213> ORGANISM: Homo sapiens

<400> SEQUENCE: 28

```
gacatccaga tgacccagtc tccatcttcc gtgtctgcat ctgtaggaga cagagtctcc      60
atcacttgtc gggcgagtca gggtattggc agctggttag cctggtatca gcagaaacca    120
gggcaagccc ctacgctcct aatctatgct gcatccagtt tgcaacgtgg ggtcccatca    180
agattcagcg gcagtggatc tgggacagat ttcactctca ccatcaacag cctgcagcct    240
gaagattttg caacttactt ttgtcaacag gctaacagtt tcccattcac tttcggccct    300
gggaccaaag tggatgtcaa ac                                              322
```

<210> SEQ ID NO 29
<211> LENGTH: 107
<212> TYPE: PRT
<213> ORGANISM: Homo sapiens

<400> SEQUENCE: 29

```
Asp Ile Gln Met Thr Gln Ser Pro Ser Ser Val Ser Ala Ser Val Gly
  1               5                  10                  15

Asp Arg Val Ser Ile Thr Cys Arg Ala Ser Gln Gly Ile Gly Ser Trp
             20                  25                  30

Leu Ala Trp Tyr Gln Gln Lys Pro Gly Gln Ala Pro Thr Leu Leu Ile
         35                  40                  45

Tyr Ala Ala Ser Ser Leu Gln Arg Gly Val Pro Ser Arg Phe Ser Gly
 50                  55                  60

Ser Gly Ser Gly Thr Asp Phe Thr Leu Thr Ile Asn Ser Leu Gln Pro
 65                  70                  75                  80

Glu Asp Phe Ala Thr Tyr Phe Cys Gln Gln Ala Asn Ser Phe Pro Phe
             85                  90                  95

Thr Phe Gly Pro Gly Thr Lys Val Asp Val Lys
            100                 105
```

<210> SEQ ID NO 30
<211> LENGTH: 349
<212> TYPE: DNA

<400> SEQUENCE: 30

```
caggtgcagc tggtggagtc tgggggaggc gtggtccagc ctggggaggtc cctgagactc    60 tcctgtgcag cgtctggatt caccttcagt agctatggca tgcactgggt ccgccaggct   120
ccaggcaagg gctggagtg gtggcagtt atatggtttg atggaaataa taaattctat    180
gcagactccg tgaagggccg attcaccatc tccagagaca attccaagaa cacgctgtat   240
ctgcaaatga acagcctgag agtcgaggac acggctgtgt attactgtgc gcgaggcggg   300
agctactggg actactgggg ccagggaacc ctggtcaccg tctcctcag               349
```

<210> SEQ ID NO 31  
<211> LENGTH: 116  
<212> TYPE: PRT  
<213> ORGANISM: Homo sapiens

<400> SEQUENCE: 31

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Phe Asp Gly Asn Asn Lys Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                 85                  90                  95

Ala Arg Gly Gly Ser Tyr Trp Asp Tyr Trp Gly Gln Gly Thr Leu Val
            100                 105                 110

Thr Val Ser Ser
        115
```

<210> SEQ ID NO 32  
<211> LENGTH: 336  
<212> TYPE: DNA  
<213> ORGANISM: Homo sapiens

<400> SEQUENCE: 32

```
gatattgtga tgacccagac tccactcttc tcatttgtca tgattggaca gccggcctcc    60
atctcctgca ggtctaggca aagcctcgta cacagtgatg aaacaccta cttgaattgg   120 cttcagcaga ggccaggcca gcctccaaga ctcctaattt ataagacttc taaccggttc   180
tctggggtcc cagatagatt cagtggcagt ggggcaggga cagatttcac actgaaaatc   240
agcagggtgg aagctgagga tgtcgggggtt tattactgta tgcaagctac acaatttcct   300
atcacgttcg gccaagggac acgactggag attaaa                             336
```

<210> SEQ ID NO 33  
<211> LENGTH: 112  
<212> TYPE: PRT  
<213> ORGANISM: Homo sapiens

<400> SEQUENCE: 33

```
Asp Ile Val Met Thr Gln Thr Pro Leu Phe Ser Phe Val Met Ile Gly
```

```
                1               5                  10                 15
Gln Pro Ala Ser Ile Ser Cys Arg Ser Arg Gln Ser Leu Val His Ser
                   20                 25                 30

Asp Gly Asn Thr Tyr Leu Asn Trp Leu Gln Gln Arg Pro Gly Gln Pro
                35                40                 45

Pro Arg Leu Leu Ile Tyr Lys Thr Ser Asn Arg Phe Ser Gly Val Pro
    50                   55                 60

Asp Arg Phe Ser Gly Ser Gly Ala Gly Thr Asp Phe Thr Leu Lys Ile
65                  70                 75                      80

Ser Arg Val Glu Ala Glu Asp Val Gly Val Tyr Tyr Cys Met Gln Ala
                85                 90                 95

Thr Gln Phe Pro Ile Thr Phe Gly Gln Gly Thr Arg Leu Glu Ile Lys
                100                105                110

<210> SEQ ID NO 34
<211> LENGTH: 370
<212> TYPE: DNA
<213> ORGANISM: Homo sapiens

<400> SEQUENCE: 34
caggtgcagc tggtggagtc tgggggaggc gtggtccagc ctggggaggtc cctgagactc       60 tcctgtgcag cctctggatt caccttcagt agctatggca tgcactgggt ccgccaggct      120
ccaggcaagg ggctggagtg ggtggcagtt atatcatatg atggaagtaa taatactat       180 gcagactccg tgaagggccg attcaccatc tccagagaca attccaagaa cacgctgtat      240
ctgcaaatga acagcctgag agttgaggac acggctgtgt attactgtgc gaaagatcac      300 ggtggggaggt acgtctacga ctacggtatg gacgtctggg gccaagggac cacggtcacc      360
gtctcctcag                                                             370

<210> SEQ ID NO 35
<211> LENGTH: 123
<212> TYPE: PRT
<213> ORGANISM: Homo sapiens

<400> SEQUENCE: 35

Gln Val Gln Leu Val Glu Ser Gly Gly Gly Val Val Gln Pro Gly Arg
1               5                  10                 15

Ser Leu Arg Leu Ser Cys Ala Ala Ser Gly Phe Thr Phe Ser Ser Tyr
                20                 25                 30

Gly Met His Trp Val Arg Gln Ala Pro Gly Lys Gly Leu Glu Trp Val
            35                 40                 45

Ala Val Ile Ser Tyr Asp Gly Ser Asn Lys Tyr Tyr Ala Asp Ser Val
    50                 55                 60

Lys Gly Arg Phe Thr Ile Ser Arg Asp Asn Ser Lys Asn Thr Leu Tyr
65                 70                 75                     80

Leu Gln Met Asn Ser Leu Arg Val Glu Asp Thr Ala Val Tyr Tyr Cys
                85                 90                 95

Ala Lys Asp His Gly Gly Arg Tyr Val Tyr Tyr Gly Met Asp Val
                100                105                110

Trp Gly Gln Gly Thr Thr Val Thr Val Ser Ser
        115                120

<210> SEQ ID NO 36
<211> LENGTH: 322
<212> TYPE: DNA
<213> ORGANISM: Homo sapiens
```

<400> SEQUENCE: 36

```
gacatccaga tgacccagtc tccatcttcc gtgtctgcat ctgtaggaga cagagtctcc      60
atcacttgtc gggcgagtca gggtattggc agctggttag cctggtatca gcagaaacca     120
gggcaagccc ctacgctcct aatctatgct gcctccagtt tgcaacgtgg ggtcccatca     180
agattcagcg gcagtggatc tgggacagat ttcactctca ccatcaacag cctgcagcct     240
gaagattttg caacttactt ttgtcaacag gctaacagtt tcccattcac tttcggccct     300
gggaccaaag tggatgtcaa ac                                               322
```

<210> SEQ ID NO 37
<211> LENGTH: 107
<212> TYPE: PRT
<213> ORGANISM: Homo sapiens

<400> SEQUENCE: 37

```
Asp Ile Gln Met Thr Gln Ser Pro Ser Ser Val Ser Ala Ser Val Gly
  1               5                  10                  15

Asp Arg Val Ser Ile Thr Cys Arg Ala Ser Gln Gly Ile Gly Ser Trp
             20                  25                  30

Leu Ala Trp Tyr Gln Gln Lys Pro Gly Gln Ala Pro Thr Leu Leu Ile
         35                  40                  45

Tyr Ala Ala Ser Ser Leu Gln Arg Gly Val Pro Ser Arg Phe Ser Gly
     50                  55                  60

Ser Gly Ser Gly Thr Asp Phe Thr Leu Thr Ile Asn Ser Leu Gln Pro
 65                  70                  75                  80

Glu Asp Phe Ala Thr Tyr Phe Cys Gln Gln Ala Asn Ser Phe Pro Phe
                 85                  90                  95

Thr Phe Gly Pro Gly Thr Lys Val Asp Val Lys
            100                 105
```

<210> SEQ ID NO 38
<211> LENGTH: 348
<212> TYPE: DNA
<213> ORGANISM: Homo sapiens

<400> SEQUENCE: 38

```
caggtgcagc tgcaggagtc gggcccagga ctggtgaagc cttcggagac cctgtccctc      60
acctgcactg tctctggtgc ctccatcagt aattactact ggagctggat ccggcagccc     120
ccagggaagg gactggagtg gattgggtat gtctcttaca gtgggagtac gtactacaac     180
ccctccctca gggtcgagt caccatgtca gtagacacgt ccaagaacca gttctccctg     240
aagctgagct ctgtgaccgc tgcggacacg gccgtgtatt actgtgcgag agaaaaactg     300
gggattggag actactgggg ccagggaacc ctggtcaccg tctcctca                  348
```

<210> SEQ ID NO 39
<211> LENGTH: 116
<212> TYPE: PRT
<213> ORGANISM: Homo sapiens

<400> SEQUENCE: 39

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Ala Ser Ile Ser Asn Tyr
             20                  25                  30
```

```
Tyr Trp Ser Trp Ile Arg Gln Pro Pro Gly Lys Gly Leu Glu Trp Ile
            35                  40                  45
Gly Tyr Val Ser Tyr Ser Gly Ser Thr Tyr Tyr Asn Pro Ser Leu Lys
        50                  55                  60
Gly Arg Val Thr Met Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Glu Lys Leu Gly Ile Gly Asp Tyr Trp Gly Gln Gly Thr Leu Val
            100                 105                 110
Thr Val Ser Ser
        115

<210> SEQ ID NO 40
<211> LENGTH: 322
<212> TYPE: DNA
<213> ORGANISM: Homo sapiens

<400> SEQUENCE: 40
gacatccaga tgacccagtc tccatcctcc ctgtctgcat ctgtaggaga cagagtcacc      60
atcacttgcc gggcaagtca gggcattaaa aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt atccgtgcag ttttggccag    300
gggaccaagc tggagatcaa ac                                              322

<210> SEQ ID NO 41
<211> LENGTH: 107
<212> TYPE: PRT
<213> ORGANISM: Homo sapiens

<400> SEQUENCE: 41

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Lys Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro Cys
                85                  90                  95
Ser Phe Gly Gln Gly Thr Lys Leu Glu Ile Lys
            100                 105

<210> SEQ ID NO 42
<211> LENGTH: 354
<212> TYPE: DNA
<213> ORGANISM: Homo sapiens

<400> SEQUENCE: 42
caggtgcagc tgcaggagtc gggcccagga ctggtgaagc cttcacagac cctgtccctc      60
```

```
acctgcactg tctctggtgc ctccatcagc agtggtgctt actactgcag ttggatccgc    120
cagcacccag ggaagggcct ggagtggatt gggtacatct ataagagtga gacctcctac    180
tacaacccgt ccctcaagag tcgacttacc ctatcagtag acacgtctaa gaaccagttc    240
tccctgaacc tgatctctgt gactgccgcg gacacggccg tgtattattg cgcgagagat    300
aaactgggga tcgcggacta ctggggccag ggaaccctgg tcaccgtctc ctca          354
```

<210> SEQ ID NO 43
<211> LENGTH: 118
<212> TYPE: PRT
<213> ORGANISM: Homo sapiens

<400> SEQUENCE: 43

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Ala Ser Ile Ser Ser Gly
             20                  25                  30

Ala Tyr Tyr Trp Ser Trp Ile Arg Gln His Pro Gly Lys Gly Leu Glu
         35                  40                  45

Trp Ile Gly Tyr Ile Tyr Lys Ser Glu Thr Ser Tyr Tyr Asn Pro Ser
     50                  55                  60

Leu Lys Ser Arg Leu Thr Leu Ser Val Asp Thr Ser Lys Asn Gln Phe
 65                  70                  75                  80

Ser Leu Asn Leu Ile Ser Val Thr Ala Ala Asp Thr Ala Val Tyr Tyr
                 85                  90                  95

Cys Ala Arg Asp Lys Leu Gly Ile Ala Asp Tyr Trp Gly Gln Gly Thr
             100                 105                 110

Leu Val Thr Val Ser Ser
         115
```

<210> SEQ ID NO 44
<211> LENGTH: 322
<212> TYPE: DNA
<213> ORGANISM: Homo sapiens

<400> SEQUENCE: 44

```
gacatccaga tgacccagtc tccatcctcc ctgtctgcat ctgtaggaga cagagtcacc     60
atcacttgcc gggcaagtca ggacattaga aatgatttag ctggtatca gcagaaacca    120 gggaaagccc ctaagcgcct gatctatgct gcatccaatt tgcaaagtgg ggtcccatca    180
aggttcagcg gcagtggatc tgggacagaa ttcactctca caatcagcag cctgcagcct    240
gaagattttg caacttatta ctgtctacag cataatagct accctcccac tttcggcgga    300
gggaccaagg tggaaatcaa ac                                              322
```

<210> SEQ ID NO 45
<211> LENGTH: 107
<212> TYPE: PRT
<213> ORGANISM: Homo sapiens

<400> SEQUENCE: 45

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
             20                  25                  30

Leu Gly Trp Tyr Gln Gln Lys Pro Gly Lys Ala Pro Lys Arg Leu Ile
```

```
            35                  40                  45
Tyr Ala Ala Ser Asn Leu Gln Ser Gly Val Pro Ser Arg Phe Ser Gly
             50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Pro
                 85                  90                  95

Thr Phe Gly Gly Gly Thr Lys Val Glu Ile Lys
                100                 105
```

<210> SEQ ID NO 46
<211> LENGTH: 349
<212> TYPE: DNA
<213> ORGANISM: Homo sapiens

<400> SEQUENCE: 46

```
caggtgcagc tgcaggagtc gggcccagga ctggtgaagc cttcggagac cctgtccctc      60
acctgcactg tctctggtgt ctccatcagt aattactact ggagctggat ccggcagtcc     120
ccagggaagg gactggagtg gattggatat atctattaca gtgggagtcc ctattacaac     180
ccctccctca agagtcgagt cactatatct gcagacacgt ccaagaacca attctccctg     240
aagctgagct ctgtgaccgc tgcggacacg gccatttatt actgtgcgag agaaaaactg     300
gggattggag actactgggg ccagggaacc ctggtcaccg tctcctcag               349
```

<210> SEQ ID NO 47
<211> LENGTH: 116
<212> TYPE: PRT
<213> ORGANISM: Homo sapiens

<400> SEQUENCE: 47

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Val Ser Ile Ser Asn Tyr
             20                  25                  30

Tyr Trp Ser Trp Ile Arg Gln Ser Pro Gly Lys Gly Leu Glu Trp Ile
         35                  40                  45

Gly Tyr Ile Tyr Tyr Ser Gly Ser Pro Tyr Tyr Asn Pro Ser Leu Lys
     50                  55                  60

Ser Arg Val Thr Ile Ser Ala Asp Thr Ser Lys Asn Gln Phe Ser Leu
 65                  70                  75                  80

Lys Leu Ser Ser Val Thr Ala Ala Asp Thr Ala Ile Tyr Tyr Cys Ala
                 85                  90                  95

Arg Glu Lys Leu Gly Ile Gly Asp Tyr Trp Gly Gln Gly Thr Leu Val
                100                 105                 110

Thr Val Ser Ser
        115
```

<210> SEQ ID NO 48
<211> LENGTH: 322
<212> TYPE: DNA
<213> ORGANISM: Homo sapiens

<400> SEQUENCE: 48

```
gacatccaga tgacccagtc tccatcctcc ctgtctgcat ctgtcggaga cagagtcacc      60
atcacttgcc gggcaagtca gggcattaga aatgatttag cctggtatca gcagaaacca    120
```

```
gggaaagccc ctaagcgcct gatctatgct gcatccagtt tgcaaagtgg ggtcccatca      180
aggttcagcg gcagtggatc tgggacagaa ttcactctca caatcagcag cctgcagcct      240
gaagattttg caacttatta ctgtctacag cataatagtt accctcccac tttcggccct      300
gggaccaagg tggatatcaa ac                                               322
```

<210> SEQ ID NO 49
<211> LENGTH: 107
<212> TYPE: PRT
<213> ORGANISM: Homo sapiens

<400> SEQUENCE: 49

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Thr Phe Gly Pro Gly Thr Lys Val Asp Ile Lys
            100                 105
```

<210> SEQ ID NO 50
<211> LENGTH: 349
<212> TYPE: DNA
<213> ORGANISM: Homo sapiens

<400> SEQUENCE: 50

```
caggtgcagc tgcaggagtc gggcccagga ctggtgaagc cttcggagac cctgtccctc       60
acctgcactg tctctggtgg ctccatcagt cgttactact ggagctggat ccggcagccc      120
ccagggaagg gactgagtg gattgggtat gtctcttaca gtgggagcac ctactacaac      180
ccctccctca agagtcgagt caccatatca gtagacacgt ccaagaacca gttctccctg      240
aagctgagct ctgtgaccgc tgcggacacg gccgtgtatt actgtgcgag agataaactg      300
gggattggag actactgggg ccagggaacc ctggtcaccg tctcctcag                  349
```

<210> SEQ ID NO 51
<211> LENGTH: 116
<212> TYPE: PRT
<213> ORGANISM: Homo sapiens

<400> SEQUENCE: 51

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Tyr
            20                  25                  30

Tyr Trp Ser Trp Ile Arg Gln Pro Pro Gly Lys Gly Leu Glu Trp Ile
        35                  40                  45

Gly Tyr Val Ser Tyr Ser Gly Ser Thr Tyr Tyr Asn Pro Ser Leu Lys
    50                  55                  60
```

```
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Lys Leu Gly Ile Gly Asp Tyr Trp Gly Gln Gly Thr Leu Val
            100                 105                 110

Thr Val Ser Ser
        115
```

<210> SEQ ID NO 52
<211> LENGTH: 322
<212> TYPE: DNA
<213> ORGANISM: Homo sapiens

<400> SEQUENCE: 52

```
gacatccaga tgacccagtc tccatcctcc ctgtctgcat ctgtaggaga cagagtcacc    60
atcacttgcc gggcaagtca gggcattaga aatgatttag gctggtatca gcagaaaccg   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgtgcag ttttggccag   300
gggaccaagc tggagatcaa ac                                            322
```

<210> SEQ ID NO 53
<211> LENGTH: 107
<212> TYPE: PRT
<213> ORGANISM: Homo sapiens

<400> SEQUENCE: 53

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Cys
                 85                  90                  95

Ser Phe Gly Gln Gly Thr Lys Leu Glu Ile Lys
            100                 105
```

<210> SEQ ID NO 54
<211> LENGTH: 355
<212> TYPE: DNA
<213> ORGANISM: Homo sapiens

<400> SEQUENCE: 54

```
caggtgcagc tgcaggagtc gggcccagga ctggtgaagc ctttacagac cctgtccctc    60
acctgcactg tctctggtgg ctccatcagc agtggtgttt actactggag ctggatccgc   120
cagcacccag ggaagggcct ggagtggatt gggtacatct ataacagtaa gacctcctat   180
tataatccgt ccctcaagag tcgacttacc ctatcagtag acacgtctaa gaaccagttc   240
tccctgaacc tgatctctgt gactgccgcg gacacggccg tgtattactg tgcgagagat   300
```
aaattgggga tcgcggacta ctggggccag ggaaccctgg tcaccgtctc ctcag    355

<210> SEQ ID NO 55
<211> LENGTH: 118
<212> TYPE: PRT
<213> ORGANISM: Homo sapiens

<400> SEQUENCE: 55

Gln Val Gln Leu Gln Glu Ser Gly Pro Gly Leu Val Lys Pro Leu Gln
1               5                   10                  15

Thr Leu Ser Leu Thr Cys Thr Val Ser Gly Gly Ser Ile Ser Ser Gly
            20                  25                  30

Val Tyr Tyr Trp Ser Trp Ile Arg Gln His Pro Gly Lys Gly Leu Glu
        35                  40                  45

Trp Ile Gly Tyr Ile Tyr Asn Ser Lys Thr Ser Tyr Tyr Asn Pro Ser
    50                  55                  60

Leu Lys Ser Arg Leu Thr Leu Ser Val Asp Thr Ser Lys Asn Gln Phe
65                  70                  75                  80

Ser Leu Asn Leu Ile Ser Val Thr Ala Ala Asp Thr Ala Val Tyr Tyr
                85                  90                  95

Cys Ala Arg Asp Lys Leu Gly Ile Ala Asp Tyr Trp Gly Gln Gly Thr
            100                 105                 110

Leu Val Thr Val Ser Ser
        115

<210> SEQ ID NO 56
<211> LENGTH: 322
<212> TYPE: DNA
<213> ORGANISM: Homo sapiens

<400> SEQUENCE: 56
gacatccaga tgacccagtc tccatcctcc ctgtctgcat ctgtaggaga cagagtcacc    60
atcacttgcc ggacaagtca gggcattaga aatgatttag ctggtatca gcagaaacca   120 gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagct accctcccac tttcggcgga   300
gggaccaagg tggagatcaa ac                                            322

<210> SEQ ID NO 57
<211> LENGTH: 107
<212> TYPE: PRT
<213> ORGANISM: Homo sapiens

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

```
Glu Asp Phe Ala Thr Tyr Tyr Cys Leu Gln His Asn Ser Tyr Pro Pro
                85                  90                  95

Thr Phe Gly Gly Gly Thr Lys Val Glu Ile Lys
        100                 105

<210> SEQ ID NO 58
<211> LENGTH: 34
<212> TYPE: PRT
<213> ORGANISM: Homo sapiens

<400> SEQUENCE: 58

Gly Ala Ser Ile Ser Ser Tyr Tyr Trp Ser Tyr Ile Tyr Ser Gly
    1               5                   10                  15
    Ser Thr Asn Tyr Asn Pro Ser Leu Lys Ser Glu Arg Leu Gly Ile Gly
                20                  25                  30
    Asp Tyr

<210> SEQ ID NO 59
<211> LENGTH: 41
<212> TYPE: PRT
<213> ORGANISM: Homo sapiens

<400> SEQUENCE: 59

Gly Phe Thr Phe Ser Ser Tyr Gly Met His Val Ile Ser Tyr Asp Gly
1               5                   10                  15

Ser Asn Lys Tyr Tyr Ala Asp Ser Val Lys Gly Asp His Gly Gly Arg
            20                  25                  30

Tyr Val Tyr Asp Tyr Gly Met Asp Val
        35                  40

<210> SEQ ID NO 60
<211> LENGTH: 34
<212> TYPE: PRT
<213> ORGANISM: Homo sapiens

<400> SEQUENCE: 60

Gly Phe Thr Phe Ser Lys Tyr Gly Met His Val Leu Trp Tyr Asp Gly
    1               5                   10                  15
    Ser Asn Lys Tyr Tyr Ala Asp Ser Val Lys Gly Asp Gly His Tyr Phe
                20                  25                  30
    Asp Tyr

<210> SEQ ID NO 61
<211> LENGTH: 34
<212> TYPE: PRT
<213> ORGANISM: Homo sapiens

<400> SEQUENCE: 61

Gly Phe Thr Phe Ser Ser Tyr Gly Met His Val Ile Trp Phe Asp Gly
1               5                   10                  15

Asn Asn Lys Phe Tyr Ala Asp Ser Val Lys Gly Ala Pro Ala Tyr Trp
            20                  25                  30

Asp Tyr

<210> SEQ ID NO 62
<211> LENGTH: 27
<212> TYPE: PRT
<213> ORGANISM: Homo sapiens

<400> SEQUENCE: 62

Arg Ala Ser Gln Gly Ile Arg Asn Asp Leu Gly Ala Ala Ser Ser Leu
1               5                   10                  15
```

```
Gln Ser Leu Gln His Asn Thr Tyr Pro Pro Thr
            20                  25

<210> SEQ ID NO 63
<211> LENGTH: 27
<212> TYPE: PRT
<213> ORGANISM: Homo sapiens

<400> SEQUENCE: 63

Arg Ala Ser Gln Gly Ile Ser Ser Trp Leu Ala Ala Ser Thr Leu
1               5                   10                  15

Gln Arg Gln Gln Ala Asn Ser Phe Pro Phe Thr
            20                  25

<210> SEQ ID NO 64
<211> LENGTH: 29
<212> TYPE: PRT
<213> ORGANISM: Homo sapiens

<400> SEQUENCE: 64

Arg Ala Ser Gln Gly Ile Ser Ser Trp Leu Val Ala Leu Ala Ala Ser
1               5                   10                  15

Ser Leu Gln Arg Gln Gln Ala Asn Ser Phe Pro Phe Thr
            20                  25

<210> SEQ ID NO 65
<211> LENGTH: 27
<212> TYPE: PRT
<213> ORGANISM: Homo sapiens

<400> SEQUENCE: 65

Arg Ala Ser Gln Gly Ile Ser Ser Trp Leu Ala Ala Ser Ser Leu
1               5                   10                  15

Gln Arg Gln Gln Ala Asn Ser Phe Pro Phe Thr
            20                  25

<210> SEQ ID NO 66
<211> LENGTH: 27
<212> TYPE: PRT
<213> ORGANISM: Homo sapiens

<400> SEQUENCE: 66

Arg Ala Ser Gln Gly Ile Gly Ser Trp Leu Ala Ala Ala Ser Ser Leu
1               5                   10                  15

Gln Arg Gln Gln Ala Asn Ser Phe Pro Phe Thr
            20                  25

<210> SEQ ID NO 67
<211> LENGTH: 32
<212> TYPE: PRT
<213> ORGANISM: Homo sapiens

<400> SEQUENCE: 67

Arg Ser Arg Gln Ser Leu Val His Ser Asp Gly Asn Thr Tyr Leu Asn
1               5                   10                  15

Lys Thr Ser Asn Arg Phe Ser Met Gln Ala Thr Gln Phe Pro Ile Thr
            20                  25                  30

<210> SEQ ID NO 68
<211> LENGTH: 28
<212> TYPE: PRT
<213> ORGANISM: Homo sapiens
```

-continued

```
<400> SEQUENCE: 68

Arg Ala Ser Gln Ser Val Ser Ser Ser Tyr Leu Ala Gly Ala Ser Ser
 1               5                  10                  15

Arg Ala Thr Gln Gln Tyr Gly Ser Ser Pro Trp Thr
             20                  25

<210> SEQ ID NO 69
<211> LENGTH: 1990
<212> TYPE: DNA
<213> ORGANISM: Homo sapiens

<400> SEQUENCE: 69
atgaagcatc tgtggttctt ccttctccta gtggcagctc ccagatgggt cctgtcccag      60
gtgcagctgc aggagtcggg cccaggactg gtgaagcctt cggagaccct gtccctcacc     120
tgcactgtct ctggtgcctc catcagtagt tactactgga gctggatccg gcagccccca     180
gggaagggac tggagtggat tgggtatatc tattacagtg ggagcaccaa ctacaacccc     240
tccctcaaga gtcgagtcac catatcagta gacacgtcca agaaccagtt ctccctgaag     300
ctgaggtctg tgaccgctgc ggacacggcc gtgtattact gtgcgagaga gcgactgggg     360
atcggggact actggggcca aggaaccctg gtcaccgtct cctcagcctc caccaagggc     420
ccatcggtct tccccctggc gccctgctct agaagcacct ccgagagcac agccgccctg     480
ggctgcctgg tcaaggacta cttccccgaa ccggtgacgg tgtcgtggaa ctcaggcgct     540
ctgaccagcg gcgtgcacac cttcccagct gtcctacagt cctcaggact ctactccctc     600
agcagcgtgg tgaccgtgcc ctccagcaac ttcggcaccc agacctacac ctgcaacgta     660
gatcacaagc ccagcaacac caaggtggac aagacagttg gtgagaggcc agctcaggga     720
gggagggtgt ctgctggaag ccaggctcag ccctcctgcc tggacgcacc ccggctgtgc     780
agccccagcc cagggcagca aggcaggccc catctgtctc ctcacccgga ggcctctgcc     840
cgccccactc atgctcaggg agagggtctt ctggcttttt ccaccaggct ccaggcaggc     900
acaggctggg tgcccctacc ccaggccctt cacacacagg gcaggtgct tggctcagac     960 ctgccaaaag ccatatccgg gaggaccctg cccctgacct aagccgaccc caaaggccaa    1020
actgtccact ccctcagctc ggacaccttc tctcctccca gatccgagta actcccaatc    1080
ttctctctgc agagcgcaaa tgttgtgtcg agtgcccacc gtgcccaggt aagccagccc    1140
aggcctcgcc ctccagctca aggcgggaca ggtgccctag agtagcctgc atccagggac    1200
aggccccagc tgggtgctga cacgtccacc tccatctctt cctcagcacc acctgtggca    1260
ggaccgtcag tcttcctctt ccccccaaaa cccaaggaca ccctcatgat ctcccggacc    1320
cctgaggtca cgtgcgtggt ggtggacgtg agccacgaag accccgaggt ccagttcaac    1380
tggtacgtgg acggcgtgga ggtgcataat gccaagacaa agccacggga ggagcagttc    1440
aacagcacgt tccgtgtggt cagcgtcctc accgttgtgc accaggactg gctgaacggc    1500
aaggagtaca agtgcaaggt ctccaacaaa ggcctcccag cccccatcga gaaaaccatc    1560
tccaaaacca aggtgggacc cgcggggta tgagggccac atggacagag gccggctcgg    1620 cccacccttct gcctgggag tgaccgctgt gccaacctct gtcctacag ggcagccccg    1680 agaaccacag gtgtacaccc tgcccccatc ccggaggag atgaccaaga ccaggtcag     1740 cctgacctgc ctggtcaaag cttctaccc cagcgacatc gccgtggagt gggagagcaa    1800
tgggcagccg gagaacaact acaagaccac acctcccatg ctggactccg acggctcctt    1860
cttcctctac agcaagctca ccgtggacaa gagcaggtgg cagcagggga acgtcttctc    1920
```

```
atgctccgtg atgcatgagg ctctgcacaa ccactacacg cagaagagcc tctccctgtc    1980
tccgggtaaa                                                           1990

<210> SEQ ID NO 70
<211> LENGTH: 1990
<212> TYPE: DNA
<213> ORGANISM: Homo sapiens

<400> SEQUENCE: 70
tttacccgga gacagggaga ggctcttctg cgtgtagtgg ttgtgcagag cctcatgcat      60
cacggagcat gagaagacgt tcccctgctg ccacctgctc ttgtccacgg tgagcttgct     120
gtagaggaag aaggagccgt cggagtccag catgggaggt gtggtcttgt agttgttctc     180
cggctgccca ttgctctccc actccacggc gatgtcgctg gggtagaagc ctttgaccag     240
gcaggtcagg ctgacctggt tcttggtcat ctcctcccgg gatggggggca gggtgtacac    300 ctgtggttct cggggctgcc ctgtagggac agaggttggc acagcggtca ctcccagggc     360
agagggtggg ccgagccggc ctctgtccat gtggccctca taccccgcgg gtcccacctt     420 tggtttttgga gatggttttc tcgatggggg ctgggaggcc tttgttggag accttgcact    480
tgtactcctt gccgttcagc cagtcctggt gcacaacggt gaggacgctg accacacgga    540
acgtgctgtt gaactgctcc tcccgtggct ttgtcttggc attatgcacc tccacgccgt    600
ccacgtacca gttgaactgg acctcggggt cttcgtggct cacgtccacc accacgcacg    660
tgacctcagg ggtccgggag atcatgaggg tgtccttggg ttttgggggg aagaggaaga   720
ctgacggtcc tgccacaggt ggtgctgagg aagagatgga ggtggacgtg tcagcaccca    780
gctggggcct gtccctggat gcaggctact ctagggcacc tgtcccgcct tgagctggag     840
ggcgaggcct gggctggctt acctgggcac ggtgggcact cgacacaaca tttgcgctct     900
gcagagagaa gattgggagt tactcggatc tgggaggaga gaaggtgtcc gagctgaggg    960
agtggacagt ttggcctttg gggtcggctt aggtcagggg cagggtcctc ccggatatgg    1020
cttttggcag gtctgagcca agcacctgcc cctgtgtgtg aagggcctgg ggtaggggca    1080
cccagcctgt gcctgcctgg agcctggtgg aaaaagccag aagaccctct ccctgagcat     1140
gagtggggcg ggcagaggcc tccgggtgag gagacagatg gggcctgcct tgctgccctg    1200
ggctggggct gcacagccgg ggtgcgtcca ggcaggaggg ctgagcctgg cttccagcag    1260
acaccctccc tccctgagct ggcctctcac caactgtctt gtccaccttg gtgttgctgg    1320
gcttgtgatc tacgttgcag gtgtaggtct gggtgccgaa gttgctggag gcacggtca    1380 ccacgctgct gagggagtag agtcctgagg actgtaggac agctgggaag gtgtgcacgc    1440
cgctggtcag agcgcctgag ttccacgaca ccgtcaccgg ttcggggaag tagtccttga    1500
ccaggcagcc cagggcggct gtgctctcgg aggtgcttct agagcagggc gccaggggga    1560
agaccgatgg gcccttggtg gaggctgagg agacggtgac cagggttcct tggccccagt    1620
agtccccgat ccccagtcgc tctctcgcac agtaatacac ggccgtgtcc gcagcggtca    1680
cagacctcag cttcagggag aactggttct tggacgtgtc tactgatatg gtgactcgac    1740
tcttgaggga ggggttgtag ttggtgctcc cactgtaata gatataccca atccactcca    1800
gtcccttccc tggggctgc cggatccagc tccagtagta actactgatg gaggcaccag    1860
agacagtgca ggtgagggac agggtctccg aaggcttcac cagtcctggg cccgactcct    1920
gcagctgcac ctgggacagg acccatctgg gagctgccac taggagaagg aagaaccaca   1980
```
gatgcttcat                                                                    1990

<210> SEQ ID NO 71
<211> LENGTH: 241
<212> TYPE: PRT
<213> ORGANISM: Homo sapiens

<400> SEQUENCE: 71

Met Lys His Leu Trp Phe Phe Leu Leu Leu Val Ala Leu Ala Ala Pro
1               5                   10                  15

Arg Trp Val Leu Ser Gln Val Gln Leu Gln Glu Ser Gly Pro Gly Leu
            20                  25                  30

Val Lys Pro Ser Glu Thr Leu Ser Leu Thr Cys Thr Val Ser Gly Ala
        35                  40                  45

Ser Ile Ser Ser Tyr Tyr Trp Ser Trp Ile Arg Gln Pro Pro Gly Lys
    50                  55                  60

Gly Leu Glu Trp Ile Gly Tyr Ile Tyr Tyr Ser Gly Ser Thr Asn Tyr
65                  70                  75                  80

Asn Pro Ser Leu Lys Ser Arg Val Thr Ile Ser Val Ala Ser Pro Thr
                85                  90                  95

Ser Lys Asn Gln Phe Ser Leu Lys Leu Arg Ser Val Thr Ala Ala Asp
            100                 105                 110

Thr Ala Val Tyr Tyr Cys Ala Arg Glu Arg Leu Gly Ile Gly Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Ala Ser Pro His Lys Pro Ser Asn Thr Lys Val Ala Ser Pro Lys Thr
225                 230                 235                 240

Val

<210> SEQ ID NO 72
<211> LENGTH: 12
<212> TYPE: PRT
<213> ORGANISM: Homo sapiens

<400> SEQUENCE: 72

Glu Arg Lys Cys Cys Val Glu Cys Pro Pro Cys Pro
1               5                   10

<210> SEQ ID NO 73
<211> LENGTH: 115
<212> TYPE: PRT
<213> ORGANISM: Homo sapiens

<400> SEQUENCE: 73

Ala Pro Pro Val Ala Leu Ala Gly Pro Ser Val Phe Leu Phe Pro Pro
1               5                   10                  15

```
Lys Pro Lys Asp Thr Leu Met Ile Ser Arg Thr Pro Glu Val Thr Cys
            20                  25                  30

Val Val Val Ala Ser Pro Val Ser His Glu Asp Pro Glu Val Gln Phe
            35                  40                  45

Asn Trp Tyr Val Ala Ser Pro Gly Val Glu Val His Asn Ala Lys Thr
 50                  55                  60

Lys Pro Arg Glu Glu Gln Phe Asn Ser Thr Phe Arg Val Val Ser Val
 65                  70                  75                  80

Leu Thr Val Val His Gln Asp Trp Leu Asn Gly Lys Glu Tyr Lys Cys
                 85                  90                  95

Lys Val Ser Asn Lys Gly Leu Pro Ala Pro Ile Glu Lys Thr Ile Ser
                100                 105                 110

Lys Thr Lys
        115

<210> SEQ ID NO 74
<211> LENGTH: 107
<212> TYPE: PRT
<213> ORGANISM: Homo sapiens

<400> SEQUENCE: 74

Gly Gln Pro Arg Glu Pro Gln Val Tyr Thr Leu Pro Pro Ser Arg Glu
 1               5                  10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
         35                  40                  45

Asn Asn Tyr Lys Thr Thr Pro Pro Met Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
                100                 105

<210> SEQ ID NO 75
<211> LENGTH: 310
<212> TYPE: PRT
<213> ORGANISM: Homo sapiens

<400> SEQUENCE: 75

Ser Thr Ser Glu Ser Thr Ala Ala Leu Gly Cys Leu Val Lys Asp Tyr
 1               5                  10                  15

Phe Pro Glu Pro Val Thr Val Ser Trp Asn Ser Gly Ala Leu Thr Ser
            20                  25                  30

Gly Val His Thr Phe Pro Ala Val Leu Gln Ser Ser Gly Leu Tyr Ser
            35                  40                  45

Leu Ser Ser Val Val Thr Val Pro Ser Ser Asn Phe Gly Thr Gln Thr
 50                  55                  60

Tyr Thr Cys Asn Val Asp His Lys Pro Ser Asn Thr Lys Val Asp Lys
 65                  70                  75                  80

Thr Val Glu Arg Lys Cys Cys Val Glu Cys Pro Pro Cys Pro Ala Pro
                 85                  90                  95

Pro Val Ala Gly Pro Ser Val Phe Leu Phe Pro Pro Lys Pro Lys Asp
                100                 105                 110
```

Thr Leu Met Ile Ser Arg Thr Pro Glu Val Thr Cys Val Val Val Asp
    115                 120                 125

Val Ser His Glu Asp Pro Glu Val Gln Phe Asn Trp Tyr Val Asp Gly
130                 135                 140

Val Glu Val His Asn Ala Lys Thr Lys Pro Arg Glu Glu Gln Phe Asn
145                 150                 155                 160

Ser Thr Phe Arg Val Val Ser Val Leu Thr Val His Gln Asp Trp
                165                 170                 175

Leu Asn Gly Lys Glu Tyr Lys Cys Lys Val Ser Asn Lys Gly Leu Pro
            180                 185                 190

Ala Pro Ile Glu Lys Thr Ile Ser Lys Thr Lys Gly Gln Pro Arg Glu
            195                 200                 205

Pro Gln Val Tyr Thr Leu Pro Pro Ser Arg Glu Glu Met Thr Lys Asn
210                 215                 220

Gln Val Ser Leu Thr Cys Leu Val Lys Gly Phe Tyr Pro Ser Asp Ile
225                 230                 235                 240

Ala Val Glu Trp Glu Ser Asn Gly Gln Pro Glu Asn Asn Tyr Lys Thr
                245                 250                 255

Thr Pro Pro Met Leu Asp Ser Asp Gly Ser Phe Phe Leu Tyr Ser Lys
            260                 265                 270

Leu Thr Val Asp Lys Ser Arg Trp Gln Gln Gly Asn Val Phe Ser Cys
        275                 280                 285

Ser Val Met His Glu Ala Leu His Asn His Tyr Thr Gln Lys Ser Leu
    290                 295                 300

Ser Leu Ser Pro Gly Lys
305                 310

<210> SEQ ID NO 76
<211> LENGTH: 552
<212> TYPE: DNA
<213> ORGANISM: Homo sapiens

<400> SEQUENCE: 76
atgagggtcc ccgctcagct cctggggctc ctgctgctct ggttcccagg tgccaggtgt      60
aagcttgaca tccagctgac ccaatctcca tcctccctgt ctgcatctgt aggagacaga     120
gtcaccatca cttgccgggc aagtcagggc attagaaatg atttaggctg gtatcagcag     180
aaaccaggga aagcccctaa gcgcctgatc tatgctgcat ccagtttgca aagtggggtc     240
ccatcaaggt tcagcggcag tggatctggg acagaattca ctctcacaat cagcagcctg     300
cagcctgaag attttgcaac ttattactgt ctacagcata tacttacccc tcgacgttc      360 ggccaaggga ccaaggtgga aatcaaacga actgtggctg caccatctgt cttcatcttc     420
ccgccatctg atgagcagtt gaaatctgga actgctagcg ttgtgtgcct gctgaataac     480
ttctatccca gagaggccaa agtacagtgg aaggtggata cgccctccaa tcgggtaac      540 tcccaggaga gt                                                         552

<210> SEQ ID NO 77
<211> LENGTH: 552
<212> TYPE: DNA
<213> ORGANISM: Homo sapiens

<400> SEQUENCE: 77
actctcctgg gagttacccg attggagggc gttatccacc ttccactgta ctttggcctc      60
tctgggatag aagttattca gcaggcacac aacgctagca gttccagatt tcaactgctc     120

-continued

```
atcagatggc gggaagatga agacagatgg tgcagccaca gttcgtttga tttccacctt    180
ggtcccttgg ccgaacgtcg gagggtaagt attatgctgt agacagtaat aagttgcaaa    240
atcttcaggc tgcaggctgc tgattgtgag agtgaattct gtcccagatc cactgccgct    300
gaaccttgat gggaccccac tttgcaaact ggatgcagca tagatcaggc gcttaggggc    360
tttccctggt ttctgctgat accagcctaa atcatttcta atgccctgac ttgcccggca    420
agtgatggtg actctgtctc ctacagatgc agacagggag gatggagatt gggtcagctg    480
gatgtcaagc ttacacctgg cacctgggaa ccagagcagc aggagcccca ggagctgagc    540
ggggaccctc at                                                        552
```

<210> SEQ ID NO 78
<211> LENGTH: 184
<212> TYPE: PRT
<213> ORGANISM: Homo sapiens

<400> SEQUENCE: 78

Met Arg Val Pro Ala Gln Leu Leu Gly Leu Leu Leu Leu Trp Phe Pro
1               5                   10                  15

Gly Ala Arg Cys Lys Leu Asp Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Thr Tyr Pro Pro Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser
            180

<210> SEQ ID NO 79
<211> LENGTH: 31
<212> TYPE: PRT
<213> ORGANISM: Homo sapiens

<400> SEQUENCE: 79

Val Val Cys Leu Leu Asn Asn Phe Tyr Pro Arg Glu Ala Lys Val Gln
1               5                   10                  15

Trp Lys Val Asp Asn Ala Leu Gln Ser Gly Asn Ser Gln Glu Ser
            20                  25                  30

<210> SEQ ID NO 80
<211> LENGTH: 2011
<212> TYPE: DNA
<213> ORGANISM: Homo sapiens

<400> SEQUENCE: 80

```
atggaattgg ggctccgctg ggttttcctc gttgctcttt taagaggtgt ccagtgtcag      60
gtgcagctgg tggagtctgg gggaggcgtg gtccagcctg gaggtccct gagactctcc      120
tgtgtagcct ctggattcac cttcagtagc tatggcatgc actgggtccg ccaggctcca     180
ggcaaggggc tggagtgggt ggcagttata tcatatgatg aagtaataa atactatgca      240
gactccgtga agggccgatt caccatctcc agagacaatt ccaagaacac gctgtatctg     300
caaatgaaca gcctgagagt tgaggacacg gctgtgtatt actgtgcgag agatcacggt    360
gggaggtacg tctacgacta cggtatggac gtctggggcc aagggaccac ggtcaccgtc    420
tcctcagcct ccaccaaggg cccatcggtc ttccccctgg cgccctgctc tagaagcacc    480
tccgagagca cagccgccct gggctgcctg gtcaaggact acttccccga accggtgacg    540
gtgtcgtgga actcaggcgc tctgaccagc ggcgtgcaca ccttcccagc tgtcctacag    600
tcctcaggac tctactccct cagcagcgtg gtgaccgtgc cctccagcaa cttcggcacc    660
cagacctaca cctgcaacgt agatcacaag cccagcaaca ccaaggtgga caagacagtt    720
ggtgagaggc cagctcaggg agggagggtg tctgctggaa gccaggctca gccctcctgc    780
ctggacgcac cccggctgtg cagccccagc caagggcagc aaggcaggcc catctgtct    840
cctcacccgg aggcctctgc ccgccccact catgctcagg gagagggtct tctggctttt    900
tccaccaggc tccaggcagg cacaggctgg gtgcccctac cccaggccct tcacacacag    960
gggcaggtgc ttggctcaga cctgccaaaa gccatatccg gaggaccct gcccctgacc    1020
taagccgacc ccaaaggcca aactgtccac tccctcagct cggacacctt ctctcctccc    1080
agatccgagt aactcccaat cttctctctg cagagcgcaa atgttgtgtc gagtgccac    1140
cgtgcccagg taagccagcc caggcctcgc cctccagctc aaggcgggac aggtgcccta   1200
gagtagcctg catccaggga caggcccag ctgggtgctg acacgtccac ctccatctct    1260
tcctcagcac cacctgtggc aggaccgtca gtcttcctct ccccccaaa acccaaggac    1320
acccctcatga tctcccggac ccctgaggtc acgtgcgtgg tggtggacgt gagccacgaa   1380
gaccccgagg tccagttcaa ctggtacgtg gacggcgtgg aggtgcataa tgccaagaca    1440
aagccacggg aggagcagtt caacagcacg ttccgtgtgg tcagcgtcct caccgttgtg   1500
caccaggact ggctgaacgg caaggagtac aagtgcaagg tctccaacaa aggcctccca   1560
gcccccatcg agaaaaccat ctccaaaacc aaaggtggga cccgcggggt atgagggcca   1620
catggacaga ggccggctcg gcccaccctc tgccctggga gtgaccgctg tgccaacctc   1680
tgtccctaca gggcagcccc gagaaccaca ggtgtacacc ctgccccccat cccgggagga   1740
gatgaccaag aaccaggtca gcctgacctg cctggtcaaa ggcttctacc ccagcgacat    1800
cgccgtggag tgggagagca atgggcagcc ggagaacaac tacaagacca cctctcccat   1860
gctggactcc gacggctcct tcttcctcta cagcaagctc accgtggaca gagcaggtg    1920
gcagcagggg aacgtcttct catgctccgt gatgcatgag gctctgcaca accactacac   1980
gcagaagagc ctctccctgt ctccgggtaa a                                    2011
```

<210> SEQ ID NO 81
<211> LENGTH: 2011
<212> TYPE: DNA
<213> ORGANISM: Homo sapiens

<400> SEQUENCE: 81

```
tttacccgga gacagggaga ggctcttctg cgtgtagtgg ttgtgcagag cctcatgcat      60
cacggagcat gagaagacgt tcccctgctg ccacctgctc ttgtccacgg tgagcttgct     120
gtagaggaag aaggagccgt cggagtccag catgggaggt gtggtcttgt agttgttctc     180
cggctgccca ttgctctccc actccacggc gatgtcgctg gggtagaagc ctttgaccag     240
gcaggtcagg ctgacctggt tcttggtcat ctcctcccgg gatggggggca gggtgtacac     300
ctgtggttct cggggctgcc ctgtaggggac agaggttggc acagcggtca ctcccagggc     360
agagggtggg ccgagccggc ctctgtccat gtggccctca taccccgcgg gtcccacctt     420
tggttttgga gatggttttc tcgatgggggg ctggaggcc tttgttggag accttgcact     480
tgtactcctt gccgttcagc cagtcctggt gcacaacggt gaggacgctg accacacgga     540
acgtgctgtt gaactgctcc tcccgtggct ttgtcttggc attatgcacc tccacgccgt     600
ccacgtacca gttgaactgg acctcggggt cttcgtggct cacgtccacc accacgcacg     660
tgacctcagg ggtccgggag atcatgaggg tgtccttggg ttttgggggg aagaggaaga     720
ctgacggtcc tgccacaggt ggtgctgagg aagagatgga ggtggacgtg tcagcaccca     780
gctggggcct gtccctggat gcaggctact ctagggcacc tgtcccgcct tgagctggag     840
ggcgaggcct gggctggctt acctgggcac ggtgggcact cgacacaaca tttgcgctct     900
gcagagagaa gattgggagt tactcggatc tgggaggaga gaaggtgtcc gagctgaggg     960
agtggacagt ttggcctttg gggtcggctt aggtcagggg cagggtcctc ccggatatgg    1020
cttttggcag gtctgagcca agcacctgcc cctgtgtgtg aagggcctgg ggtagggggca    1080
cccagcctgt gcctgcctgg agcctggtgg aaaaagccag aagaccctct ccctgagcat    1140
gagtgggggcg ggcagaggcc tccgggtgag gagacagatg gggcctgcct tgctgccctg    1200
ggctggggct gcacagccgg ggtgcgtcca ggcaggaggg ctgagcctgg cttccagcag    1260
acaccctccc tccctgagct ggcctctcac caactgtctt gtccaccttg tgttgctgg     1320
gcttgtgatc tacgttgcag gtgtaggtct gggtgccgaa gttgctggag ggcacggtca    1380
ccacgctgct gagggagtag agtcctgagg actgtaggac agctgggaag gtgtgcacgc    1440
cgctggtcag agcgcctgag ttccacgaca ccgtcaccgg ttcggggaag tagtccttga    1500
ccaggcagcc cagggcggct gtgctctcgg aggtgcttct agagcagggc gccaggggga    1560
agaccgatgg gcccttggtg gaggctgagg agacggtgac cgtggtccct tggccccaga    1620
cgtccatacc gtagtcgtag acgtacctcc caccgtgatc tctcgcacag taatacacag    1680
ccgtgtcctc aactctcagg ctgttcattt gcagatacag cgtgttcttg gaattgtctc    1740
tggagatggt gaatcggccc ttcacggagt ctgcatagta tttattactt ccatcatatg    1800
atataactgc cacccactcc agccccttgc ctggagcctg gcggacccag tgcatgccat    1860
agctactgaa ggtgaatcca gaggctacac aggagagtct cagggacctc ccaggctgga    1920
ccacgcctcc cccagactcc accagctgca cctgacactg gacacctctt aaaagagcaa    1980
cgaggaaaac ccagcggagc cccaattcca t                                   2011
```

<210> SEQ ID NO 82
<211> LENGTH: 252
<212> TYPE: PRT
<213> ORGANISM: Homo sapiens

<400> SEQUENCE: 82

Met Glu Leu Gly Leu Arg Trp Val Phe Leu Val Ala Leu Ala Leu Leu
1               5                   10                  15

```
Arg Gly Val Gln Cys Gln Val Gln Leu Val Glu Ser Gly Gly Gly Val
            20                  25                  30
Val Gln Pro Gly Arg Ser Leu Arg Leu Ser Cys Val Ala Leu Ala Ser
        35                  40                  45
Gly Phe Thr Phe Ser Ser Tyr Gly Met His Trp Val Ala Arg Gly Gln
    50                  55                  60
Ala Pro Gly Lys Gly Leu Glu Trp Val Ala Leu Ala Val Ile Ser Tyr
65                  70                  75                  80
Asp Gly Ser Asn Lys Tyr Tyr Ala Asp Ser Val Lys Gly Arg Phe Thr
                85                  90                  95
Ile Ser Arg Asp Asn Ser Lys Asn Thr Leu Tyr Leu Gln Met Asn Ser
            100                 105                 110
Leu Arg Val Glu Asp Thr Ala Val Tyr Tyr Cys Ala Arg Asp His Gly
        115                 120                 125
Gly Arg Tyr Val Tyr Asp Tyr Gly Met Asp Val Trp Gly Gln Gly Thr
    130                 135                 140
Thr Val Thr Val Ser Ser Ala Ser Thr Lys Gly Pro Ser Val Phe Pro
145                 150                 155                 160
Leu Ala Pro Cys Ser Arg Ser Thr Ser Glu Ser Thr Ala Ala Leu Gly
                165                 170                 175
Cys Leu Val Lys Asp Tyr Phe Pro Glu Pro Val Thr Val Ser Trp Asn
            180                 185                 190
Ser Gly Ala Leu Thr Ser Gly Val His Thr Phe Pro Ala Val Leu Gln
        195                 200                 205
Ser Ser Gly Leu Tyr Ser Leu Ser Ser Val Val Thr Val Pro Ser Ser
    210                 215                 220
Asn Phe Gly Thr Gln Thr Tyr Thr Cys Asn Val Ala Ser Pro His Lys
225                 230                 235                 240
Pro Ser Asn Thr Lys Val Ala Ser Pro Lys Thr Val
                245                 250
```

<210> SEQ ID NO 83
<211> LENGTH: 752
<212> TYPE: DNA
<213> ORGANISM: Homo sapiens

<400> SEQUENCE: 83

```
atgagggtcc ccgctcagct cctggggctc ctgctgctct ggttcccagg ttccagatgc     60
gacatccaga tgacccaatc tccatcttcc gtgtctgcat ctataggaga cagagtctcc    120
atcacttgtc gggcgagtca gggtattagc agctggttag cctggtatca gcagaaacca    180
gggaaagccc ctacgctcct tatctatgct gcatccactt tgcaacgtgg ggtcccatca    240
aggttcagcg gcagtggatc tgggacagat ttcactctca ccatcagcag cctgcagcct    300
gaagattttg caacttactt ttgtcaacag gctaacagtt tcccattcac tttcggccct    360
gggaccaaag tggatatcaa acgaactgtg gctgcaccat ctgtcttcat cttcccgcca    420
tctgatgagc agttgaaatc tggaactgct agcgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggaagtg gtagtcccg gactcgagcg    720
ggcagtgttt ctcgaagttg tccctgagt gt                                  752
```

<210> SEQ ID NO 84
<211> LENGTH: 752
<212> TYPE: DNA
<213> ORGANISM: Homo sapiens

<400> SEQUENCE: 84
acactcaggg gacaacttcg agaaacactg cccgctcgag tccgggacta cccacttccc    60
ctgttgaagc tctttgtgac gggcgagctc aggccctgat gggtgacttc gcaggcgtag   120
actttgtgtt tctcgtagtc tgctttgctc agcgtcaggg tgctgctgag gctgtaggtg   180
ctgtccttgc tgtcctgctc tgtgacactc tcctgggagt tacccgattg gagggcgtta   240
tccaccttcc actgtacttt ggcctctctg ggatagaagt tattcagcag gcacacaacg   300
ctagcagttc cagatttcaa ctgctcatca gatggcggga agatgaagac agatggtgca   360
gccacagttc gtttgatatc cactttggtc ccagggccga aagtgaatgg gaaactgtta   420
gcctgttgac aaaagtaagt tgcaaaatct tcaggctgca ggctgctgat ggtgagagtg   480
aaatctgtcc cagatccact gccgctgaac cttgatggga ccccacgttg caaagtggat   540
gcagcataga taaggagcgt aggggctttc cctggtttct gctgataccaa ggctaaccag   600
ctgctaatac cctgactcgc ccgacaagtg atggagactc tgtctcctat agatgcagac   660
acggaagatg gagattgggt catctggatg tcgcatctgg aacctgggaa ccagagcagc   720
aggagcccca ggagctgagc ggggaccctc at                                  752

<210> SEQ ID NO 85
<211> LENGTH: 234
<212> TYPE: PRT
<213> ORGANISM: Homo sapiens

<400> SEQUENCE: 85

Met Arg Val Pro Ala Gln Leu Leu Gly Leu Leu Leu Leu Trp Phe Pro
 1               5                  10                  15

Gly Ser Arg Cys Asp Ile Gln Met Thr Gln Ser Pro Ser Ser Val Ser
            20                  25                  30

Ala Ser Ile Gly Asp Arg Val Ser Ile Thr Cys Arg Ala Ser Gln Gly
        35                  40                  45

Ile Ser Ser Trp Leu Ala Trp Tyr Gln Gln Lys Pro Gly Lys Ala Pro
    50                  55                  60

Thr Leu Leu Ile Tyr Ala Ala Ser Thr Leu Gln Arg Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Phe Cys Gln Gln Ala Asn
            100                 105                 110

Ser Phe Pro Phe Thr Phe Gly Pro Gly Thr Lys Val Asp Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys

```
              195                 200                 205
    His Lys Val Tyr Ala Cys Glu Val Thr His Gln Gly Leu Ser Ser Pro
        210                 215                 220

Val Thr Lys Ser Phe Asn Arg Gly Glu Cys
    225                 230

<210> SEQ ID NO 86
<211> LENGTH: 1990
<212> TYPE: DNA
<213> ORGANISM: Homo sapiens

<400> SEQUENCE: 86
atgaagcatc tgtggttctt ccttctcctg gtggcagctc ccagatgggt cctgtcccag      60
gtgcagctgc aggagtcggg cccaggactg gtgaagcctt cggagaccct gtccctcacc     120
tgcactgtct ctggtgcctc catcagtaat tactactgga gctggatccg cagcccccca     180
gggaagggac tggagtggat tgggtatgtc tcttacagtg ggagtacgta ctacaacccc     240
tccctcaagg gtcgagtcac catgtcagta gacacgtcca agaaccagtt ctccctgaag     300
ctgagctctg tgaccgctgc ggacacggcc gtgtattact gtgcgagaga aaaactgggg     360
attggagact actggggcca gggaaccctg gtcaccgtct cctcagcctc caccaagggc     420
ccatcggtct tccccctggc gccctgctct agaagcacct ccgagagcac agccgccctg     480
ggctgcctgg tcaaggacta cttccccgaa ccggtgacgg tgtcgtggaa ctcaggcgct     540
ctgaccagcg gcgtgcacac cttcccagct gtcctacagt cctcaggact ctactccctc     600
agcagcgtgg tgaccgtgcc ctccagcaac ttcggcaccc agacctacac ctgcaacgta     660
gatcacaagc ccagcaacac caaggtggac aagacagttg tgagaggcc agctcaggga     720 gggagggtgt ctgctggaag ccaggctcag ccctcctgcc tggacgcacc ccggctgtgc     780
agccccagcc cagggcagca aggcaggccc catctgtctc ctcacccgga ggcctctgcc     840 cgcccccactc atgctcaggg agagggtctt ctggcttttt ccaccaggct ccaggcaggc     900
acaggctggg tgcccctacc ccaggccctt cacacacagg ggcaggtgct tggctcagac     960
ctgccaaaag ccatatccgg gaggaccctg cccctgacct aagccgaccc caaaggccaa    1020
actgtccact ccctcagctc ggacaccttc tctcctccca gatccgagta actcccaatc    1080
ttctctctgc agagcgcaaa tgttgtgtcg agtgcccacc gtgcccaggt aagccagccc    1140
aggcctcgcc ctccagctca aggcgggaca ggtgccctag agtagcctgc atccagggac    1200
aggccccagc tgggtgctga cacgtccacc tccatctctt cctcagcacc acctgtggca    1260
ggaccgtcag tcttcctctt ccccccaaaa cccaaggaca ccctcatgat ctcccggacc    1320
cctgaggtca cgtgcgtggt ggtggacgtg agccacgaag acccgaggt ccagttcaac    1380 tggtacgtgg acggcgtgga ggtgcataat gccaagacaa agccacggga ggagcagttc    1440
aacagcacgt tccgtgtggt cagcgtcctc accgttgtgc accaggactg gctgaacggc    1500
aaggagtaca agtgcaaggt ctccaacaaa ggcctcccag ccccatcga gaaaaccatc    1560 tccaaaacca aagtgggac ccgcgggta tgagggccac atggacagag gccggctcgg    1620 cccacccctct gcctgggag tgaccgctgt gccaacctct gtccctacag ggcagccccg    1680
agaaccacag gtgtacaccc tgcccccatc ccggaggag atgaccaaga accaggtcag    1740
cctgacctgc ctggtcaaag gcttctaccc cagcgacatc gccgtggagt gggagagcaa    1800
tgggcagccg gagaacaact acaagaccac acctcccatg ctggactccg acggctcctt    1860
cttcctctac agcaagctca ccgtggacaa gagcaggtgg cagcagggga acgtcttctc    1920
```

```
atgctccgtg atgcatgagg ctctgcacaa ccactacacg cagaagagcc tctccctgtc    1980
tccgggtaaa                                                            1990

<210> SEQ ID NO 87
<211> LENGTH: 1990
<212> TYPE: DNA
<213> ORGANISM: Homo sapiens

<400> SEQUENCE: 87
tttacccgga gacagggaga ggctcttctg cgtgtagtgg ttgtgcagag cctcatgcat      60
cacggagcat gagaagacgt tcccctgctg ccacctgctc ttgtccacgg tgagcttgct     120
gtagaggaag aaggagccgt cggagtccag catgggaggt gtggtcttgt agttgttctc     180
cggctgccca ttgctctccc actccacggc gatgtcgctg gggtagaagc ctttgaccag     240
gcaggtcagg ctgacctggt tcttggtcat ctcctcccgg gatgggggca gggtgtacac     300
ctgtggttct cggggctgcc ctgtagggac agaggttggc acagcggtca ctcccagggc     360
agagggtggg ccgagccggc ctctgtccat gtggccctca taccccgcgg gtcccacctt     420
tggttttgga gatggttttc tcgatggggg ctgggaggcc tttgttggag accttgcact     480
tgtactcctt gccgttcagc cagtcctggt gcacaacggt gaggacgctg accacacgga     540
acgtgctgtt gaactgctcc tcccgtggct ttgtcttggc attatgcacc tccacgccgt     600
ccacgtacca gttgaactgg acctcggggt cttcgtggct cacgtccacc accacgcacg     660
tgacctcagg ggtccgggag atcatgaggg tgtccttggg ttttgggggg aagaggaaga     720
ctgacggtcc tgccacaggt ggtgctgagg aagagatgga ggtggacgtg tcagcaccca     780
gctggggcct gtccctggat gcaggctact ctagggcacc tgtcccgcct tgagctggag     840
ggcgaggcct gggctggctt acctgggcac ggtgggcact cgacacaaca tttgcgctct     900
gcagagagaa gattgggagt tactcggatc tgggaggaga gaaggtgtcc gagctgaggg     960
agtggacagt ttggcctttg gggtcggctt aggtcagggg cagggtcctc ccggatatgg    1020
cttttggcag gtctgagcca agcacctgcc cctgtgtgtg aagggcctgg ggtaggggca    1080
cccagcctgt gcctgcctgg agcctggtgg aaaaagccag aagaccctct ccctgagcat    1140
gagtggggcg gcagaggcc  tccgggtgag gagacagatg gggcctgcct tgctgccctg    1200
ggctggggct gcacagccgg ggtgcgtcca ggcaggaggg ctgagcctgg cttccagcag    1260
acaccctccc tccctgagct ggcctctcac caactgtctt gtccaccttg tgttgctgg     1320 gcttgtgatc tacgttgcag gtgtaggtct gggtgccgaa gttgctggag gcacggtca    1380 ccacgctgct gagggagtag agtcctgagg actgtaggac agctgggaag gtgtgcacgc    1440
cgctggtcag agcgcctgag ttccacgaca ccgtcaccgg ttcggggaag tagtccttga    1500
ccaggcagcc cagggcggct gtgctctcgg aggtgcttct agagcagggc gccaggggga    1560
agaccgatgg gcccttggtg gaggctgagg agacggtgac cagggttccc tggccccagt    1620
agtctccaat cccagttttt tctctcgcac agtaatacac ggccgtgtcc gcagcggtca    1680
cagagctcag cttcagggag aactggttct tggacgtgtc tactgacatg gtgactcgac    1740
ccttgaggga ggggttgtag tacgtactcc cactgtaaga gacataccca atccactcca    1800
gtcccttccc tggggctgc cggatccagc tccagtagta attactgatg gaggcaccag    1860
agacagtgca ggtgagggac agggtctccg aaggcttcac cagtcctggg cccgactcct    1920
gcagctgcac ctgggacagg acccatctgg gagctgccac caggagaagg aagaaccaca    1980
```

```
gatgcttcat                                                              1990
```

<210> SEQ ID NO 88
<211> LENGTH: 241
<212> TYPE: PRT
<213> ORGANISM: Homo sapiens

<400> SEQUENCE: 88

Met Lys His Leu Trp Phe Phe Leu Leu Val Ala Leu Ala Ala Pro
1               5                   10                  15

Arg Trp Val Leu Ser Gln Val Gln Leu Gln Glu Ser Gly Pro Gly Leu
            20                  25                  30

Val Lys Pro Ser Glu Thr Leu Ser Leu Thr Cys Thr Val Ser Gly Ala
        35                  40                  45

Ser Ile Ser Asn Tyr Tyr Trp Ser Trp Ile Arg Gln Pro Pro Gly Lys
    50                  55                  60

Gly Leu Glu Trp Ile Gly Tyr Val Ser Tyr Ser Gly Ser Thr Tyr Tyr
65                  70                  75                  80

Asn Pro Ser Leu Lys Gly Arg Val Thr Met Ser Val Ala Ser Pro Thr
                85                  90                  95

Ser Lys Asn Gln Phe Ser Leu Lys Leu Ser Ser Val Thr Ala Ala Asp
            100                 105                 110

Thr Ala Val Tyr Tyr Cys Ala Arg Glu Lys Leu Gly Ile Gly Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Ala Ser Pro His Lys Pro Ser Asn Thr Lys Val Ala Ser Pro Lys Thr
225                 230                 235                 240

Val

<210> SEQ ID NO 89
<211> LENGTH: 702
<212> TYPE: DNA
<213> ORGANISM: Homo sapiens

<400> SEQUENCE: 89

```
atgaggctcc ccgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaagtca gggcattaaa aatgatttag gctggtatca gcagaaacca   180
gggaaagccc ctaagcgcct gatctatgct gcatccagtt tgcaaagtgg ggtcccatca   240
aggttcagcg gcagtggatc tgggacagaa ttcactctca caatcagcag cctgcagcct   300
gaagattttg caacttatta ctgtctacag cataatagtt atccgtgcag ttttggccag   360
gggaccaagc tggagatcaa acgaactgtg gctgcaccat ctgtcttcat cttcccgcca   420
```

```
tctgatgagc agttgaaatc tggaactgct agcgttgtgt gcctgctgaa taacttctat      480
cccagagagg ccaaagtaca gtggaaggtg ataacgccc tccaatcggg taactcccag      540
gagagtgtca cagagcagga cagcaaggac agcacctaca gcctcagcag caccctgacg      600
ctgagcaaag cagactacga gaaacacaaa gtctacgcct gcgaagtcac ccatcagggc      660
ctgagctcgc ccgtcacaaa gagcttcaac aggggagagt gt                        702
```

<210> SEQ ID NO 90
<211> LENGTH: 702
<212> TYPE: DNA
<213> ORGANISM: Homo sapiens

<400> SEQUENCE: 90

```
acactctccc ctgttgaagc tctttgtgac gggcgagctc aggccctgat gggtgacttc       60
gcaggcgtag actttgtgtt tctcgtagtc tgctttgctc agcgtcaggg tgctgctgag      120
gctgtaggtg ctgtccttgc tgtcctgctc tgtgacactc tcctgggagt tacccgattg      180
gagggcgtta tccaccttcc actgtacttt ggcctctctg ggatagaagt tattcagcag      240
gcacacaacg ctagcagttc cagatttcaa ctgctcatca gatggcggga agatgaagac      300
agatggtgca gccacagttc gtttgatctc cagcttggtc ccctggccaa aactgcacgg      360
ataactatta tgctgtagac agtaataagt tgcaaaatct tcaggctgca ggctgctgat      420
tgtgagagtg aattctgtcc cagatccact gccgctgaac cttgatggga ccccactttg      480
caaactggat gcagcataga tcaggcgctt aggggctttc cctggtttct gctgatacca      540
gcctaaatca ttttttaatgc cctgacttgc ccggcaagtg atggtgactc tgtctcctac      600
agatgcagac aggaggatg gagactgggt catctggatg tcacacctgg cacctgggaa      660
ccagagcagc aggagcccca ggagctgagc ggggagcctc at                        702
```

<210> SEQ ID NO 91
<211> LENGTH: 234
<212> TYPE: PRT
<213> ORGANISM: Homo sapiens

<400> SEQUENCE: 91

```
Met Arg Leu Pro Ala Gln Leu Leu Gly Leu Leu Leu Leu Trp Phe Pro
 1               5                  10                  15

Gly Ala Arg Cys Asp Ile Gln Met Thr Gln Ser Pro Ser Ser Leu Ser
             20                  25                  30

Ala Ser Val Gly Asp Arg Val Thr Ile Thr Cys Arg Ala Ser Gln Gly
         35                  40                  45

Ile Lys Asn Asp Leu Gly Trp Tyr Gln Gln Lys Pro Gly Lys Ala Pro
     50                  55                  60

Lys Arg Leu Ile Tyr Ala Ala Ser Ser Leu Gln Ser Gly Val Pro Ser
 65                  70                  75                  80

Arg Phe Ser Gly Ser Gly Ser Gly Thr Glu Phe Thr Leu Thr Ile Ser
                 85                  90                  95

Ser Leu Gln Pro Glu Asp Phe Ala Thr Tyr Tyr Cys Leu Gln His Asn
            100                 105                 110

Ser Tyr Pro Cys Ser Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160
```

```
Pro Arg Glu Ala Lys Val Gln Trp Lys Val Asp Asn Ala Leu Gln Ser
            165                 170                 175
Gly Asn Ser Gln Glu Ser Val Thr Glu Gln Asp Ser Lys Asp Ser Thr
        180                 185                 190
Tyr Ser Leu Ser Ser Thr Leu Thr Leu Ser Lys Ala Asp Tyr Glu Lys
    195                 200                 205
His Lys Val Tyr Ala Cys Glu Val Thr His Gln Gly Leu Ser Ser Pro
210                 215                 220
Val Thr Lys Ser Phe Asn Arg Gly Glu Cys
225                 230

<210> SEQ ID NO 92
<211> LENGTH: 1996
<212> TYPE: DNA
<213> ORGANISM: Homo sapiens

<400> SEQUENCE: 92
```

| | |
|---|---:|
| atgaaacatc tgtggttctt cctcctgctg gtggcagctc ccagatgggt cctgtcccag | 60 |
| gtgcagctgc aggagtcggg cccaggactg gtgaagcctt cacagaccct gtccctcacc | 120 |
| tgcactgtct ctggtgcctc catcagcagt ggtgcttact actggagttg gatccgccag | 180 |
| cacccaggga agggcctgga gtggattggg tacatctata agagtgagac ctcctactac | 240 |
| aacccgtccc tcaagagtcg acttacccta tcagtagaca cgtctaagaa ccagttctcc | 300 |
| ctgaacctga tctctgtgac tgccgcggac acggccgtgt attattgtgc gagagataaa | 360 |
| ctggggatcg cggactactg gggccaggga accctggtca ccgtctcctc agcctccacc | 420 |
| aagggcccat cggtcttccc cctggcgccc tgctctagaa gcacctccga gagcacagcc | 480 |
| gccctgggct gcctggtcaa ggactacttc cccgaaccgg tgacggtgtc gtggaactca | 540 |
| ggcgctctga ccagcggcgt gcacaccttc ccagctgtcc tacagtcctc aggactctac | 600 |
| tccctcagca gcgtggtgac cgtgccctcc agcaacttcg gcacccagac ctacacctgc | 660 |
| aacgtagatc acaagcccag caacaccaag gtggacaaga cagttggtga gaggccagct | 720 |
| cagggaggga gggtgtctgc tggaagccag gctcagccct cctgcctgga cgcaccccgg | 780 |
| ctgtgcagcc ccagcccagg cagcaaggc aggccccatc tgtctcctca cccggaggcc | 840 |
| tctgcccgcc ccactcatgc tcagggagag ggtcttctgg cttttttccac caggctccag | 900 |
| gcaggcacag ctgggtgcc ctaccccag gccttcaca cacagggca ggtgcttggc | 960 |
| tcagacctgc caaaagccat atccgggagg accctgcccc tgacctaagc cgaccccaaa | 1020 |
| ggccaaactg tccactccct cagctcggac accttctctc ctcccagatc cgagtaactc | 1080 |
| ccaatcttct ctctgcagag cgcaaatgtt gtgtcgagtg cccaccgtgc ccaggtaagc | 1140 |
| cagcccaggc ctcgccctcc agctcaaggc gggacaggtg ccctagagta gcctgcatcc | 1200 |
| agggacaggc cccagctggg tgctgacacg tccacctcca tctcttcctc agcaccacct | 1260 |
| gtggcaggac cgtcagtctt cctcttcccc ccaaaaccca aggacaccct catgatctcc | 1320 |
| cggacccctg aggtcacgtg cgtggtggtg gacgtgagcc acgaagaccc cgaggtccag | 1380 |
| ttcaactggt acgtggacgg cgtggaggtg cataatgcca agacaaagcc acgggaggag | 1440 |
| cagttcaaca gcacgttccg tgtggtcagc gtcctcaccg ttgtgcacca ggactggctg | 1500 |
| aacggcaagg agtacaagtg caaggtctcc aacaaaggcc tcccagcccc catcgagaaa | 1560 |
| accatctcca aaaccaaagg tgggacccgc ggggtatgag ggccacatgg acagaggccg | 1620 |
| gctcggccca ccctctgccc tgggagtgac cgctgtgcca acctctgtcc ctacagggca | 1680 |

-continued

| | |
|---|---|
| gccccgagaa ccacaggtgt acaccctgcc cccatcccgg gaggagatga ccaagaacca | 1740 |
| ggtcagcctg acctgcctgg tcaaaggctt ctaccccagc gacatcgccg tggagtggga | 1800 |
| gagcaatggg cagccggaga caactacaa gaccacacct cccatgctgg actccgacgg | 1860 |
| ctccttcttc ctctacagca agctcaccgt ggacaagagc aggtggcagc aggggaacgt | 1920 |
| cttctcatgc tccgtgatgc atgaggctct gcacaaccac tacacgcaga gagcctctc | 1980 |
| cctgtctccg ggtaaa | 1996 |

<210> SEQ ID NO 93
<211> LENGTH: 1996
<212> TYPE: DNA
<213> ORGANISM: Homo sapiens

<400> SEQUENCE: 93

| | |
|---|---|
| tttacccgga gacagggaga ggctcttctg cgtgtagtgg ttgtgcagag cctcatgcat | 60 |
| cacggagcat gagaagacgt tcccctgctg ccacctgctc ttgtccacgg tgagcttgct | 120 |
| gtagaggaag aaggagccgt cggagtccag catgggaggt gtggtcttgt agttgttctc | 180 |
| cggctgccca ttgctctccc actccacggc gatgtcgctg gggtagaagc ctttgaccag | 240 |
| gcaggtcagg ctgacctggt tcttggtcat ctcctcccgg gatgggggca gggtgtacac | 300 |
| ctgtggttct cggggctgcc ctgtaggac agaggttggc acagcggtca ctcccagggc | 360 |
| agagggtggg ccgagccggc ctctgtccat gtggccctca tacccgcgg gtcccacctt | 420 |
| tggttttgga gatggttttc tcgatggggg ctgggaggcc tttgttggag accttgcact | 480 |
| tgtactcctt gccgttcagc cagtcctggt gcacaacggt gaggacgctg accacacgga | 540 |
| acgtgctgtt gaactgctcc tcccgtggct ttgtcttggc attatgcacc tccacgcgt | 600 |
| ccacgtacca gttgaactgg acctcggggt cttcgtggct cacgtccacc accacgcacg | 660 |
| tgacctcagg ggtccgggag atcatgaggg tgtccttggg ttttgggggg aagaggaaga | 720 |
| ctgacggtcc tgccacaggt ggtgctgagg aagagatgga ggtggacgtg tcagcaccca | 780 |
| gctggggcct gtccctggat gcaggctact ctagggcacc tgtcccgcct tgagctggag | 840 |
| ggcgaggcct gggctggctt acctgggcac ggtgggcact cgacacaaca tttgcgctct | 900 |
| gcagagagaa gattgggagt tactcggatc tgggaggaga gaaggtgtcc gagctgaggg | 960 |
| agtggacagt ttggcctttg gggtcggctt aggtcagggg cagggtcctc ccggatatgg | 1020 |
| cttttggcag gtctgagcca agcacctgcc cctgtgtgtg aagggcctgg ggtaggggca | 1080 |
| cccagcctgt gcctgcctgg agcctggtgg aaaaagccag aagaccctct ccctgagcat | 1140 |
| gagtggggcg ggcagaggcc tccgggtgag gagacagatg gggcctgcct tgctgccctg | 1200 |
| ggctggggct gcacagccgg ggtgcgtcca ggcaggaggg ctgagcctgg cttccagcag | 1260 |
| acaccctccc tccctgagct ggcctctcac caactgtctt gtccaccttg gtgttgctgg | 1320 |
| gcttgtgatc tacgttgcag gtgtaggtct gggtgccgaa gttgctggag gcacggtca | 1380 |
| ccacgctgct gagggagtag agtcctgagg actgtaggac agctgggaag gtgtgcacgc | 1440 |
| cgctggtcag agcgcctgag ttccacgaca ccgtcaccgg ttcggggaag tagtccttga | 1500 |
| ccaggcagcc cagggcggct gtgctctcgg aggtgcttct agagcagggc gccagggga | 1560 |
| agaccgatgg gcccttggtg gaggctgagg agacggtgac cagggttccc tggccccagt | 1620 |
| agtccgcgat ccccagttta tctctcgcac aataatacac ggccgtgtcc gcggcagtca | 1680 |
| cagagatcag gttcagggag aactggttct tagacgtgtc tactgatagg gtaagtcgac | 1740 |

```
tcttgaggga cgggttgtag taggaggtct cactcttata gatgtaccca atccactcca    1800
ggcccttccc tgggtgctgg cggatccaac tccagtagta agcaccactg ctgatggagg    1860
caccagagac agtgcaggtg agggacaggg tctgtgaagg cttcaccagt cctgggcccg    1920
actcctgcag ctgcacctgg gacaggaccc atctgggagc tgccaccagc aggaggaaga    1980
accacagatg tttcat                                                    1996
```

<210> SEQ ID NO 94
<211> LENGTH: 243
<212> TYPE: PRT
<213> ORGANISM: Homo sapiens

<400> SEQUENCE: 94

```
Met Lys His Leu Trp Phe Phe Leu Leu Leu Val Ala Leu Ala Ala Pro
 1               5                  10                  15

Arg Trp Val Leu Ser Gln Val Gln Leu Gln Glu Ser Gly Pro Gly Leu
            20                  25                  30

Val Lys Pro Ser Gln Thr Leu Ser Leu Thr Cys Thr Val Ser Gly Ala
        35                  40                  45

Ser Ile Ser Ser Gly Ala Tyr Tyr Trp Ser Trp Ile Arg Gln His Pro
    50                  55                  60

Gly Lys Gly Leu Glu Trp Ile Gly Tyr Ile Tyr Lys Ser Glu Thr Ser
 65                  70                  75                  80

Tyr Tyr Asn Pro Ser Leu Lys Ser Arg Leu Thr Leu Ser Val Ala Ser
                85                  90                  95

Pro Thr Ser Lys Asn Gln Phe Ser Leu Asn Leu Ile Ser Val Thr Ala
           100                 105                 110

Ala Asp Thr Ala Val Tyr Tyr Cys Ala Arg Asp Lys Leu Gly Ile Ala
       115                 120                 125

Asp Tyr Trp Gly Gln Gly Thr Leu Val Thr Val Ser Ser Ala Ser Thr
   130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
               165                 170                 175

Pro Val Thr Val Ser Trp Asn Ser Gly Ala Leu Thr Ser Gly Val His
           180                 185                 190

Thr Phe Pro Ala Val Leu Gln Ser Ser Gly Leu Tyr Ser Leu Ser Ser
       195                 200                 205

Val Val Thr Val Pro Ser Ser Asn Phe Gly Thr Gln Thr Tyr Thr Cys
   210                 215                 220

Asn Val Ala Ser Pro His Lys Pro Ser Asn Thr Lys Val Ala Ser Pro
225                 230                 235                 240

Lys Thr Val
```

<210> SEQ ID NO 95
<211> LENGTH: 702
<212> TYPE: DNA
<213> ORGANISM: Homo sapiens

<400> SEQUENCE: 95

```
atgagggtcc ccgctcagct cctggggctc ctgctgctct ggttcccagg cgccaggtgt     60
gacatccaga tgacccagtc tccatcctcc ctgtctgcat ctgtaggaga cagagtcacc    120
atcacttgcc gggcaagtca ggacattaga aatgatttag gctggtatca gcagaaacca    180
```

```
gggaaagccc ctaagcgcct gatctatgct gcatccaatt tgcaaagtgg ggtcccatca      240
aggttcagcg gcagtggatc tgggacagaa ttcactctca caatcagcag cctgcagcct      300
gaagattttg caacttatta ctgtctacag cataatagct accctcccac tttcggcgga      360
gggaccaagg tggaaatcaa acgaactgtg gctgcaccat ctgtcttcat cttcccgcca      420
tctgatgagc agttgaaatc tggaactgct agcgttgtgt gcctgctgaa taacttctat      480
cccagagagg ccaaagtaca gtggaaggtg gataacgccc tccaatcggg taactcccag      540
gagagtgtca cagagcagga cagcaaggac agcacctaca gcctcagcag caccctgacg      600
ctgagcaaag cagactacga gaaacacaaa gtctacgcct gcgaagtcac ccatcagggc      660
ctgagctcgc ccgtcacaaa gagcttcaac aggggagagt gt                        702

<210> SEQ ID NO 96
<211> LENGTH: 702
<212> TYPE: DNA
<213> ORGANISM: Homo sapiens

<400> SEQUENCE: 96
acactctccc ctgttgaagc tctttgtgac gggcgagctc aggccctgat gggtgacttc       60
gcaggcgtag actttgtgtt tctcgtagtc tgctttgctc agcgtcaggg tgctgctgag      120
gctgtaggtg ctgtccttgc tgtcctgctc tgtgacactc tcctgggagt tacccgattg      180
gagggcgtta tccaccttcc actgtacttt ggcctctctg ggatagaagt tattcagcag      240
gcacacaacg ctagcagttc cagatttcaa ctgctcatca gatggcggga agatgaagac      300
agatggtgca gccacagttc gtttgatttc caccttggtc cctccgccga aagtgggagg      360
gtagctatta tgctgtagac agtaataagt tgcaaaatct tcaggctgca ggctgctgat      420
tgtgagagtg aattctgtcc cagatccact gccgctgaac cttgatggga ccccactttg      480
caaattggat gcagcataga tcaggcgctt aggggctttc cctggtttct gctgataccag      540 gcctaaatca tttctaatgt cctgacttgc ccggcaagtg atggtgactc tgtctcctac      600
agatgcagac agggaggatg gagactgggt catctggatg tcacacctgg cgcctgggaa      660
ccagagcagc aggagcccca ggagctgagc ggggaccctc at                         702

<210> SEQ ID NO 97
<211> LENGTH: 234
<212> TYPE: PRT
<213> ORGANISM: Homo sapiens

<400> SEQUENCE: 97

Met Arg Val Pro Ala Gln Leu Leu Gly Leu Leu Leu Leu Trp Phe Pro
  1               5                  10                  15

Gly Ala Arg Cys Asp Ile Gln Met Thr Gln Ser Pro Ser Ser Leu Ser
             20                  25                  30

Ala Ser Val Gly Asp Arg Val Thr Ile Thr Cys Arg Ala Ser Gln Asp
         35                  40                  45

Ile Arg Asn Asp Leu Gly Trp Tyr Gln Gln Lys Pro Gly Lys Ala Pro
     50                  55                  60

Lys Arg Leu Ile Tyr Ala Ala Ser Asn Leu Gln Ser Gly Val Pro Ser
 65                  70                  75                  80

Arg Phe Ser Gly Ser Gly Ser Gly Thr Glu Phe Thr Leu Thr Ile Ser
                 85                  90                  95

Ser Leu Gln Pro Glu Asp Phe Ala Thr Tyr Tyr Cys Leu Gln His Asn
            100                 105                 110
```

```
Ser Tyr Pro Pro Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 98
<211> LENGTH: 1990
<212> TYPE: DNA
<213> ORGANISM: Homo sapiens

<400> SEQUENCE: 98

```
atgaaacacc tgtggttctt ccttctcctg gtggcagctc ccagatgggt cctgtcccag    60
gtgcagctgc aggagtcggg cccaggactg gtgaagcctt cggagaccct gtccctcacc   120
tgcactgtct ctggtgtctc catcagtaat tactactgga gctggatccg gcagtcccca   180
gggaagggac tggagtggat tggatatatc tattacagtg ggagtcccta ttacaacccc   240
tccctcaaga gtcgagtcac tatatctgca gacacgtcca agaaccaatt ctccctgaag   300
ctgagctctg tgaccgctgc ggacacggcc atttattact gtgcgagaga aaaactgggg   360
attggagact actggggcca gggaaccctg gtcaccgtct cctcagcctc caccaagggc   420
ccatcggtct tccccctggc gccctgctct agaagcacct ccgagagcac agccgccctg   480
ggctgcctgg tcaaggacta cttccccgaa ccggtgacgg tgtcgtggaa ctcaggcgct   540
ctgaccagcg gcgtgcacac cttcccagct gtcctacagt cctcaggact ctactccctc   600
agcagcgtgg tgaccgtgcc ctccagcaac ttcggcaccc agacctacac ctgcaacgta   660
gatcacaagc ccagcaacac caaggtggac aagacagttg tgagaggcc agctcaggga   720
gggagggtgt ctgctggaag ccaggctcag ccctcctgcc tggacgcacc ccggctgtgc   780
agccccagcc cagggcagca aggcaggccc catctgtctc ctcacccgga ggcctctgcc   840
cgccccactc atgctcaggg agagggtctt ctggcttttt ccaccaggct ccaggcaggc   900
acaggctggg tgcccctacc ccaggccctt cacacacagg gcaggtgct tggctcagac    960
ctgccaaaag ccatatccgg gaggaccctg cccctgacct aagccgaccc caaaggccaa  1020
actgtccact ccctcagctc ggacaccttc tctcctccca gatccgagta actcccaatc  1080
ttctctctgc agagcgcaaa tgttgtgtcg agtgcccacc gtgcccaggt aagccagccc  1140
aggcctcgcc ctccagctca aggcgggaca ggtgccctag agtagcctgc atccagggac  1200
aggccccagc tgggtgctga cacgtccacc tccatctctt cctcagcacc acctgtggca  1260
ggaccgtcag tcttcctctt ccccccaaaa cccaaggaca cctcatgat ctcccggacc   1320
cctgaggtca cgtgcgtggt ggtggacgtg agccacgaag accccgaggt ccagttcaac  1380
tggtacgtgg acggcgtgga ggtgcataat gccaagacaa agccacggga ggagcagttc  1440
```

```
aacagcacgt tccgtgtggt cagcgtcctc accgttgtgc accaggactg gctgaacggc    1500
aaggagtaca agtgcaaggt ctccaacaaa ggcctcccag cccccatcga gaaaaccatc    1560
tccaaaacca aaggtgggac ccgcggggta tgagggccac atggacagag gccggctcgg    1620 cccacccctct gccctgggag tgaccgctgt gccaacctct gtccctacag ggcagccccg    1680
agaaccacag gtgtacaccc tgcccccatc ccgggaggag atgaccaaga accaggtcag    1740
cctgacctgc ctggtcaaag gcttctaccc cagcgacatc gccgtggagt gggagagcaa    1800
tgggcagccg gagaacaact acaagaccac acctcccatg ctggactccg acggctcctt    1860
cttcctctac agcaagctca ccgtggacaa gagcaggtgg cagcagggga acgtcttctc    1920
atgctccgtg atgcatgagg ctctgcacaa ccactacacg cagaagagcc tctccctgtc    1980
tccgggtaaa                                                          1990
```

<210> SEQ ID NO 99
<211> LENGTH: 1990
<212> TYPE: DNA
<213> ORGANISM: Homo sapiens

<400> SEQUENCE: 99

```
tttacccgga gacagggaga ggctcttctg cgtgtagtgg ttgtgcagag cctcatgcat      60
cacggagcat gagaagacgt tcccctgctg ccacctgctc ttgtccacgg tgagcttgct     120
gtagaggaag aaggagccgt cggagtccag catgggaggt gtggtcttgt agttgttctc     180
cggctgccca ttgctctccc actccacggc gatgtcgctg gggtagaagc ctttgaccag     240
gcaggtcagg ctgacctggt tcttggtcat ctcctcccgg gatggggca gggtgtacac     300 ctgtggttct cggggctgcc ctgtaggac agaggttggc acagcggtca ctcccagggc     360
agagggtggg ccgagccggc ctctgtccat gtggccctca taccccgcgg gtcccacctt     420
tggttttgga gatggttttc tcgatggggg ctggaggcc tttgttggag accttgcact     480
tgtactcctt gccgttcagc cagtcctggt gcacaacggt gaggacgctg accacacgga    540
acgtgctgtt gaactgctcc tcccgtggct ttgtcttggc attatgcacc tccacgccgt    600
ccacgtacca gttgaactgg acctcgggt cttcgtggct cacgtccacc accacgcacg    660
tgacctcagg ggtccgggag atcatgaggg tgtccttggg ttttgggggg aagaggaaga    720
ctgacggtcc tgccacaggt ggtgctgagg aagagatgga ggtggacgtg tcagcaccca    780 gctgggggcct gtccctggat gcaggctact ctagggcacc tgtcccgcct tgagctggag    840
ggcgaggcct gggctggctt acctgggcac ggtgggcact cgacacaaca tttgcgctct    900
gcagagagaa gattgggagt tactcggatc tgggaggaga gaaggtgtcc gagctgaggg    960
agtggacagt ttggcctttg ggtcggctt aggtcagggg cagggtcctc ccggatatgg   1020
cttttggcag gtctgagcca agcacctgcc cctgtgtgtg aagggcctgg ggtaggggca   1080
cccagcctgt gcctgcctgg agcctggtgg aaaaagccag aagaccctct ccctgagcat   1140 gagtgggggcg ggcagaggcc tccggtgag gagacagatg gggcctgcct tgctgccctg   1200 ggctgggggct gcacagccgg ggtgcgtcca ggcaggaggg ctgagcctgg cttccagcag   1260
acaccctccc tccctgagct ggcctctcac caactgtctt gtccaccttg tgttgctgg   1320 gcttgtgatc tacgttgcag gtgtaggtct gggtgccgaa gttgctggag gcacggtca   1380 ccacgctgct gagggagtag agtcctgagg actgtaggac agctgggaag gtgtgcacgc   1440
cgctggtcag agcgcctgag ttccacgaca ccgtcaccgg ttcggggaag tagtccttga   1500
```

```
ccaggcagcc cagggcggct gtgctctcgg aggtgcttct agagcagggc gccaggggga      1560
agaccgatgg gcccttggtg gaggctgagg agacggtgac cagggttccc tggccccagt      1620
agtctccaat ccccagtttt tctctcgcac agtaataaat ggccgtgtcc gcagcggtca      1680
cagagctcag cttcagggag aattggttct tggacgtgtc tgcagatata gtgactcgac      1740
tcttgaggga ggggttgtaa tagggactcc cactgtaata gatatatcca atccactcca      1800
gtcccttccc tggggactgc cggatccagc tccagtagta attactgatg agacaccag       1860 agacagtgca ggtgagggac agggtctccg aaggcttcac cagtcctggg cccgactcct      1920
gcagctgcac ctgggacagg acccatctgg gagctgccac caggagaagg aagaaccaca     1980
ggtgtttcat                                                             1990
```

<210> SEQ ID NO 100
<211> LENGTH: 239
<212> TYPE: PRT
<213> ORGANISM: Homo sapiens

<400> SEQUENCE: 100

```
Met Lys His Leu Trp Phe Phe Leu Leu Leu Val Ala Leu Ala Ala Pro
 1               5                  10                  15

Arg Trp Val Leu Ser Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Ile Ser Asn Tyr Tyr Trp Ser Trp Ile Arg Gln Ser Pro Gly Lys
    50                  55                  60

Gly Leu Glu Trp Ile Gly Tyr Ile Tyr Tyr Ser Gly Ser Pro Tyr Tyr
65                  70                  75                  80

Asn Pro Ser Leu Lys Ser Arg Val Thr Ile Ser Ala Asp Thr Ser Lys
                85                  90                  95

Asn Gln Phe Ser Leu Lys Leu Ser Ser Val Thr Ala Ala Asp Thr Ala
            100                 105                 110

Ile Tyr Tyr Cys Ala Arg Glu Lys Leu Gly Ile Gly Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Ala Ser
    210                 215                 220

Pro His Lys Pro Ser Asn Thr Lys Val Ala Ser Pro Lys Thr Val
225                 230                 235
```

<210> SEQ ID NO 101
<211> LENGTH: 702
<212> TYPE: DNA
<213> ORGANISM: Homo sapiens

<400> SEQUENCE: 101

-continued

```
atgagggtcc ccgctcagct cctggggctc ctgctgctct ggttcccagg tgccaggtgt    60
gacatccaga tgacccagtc tccatcctcc ctgtctgcat ctgtcggaga cagagtcacc   120
atcacttgcc gggcaagtca gggcattaga aatgatttag ctggtatcag cagaaaccag   180
gggaaagccc ctaagcgcct gatctatgct gcatccagtt tgcaaagtgg ggtcccatca   240
aggttcagcg gcagtggatc tgggacagaa ttcactctca caatcagcag cctgcagcct   300
gaagattttg caacttatta ctgtctacag cataatagtt accctcccac tttcggccct   360
gggaccaagg tggatatcaa acgaactgtg gctgcaccat ctgtcttcat cttcccgcca   420
tctgatgagc agttgaaatc tggaactgct agcgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga aaacacaaa gtctacgcct gcgaagtcac ccatcagggc   660
ctgagctcgc ccgtcacaaa gagcttcaac aggggagagt gt                     702
```

<210> SEQ ID NO 102
<211> LENGTH: 702
<212> TYPE: DNA
<213> ORGANISM: Homo sapiens

<400> SEQUENCE: 102

```
acactctccc ctgttgaagc tctttgtgac gggcgagctc aggccctgat gggtgacttc    60
gcaggcgtag actttgtgtt ctcgtagtc tgctttgctc agcgtcaggg tgctgctgag    120
gctgtaggtg ctgtccttgc tgtcctgctc tgtgacactc tcctgggagt tacccgattg   180
gagggcgtta tccaccttcc actgtacttt ggcctctctg ggatagaagt tattcagcag   240
gcacacaacg ctagcagttc cagatttcaa ctgctcatca gatggcggga agatgaagac   300
agatggtgca gccacagttc gtttgatatc caccttggtc ccagggccga agtgggagg    360
gtaactatta tgctgtagac agtaataagt tgcaaaatct tcaggctgca ggctgctgat   420
tgtgagagtg aattctgtcc cagatccact gccgctgaac cttgatggga ccccactttg   480
caaactggat gcagcataga tcaggcgctt aggggctttc cctggtttct gctgatacca   540
gcctaaatca tttctaatgc cctgacttgc ccggcaagtg atggtgactc tgtctccgac   600
agatgcagac agggaggatg gagactgggt catctggatg tcacacctgg cacctgggaa   660
ccagagcagc aggagcccca ggagctgagc ggggaccctc at                    702
```

<210> SEQ ID NO 103
<211> LENGTH: 234
<212> TYPE: PRT
<213> ORGANISM: Homo sapiens

<400> SEQUENCE: 103

```
Met Arg Val Pro Ala Gln Leu Leu Gly Leu Leu Leu Leu Trp Phe Pro
 1               5                  10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Arg Asn Asp Leu Gly Trp Tyr Gln Gln Lys Pro Gly Lys Ala Pro
    50                  55                  60

Lys Arg Leu Ile Tyr Ala Ala Ser Ser Leu Gln Ser Gly Val Pro Ser
65                  70                  75                  80
```

```
Arg Phe Ser Gly Ser Gly Ser Gly Thr Glu Phe Thr Leu Thr Ile Ser
                 85                  90                  95
Ser Leu Gln Pro Glu Asp Phe Ala Thr Tyr Tyr Cys Leu Gln His Asn
            100                 105                 110
Ser Tyr Pro Pro Thr Phe Gly Pro Gly Thr Lys Val Asp Ile Lys Arg
        115                 120                 125
Thr Val Ala Ala Pro Ser Val Phe Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
    210                 215                 220
Val Thr Lys Ser Phe Asn Arg Gly Glu Cys
225                 230

<210> SEQ ID NO 104
<211> LENGTH: 1990
<212> TYPE: DNA
<213> ORGANISM: Homo sapiens

<400> SEQUENCE: 104
atgaaacatc tgtggttctt ccttctcctg gtggcagctc ccagatgggt cctgtcccag     60
gtgcagctgc aggagtcggg cccaggactg gtgaagcctt cggagaccct gtccctcacc    120
tgcactgtct ctggtggctc catcagtcgt tactactgga gctggatccg cagcccccca    180
gggaagggac tggagtggat tgggtatgtc tcttacagtg ggagcaccta ctacaacccc    240
tccctcaaga gtcgagtcac catatcagta gacacgtcca agaaccagtt ctccctgaag    300
ctgagctctg tgaccgctgc ggacacggcc gtgtattact gtgcgagaga taaactgggg    360
attggagact actggggcca gggaaccctg gtcaccgtct cctcagcctc caccaagggc    420
ccatcggtct tccccctggc gccctgctct agaagcacct ccgagagcac agccgccctg    480
ggctgcctgg tcaaggacta cttccccgaa ccggtgacgg tgtcgtggaa ctcaggcgct    540
ctgaccagcg gcgtgcacac cttccagct gtcctacagt cctcaggact ctactccctc    600
agcagcgtgg tgaccgtgcc ctccagcaac ttcggcaccc agacctacac ctgcaacgta    660
gatcacaagc ccagcaacac caaggtggac aagacagttg gtgagaggcc agctcaggga    720
gggagggtgt ctgctggaag ccaggctcag ccctcctgcc tggacgcacc ccggctgtgc    780
agccccagcc cagggcagca aggcaggccc catctgtctc ctcacccgga ggcctctgcc    840
cgccccactc atgctcaggg agagggtctt ctggcttttt ccaccaggct ccaggcaggc    900
acaggctggg tgcccctacc ccaggccctt cacacacagg gcaggtgct ggctcagac     960
ctgccaaaag ccatatccgg gaggaccctg ccctgacct aagccgaccc caaaggccaa    1020
actgtccact ccctcagctc ggacaccttc tctcctccca gatccgagta actcccaatc    1080
ttctctctgc agagcgcaaa tgttgtgtcg agtgcccacc gtgcccaggt aagccagccc    1140
aggcctcgcc ctccagctca aggcgggaca ggtgccctag agtagcctgc atccaggac     1200
aggccccagc tgggtgctga cacgtccacc tccatctctt cctcagcacc acctgtggca    1260
```

```
ggaccgtcag tcttcctctt cccccccaaaa cccaaggaca ccctcatgat ctcccggacc   1320
cctgaggtca cgtgcgtggt ggtggacgtg agccacgaag accccgaggt ccagttcaac   1380
tggtacgtgg acggcgtgga ggtgcataat gccaagacaa agccacggga ggagcagttc   1440
aacagcacgt tccgtgtggt cagcgtcctc accgttgtgc accaggactg gctgaacggc   1500
aaggagtaca agtgcaaggt ctccaacaaa ggcctcccag cccccatcga gaaaaccatc   1560
tccaaaacca aggtgggac cgcggggta tgagggccac atggacagag gccggctcgg   1620 cccacccctct gccctgggag tgaccgctgt gccaacctct gtccctacag ggcagccccg   1680
agaaccacag gtgtacaccc tgcccccatc ccggaggag atgaccaaga accaggtcag   1740
cctgacctgc ctggtcaaag gcttctaccc cagcgacatc gccgtggagt gggagagcaa   1800
tgggcagccg gagaacaact acaagaccac acctcccatg ctggactccg acggctcctt   1860
cttcctctac agcaagctca ccgtggacaa gagcaggtgg cagcagggga acgtcttctc   1920
atgctccgtg atgcatgagg ctctgcacaa ccactacacg cagaagagcc tctccctgtc   1980
tccgggtaaa                                                          1990

<210> SEQ ID NO 105
<211> LENGTH: 1990
<212> TYPE: DNA
<213> ORGANISM: Homo sapiens

<400> SEQUENCE: 105
tttacccgga gacagggaga ggctcttctg cgtgtagtgg ttgtgcagag cctcatgcat     60
cacggagcat gagaagacgt tccctgctg ccacctgctc ttgtccacgg tgagcttgct    120
gtagaggaag aaggagccgt cggagtccag catgggaggt gtggtcttgt agttgttctc    180
cggctgccca ttgctctccc actccacggc gatgtcgctg gggtagaagc ctttgaccag    240
gcaggtcagg ctgacctggt tcttggtcat ctcctcccgg gatgggggca gggtgtacac    300
ctgtggttct cggggctgcc ctgtagggac agaggttggc acagcggtca ctcccagggc    360
agagggtggg ccgagccggc ctctgtccat gtggccctca tacccgcgg gtcccacctt    420 tggttttgga gatggttttc tcgatggggg ctgggaggcc tttgttggag accttgcact    480
tgtactcctt gccgttcagc cagtcctggt gcacaacggt gaggacgctg accacacgga    540
acgtgctgtt gaactgctcc tcccgtggct ttgtcttggc attatgcacc tccacgccgt    600
ccacgtacca gttgaactgg acctcgggt cttcgtggct cacgtccacc accacgcacg    660
tgacctcagg ggtccgggag atcatgaggg tgtccttggg ttttgggggg aagaggaaga    720 ctgacgtcc tgccacaggt ggtgctgagg aagagatgga ggtggacgtg tcagcaccca    780
gctggggcct gtccctggat gcaggctact ctagggcacc tgtcccgcct tgagctggag    840
ggcgaggcct gggctggctt acctgggcac ggtgggcact cgacacaaca tttgcgctct    900
gcagagagaa gattgggagt tactcggatc tgggaggaga gaaggtgtcc gagctgaggg    960
agtggacagt ttggcctttg gggtcggctt aggtcagggg cagggtcctc ccggatatgg   1020
cttttggcag gtctgagcca agcacctgcc cctgtgtgtg aagggcctgg ggtaggggca   1080
cccagcctgt gcctgcctgg agcctggtgg aaaaagccag aagaccctct ccctgagcat   1140
gagtggggcg ggcagaggcc tccggtgag gagacagatg gggcctgcct tgctgccctg   1200
ggctggggct gcacagccgg ggtgcgtcca ggcaggaggg ctgagcctgg cttccagcag   1260
acaccctccc tccctgagct ggcctctcac caactgtctt gtccaccttg gtgttgctgg   1320
```

```
gcttgtgatc tacgttgcag gtgtaggtct gggtgccgaa gttgctggag ggcacggtca    1380
ccacgctgct gagggagtag agtcctgagg actgtaggac agctgggaag gtgtgcacgc    1440
cgctggtcag agcgcctgag ttccacgaca ccgtcaccgg ttcggggaag tagtccttga    1500
ccaggcagcc cagggcggct gtgctctcgg aggtgcttct agagcagggc gccaggggaa    1560
agaccgatgg gcccttggtg gaggctgagg agacggtgac cagggttccc tggccccagt    1620
agtctccaat ccccagttta tctctcgcac agtaatacac ggccgtgtcc gcagcggtca    1680
cagagctcag cttcagggag aactggttct tggacgtgtc tactgatatg gtgactcgac    1740
tcttgaggga ggggttgtag taggtgctcc cactgtaaga gacataccca atccactcca    1800
gtcccttccc tgggggctgc cggatccagc tccagtagta acgactgatg gagccaccag    1860
agacagtgca ggtgagggac agggtctccg aaggcttcac cagtcctggg cccgactcct    1920
gcagctgcac ctgggacagg acccatctgg gagctgccac caggagaagg aagaaccaca    1980
gatgtttcat                                                          1990
```

<210> SEQ ID NO 106
<211> LENGTH: 241
<212> TYPE: PRT
<213> ORGANISM: Homo sapiens

<400> SEQUENCE: 106

```
Met Lys His Leu Trp Phe Phe Leu Leu Leu Val Ala Leu Ala Ala Pro
1               5                   10                  15

Arg Trp Val Leu Ser Gln Val Gln Leu Gln Glu Ser Gly Pro Gly Leu
            20                  25                  30

Val Lys Pro Ser Glu Thr Leu Ser Leu Thr Cys Thr Val Ser Gly Gly
        35                  40                  45

Ser Ile Ser Arg Tyr Tyr Trp Ser Trp Ile Arg Gln Pro Pro Gly Lys
    50                  55                  60

Gly Leu Glu Trp Ile Gly Tyr Val Ser Tyr Ser Gly Ser Thr Tyr Tyr
65                  70                  75                  80

Asn Pro Ser Leu Lys Ser Arg Val Thr Ile Ser Val Ala Ser Pro Thr
                85                  90                  95

Ser Lys Asn Gln Phe Ser Leu Lys Leu Ser Ser Val Thr Ala Ala Asp
            100                 105                 110

Thr Ala Val Tyr Tyr Cys Ala Arg Asp Lys Leu Gly Ile Gly Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Ala Ser Pro His Lys Pro Ser Asn Thr Lys Val Ala Ser Pro Lys Thr
225                 230                 235                 240

Val
```

<210> SEQ ID NO 107
<211> LENGTH: 702
<212> TYPE: DNA
<213> ORGANISM: Homo sapiens

<400> SEQUENCE: 107

```
atgaggctcc ctgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaagtca gggcattaga aatgatttag ctggtatca gcagaaaccg   180
gggaaagccc ctaagcgcct gatctatgct gcatccagtt tgcaaagtgg ggtcccatca   240
aggttcagcg gcagtggatc tgggacagaa ttcactctca caatcagcag cctgcagcct   300
gaagattttg caacttatta ctgtctacag cataatagtt acccgtgcag ttttggccag   360
gggaccaagc tggagatcaa acgaactgtg gctgcaccat ctgtcttcat cttcccgcca   420
tctgatgagc agttgaaatc tggaactgct agcgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaaacacaaa gtctacgcct gcgaagtcac ccatcagggc   660
ctgagctcgc ccgtcacaaa gagcttcaac aggggagagt gt                      702
```

<210> SEQ ID NO 108
<211> LENGTH: 702
<212> TYPE: DNA
<213> ORGANISM: Homo sapiens

<400> SEQUENCE: 108

```
acactctccc ctgttgaagc tctttgtgac gggcgagctc aggccctgat gggtgacttc    60
gcaggcgtag actttgtgtt ctcgtagtc tgctttgctc agcgtcaggg tgctgctgag   120
gctgtaggtg ctgtccttgc tgtcctgctc tgtgacactc tcctgggagt tacccgattg   180
gagggcgtta tccaccttcc actgtacttt ggcctctctg ggatagaagt tattcagcag   240
gcacacaacg ctagcagttc cagatttcaa ctgctcatca gatggcggga agatgaagac   300
agatggtgca gccacagttc gtttgatctc agcttggtc ccctggccaa aactgcacgg   360
gtaactatta tgctgtagac agtaataagt tgcaaaatct tcaggctgca ggctgctgat   420
tgtgagagtg aattctgtcc cagatccact gccgctgaac cttgatggga ccccactttg   480
caaactggat gcagcataga tcaggcgctt aggggctttc ccggtttct gctgatacca   540
gcctaaatca tttctaatgc cctgacttgc ccggcaagtg atggtgactc tgtctcctac   600
agatgcagac agggaggatg gagactgggt catctgatt tcacacctgg cacctgggaa   660
ccagagcagc aggagcccca ggagctgagc agggagcctc at                      702
```

<210> SEQ ID NO 109
<211> LENGTH: 234
<212> TYPE: PRT
<213> ORGANISM: Homo sapiens

<400> SEQUENCE: 109

```
Met Arg Leu Pro Ala Gln Leu Leu Gly Leu Leu Leu Leu Trp Phe Pro
  1               5                  10                  15
Gly Ala Arg Cys Asp Ile Gln Met Thr Gln Ser Pro Ser Ser Leu Ser
             20                  25                  30
Ala Ser Val Gly Asp Arg Val Thr Ile Thr Cys Arg Ala Ser Gln Gly
```

-continued

```
                35                  40                  45
Ile Arg Asn Asp Leu Gly Trp Tyr Gln Gln Lys Pro Gly Lys Ala Pro
 50                  55                  60

Lys Arg Leu Ile Tyr Ala Ala Ser Ser Leu Gln Ser Gly Val Pro Ser
 65                  70                  75                  80

Arg Phe Ser Gly Ser Gly Ser Gly Thr Glu Phe Thr Leu Thr Ile Ser
                 85                  90                  95

Ser Leu Gln Pro Glu Asp Phe Ala Thr Tyr Tyr Cys Leu Gln His Asn
            100                 105                 110

Ser Tyr Pro Cys Ser Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 110
<211> LENGTH: 1996
<212> TYPE: DNA
<213> ORGANISM: Homo sapiens

<400> SEQUENCE: 110

```
atgaagcatc tgtggttctt cctcctgctg gtggcagctc ccagatgggt cctgtcccag      60
gtgcagctgc aggagtcggg cccaggactg gtgaagcctt cacagaccct gtccctcacc     120
tgcactgtct ctggtggctc catcagcagt ggtgtttact actggagctg gatccgccag     180
cacccaggga agggcctgga gtggattggg tacatctata cagtaagac ctcctattat     240
aatccgtccc tcaagagtcg acttacccta tcagtagaca cgtctaagaa ccagttctcc     300
ctgaacctga tctctgtgac tgccgcggac acggccgtgt attactgtgc gagagataaa     360
ttggggatcg cggactactg gggccaggga accctggtca ccgtctcctc agcctccacc     420
aagggcccat cggtcttccc cctggcgccc tgctctagaa gcacctccga gagcacagcc     480
gccctgggct gcctggtcaa ggactacttc cccgaaccgg tgacggtgtc gtggaactca     540
ggcgctctga ccagcggcgt gcacaccttc ccagctgtcc tacagtcctc aggactctac     600
tccctcagca gcgtggtgac cgtgccctcc agcaacttcg gcacccagac ctacacctgc     660
aacgtagatc acaagcccag caacaccaag gtggacaaga cagttggtga gaggccagct     720
cagggaggga gggtgtctgc tggaagccag gctcagccct cctgcctgga cgcaccccgg     780
ctgtgcagcc ccagcccagg gcagcaaggc aggccccatc tgtctcctca cccggaggcc     840
tctgcccgcc ccactcatgc tcagggagag gtcttctgg ctttttccac caggctccag     900
gcaggcacag gctgggtgcc cctacccag gccttcaca cacaggggca ggtgcttggc     960
tcagacctgc caaaagccat atccgggagg accctgcccc tgacctaagc cgaccccaaa    1020
```

```
ggccaaactg tccactccct cagctcggac accttctctc ctcccagatc cgagtaactc  1080
ccaatcttct ctctgcagag cgcaaatgtt gtgtcgagtg cccaccgtgc ccaggtaagc  1140
cagcccaggc ctcgccctcc agctcaaggc gggacaggtg ccctagagta gcctgcatcc  1200
agggacaggc cccagctggg tgctgacacg tccacctcca tctcttcctc agcaccacct  1260
gtggcaggac cgtcagtctt cctcttcccc caaaaccca aggacaccct catgatctcc  1320
cggacccctg aggtcacgtg cgtggtggtg gacgtgagcc acgaagaccc cgaggtccag  1380
ttcaactggt acgtggacgg cgtggaggtg cataatgcca agacaaagcc acgggaggag  1440
cagttcaaca gcacgttccg tgtggtcagc gtcctcaccg ttgtgcacca ggactggctg  1500
aacggcaagg agtacaagtg caaggtctcc aacaaaggcc tcccagcccc catcgagaaa  1560
accatctcca aaccaaagg tgggacccgc ggggtatgag gccacatgg acagaggccg  1620
gctcggccca cctctgcccc tgggagtgac cgctgtgcca acctctgtcc ctacagggca  1680
gccccgagaa ccacaggtgt acaccctgcc cccatcccgg gaggagatga ccaagaacca  1740
ggtcagcctg acctgcctgg tcaaaggctt ctaccccagc gacatcgccg tggagtggga  1800
gagcaatggg cagccggaga caactacaa gaccacacct cccatgctgg actccgacgg  1860
ctccttcttc ctctacagca agctcaccgt ggacaagagc aggtggcagc aggggaacgt  1920
cttctcatgc tccgtgatgc atgaggctct gcacaaccac tacacgcaga agagcctctc  1980
cctgtctccg ggtaaa                                                  1996
```

<210> SEQ ID NO 111
<211> LENGTH: 1996
<212> TYPE: DNA
<213> ORGANISM: Homo sapiens

<400> SEQUENCE: 111

```
tttacccgga gacagggaga ggctcttctg cgtgtagtgg ttgtgcagag cctcatgcat    60
cacggagcat gagaagacgt tccccctgctg ccacctgctc ttgtccacgg tgagcttgct  120
gtagaggaag aaggagccgt cggagtccag catgggaggt gtggtcttgt agttgttctc  180
cggctgccca ttgctctccc actccacggc gatgtcgctg gggtagaagc ctttgaccag  240
gcaggtcagg ctgacctggt tcttggtcat ctcctcccgg gatgggggca gggtgtacac  300
ctgtggttct cggggctgcc ctgtagggac agaggttggc acagcggtca ctcccagggc  360
agagggtggg ccgagccggc ctctgtccat gtggccctca tacccgcgg gtcccacctt  420
tggttttgga gatggttttc tcgatggggg ctgggaggcc tttgttggag accttgcact  480
tgtactcctt gccgttcagc cagtcctggt gcacaacggt gaggacgctg accacacgga  540
acgtgctgtt gaactgctcc tcccgtggct ttgtcttggc attatgcacc tccacgccgt  600
ccacgtacca gttgaactgg acctcggggt cttcgtggct cacgtccacc accacgcacg  660
tgacctcagg ggtccgggag atcatgaggg tgtccttggg ttttgggggg aagaggaaga  720
ctgacggtcc tgccacaggt ggtgctgagg aagagatgga ggtggacgtg tcagcaccca  780
gctggggcct gtccctggat gcaggctact ctagggcacc tgtcccgcct tgagctggag  840
ggcgaggcct gggctggctt acctgggcac ggtgggcact cgacacaaca tttgcgctct  900
gcagagagaa gattgggagt tactcggatc tgggaggaga aaggtgtcc gagctgaggg  960
agtggacagt ttggcctttg gggtcggctt aggtcagggg cagggtcctc ccggatatgg 1020
cttttggcag gtctgagcca agcacctgcc cctgtgtgtg aagggcctgg ggtaggggca 1080
```

-continued

```
cccagcctgt gcctgcctgg agcctggtgg aaaaagccag aagaccctct ccctgagcat   1140
gagtggggcg ggcagaggcc tccgggtgag gagacagatg gggcctgcct tgctgccctg   1200
ggctggggct gcacagccgg ggtgcgtcca ggcaggaggg ctgagcctgg cttccagcag   1260
acaccctccc tccctgagct ggcctctcac caactgtctt gtccaccttg gtgttgctgg   1320
gcttgtgatc tacgttgcag gtgtaggtct gggtgccgaa gttgctggag ggcacggtca   1380
ccacgctgct gagggagtag agtcctgagg actgtaggac agctgggaag gtgtgcacgc   1440
cgctggtcag agcgcctgag ttccacgaca ccgtcaccgg ttcggggaag tagtccttga   1500
ccaggcagcc cagggcggct gtgctctcgg aggtgcttct agagcagggc gccaggggga   1560
agaccgatgg gcccttggtg gaggctgagg agacggtgac cagggttccc tggccccagt   1620
agtccgcgat ccccaattta tctctcgcac agtaatacac ggccgtgtcc gcggcagtca   1680
cagagatcag gttcagggag aactggttct tagacgtgtc tactgatagg gtaagtcgac   1740
tcttgaggga cggattataa taggaggtct tactgtttata gatgtaccca atccactcca   1800
ggcccttccc tgggtgctgg cggatccagc tccagtagta acaccactg ctgatggagc   1860 caccagagac agtgcaggtg agggacaggg tctgtaaagg cttcaccagt cctgggcccg   1920
actcctgcag ctgcacctgg gacaggaccc atctgggagc tgccaccagc aggaggaaga   1980
accacagatg cttcat                                                  1996
```

<210> SEQ ID NO 112
<211> LENGTH: 235
<212> TYPE: PRT
<213> ORGANISM: homo sapiens

<400> SEQUENCE: 112

```
Met Lys His Leu Trp Phe Phe Leu Leu Leu Val Ala Ala Pro Arg Trp
  1               5                  10                  15

Val Leu Ser Gln Val Gln Leu Gln Glu Ser Gly Pro Gly Leu Val Lys
             20                  25                  30

Pro Leu Gln Thr Leu Ser Leu Thr Cys Thr Val Ser Gly Gly Ser Ile
         35                  40                  45

Ser Ser Gly Val Tyr Tyr Trp Ser Trp Ile Arg Gln His Pro Gly Lys
     50                  55                  60

Gly Leu Glu Trp Ile Gly Tyr Ile Tyr Asn Ser Lys Thr Ser Tyr Tyr
 65                  70                  75                  80

Asn Pro Ser Leu Lys Ser Arg Leu Thr Leu Ser Val Asp Thr Ser Lys
                 85                  90                  95

Asn Gln Phe Ser Leu Asn Leu Ile Ser Val Thr Ala Ala Asp Thr Ala
            100                 105                 110

Val Tyr Tyr Cys Ala Arg Asp Lys Leu Gly Ile Ala Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205
```

Pro Ser Ser Asn Phe Gly Thr Gln Thr Tyr Thr Cys Asn Val Asp His
    210                 215                 220

Lys Pro Ser Asn Thr Lys Val Asp Lys Thr Val
225                 230                 235

<210> SEQ ID NO 113
<211> LENGTH: 702
<212> TYPE: DNA
<213> ORGANISM: Homo sapiens

<400> SEQUENCE: 113
atgagggtcc ctgctcagct cctggggctc ctgctgctct ggttcccagg tgccaggtgt     60
gacatccaga tgacccagtc tccatcctcc ctgtctgcat ctgtaggaga cagagtcacc    120
atcacttgcc ggacaagtca gggcattaga aatgatttag ctggtatca gcagaaacca    180 gggaaagccc ctaagcgcct gatctatgct gcatccagtt tgcaaagtgg ggtcccatca    240
aggttcagcg gcagtggatc tgggacagaa ttcactctca caatcagcag cctgcagcct    300
gaagattttg caacttatta ctgtctacag cataatagct accctcccac tttcggcgga    360
gggaccaagg tggagatcaa acgaactgtg gctgcaccat ctgtcttcat cttcccgcca    420
tctgatgagc agttgaaatc tggaactgct agcgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga aaacacaaa gtctacgcct gcgaagtcac ccatcagggc    660
ctgagctcgc ccgtcacaaa gagcttcaac aggggagagt gt                      702

<210> SEQ ID NO 114
<211> LENGTH: 702
<212> TYPE: DNA
<213> ORGANISM: Homo sapiens

<400> SEQUENCE: 114
acactctccc ctgttgaagc tctttgtgac gggcgagctc aggccctgat gggtgacttc     60
gcaggcgtag actttgtgtt tctcgtagtc tgctttgctc agcgtcaggg tgctgctgag    120
gctgtaggtg ctgtccttgc tgtcctgctc tgtgacactc tcctgggagt tacccgattg    180
gagggcgtta tccaccttcc actgtacttt ggcctctctg ggatagaagt tattcagcag    240
gcacacaacg ctagcagttc cagatttcaa ctgctcatca gatggcggga agatgaagac    300
agatggtgca gccacagttc gtttgatctc caccttggtc cctccgccga agtgggagg    360 gtagctatta tgctgtagac agtaataagt tgcaaaatct tcaggctgca ggctgctgat    420
tgtgagagtg aattctgtcc cagatccact gccgctgaac cttgatggga ccccactttg    480
caaactggat gcagcataga tcaggcgctt aggggctttc cctggtttct gctgatacca    540
gcctaaatca tttctaatgc cctgacttgt ccggcaagtg atggtgactc tgtctcctac    600
agatgcagac agggaggatg gagactgggt catctggatg tcacacctgg cacctgggaa    660
ccagagcagc aggagcccca ggagctgagc agggaccctc at                      702

<210> SEQ ID NO 115
<211> LENGTH: 234
<212> TYPE: PRT
<213> ORGANISM: Homo sapiens

<400> SEQUENCE: 115

Met Arg Val Pro Ala Gln Leu Leu Gly Leu Leu Leu Leu Trp Phe Pro

-continued

```
1               5                   10                  15
Gly Ala Arg Cys Asp Ile Gln Met Thr Gln Ser Pro Ser Ser Leu Ser
            20                  25              30

Ala Ser Val Gly Asp Arg Val Thr Ile Thr Cys Arg Thr Ser Gln Gly
            35              40                  45

Ile Arg Asn Asp Leu Gly Trp Tyr Gln Gln Lys Pro Gly Lys Ala Pro
            50              55                  60

Lys Arg Leu Ile Tyr Ala Ala Ser Ser Leu Gln Ser Gly Val Pro Ser
65                      70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Tyr Cys Leu Gln His Asn
            100                 105                 110

Ser Tyr Pro Pro Thr Phe Gly Gly Gly Thr Lys Val Glu Ile Lys Arg
            115                 120                 125

Thr Val Ala Ala Pro Ser Val Phe Ile Phe Pro Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230
```